US012084519B2

(12) United States Patent
Shoemaker et al.

(10) Patent No.: US 12,084,519 B2
(45) **Date of Patent: *Sep. 10, 2024**

(54) METHODS, COMPOSITIONS AND KITS FOR TREATING A SUBJECT USING A RECOMBINANT HETEROMULTIMERIC NEUTRALIZING BINDING PROTEIN

(71) Applicant: TRUSTEES OF TUFTS COLLEGE, Medford, MA (US)

(72) Inventors: Charles B. Shoemaker, Medford, MA (US); Hanping Feng, Medford, MA (US)

(73) Assignee: Trustees of Tufts College, Medford, MA (US)

(*) Notice: Subject to any disclaimer, the term of this patent is extended or adjusted under 35 U.S.C. 154(b) by 105 days.

This patent is subject to a terminal disclaimer.

(21) Appl. No.: 17/371,762

(22) Filed: Jul. 9, 2021

(65) Prior Publication Data

US 2021/0363275 A1 Nov. 25, 2021

Related U.S. Application Data

(60) Continuation of application No. 15/475,664, filed on Mar. 31, 2017, now Pat. No. 11,091,563, which is a continuation of application No. 14/665,542, filed on Mar. 23, 2015, now Pat. No. 9,834,616, which is a division of application No. 13/566,524, filed on Aug. 3, 2012, now Pat. No. 9,023,352, which is a continuation-in-part of application No. 12/889,511, filed on Sep. 24, 2010, now Pat. No. 8,349,326, which is a continuation-in-part of application No. 12/032,744, filed on Feb. 18, 2008, now Pat. No. 8,865,169.

(60) Provisional application No. 61/514,949, filed on Aug. 4, 2011, provisional application No. 60/890,626, filed on Feb. 20, 2007.

(51) Int. Cl.

| | |
|---|---|
| ***A61K 39/00*** | (2006.01) |
| ***A61K 38/16*** | (2006.01) |
| ***A61K 39/395*** | (2006.01) |
| ***C07K 16/12*** | (2006.01) |
| ***C07K 16/40*** | (2006.01) |
| ***C07K 16/44*** | (2006.01) |
| ***C07K 16/46*** | (2006.01) |

(52) U.S. Cl.

CPC ............ *C07K 16/468* (2013.01); *A61K 38/16* (2013.01); *A61K 39/39591* (2013.01); *C07K 16/1282* (2013.01); *C07K 16/40* (2013.01); *C07K 16/44* (2013.01); *A61K 2039/505* (2013.01); *A61K 2039/507* (2013.01); *C07K 2317/31* (2013.01); *C07K 2317/569* (2013.01); *C07K 2317/62* (2013.01); *C07K 2317/622* (2013.01); *C07K 2317/76* (2013.01); *C07K 2317/92* (2013.01); *C07K 2319/40* (2013.01)

(58) Field of Classification Search

None

See application file for complete search history.

(56) References Cited

U.S. PATENT DOCUMENTS

| | | | |
|---|---|---|---|
| 5,194,596 | A | 3/1993 | Tischer et al. |
| 5,196,193 | A | 3/1993 | Carroll |
| 5,225,539 | A | 7/1993 | Winter |
| 5,455,030 | A | 10/1995 | Ladner et al. |
| 5,530,101 | A | 6/1996 | Queen et al. |
| 5,585,089 | A | 12/1996 | Queen et al. |
| 5,624,659 | A | 4/1997 | Bigner et al. |
| 5,693,761 | A | 12/1997 | Queen et al. |
| 5,693,762 | A | 12/1997 | Queen et al. |
| 5,731,168 | A | 3/1998 | Carter et al. |
| 5,840,526 | A | 11/1998 | Casterman et al. |
| 6,015,695 | A | 1/2000 | Casterman et al. |
| 6,180,370 | B1 | 1/2001 | Queen et al. |

(Continued)

FOREIGN PATENT DOCUMENTS

| | | |
|---|---|---|
| CN | 103866401 A | 6/2014 |
| EP | 0239400 B1 | 9/1987 |

(Continued)

OTHER PUBLICATIONS

Schmidt et al. Clin. Vaccine Immunol. 23: 774-784, pre-published online Jul. 13, 2016.*

(Continued)

*Primary Examiner* — S. Devi

(74) *Attorney, Agent, or Firm* — Melissa Hunter-Ensor; Leslie Serunian; Greenberg Traurig, LLP

(57) ABSTRACT

Methods, compositions and kits are provided for treating a subject exposed to or at risk for exposure to a disease agent using a pharmaceutical composition including at least one recombinant heteromultimeric neutralizing binding protein including two or multiple binding regions, such that the binding regions are not identical, and each binding region specifically binds a non-overlapping portion of the disease agent, thereby treating the subject for exposure to the disease agent. In a related embodiment, the heteromultimeric neutralizing binding protein includes two or multiple binding regions that neutralize a plurality of disease agents. In certain embodiments, the disease agent includes a bacterium, a bacterial protein, a virus, a viral protein, a cancer cell, and a protein or molecule produced therefrom. In certain embodiments, the disease agent is a plurality of different disease agents.

24 Claims, 41 Drawing Sheets

Specification includes a Sequence Listing.

(56) References Cited

U.S. PATENT DOCUMENTS

| | | | | |
|---|---|---|---|---|
| 6,187,287 | B1 | 2/2001 | Leung et al. | |
| 7,345,161 | B2 | 3/2008 | Masuda et al. | |
| 7,745,587 | B2 | 6/2010 | Devy et al. | |
| 7,763,445 | B2 | 7/2010 | Moore et al. | |
| 7,807,184 | B2 | 10/2010 | Vermeij | |
| 7,867,724 | B2 | 1/2011 | Alexandru et al. | |
| 7,879,333 | B2 | 2/2011 | Gerber | |
| 7,943,345 | B2 | 5/2011 | Park et al. | |
| 8,114,634 | B2 | 2/2012 | Park et al. | |
| 8,349,326 | B2 | 1/2013 | Shoemaker et al. | |
| 8,865,169 | B2 | 10/2014 | Shoemaker et al. | |
| 8,865,871 | B2 | 10/2014 | Park et al. | |
| 8,975,382 | B2 | 3/2015 | Revets et al. | |
| 9,023,352 | B2 | 5/2015 | Shoemaker et al. | |
| 9,834,616 | B2 | 12/2017 | Shoemaker et al. | |
| 10,131,870 | B2 | 11/2018 | Takeuchi et al. | |
| 10,202,441 | B2 | 2/2019 | Shoemaker | |
| 10,550,174 | B2 | 2/2020 | Stortelers et al. | |
| 10,766,950 | B2 | 9/2020 | Shoemaker | |
| 11,001,625 | B2 | 5/2021 | Shoemaker | |
| 11,091,563 | B2 * | 8/2021 | Shoemaker | C07K 16/1282 |
| 2004/0053340 | A1 | 3/2004 | De Haard et al. | |
| 2005/0287129 | A1 | 12/2005 | Ciccarelli et al. | |
| 2006/0018911 | A1 | 1/2006 | Ault-Riche et al. | |
| 2006/0149041 | A1 | 7/2006 | Silence | |
| 2009/0098608 | A1 | 4/2009 | Park et al. | |
| 2010/0092511 | A1 | 4/2010 | Waldor et al. | |
| 2010/0136018 | A1 | 6/2010 | Dolk et al. | |
| 2010/0278830 | A1 | 11/2010 | Shoemaker et al. | |
| 2011/0010782 | A1 | 1/2011 | Horvitz et al. | |
| 2011/0129474 | A1 | 6/2011 | Shoemaker et al. | |
| 2013/0058962 | A1 | 3/2013 | Shoemaker et al. | |
| 2014/0072581 | A1 | 3/2014 | Dixit et al. | |
| 2014/0294826 | A1 * | 10/2014 | Shoemaker | C07K 16/1278 424/134.1 |
| 2015/0093384 | A1 | 4/2015 | Shoemaker et al. | |
| 2016/0031971 | A9 | 2/2016 | Shoemaker | |
| 2016/0159866 | A1 | 6/2016 | Ichtchenko et al. | |
| 2016/0362501 | A1 | 12/2016 | Shoemaker et al. | |
| 2016/0368972 | A1 | 12/2016 | Shoemaker | |
| 2017/0204169 | A1 | 7/2017 | Shoemaker et al. | |
| 2017/0362310 | A1 | 12/2017 | Shoemaker | |
| 2019/0225675 | A1 | 7/2019 | Shoemaker | |
| 2020/0129444 | A1 | 4/2020 | Whitehead et al. | |
| 2021/0188953 | A1 | 6/2021 | Shoemaker | |
| 2021/0221874 | A1 | 7/2021 | Shoemaker | |
| 2023/0192825 | A1 | 6/2023 | Shoemaker | |

FOREIGN PATENT DOCUMENTS

| | | | |
|---|---|---|---|
| EP | 0592106 | B1 | 4/1994 |
| EP | 0519596 | B1 | 2/2005 |
| WO | 1991009967 | A1 | 7/1991 |
| WO | 2009139919 | A2 | 11/2009 |
| WO | 2011068953 | A2 | 6/2011 |
| WO | 2015100409 | A2 | 7/2015 |
| WO | 2016040499 | A1 | 3/2016 |
| WO | 2019094095 | A1 | 5/2019 |
| WO | 2022006219 | A2 | 1/2022 |

OTHER PUBLICATIONS

Sandvig et al., "Entry of ricin and Shiga toxin into cells: molecular mechanisms and medical perspectives" EMBO J, vol. 19, pp. 5943-5950 (2000).

Savidge et al., "Clostridium difficile toxin B is an inflammatory enterotoxin in human intestine" Gastroenterology, vol. 125, pp. 413-420, (2003).

Sehr et al., "Glucosylation and ADP ribosylation of rho proteins: effects on nucleotide binding, GTPase activity, and effector coup-ing" Biochemistry, vol. 37, pp. 5296-5304 (1998).

Siemann et al. "Clostridium difficil-associated diseases. The clinical courses of 18 fatal cases" Inten Car Med, vol. 26, pp. 416-421, (2000).

Simpson, "Identification of the major steps in botulinum toxin action" Annu Rev Parmacol Toxicol, vol. 44, pp. 167-193, (2004).

Spears et al., "A comparison of enteropathogenic and enterohaemorrhagic *Escherichia coli* pathogenesis" FEMS Microbiol Lett, vol. 255, pp. 187-202, (2006).

Stancovski et al., Proceedings of the National Academy of Science USA 88: pp. 8691-8695, (1991).

Tonegawa, S. "The genetic principle for generation of antibody diversity", The Nobel Assembly at the Karolinkska Institute, (retrieved May 23, 2008 from online at nobelprize.org/nobel_prizes/medicine/laureates/1987/press.html), (1987).

Tonna et al., "Pathogenesis and treatment of Clostridium difficile infection" Postgrad Med J, vol. 81, pp. 367-369 (2005).

Tucker et al., "Toxin A of Clostridium difficile Binds to the Human Carbohydrate Antigens I, X, and Y" Infect Immun., vol. 59, pp. 73-78 (1991).

Von Eichel-Streiber et al., "Large clostridial cytotoxins—a family of glycosyltransferases modifying small GTP-binding proteins" Trends Microbiol, vol. 4, pp. 375-382 (1996).

Voth et al., "Clostridium difficile Toxins: Mechanism of Action and Role in Disease" Clin Microbio Rev, vol. 18, pp. 247-263 (2005).

Walker et al., "Interscience Conference on Antimicrobial Agents and Chemotherapy—50th Annual Meetings—Research on Promising New Agents: Part 1" IDRUGS, vol. 13, pp. 743-745 (2010).

Witte et al., Cancer and Metastasis Reviews 17: pp. 155-161 (1998).

Yu et al., Investigative Opthamology & Visual Science, vol. 49(2): pp. 522-527, Feb. 2008.

Zar et al., "A comparison of vancomycin and metronidazole for the treatment of Clostridium difficile-associated diarrhea, stratified by disease severity" Clin Infect Dis, vol. 45, pp. 302-307 (2007).

Lederman et al., Mol. Immunol., vol. 28, pp. 1171-1181 (1991).

Li et al., PNAS, vol. 77, pp. 3211-3214 (1980).

Skolnick et al., Trends in Biology, vol. 18, pp. 34-39 (2000).

Abaza et al., J. Protein Chem., vol. 11, pp. 433-444 (1992).

Colman et al., Res. Immunol., vol. 245, pp. 33-36 (1964).

Brown et al., Hybridoma, vol. 16(5), pp. 447-456 (1997).

Hussack et al., Toxins, vol. 2, pp. 998-1018 (2010).

Dupuy et al., Research in Microbiology, vol. 157, pp. 201-205 (2006).

Adelman et al., "In vitro deletional mutagensis for bacterial production of the 20,000-dalton form of human pituitary growth hormone," DNA, vol. 2, pp. 183-193 (1983).

Altschul et al., "Basic local alignment search tool," J. Mol. Biol., vol. 215, pp. 403-410 (1990).

Altschul et al., "Gapped BLAST and PSI-BLAST: a new generation of protein database search programs," Nucleic Acids Res. vol. 25(17), pp. 3389-3402 (1997).

Brown et al., "Cloning and characterization of an extracellular Ca(2+)-sensing receptor from bovine parathyroid," Nature, vol. 366, pp. 575-580 (1993).

Higgins et al., "CLUSTAL: a package for performing multiple sequence alignment on a microcomputer," Gene, vol. 73, pp. 237-244 (1988).

Bilge et al., "Translocation of Ricin A-chain Into Proteoliposomes Reconstitute from Golgi and Endoplasmic Reticulum," Journal of Biological Chemistry, vol. 270, pp. 23720-23725 (1995).

Boerlin et al., "Associations between Virulence Factors of Shiga Toxin-Producing *Escherichida coli* and Disease in Humans," Journal of clinical microbiolgy, vol. 27, pp. 497-503 (1999).

Bucholz et al., "German Outbreak of *Escherichia coli* O104:H4 Associated with Sprouts," N. Engl. J. Med., vol. 365 (19), pp. 1763-1770 (2011).

Butterworth et al., "Ricin and Ricinus communis agglutinin subunits are all derived from a single-size polypeptide precursor," Eur. J. Blochem., vol. 137, pp. 57-65 (1983).

Cherla et al., "Shiga toxins and apoptosis," FEMS microbiology letters, vol. 228, pp. 159-166 (2003).

Cohen et al., "Roles of globtriosyl- and galabiosylceramide in verotoxin binding and high affinity interferon receptor," J. Biol. Chem., vol. 262, pp. 17088-17091 (1987).

(56) References Cited

OTHER PUBLICATIONS

Donohue-Rolfe et al., Purification of Shiga toxin and Shiga-like toxins I and II by receptor analog affinity chromatography with immobolized P1 glycoprotein and production of cross-reactive monoclonal antibodies, vol. 57 (12), pp. 3888-3693 (1989).
Dowling et al., "Phase 1 safety and pharmacokinetic study of chimeric murine-human monoclonal antibody c alpha Stx2 administered intravelously to healthy adult volunteers," Antimicrobial agents and chemoterhapy, vol. 49, pp. 1808-1812 (2005).
Eubanks et al., "Identification of a Natural Product Antagonist against the Botulinum Neurotoxin Light Chain Protease," ACS Med Chem Lett. vol. 1(6), pp. 268-272 (2010).
Eubanks et al., "An in vitro and in vitro disconnect uncovered through high-throughput identification of botulinum neurotoxin A antagonists," Proc. Natl. Acad. Sci., vol. 104, pp. 2602-2607 (2007).
Fernie et al., Active and passive immunization to protect against antiobiotic associated caecitis in hamsters, Dev. Biol. Stand., vol. 53, pp. 325-332 (1983).
Frank et al., "Epidemic Profile of Shiga-Toxin-Producing *Escherchia coli* O104:H4 Outbreak in Germany," N. Engl. J. Med., vol. 365, pp. 1771-1780 (2011).
Friedrich et al., "*Escherichia coli* Harboring Shiga Toxin 2 Gene Variants: Frequency and Association with Clinical Symptoms," J. Infect. Dis., vol. 185(1), pp. 74-84 (2002).
Gibbs, "Nanobodies," Sci. Am., vol. 293(2), pp. 78-83 (2005).
Hedican et al., Characteristics of O157 verus Non-O157 Shiga Toxin-Producing *Escherichia coli* Infections in Minnesota, 2000-2006, vol. 49(3), pp. 358-364 (2009).
Hunt, "Shiga Toxin-Producing *Escherichida coli*," Clinics in laboratory medicine, vol. 30(1), pp. 21-45 (2010).
Karmali et al., "The association between idiopathic hemolytic uremic syndrome and infection by verotoxin-producing *Escherichia coli*," J. Infect. Dis., vol. 151, pp. 775-782 (1985).
Kawano et al., "Relationship between pathogenicity for humans and stx genotype in Shiga toxin-producing *Escherichia coli* serotype O157." European journal of clinical microbiology & Infectious diseases, vol. 27(3), pp. 227-232 (2008).
Babcock et al., "Human Monoclonal Antibodies Directed against Toxins A and B Prevent Clostridum difficile-induced Mortality in Hamsters," Infect. Immun., vol. 74, pp. 6339-6347 (2006).
Notice of Allowance in U.S. Appl. No. 15/475,664, mailed on Apr. 7, 2021 (10 pages).
Non-Final Office Action in U.S. Appl. No. 15/475,664, mailed on Feb. 23, 2018 (16 pages).
Babcock et al., "Human Monoclonal Antibodies Directed against Toxins A and B Prevent Clostridium difficile-Induced Mortality in Hamsters," Infect. Immun., vol. 74, pp. 6339-6347 (2006).
Barbut et al., "Epidemiology of Recurrences or Reinfections of Clostridium difficule-Associated Diarrhea," J. Clin. Microbiol., vol. 38, pp. 2386-2388 (2000).
Bartlett, "Antibiotic-Associated Diarrhea." New England J. Med, vol. 346, pp. 334-339 (2002).
Borriello et al., "Clostridium difficile infections of the gut: the unanswered questions." J. Antimicrob. Chemother., vol. 41, Suppl C, pp. 67-69 (1998).
Clark, M. "Animal Models", (retrieved online May 23, 2008), Retrieved from www.path.cam.ac.uk/~mrc7/iggfunctions/models.html (1998).
Cogburn et al., Journal of Nutrition, vol. 119, p. 1213 (1989).
Cohn, M. and Langman, R.E., "The Immune System: A look from a distance", Fronteirs in Bioscience 1, d318-323, (Oct. 1, 1996).
Cunney et al., "Clostridium difficile infections of the gut: the unanswered questions," Nephrol Dial Transplant, vol. 13, pp. 2842-2846 (1998).
Daeron, "Fc Receptor Biology," Anny Rev Immunol., vol. 15, pp. 203-234 (1997).
Davies et al., "Defective Fc-Dependent Processing of Immune Complexes in Patients with Systemic Lupus Erythematosus," Arth. Rheum., vol. 46, pp. 1028-1038 (2002).
Dobson et al., "Clostridium difficile colitis causing toxic megacolon, severe sepsis and multiple organ dysfunction syndrome," Inten. Car. Med., vol. 29, p. 1030 (2003).
Donnenberg, "Infections Due to *Escherichia colu* and Other Enteric Gram-Negative Bacilli,", Chapter 138 in ACP Medicine Principles and Practice, pp. 1626-1633; BC Decker (Jul. 2007).
Feng, "*Escherichia coli*,", Chapter 10 in 'Guide to Foodborne Pathogens', edited by Labbe et al., John Wiley and Sons, Inc., pp. 143-163 (2001).
Florin et al., "Internalization of Clostridium difficile cytotoxin into cultured human lung fibroblasts," Biochim, Biophys, Acta, vol. 763, pp. 383-392 (1983).
Florin et al., "Lysosomal involvement in cellular intoxication with Clostridium difficile toxin B," Microb Pathogen, vol. 1, pp. 373-385 (1986).
Friedman et al., "Bacteriophage lambda: alive and well and still doing its thing," Curr Opin Microbiol, vol. 4, pp. 201-207 (2001).
Gerding et al., "Treatment of Clostridium difficile Infection," Clin. Infect. Dis., vol. 46, S32-42 (2008).
Giesemann et al., "Cholesterol-dependent Pore Formation of Clostridium difficile Toxin A," J. Biol. Chem., vol. 281, pp. 10808-10815 (2006).
Hamm et al., "Identification of Clostridium difficile toxin B cari-otoxicity using zebrafish embryo model of intoxication," Proc. Natl. Acad. Sci., vol. 103, pp. 14176-14181 (2006).
He et al., "Antibody-Enhanced, Fc Gamma Receptor-Mediated Enocytosis of Clostridium difficile Toxin A," Infect Immun., vol. 77, pp. 2294-2303 (2009).
Henriques et al., "Cellular Internalisation of Clostridium difficile toxin A," Microb Pathogen, vol. 2, pp. 455-463 (1987).
Jacob et al., "Clostridium difficile and acute respiratory distress syndrome," Heart Lung, vol. 33, pp. 265-268 (2004).
Jank et al., "Structure and mode of action of clostridial glucosylating toxins: the ABCD model," Trends Microbiol., pp. 222-229 (2008).
Johansson et al., "Liver Cell Uptake and Degradation of Soluble Immunoglobulin G Immune Complexes In Vivo and In Vitro in Rats,", Hepatology, vol. 24, pp. 169-175 (1996).
Johnson et al., "Fatal Pseudomembranous Colitis Associated with a Variant Clostridium difficile Strain Not Detected by Toxin A Immunoassay," Ann Intern Med, vol. 135, pp. 434-438 (2001).
Jubala et al., Vet Pathol., vol. 42: pp. 468-476 (2005).
Just et al.,"Glucosylation of Rho proteins by Clostridium difficile toxin B," Nature, vol. 375, pp. 500-503 (1995).
Karlsson et al., "Microbial recognition of target-cell glycoconjugates," Curr. Opin. Struct. Biol., vol. 5, pp. 622-635 (1995).
Kelly et al., "Clostridium Difficile Infection," Annu. Rev. Med., vol. 49, pp. 375-390 (1998).
Kelly et al., "Neutrophil Recruitment in Clostridium difficile Toxin A Enteritis in the Rabbit," J, Clin, Invest, vol. 93, pp. 1257-1265 (1994).
Krautz-Peterson et al., "Intracellular Neutralization of Shiga Toxin 2 by a Subunit-Specific Human Monoclonal Antibody," Infect, Immun, vol. 76, pp. 1931-1939 (2008).
Kuijper et al., "Clostridium difficile: changing epidemiology and new treatment options," Curr. Opin. Infect. Dis., vol. 20, pp. 376-383 (2007).
Kyne et al. "Health Care Costs and Mortality Associated with Nosocomial Diarrhea Due to Clostridium difficile," Clin. Infect. Dis., vol. 34, pp. 346-353 (2002).
Libby et al., "Effects of the Two Toxins of Clostridium difficile in Antibiotic-Associated Cecitis in Hamsters," Infect. Immun., vol. 36, pp. 822-829 (1982).
Loo et al., "A Predominantly Clonal Multi-Institutional Outbreak of Clostridium difficil-Associated Diarrhea with High Morbidity and Mortality," N. Eng. J. Med., vol. 353, pp. 2442-2449 (2005).
Lovdal et al., "FC Receptor mediated endocytosis of small soluble immunoglobulin G immune complexes in Kupffer and endothelial cells from rat liver" J. Cell Scl., vol. 113, pp. 3255-3266 (2000).
Lowy et al., "Treatment with Monoclonal Antibodies against Clostridium difficile and Toxins," New. Eng. J. Med., vol. 362, pp. 197-205 (2010).

(56) References Cited

OTHER PUBLICATIONS

McDonald et al., "An Epidemic, Toxin Gene-Variant Strain of Clostridium difficile," New. Eng. J. Med., vol. 353, pp. 2433-2441 (2005).
Mohamed et al., "A High-Affinity Monoclonal Antibody to Anthrax Protective Antigen Passively Protects Rabbits before and after Aerosolized Bacillus anthracis Spire Challenge," Infect. Immun., vol. 73, pp. 795-802 (2005).
Mukherjee et al., "Human Stx2-Specific Monoclonal Antibodies Prevent Systemic Complications of *Escherichia coli* O157:H7 Infection," Infect. Immun., vol. 70, pp. 612-619 (2002).
Nowakowski et al., "Potent neutralization of botulinum neurotoxin by recombinant oligocional antibody," Proc Natl Acad Sci, vol. 99, pp. 11346-11350 (2002).
Owens Jr. et al., "Antimicrobal-Associated Risk Factors for Clostridium difficile Infection," Clin. Infect. Dis., vol. 46, S19-31 (2008).
Pfeifer et al., "Cellular Uptake of Clostridium difficile Toxin B: Translocation of the N-Terminal Catalytic Domain Into the Cytosol of Eukaryotic Cells," J. Biol. Chem., vol. 45, pp. 44535-44541 (2003).
Pothoulakis et al., "Microbes and Microbial Toxins: Paradigms for Microbial-Mucosal Interactions II. The integrated response of the intesting to Clostridium difficile toxins," Am. J. Physiol. Gastrointest Liver Physiol, vol. 280, G178-G183 (2001).
Qa'Dan et al., "pH-Induced Conformational Changes in Clostridium difficile Toxin B," Infect Immun., vol. 68, pp. 2470-2474 (2001).
Reineke et al., "Autocatalytic cleavage of Clostridium difficile toxin B," Nature, vol. 446, pp. 415-419 (2007).
Riegler et al., "Claostridium difficile Toxin B Is More Potent than Toxin A Damagine Human Colonic Epithelium In Vitro," J. Clin. Invest., vol. 95, pp. 2004-2011 (1995).
Riemer et al., Mol. Immunol., vol. 42, pp. 1121-1124 (2005).
Rupkin et al., "Characterization of the cleavage site and function of resulting cleavage fragments after limited proteolysis of Clostridium difficile toxin B (TcdB) by host cells," Microbiology, vol. 151, pp. 199-208 (2005).
Sakuri et al., "Liver abscess caused by Clostridium difficile," Scand. J. Infect Dis., vol. 33, pp. 69-70 (2001).
Final Office Action in U.S. Appl. No. 15/475,664, malled on Oct. 19, 2018 (21 pages).
Non-Final Office Action in U.S. Appl. No. 15/475,664, mailed on Dec. 30, 2019 (21 pages).
Final Office Action in U.S. Appl. No. 15/475,664, mailed on Apr. 22, 2020 (7 pages).
Rossolini et al., "Use of deoxyinosine-containing primers vs degenerate primers for polymerase chain reaction based on ambiguous sequence information," Molecular and Cellular Probes, 1994, vol. 8, pp. 91-98.
Sikorra et al., "Identification of the Amino Acid Residues Rendering TI-VAMP Insensitive toward Botulinum Neurotoxin B," Journal of Molecular Biology, 2006, vol. 357, pp. 574-582.
Sikorra et al., "Substrate Recognition Mechanism of VAMP/Synaptobrevin-cleaving Clostridial Neurotoxins," The Journal of Biological Chemistry, Jul. 25, 2008, vol. 283, No. 30, pp. 21145-21152.
Silvaggi et al., "Structures of Clostridium botulinum Neurotoxin Serotype A Light Chain Complexed with Small-Molecule Inhibitors Highlight Active-Site Flexibility," Chemistry & Biology, May 2007, vol. 14, pp. 533-542.
Vagin et al., "Recruitment of septin cytoskeletal proteins by botulinum toxin A protease determines its remarkable stability," Journal of Cell Science, 2014, vol. 127, pp. 3294-3308.
Wang et al., "A Dileucine in the Protease of Botulinum Toxin A Underlies Its Long-lived Neuroparalysis," The Journal of Biological Chemistry, Feb. 25, 2011, vol. 286, No. 8, pp. 6375-6385.
Winn et al., "Overview of the CCP4 suite and current developments," Acta Crystallographica Section D: Biological Crystallography, 2011, vol. 67, pp. 235-242.
Yao et al., "A camelid single-domain antibody neutralizes botulinum neurotoxin A by blocking host receptor binding," Scientific Reports, 2017, vol. 7, Article No. 7438, pp. 1-12.
Zuniga et al., "A Potent Peptidomimetic Inhibitor of Botulinum Neurotoxin Serotype A Has a Very Different Conformation than SNAP-25 Substrate," Structure, Oct. 8, 2008, vol. 16, pp. 1588-1597.
Zuniga et al., "Iterative Structure-Based Peptide-Like Inhibitor Design against the Botulinum Neurotoxin Serotype A," PLoS One, Jun. 2010, vol. 5, No. 6, e11378, pp. 1-15.
Adams et al., "PHENIX: a comprehensive Python-based system for macromolecular structure solution," Acta Crystallographica Section D: Biological Crystallography, 2010, vol. 66, pp. 213-221.
Agarwal et al., "Mode of VAMP substrate recognition and inhibition of Clostridium botulinum neurotoxin F," Nature Structural & Molecular Biology, Jul. 2009, vol. 16, No. 7, pp. 789-794.
Ahmed et al., "Identification of Residues Surrounding the Active Site of Type A Botulinum Neurotoxin Important for Substrate Recognition and Catalytic Activity," The Protein Journal, 2008, vol. 27, pp. 151-162.
Baldwin et al., "The C-terminus of botulinum neurotoxin type A light chain contributes to solubility, catalysis, and stability," Protein Expression and Purification, 2004, vol. 37, pp. 187-195.
Battye et al., "iMOSFLM: a new graphical interface for diffraction-image processing with MOSFLM," Acta Crystallographica Section D: Biological Crystallography, 2011, vol. 67, pp. 271-281.
Batzer et al., "Enhanced evolutionary PCR using oligonucleotides with inosine at the 3'-terminus," Nucleic Acids Research, 1991, vol. 19, No. 18, p. 5081.
Breidenbach et al., "Substrate recognition strategy for botulinum neurotoxin serotype A," Nature, Dec. 16, 2004, vol. 432, pp. 925-929.
Brizzard et al., "Epitope Tagging of Recombinant Proteins," Current Protocols in Neuroscience, 1997, Unit 5.8, pp. 5.8.1-5.8.10.
Brunger et al., "Botulinum Neurotoxin Heavy Chain Belt as an Intramolecular Chaperone for the Light Chain," PLoS Pathogens, Sep. 2007, vol. 3, No. 9, e113, pp. 1191-1194.
Brünger, Axel T., "Free R value: a novel statistical quantity for assessing the accuracy of crystal structures," Nature, Jan. 30, 1992, vol. 355, pp. 472-475.
Chen et al., "Insights into the Different Catalytic Activities of Clostridium Neurotoxins," Biochemistry, 2012, vol. 51, pp. 3941-3947.
Chen et al., "Mechanism of Substrate Recognition by Botulinum Neurotoxin Serotype A," The Journal of Biological Chemistry, Mar. 30, 2007, vol. 282, No. 13, pp. 9621-9627.
Chen et al., "MolProbity: all-atom structure validation for macromolecular crystallography," Acta Crystallographica Section D: Biological Crystallography, 2010, vol. 66, pp. 12-21.
Chen et al., "Substrate Recognition of VAMP-2 by Botulinum Neurotoxin B and Tetanus Neurotoxin," The Journal of Biological Chemistry, Jul. 25, 2008, vol. 283, No. 30, pp. 21153-21159.
Desmyter et al., "Camelid nanobodies: killing two birds with one stone," Current Opinion in Structural Biology, 2015, vol. 32, pp. 1-8.
Dong et al., "A Single-Domain Llama Antibody Potently Inhibits the Enzymatic Activity of Botulinum Neurotoxin by Binding to the Non-Catalytic α-Exosite Binding Region," Journal of Molecular Biology, 2010, vol. 397, pp. 1106-1118.
Einhauer et al., "The FLAG™ peptide, a versatile fusion tag for the purification of recombinant proteins," Journal of Biochemical and Biophysical Methods, 2001, vol. 49, pp. 455-465.
Emsley et al., "Features and development of Coot," Acta Crystallographica Section D: Biological Crystallography, 2010, vol. 66, pp. 486-501.
Fernández-Salas et al., "Plasma membrane localization signals in the light chain of botulinum neurotoxin," Proceedings of the National Academy of Sciences of the United States of America, Mar. 2, 2004, vol. 101, No. 9, pp. 3208-3213.
Fritze et al., "Epitope Tagging: General Method for Tracking Recombinant Proteins," Methods in Enzymology, 2000, vol. 327, pp. 3-16.

(56) References Cited

OTHER PUBLICATIONS

Gu et al., "Botulinum Neurotoxin Is Shielded by NTNHA in an Interlocked Complex," Science, Feb. 24, 2012, vol. 335, pp. 977-981.
Hernan et al., "Multiple Epitope Tagging of Expressed Proteins for Enhanced Detection," BioTechniques, Apr. 2000, vol. 28, No. 4, pp. 789-793.
Kabsch, Wolfgang, "XDS," Acta Crystallographica Section D: Biological Crystallography, 2010, vol. 66, pp. 125-132.
Kashmiri et al., "SDR grafting—a new approach to antibody humanization," Methods, 2005, vol. 36, pp. 25-34.
Kimmel, Alan R., "Identification and Characterization of Specific Clones: Strategy for Confirming the Validity of Presumptive Clones," Methods in Enzymology, 1987, vol. 152, pp. 507-511.
Kumaran et al., "Interactions of a potent cyclic peptide inhibitor with the light chain of botulinum neurotoxin A: Insights from X-ray crystallography," Bioorganic & Medicinal Chemistry, 2015, vol. 23, pp. 7264-7273.
Kumaran et al., "Substrate Binding Mode and Its Implication on Drug Design for Botulinum Neurotoxin A," PLoS Pathogens, Sep. 2008, vol. 4, No. 9, e1000165, pp. 1-9.
Kuroda et al., "Shape complementarity and hydrogen bond preferences in protein-protein interfaces: implications for antibody modeling and protein-protein docking," Bioinformatics, 2016, vol. 32, No. 16, pp. 2451-2456.
Lacy et al., "Crystal structure of botulinum neurotoxin type A and implications for toxicity," Nature Structural Biology, Oct. 1998, vol. 5, No. 10, pp. 898-902.
Lauwereys et al., "Potent enzyme inhibitors derived from dromedary heavy-chain antibodies," The EMBO Journal, 1998, vol. 17, No. 13, pp. 3512-3520.
Lawrence et al., "Shape Complementarity at Protein/Protein Interfaces," Journal of Molecular Biology, 1993, vol. 234, pp. 946-950.
Maass et al., "Alpaca (*Lama pacos*) as a convenient source of recombinant camelid heavy chain antibodies (VHHs)," Journal of Immunological Methods, 2007, vol. 324, pp. 13-25.
McCoy et al., "Phaser crystallographic software," Journal of Applied Crystallography, 2007, vol. 40, pp. 658-674.
Mizanur et al., "The C Terminus of the Catalytic Domain of Type A Botulinum Neurotoxin May Facilitate Product Release from the Active Site," The Journal of Biological Chemistry, Aug. 16, 2013, vol. 288, No. 33, pp. 24223-24233.
Mukherjee et al., "A Novel Strategy for Development of Recombinant Antitoxin Therapeutics Tested in a Mouse Botulism Model," PLoS One, Jan. 2012, vol. 7, No. 1, e29941, pp. 1-12.
Nayak et al., "Safety and Pharmacokinetics of XOMA 3AB, a Novel Mixture of Three Monoclonal Antibodies against Botulinum Toxin A," Antimicrobial Agents and Chemotherapy, Sep. 2014, vol. 58, No. 9, pp. 5047-5053.
Ohtsuka et al., "An Alternative Approach to Deoxyoligonucleotides as Hybridization Probes by Insertion of Deoxyinosine at Ambiguous Codon Positions," The Journal of Biological Chemistry, Mar. 10, 1985, vol. 260, No. 5, pp. 2605-2608.
Pardon et al., "A general protocol for the generation of Nanobodies for structural biology," Nature Protocols, 2014, vol. 9, No. 3, pp. 674-693.
Riechmann et al., "Reshaping human antibodies for therapy," Nature, Mar. 24, 1988, vol. 332, pp. 323-327.
Benton et al., "Screening λgt Recombinant Clones by Hybridization to Single Plaques in situ," Science, Apr. 8, 1977, vol. 196, pp. 180-182.
Buck et al., "Fusion of an Fc chain to a VHH boosts the accumulation levels in *Arabidopsis* seeds," Plant Biotechnology Journal, 2013, vol. 11, pp. 1006-1016.
Chen et al., "A Mouse Model of Clostridium difficile—Associated Disease," Gastroenterology, Dec. 2008, vol. 135, No. 6, pp. 1984-1992.
Chen et al., "Novel Chimpanzee/Human Monoclonal Antibodies That Neutralize Anthrax Lethal Factor, and Evidence for Possible Synergy with Anti-Protective Antigen Antibody," Infection and Immunity, Sep. 2009, vol. 77, No. 9, pp. 3902-3908.
Cohen, Jon, "Naked DNA Points Way to Vaccines," Science, Mar. 19, 1993, vol. 259, pp. 1691-1692.
Gronbach et al., "Safety of Probiotic *Escherichia coli* Strain Nissle 1917 Depends on Intestinal Microbiota and Adaptive Immunity of the Host," Infection and Immunity, Jul. 2010, vol. 78, No. 7, pp. 3036-3046.
Grunstein et al., "Colony hybridization: a method for the isolation of cloned DNAs that contain a specific gene," Proceedings of the National Academy of Sciences of the United States of America, Oct. 1975, vol. 72, No. 10, pp. 3961-3965.
Hoerr et al., "In vivo application of RNA leads to induction of specific cytotoxic T lymphocytes and antibodies," European Journal of Immunology, 2000, vol. 30, pp. 1-7.
Janeway et al., "The interaction of the antibody molecule with specification antigen," Immunobiology: The Immune System in Health and Disease, 2001, 5th edition, 5 pages.
Jirikowski et al., "Reversal of Diabetes Insipidus in Brattleboro Rats: Intrahypothalamic Injection of Vasopressin mRNA," Science, Feb. 21, 1992, vol. 255, pp. 996-998.
Karikó et al., "Increased Erythropoiesis in Mice Injected With Submicrogram Quantities of Pseudouridine-containing mRNA Encoding Erythropoietin," Molecular Therapy, May 2012, vol. 20, No. 5, pp. 948-953.
Killgore et al., "Comparison of Seven Techniques for Typing International Epidemic Strains of Clostridium difficile: Restriction Endonuclease Analysis, Pulsed-Field Gel Electrophoresis, PCR-Ribotyping, Multilocus Sequence Typing, Multilocus Variable-Number Tandem-Repeat Analysis, Amplified Fragment Length Polymorphism, and Surface Layer Protein A Gene Sequence Typing," Journal of Clinical Microbiology, Feb. 2008, vol. 46, No. 2, pp. 431-437.
Little et al., "Production and Characterization of Monoclonal Antibodies to the Protective Antigen Component of Bacillus anthracis Toxin," Infection and Immunity, Jul. 1988, vol. 56, No. 7, pp. 1807-1813.
Maass et al., "Three surface antigens dominate the mucosal antibody response to gastrointestinal L3-stage strongylid nematodes in field immune sheep," International Journal for Parasitology, 2007, vol. 37, pp. 953-962.
Mitchell et al., "Comparative analysis of nanobody sequence and structure data," Proteins: Structure, Function, and Bioinformatics, 2018, vol. 86, pp. 697-706.
Moayeri et al., "A Heterodimer of a VHH (Variable Domains of Camelid Heavy Chain-only) Antibody That Inhibits Anthrax Toxin Cell Binding Linked to a VHH Antibody That Blocks Oligomer Formation Is Highly Protective in an Anthrax Spore Challenge Model," The Journal of Biological Chemistry, Mar. 6, 2015, vol. 290, No. 10, pp. 6584-6595.
Moayeri et al., "Adenoviral Expression of a Bispecific VHH-Based Neutralizing Agent That Targets Protective Antigen Provides Prophylactic Protection from Anthrax in Mice," Clinical and Vaccine Immunology, Mar. 2016, vol. 23, No. 3, pp. 213-218.
Mukherjee et al., "Prolonged Prophylactic Protection from Botulism with a Single Adenovirus Treatment Promoting Serum Expression of a VHH-Based Antitoxin Protein," PLoS One, Aug. 2014, vol. 9, No. 8, e106422, pp. 1-13.
Nguyen et al., "The pharmacokinetics of an albumin-binding Fab (AB.Fab) can be modulated as a function of affinity for albumin," Protein Engineering, Design & Selection, 2006, vol. 19, No. 7, pp. 291-297.
Park et al., "Generation and Application of New Rat Monoclonal Antibodies Against Synthetic FLAG and OLLAS Tags for Improved Immunodetection," Journal of Immunological Methods, Feb. 2008, vol. 331, Nos. 1-2, pp. 27-38.
Park et al., "Optimized Production and Purification of Bacillus anthracis Lethal Factor," Protein Expression and Purification, 2000, vol. 18, pp. 293-302.
Patra et al., "Nano based drug delivery systems: recent developments and future prospects," Journal of Nanobiotechnology, 2018, vol. 16, Article No. 71, pp. 1-33.

(56) References Cited

OTHER PUBLICATIONS

Petsch et al., "Protective efficacy of in vitro synthesized, specific mRNA vaccines against influenza A virus infection," Nature Biotechnology, Dec. 2012, vol. 30, No. 12, pp. 1210-1216.
Pomerantsev et al., "Genome Engineering in Bacillus anthracis Using Cre Recombinase," Infection and Immunity, Jan. 2006, vol. 74, No. 1, pp. 682-693.
Sepulveda et al., "Efficient Serum Clearance of Botulinum Neurotoxin Achieved Using a Pool of Small Antitoxin Binding Agents," Infection and Immunity, Feb. 2010, vol. 78, No. 2, pp. 756-763.
Sponseller et al., "Hyperimmune Bovine Colostrum as a Novel Therapy to Combat Clostridium difficile Infection," The Journal of Infectious Diseases, Apr. 15, 2015, vol. 211, pp. 1334-1341.
Thess et al., "Sequence-engineered mRNA Without Chemical Nucleoside Modifications Enables an Effective Protein Therapy in Large Animals," Molecular Therapy, Sep. 2015, vol. 23, No. 9, pp. 1456-1464.
Thran et al., "mRNA mediates passive vaccination against infectious agents, toxins, and tumors," EMBO Molecular Medicine, 2017, vol. 9, No. 10, pp. 1434-1447.
Tremblay et al., "A Single VHH-Based Toxin-Neutralizing Agent and an Effector Antibody Protect Mice against Challenge with Shiga Toxins 1 and 2," Infection and Immunity, Dec. 2013, vol. 81, No. 12, pp. 4592-4603.
Tremblay et al., "Camelid single domain antibodies (VHHs) as neuronal cell intrabody binding agents and inhibitors of Clostridium botulinum neurotoxin (BoNT) proteases," Toxicon, Nov. 2010, vol. 56, No. 6, pp. 990-998.
Tzipori et al., "The Role of the eaeA Gene in Diarrhea and Neurological Complications in a Gnotobiotic Piglet Model of Enterohemorrhagic *Escherichia coli* Infection," Infection and Immunity, Sep. 1995, vol. 63, No. 9, pp. 3621-3627.
Ulmer et al., "Heterologous Protection Against Influenza by Injection of DNA Encoding a Viral Protein," Science, Mar. 19, 1993, vol. 259, pp. 1745-1749.
Vance et al., "Stepwise Engineering of Heterodimeric Single Domain Camelid VHH Antibodies That Passively Protect Mice from Ricin Toxin," The Journal of Biological Chemistry, Dec. 20, 2013, vol. 288, No. 51, pp. 36538-36547.
Vattekatte et al., "Discrete analysis of camelid variable domains: sequences, structures, and in-silico structure prediction," PeerJ, 2020, vol. 8, e8408, pp. 1-28.
Wahl et al., "Molecular Hybridization of Immobilized Nucleic Acids: Theoretical Concepts and Practical Considerations," Methods in Enzymology, 1987, vol. 152, pp. 399-407.
Wolff et al., "Direct Gene Transfer into Mouse Muscle in Vivo," Science, Mar. 23, 1990, vol. 247, pp. 1465-1468.
Yang et al., "A Novel Multivalent, Single-Domain Antibody Targeting TcdA and TcdB Prevents Fulminant Clostridium difficile Infection in Mice," The Journal of Infectious Diseases, Sep. 15, 2014, vol. 210, pp. 964-972.

* cited by examiner

Anti-BoNT/A sheep scFv coding nucleotide sequences

>scFv#2
CAGGCTGTGCTGACTCAGCCGTCCTCCGTGTCCGGGTCCCCGGGCCNNANGG
TCTCCATCACCTGCTCTGGAAGCAGGAGTAACGTTGGCACATATGGTGTAGG
TTGGTTCCAACAGCTCCCAGGATCGGGCCTCAGAACCATCATCTATTATAATG
ACAAACGACCCTCAGGGGTCCCCGACCGATTCTCTGCCTCCAAATCGGGCAA
CACAGCCACCCTGATCATCAGCTCGCTCCAGGCTGAGGATGAGGCCGATTAT
TTCTGTGGAAGTGCCGACGGTAGTAGTTATGGTATTTTCGGCAGTGGACCA
GACTGACCGTCCTGGGTCAGCCCGCGGCCGCTGGTGGAGGCGGTTCAGGCGG
AGGTGGCTCTGGCGGTGGCGGATCGGCGCGCCAGGTGGGGCTGCAGGAGTCG
GGACCCAGCCTGGTGAAGCCCTCACAGACCCTCTCCCTCACCTGCACGGTCTC
TGGATTCTCATTGTCCAACAGTGTTGTAGGCTGGGTCCGCCAGGCTCCAGGAA
AGGTGCCGGAGTGGCTTGGTAGTATAGACAGTGGTGGTTACACAGTCGCTGA
CCCGGCCCTGAAATCCCGACTCAGCATCACAAGGGACACTTCCAAGAGCCAA
GTCTCCCTGTCACTGAACAGCGTGACAACTGAGGACACGGCCGTGTACTACT
GTACAAGGGCTTATAGTATTACTTATTATGCGTATCCCCCCTATATCGACTAC
TGGGGCCCAGGACTCCTGGTCACCGTCTCCTCAACTAGTGGTGCGCCGGTGC
CGTATCCGGATCCGCTGGAACCGCGTGCCGCA (SEQ ID NO:1)

>scFv#3
CAGGCTGTGCTGACTCAGCCGTCCTCCGTGTCCAGGTCCCTGGGCCAGAGTGT
CTCCATCACCTGCTCTGGAAGCAGCAGCAACGTTGGATATGGTGATTATGTG
GGCTGGTTCCAACGGGTCCCAGGATCAGCCCCCAAACTCCTCATCTATGGTG
CAACCACTCGAGCCTCGGGGGTCCCCGACCGATTCTCCGGCTCCAGGTCTGG
CAACACAGCGACTCTGACCATCAGCTCGCTCCAGGCTGAGGACGAGGCCGAT
TATTACTGTTCATCTTACGACAGTAGTCACTATAGTATTTTCGGCAGTGGAC
CAGCCTGACCGTCCTGGGTCAGCCCGCGGCCGCTGGTGGAGGCGGTTCAGGC
GGAGGTGGCTCTGGCGGTGGCGGATCGGCGCGCCAGGTGGAGCTGCAGGAG
TCGGGACCCAGCCTGGTGAAGCCCTCACAGACCCTCTCCCTCACCTGCACGG
TCTCTGGATTCTCATTAAGTAGCAATGCTGTAGGCTGGGTCCGCCAGGCTCCA
GGAAAGGCGCCGGAGTGGGTTGGTGGTATAGATATAGATGGAAGGCCGGTCT
ATAAACCAGGCCTTAAGTCCCGGCTCAGCATCACCAGGGACACCTCCAACGC
TCAAGTCTCCCTGTCACTGAGCAGCGTGACAACTGAGGACACGGCCGTGTAC
TTCTGTGCAAGTTATTATGGTGGTTATCTTTATAATTATGCCCCTGGGGCATAT
ATCGAGCACTTGAGCCCAGGACTCCTGATCACCGTCTCCTCAACTAGTGGTGC
GCCGGTGCCGTATCCGGATCCGCTGGAAACCGCGTGCCGCA (SEQ ID NO:3)

Fig. 1A

>scFv#7
TCCTATGAACTGACCCAGCCGCCTTCAATGTCGGTGGCCTTGGGACAGACGG
CCAAGGTCACCTGCCAGGGAGACAACTTAGAAAACTTTTATGTTCAGTGGCA
CCAGCAGAAGCCGGGCCAGGCCCCTGTGACGGTCATTTTTCAGGATAATAAG
AGGCCCTCGGGGATCCCTGACCGGTTCTCTGGCTCCAACTCGGGGAACACGG
CCACCCTGACCATCAGCGGGGCCCGGACCGAGGACGAGGCCGACTATTACTG
TCAGTCAGGCCACAGCAGTATCGGTGGTGTTTTCGGCAGCGGGACCAGCCTG
ACCGTCCTGGGTCAGCCCGCGGCCGCTGGTGGAGGCGGTTCAGGCGGAGGTG
GCTCTGGCGGTGGCGGATCGGCGCGCCAGGTGCAGCTGCAGGAGTCGGGACC
CAGCCTGGTGAAGCCCTCACAGACCCTCTCCCTCACCTGCACGGTCTCTGGCT
TCTCATTAACGGGAAATTCTGTAACCTGGGTCCGCCAGGCTCCAGGAAACGT
GCCGGAGTGGCTTGGTGGTATAAGCCGCGGTGGACGCACATACTATGATACG
GCCCTGAAGTCCCGGCTCAGCATCACCAGGGACACCTCCAAGAGGCAAGTCT
CCCTATCACTGAGCAGCGTGACGACTGAGGACACGGCCATGTACTTCTGTGC
AAGATCGGCATATAGTACTCTTTATGATTATGAGTATGCCGCTGATATCTACG
ACTGGGGCCCAGGACTCCTGGTCACCGTCTCCTCAACTAGTGGTGCGCCGGT
GCCGTATCCGGATCCGCTGGAACCGCGTGCCGCA (SEQ ID NO:5)

>scFv#8
TCCTATGAACTGACCCAGCCGCCTTCAGTGTCGGTGGTTTGGGGNCNGANGG
CCGAGATCACCTGCCAGGGAGACCTACTGGATAAAAAATATACAGCTTGGTA
CCAGCAGAAGCCGGGCCAGGCTCCTATGAAAATCATTAATAAAGACAGTGAG
CGGCCTTCAGGGATCCGGGACCGGTTCTCGGGCTCCAGCTCAGGCAAAACAG
CCACCCTAACCATCAACGGGGCCCGGCCTGAGGACGAGGCCGACTATTACTG
TTTATCAGGTGACAGCAATAATAATGGTGTCTTCGGCAGCGGGACCAGCCTG
ACCGTCCTGGGTCAGCCCGCGGCCGCTGGTGGAGGCGGTTCAGGCGGAGGTG
GCTCTGGCGGTGGCGGATCGGCGCGCCAGGTGGAGCTGCAGGGGTCGGGAC
CCAGCCTGGTGAAGCCCTCGCAGACCCTCTCCCTCACCTGCACGGTCTCTGGA
TTCTCATGGCCCAACAATGCTGTGGATTGGGTCCGCCAGGCTCCAGGAAAGG
CGCCGGAGTGGCTTGGTGGTATTGCCGATAATGGAAGAACAAACTACAACAC
GGCCCTAAAAGCCCGGCTCAGCATCACTAGGGACACCGCCAAGAGCCATGTC
TCCCTATCGCTGAGCAGCGTGACAGCTGAGGATACGGCCGTTTACTATTGTAC
AGCGGGGGTTATGGTCATGCACGCCACTGACTACTGGGGCCCGGGACTCCTG
GTCACCGTCTCCTCAACTAGTGGTGCGCCGGTGCCGTATCCGGATCCGCTGGA
ACCGCGTGCCGCA (SEQ ID NO:7)

Fig. 1B

>scFv#21

CAGGCTGTGGTGACTCAGCCGTCCTCCGTGTCCGGGTCCCCGGGCCNNANAG
TCTCCATCACCTGCTCTGGAAGCAGCAGCAACGTTGGTAGATATGCTGTAGG
CTGGTTCCAACAGCTCCCAGGATCGGGCCTCAGAACCGTCATCTATTATAATA
GCAATCGACCCTCAGGGGTCCCCGACCGATTCTCTGGCTCCAAATCGGGCAA
CACAGCCACCCTGACCATCAGCTCGCTCCAGGCTGAGGATGAGGCCGATTAT
TTCTGTGGAAGTTATGACAGTAGTATCTATGGTGTTTTCGGCAGCGGGACCAG
GCTGACCGTCCTGGGTCAGCCCGCGGCCGCTGGTGGAGGCGGTTCAGGCGGA
GGTGGCTCTGGCGGTGGCGGATCGGCGCGCCAGGTGCAGCTGCAGGAGTCGG
GACCCAGCCTGGTGAGGCCCTCACAGACCCTCTCCCTCACCTGCACGATCTCT
GGATTCTCTTTAAGAGAGTATGGTGTAGGTTGGGTCCGCCAGGCTCCAGGAA
AGGCGTTGGAGTGGCTTGGGCGAATAGATGATTCTGGATACACATTACATAA
TCCTGCCCTTAAGTCCCGGCTCACCATAACTAGGGACATCTCCAAGAGCCAA
GTCTCCCTGTCACTGAGCAGCGTGACACTTGAGGACACGGCCGAATATTACT
GCGTATATGCTAGTCGTGGTACTGCTTGGTTGGGAGACATCGATGTCTGGGGC
CCAGGACTCCTGCTCACTGTCTCCTCAACTAGTGGTGCGCCGGTGCCGTATCC
GGATCCGCTGGAACCGCGTGCCGCA (SEQ ID NO:9)

>scFv#E

CAGGCTGTGCTGACTCAGCCGTCCTCCGTGTCCAGGTCCCTGGGCCNNANTGT
CTCGATCACCTGCTCTGGAGGCAGCAGCAACGTTGGACAAGGTGATTATGTG
GCCTGGTTCCAACAGGTCCCAGGATCAGCCCCCAAACTCCTCATCTATGATGC
GACGAATCGAGCCTCGGGGGTCCCCGACCGATTCGTCGGCTCCAGATATGGC
AACTCAGCGACTCTGATCATCACCTCGGTCCAGGCTGAGGACGAGGCCGATT
ATTATTGTGCATCTTATGACAGTAGTATGTATACGATTTTCGGCAGCGGGACC
AGCCTGACCGTCCTGGGTCAGCCCGCGGCCGCTGGTGGAGGCGGTTCAGGCG
GAGGTGGCTCTGGCGGTGGCGGATCGGCGCGCCAGGTGGAGCTGCAGGGGTC
GGGACCCAGCCAGGTGAAGCCCTCACAGACCCTCTCCCTCATCTGCACGATC
TCTGGATTCTCATTAACCAGCAATAATGTAGCCTGGGTCCGCCAGGCTCCAGG
AAAGGGACTGGAGTGGGTTGGTGTCATAAGTGATGGTGGAACTCCATACTAT
AACTCGGCCCTGAAATCCCGGCTCAGCATCACCAGGGACACCTCCAAGAGCC
AGGTCTCCCTGTCACTGAGCAGCGTGACAACTGAGGACACGGCCGTGTACTA
CTGTGCACGGACGTTGGATTATAGTCATATTTGGTTGTACTCCGCCGACCAAT
GGGGCCCAGGACTCCTGGTCACCGTCTCCTCAACTAGTGGTGCGCCGGTGCC
GTATCCGGATCCGCTGGAACCGCGTGCCGCA (SEQ ID NO:11)

Fig. 1C

Anti-BoNT/A sheep scFv amino acid sequences

>scFv#2
QAVLTQPSSVSGSPGXXVSITCSGSRSNVGTYGVGWFQQLPGSGLRTIIYYNDKR
PSGVPDRFSASKSGNTATLIISSLQAEDEADYFCGSADGSSYGIFGSGTRLTVLGQ
PAAAGGGGSGGGGSGGGGSARQVGLQESGPSLVKPSQTLSLTCTVSGFSLSNSV
VGWVRQAPGKVPEWLGSIDSGGYTVADPALKSRLSITRDTSKSQVSLSLNSVTTE
DTAVYYCTRAYSITYYAYPPYIDYWGPGLLVTVSSTSGAPVPYPDPLEPRAA
(SEQ ID NO:2)

>scFv#3
QAVLTQPSSVSRSLGQSVSITCSGSSSNVGYGDYVGWFQRVPGSAPKLLIYGATT
RASGVPDRFSGSRSGNTATLTISSLQAEDEADYYCSSYDSSHYSIFGSGTSLTVLG
QPAAAGGGGSGGGGSGGGGSARQVELQESGPSLVKPSQTLSLTCTVSGFSLSSN
AVGWVRQAPGKAPEWVGGIDIDGRPVYKPGLKSRLSITRDTSNAQVSLSLSSVTT
EDTAVYFCASYYGGYLYNYAPGAYIEHLSPGLLITVSSTSGAPVPYPDPLEPRAA
(SEQ ID NO:4)

>scFv#7
SYELTQPPSMSVALGQTAKVTCQGDNLENFYVQWHQQKPGQAPVTVIFQDNKR
PSGIPDRFSGSNSGNTATLTISGARTEDEADYYCQSGHSSIGGVFGSGTSLTVLGQ
PAAAGGGGSGGGGSGGGGSARQVQLQESGPSLVKPSQTLSLTCTVSGFSLTGNS
VTWVRQAPGNVPEWLGGISRGGRTYYDTALKSRLSITRDTSKRQVSLSLSSVTTE
DTAMYFCARSAYSTLYDYEYAADIYDWGPGLLVTVSSTSGAPVPYPDPLEPRAA
(SEQ ID NO:6)

>scFv#8
SYELTQPPSVSVVWGXXAEITCQGDLLDKKYTAWYQQKPGQAPMKIINKDSERP
SGIRDRFSGSSSGKTATLTINGARPEDEADYYCLSGDSNNNGVFGSGTSLTVLGQ
PAAAGGGGSGGGGSGGGGSARQVELQGSGPSLVKPSQTLSLTCTVSGFSWPNNA
VDWVRQAPGKAPEWLGGIADNGRTNYNTALKARLSITRDTAKSHVSLSLSSVTA
EDTAVYYCTAGVMVMHATDYWGPGLLVTVSSTSGAPVPYPDPLEPRAA
(SEQ ID NO:8)

>scFv#21
QAVVTQPSSVSGSPGXXVSITCSGSSSNVGRYAVGWFQQLPGSGLRTVIYYNSNR
PSGVPDRFSGSKSGNTATLTISSLQAEDEADYFCGSYDSSIYGVFGSGTRLTVLGQ
PAAAGGGGSGGGGSGGGGSARQVQLQESGPSLVRPSQTLSLTCTISGFSLREYGV
GWVRQAPGKALEWLGRIDDSGYTLHNPALKSRLTITRDISKSQVSLSLSSVTLED
TAEYYCVYASRGTAWLGDIDVWGPGLLLTVSSTSGAPVPYPDPLEPRAA
(SEQ ID NO:10)

Fig. 1D

>scFv#E
QAVLTQPSSVSRSLGXXVSITCSGGSSNVGQGDYVAWFQQVPGSAPKLLIYDAT
NRASGVPDRFVGSRYGNSATLIITSVQAEDEADYYCASYDSSMYTIFGSGTSLTV
LGQPAAAGGGGSGGGGSGGGGSARQVELQGSGPSQVKPSQTLSLICTISGFSLTS
NNVAWVRQAPGKGLEWVGVISDGGTPYYNSALKSRLSITRDTSKSQVSLSLSSV
TTEDTAVYYCARTLDYSHIWLYSADQWGPGLLVTVSSTSGAPVPYPDPLEPRAA
(SEQ ID NO:12)

Fig. 1E

Nucleotide sequence of scFv#7-2E is:

GGTGCGCCGGTGCCGTATCCGGATCCGCTCGAGCCGCGTGCCGGCTCCTATGAACTG
ACCCAGCCGCCTTCAATGTCGGTGGCCTTGGGACAGACGGCCAAGGTCACCTGCCAG
GGAGACAACTTAGAAAACTTTTATGTTCAGTGGCACCAGCAGAAGCCGGGCCAGGC
CCCTGTGACGGTCATTTTTCAGGATAATAAGAGGCCCTCGGGGATCCCTGACCGGTT
CTCTGGCTCCAACTCGGGGAACACGGCCACCCTGACCATCAGCGGGGCCCGGACCG
AGGACGAGGCCGACTATTACTGTCAGTCAGGCCACAGCAGTATCGGTGGTGTTTTCG
GCAGCGGGACCAGCCTGACCGTCCTGGGTCAGCCCGCGGCCGCTGGTGGAGGCGGT
TCAGGCGGAGGTGGCTCTGGCGGTGGCGGATCGGCGCGCCAGGTGCAGCTGCAGGA
GTCGGGACCCAGCCTGGTGAAGCCCTCACAGACCCTCTCCCTCACCTGCACGGTCTC
TGGCTTCTCATTAACGGGAAATTCTGTAACCTGGGTCCGCCAGGCTCCAGGAAACGT
GCCGGAGTGGCTTGGTGGTATAAGCCGCGGTGGACGCACATACTATGATACGGCCCT
GAAGTCCCGGCTCAGCATCACCAGGGACACCTCCAAGAGGCAAGTCTCCCTATCACT
GAGCAGCGTGACGACTGAGGACACGGCCATGTACTTCTGTGCAAGATCGGCATATA
GTACTCTTTATGATTATGAGTATGCCGCTGATATCTACGACTGGGGCCCAGGACTCC
TGGTCACCGTCTCCTCAACTAGTGGTGCGCCGGTGCCGTATCCGGATCCGCTGGAAC
CGCGTGCCGCA (SEQ ID NO:13)

Amino acid sequence of scFv#7-2E is:

GAPVPYPDPLEPRAGSYELTQPPSMSVALGQTAKVTCQGDNLENFYVQWHQQKPGQAP
VTVIFQDNKRPSGIPDRFSGSNSGNTATLTISGARTEDEADYYCQSGHSSIGGVFGSGTSL
TVLGQPAAAGGGGSGGGGSGGGGSARQVQLQESGPSLVKPSQTLSLTCTVSGFSLTGNS
VTWVRQAPGNVPEWLGGISRGGRTYYDTALKSRLSITRDTSKRQVSLSLSSVTTEDTAM
YFCARSAYSTLYDYEYAADIYDWGPGLLVTVSSTSGAPVPYPDPLEPRAA
(SEQ ID NO:14)

Fig. 2

BoNT/A holotoxin binding VHHs:

JDA-D12

Nucleotide sequence:

CAGGTGCAGCTCGTGGAGTCAGGAGGAGGCTTGGTGCAGCCTGGGGGATCTCTGAGACTCTCGTGTGTAGTCTCTGGAAGTG
ACTTCAATACCTATATCATGGGCTGGTACCGCCAGGTTCCAGGGAAGCCGCGCGAGTTGGTCGCAGATATTACTACTGAAGGA
AAAACAAACTATGGCGGCTCCGTAAAGGGACGATTCACCATCTCCAGAGACAACGCCAAAAACACGGTGTATCTGCAAATGTTC
GGCCTGAAACCTGAGGACGCGGGTAATTATGTCTGTAACGCAGACTGGAAGATGGGTGCATGGACCGCGGGGGACTACGGTA
TCGACTACTGGGGCAAAGGGACCCTGGTCACCGTCTCCTCAGAACCCAAGACACCAAAACCACAA (SEQ ID NO:19)

amino acid sequence:

QVQLVESGGGLVQPGGSLRLSCVVSGSDFNTYIMGWYRQVPGKPRELVADITTEGKTNYGGSVKGRFTISRDNAKNTVYLQMFGLK
PEDAGNYVCNADWKMGAWTAGDYGIDYWGKGTLVTVSSEPKTPKPQ (SEQ ID NO:20)

JDQ-A5

Nucleotide sequence:

CAGGTGCAGCTCGTGGAGTCCGGTGGAGGCTTGGTGCAGCCTGGGGGGTCTCTGAGACTCTCCTGTGCAGCCTCTGCAGGCA
ATCTGGATTATTATGCCATAGGCTGGTTCCGCCAGGCCCCAGGGAAGGAGCGCGAGGGGGTCTCATGTATTAGTAGTAGTGAT
GGTAGCACTGTCTATACAGACTCCGTGAAGGGCCGATTCACCATCTCCAGAGACAATACCAAGAACACGGTAGATCTGCAAATG
GACAATTTGAAACCTGAGGACACGGCCGTTTATTACTGTGCGACAGTCGTTAACTACTACTGCACAGCCGGTGGGTCCATTCAC
GCGAGCCCGTATGAAATCTGGGGCCAGGGGACCCAGGTCACCGTCTCCTCAGCGCACCACAGCGAAGACCCCTCG
(SEQ ID NO:21)

amino acid sequence:

QVQLVESGGGLVQPGGSLRLSCAASAGNLDYYAIGWFRQAPGKEREGVSCISSSDGSTVYTDSVKGRFTISRDNTKNTVDLQMDNL
KPEDTAVYYCATVVNYYCTAGGSIHASPYEIWGQGTQVTVSSAHHSEDPS (SEQ ID NO:22)

FIG. 3A (cont.)

JDQ-B5
Nucleotide sequence:

CAGGTGCAGCTCGTGGAGTCCGGCGGAGGCTTGGTGCACCCTGGGGGGTCTCTGAGACTCTCTTGTGCACCCTCTGCCAGTC
TACCATCAACACCCTTCAACCCCTTCAACAATATGGTGGGCTGGTACCGTCAGGCTCCAGGTAAACAGCGCGAAATGGTCGCA
AGTATTGGTCTACGAATAAACTATGCAGACTCCGTGAAGGGCCGATTCACCATCTCCAGAGACAACGCCAAGAACACGGTGGA
TCTGCAGATGGACAGCCTGCGACCTGAGGACTCAGCCACATACTACTGTCATATAGAATACACCCACTACTGGGGCAAAGGGA
CCCTGGTCACCGTCTCCTCGGAACCCAAGACACCAAAACCACAA (SEQ ID NO:23)

amino acid sequence:

QVQLVESGGGLVHPGGSLRLSCAPSASLPSTPFNPFNNMVGWYRQAPGKQREMVASIGLRINYADSVKGRFTISRDNAKNTVDLQM
DSLRPEDSATYYCHIEYTHYWGKGTLVTVSSEPKTPKPQ (SEQ ID NO:24)

JDQ-C2
Nucleotide sequence:

CAGGTGCAGCTCGTGGAGTCTGGTGGAGGCTTGGCGCAGCCTGGGGGGTCTCTGAGACTCTCCTGTGAAGCGTCTGGTTTTG
GGACATGGTTCAGGTTCGATGAGAACACCGTGAACTGGTACCGCCAGCCTCCAGGAAAGTCGCGCGAGTTCGACGAGTTGGT
CGCTCGTTACCCAAAAAGTGGCATCGTAACCTATTTAGACTCCGTGAAGGGCCGATTCACGATCTCCAGAGACAACGCCAAAAA
AATGGCGTTTCTGCAAATGGACAACCTGAAACCTGAGGACACGGCCGTCTATTATTGCAATGTCGGTGAATTTTGGGGCCAGG
GGACCCAGGTCACGATCTCCTCAGAACCCAAGACACCAAAACCACAA (SEQ ID NO:25)

amino acid sequence:

QVQLVESGGGLAQPGGSLRLSCEASGFGTWFRFDENTVNWYRQPPGKSREFDELVARYPKSGIVTYLDSVKGRFTISRDNAKKMAF
LQMDNLKPEDTAVYYCNVGEFWGQGTQVTISSEPKTPKPQ (SEQ ID NO:26)

FIG. 3A-1

JDQ-F12

Nucleotide sequence:

CAGGTGCAGCTCGTGGAGTCGGGGGGAGGCTTGGTGCAGCCTGGGGGGTCTCTGAGACTCTCCTGTGCAGCCTCTGGATTCA
CCCTAGGGTCGCGTTACATGAGCTGGGTCCGCCAGGCTCCAGGAGAGGGGTTCGAGTGGGTCTCAAGTATTGAACCCTCTGG
TACCGCATGGGATGGAGACTCCGCGAAGGGACGATTCACCACTTCCAGAGACGACGCCAAGAACACGCTTTATCTGCAAATGA
GCAACCTGCAACCCGAGGACACGGGTGTTTATTACTGTGCAACAGGGTATCGGACGGACACGAGGATTCCGGGTGGCTCGTG
GGGCCAGGGGACCCAGGTCACCGTCTCCTCAGAACCCAAGACACCAAAACCACAA (SEQ ID NO:27)

amino acid sequence:

QVQLVESGGGLVQPGGSLRLSCAASGFTLGSRYMSWVRQAPGEGFEWVSSIEPSGTAWDGDSAKGRFTTSRDDAKNTLYLQMSN
LQPEDTGVYYCATGYRTDTRIPGGSWGQGTQVTVSSEPKTPKPQ (SEQ ID NO:28)

JDQ-G5

Nucleotide sequence:

CAGGTGCAGCTCGTGGAGTCTGGAGGAGGCTTGGTGCAGCCTGGGGGGTCTCTGAGACTCTCCTGTCAAGTCTCTGGATTCA
CCTTCGGTGACTGGGTCATGAGCTGGTTCCGCCAGGCTCCGGGGAAGGAGCGCGAATTCGTCGCAAGTATTACGGCTACTAG
TAGTCTAAAGTATTATGCAGACTCCGTGAAGGGCCGATTCACCATCTCCAGAGACAATGTCAACAACACACTGTTTCTGCAAATG
GATCGCCTGAAATCTGAGGACACGGCCGTTTATTACTGTCGGTCCCCCAACTACTGGGGCCAGGGGACCCAGGTCACCGTCTC
CGCCGAACCCAAGACACCAAAACCACAA (SEQ ID NO:29)

amino acid sequence:

QVQLVESGGGLVQPGGSLRLSCQVSGFTFGDWVMSWFRQAPGKEREFVASITATSSLKYYADSVKGRFTISRDNVNNTLFLQMDRL
KSEDTAVYYCRSPNYWGQGTQVTVSAEPKTPKPQ (SEQ ID NO:30)

JDQ-H7

Nucleotide sequence:

CAGGTGCAGCTCGTGGAGTCAGGTGGAGGCTTGGTGCAGGTTGGGGGGTCTCTGAGACTCTCCTGTGTAGTTTCTGGAAGCG
ACATCAGTGGCATTGCGATGGGCTGGTACCGCCAGGCTCCAGGGAAGCGGCGCGAAATGGTCGCAGATATTTTTTCTGGCGG
TAGTACAGACTATGCAGGCTCCGTGAAGGGCCGATTCACCATCTCCAGAGACAACGCCAAGAAGACGAGCTATCTGCAAATGA
ACAACGTGAAACCTGAGGACACCGGAGTCTACTACTGTAGGCTGTACGGGAGCGGTGACTACTGGGGCCAGGGGACCCAGGT
CACCGTCTCCTCAGCGCACCACAGCGAAGACCCCTCG (SEQ ID NO:31)

amino acid sequence:

QVQLVESGGGLVQVGGSLRLSCVVSGSDISGIAMGWYRQAPGKRREMVADIFSGGSTDYAGSVKGRFTISRDNAKKTSYLQMNNV
KPEDTGVYYCRLYGSGDYWGQGTQVTVSSAHHSEDPS (SEQ ID NO:32)

Fig. 3B

BoNT/B holotoxin binding VHHs:

JEQ-A5
Nucleotide sequence:

CAGGTGCAGCTCGTGGAGTCAGGCGGAGGCTTGGTGCAGCCTGGGGGGTCTCTGAAACTCTCCTGTGCAGCCTCTGGATTCA
CTTTGGGACACCATCGCGTTGGCTGGTTCCGCCAGGCCCCAGGAAAGAAGCGTGAGGGGGTCGCGTGTATTAGCGCCACTGG
TCTTAGCACACACTATTCAGACTCCGTGACCGGCCGATTTACCGTCTCCAGAGACAACCTCAACAACGTGGCGTATCTGCAGCT
GAACAGCCTGAAACCTGAGGACGCAGGTGTTTATTACTGTGCAAGCAGATTCTCCCTTAATTCGGTCGATGCGAATATGTGCCT
TTCAGAGCCTCAGTATGACAACTGGGGCCAGGGGACCCAGGTCAGAATCTCCTCAGAACCCAAGACACCAAAACCACAA
(SEQ ID NO:33)

amino acid sequence:

QVQLVESGGGLVQPGGSLKLSCAASGFTLGHHRVGWFRQAPGKKREGVACISATGLSTHYSDSVTGRFTVSRDNLNNVAYLQLNSL
KPEDAGVYYCASRFSLNSVDANMCLSEPQYDNWGQGTQVRISSEPKTPKPQ (SEQ ID NO:34)

JEQ-H11
Nucleotide sequence:

CAGGTGCAGCTCGTGGAGACGGGTGGAGGATTGGTGCAGGCCGGGGGCTCTCTGAGACTCTCCTGCGCAGGCTCTGGACGC
TCCTTCAGCGCCGCTGTCATGGGCTGGTTCCGCCAGGCGCCAGGGAAGGAGCGAGAATTCGTAGCAGCACTTAGACAAATTAT
TGGTAGCACACACTATGCAGACTCCGTGAAGGGCCGATTCACCATCTCCAGAGACAACGCCAAGAACATGTTGTATCTCGACAT
GAACAGCCTGAAACCTACGGACACGGCCGCGTATTACTGCACAGCGGGACCTCCGACTATGCTGGACGTTTCTACCGACCGG
GAGTATGACACCTGGGGTCAGGGGACTCAGGTCACCGTCTCCTCAGCGCACCACAGCGAAGACCCCTCG (SEQ ID NO:35)

amino acid sequence:

QVQLVESGGGLVQAGGSLRLSCAGSGRSFSAAVMGWFRQAPGKEREFVAALRQIIGSTHYADSVKGRFTISRDNAKNMLYLDMNSL
KPTDTAAYYCTAGPPTMLDVSTDREYDTWGQGTQVTVSSAHHSEDPS (SEQ ID NO:36)

Fig. 3C

JDQ-B5
Nucleotide sequence:

CAGGTGCAGCTCGTGGAGTCCGGCGGAGGCTTGGTGCACCCTGGGGGGTCTCTGAGACTCTCTTGTGCACCCTCTGCCAGTC
TACCATCAACACCCTTCAACCCCTTCAACAATATGGTGGGCTGGTACCGTCAGGCTCCAGGTAAACAGCGCGAAATGGTCGCA
AGTATTGGTCTACGAATAAACTATGCAGACTCCGTGAAGGGCCGATTCACCATCTCCAGAGACAACGCCAAGAACACGGTGGA
TCTGCAGATGGACAGCCTGCGACCTGAGGACTCAGCCACATACTACTGTCATATAGAATACACCCACTACTGGGGCAAAGGGA
CCCTGGTCACCGTCTCCTCGGAACCCAAGACACCAAAACCACAA (SEQ ID NO:23)

amino acid sequence:

QVQLVESGGGLVHPGGSLRLSCAPSASLPSTPFNPFNNMVGWYRQAPGKQREMVASIGLRINYADSVKGRFTISRDNAKNTVDLQM
DSLRPEDSATYYCHIEYTHYWGKGTLVTVSSEPKTPKPQEPKTPKPQ (SEQ ID NO:24)

JDQ-E9
Nucleotide sequence:

CAGGTGCAGCTCGTGGAGTCCGGAGGAGGCTTGGTGCGACCTGGGGGGTCTCTGAGACTCTCTTGTGTAGTCTCTGGATTCG
CCTACGAAATGCCCATGATGGGCTGGTACCGCCAGGCTCCAGGGAATCAGCGCGAGTTGGTCGCAACTATTGGTACAGGTGG
TAGGATGAACTATGCAGACTCCGTGAAGGGCCGATTCACCATCTCCAGAGACAACGCCAAGAACACGGTGTATCTGCAAATGA
ACAGCCTGAAACCTGAGGACACAGCCGCCTATTACTGTAAAATCGAGTTTACAAATTACTGGGGCCAGGGGACCCAAGTCACC
GTCTCCTCAGAACCCAAGACACCAAAACCACAA (SEQ ID NO:37)

amino acid sequence:

QVQLVESGGGLVRPGGSLRLSCVVSGFAYEMPMMGWYRQAPGNQRELVATIGTGGRMNYADSVKGRFTISRDNAKNTVYLQMNS
LKPEDTAAYYCKIEFTNYWGQGTQVTVSSEPKTPKPQ (SEQ ID NO:38)

JDQ-B2
Nucleotide sequence:

CAGGTGCAGCTCGTGGAGTCAGGTGGAGGCTTGGTGCAGCCGGGGGGATCTCTGAGACTGTCCTGTACAGTCTCTGGAAGCA
TCTTCGATCTACCTGGAATGAACTGGTATCGCCAGGCTCCAGGGGCGCAGCGCGAGTTGGTCGCAGATATTAGTAGTGATGGT
AGGAGGACAAACTATGCAGACTCCGTGAAGGGCCGATTCACCATGTCCAGAGACAATGCCAAGAAAACGGTGTATCTGCAAAT
GGACAGCCTGAAACCTGACGACACGGCCGTCTATTACTGTAATGTGAAATTTACTCACCACTGGGGCCAGGGGATCCAGGTCA
CCGTCTCCTCAGAACCCAAGACACCAAAACCACAA (SEQ ID NO:39)

amino acid sequence:

QVQLVESGGGLVQPGGSLRLSCTVSGSIFDLPGMNWYRQAPGAQRELVADISSDGRRTNYADSVKGRFTMSRDNAKKTVYLQMDS
LKPDDTAVYYCNVKFTHHWGQGIQVTVSSEPKTPKPQ (SEQ ID NO:40)

Fig. 4A

JDQ-C5
Nucleotide sequence:

CAGGTGCAGCTCGTGGAGTCAGGCGGAGGCTTGGTGCAGCCGGGGGGATCTCTGAGGCTGTCCTGTACGGTCTCTGGAAGC
ATCTTCGGCCTACCTGGCATGAGCTGGTATCGCCAGGCTCCAGGGGCGCAGCGCGAGTTGGTCGCAGATATTAGTAGTGATG
GTGGGAGGACGCACTATGCAGACTCCGTGAAGGGCCGCTTCACCATCTCCAGAGACAATGACAAGAAAACGGTGTATCTGCAG
ATGGACAGCCTGAAACCTGACGACACGGCCGTCTATTACTGTAATGTGAAATTTACTCACCACTGGGGCCAGGGGATCCAGGT
CACCGTCTCCTCAGAACCCAAGACACCAAAACCACAA (SEQ ID NO:41)

amino acid sequence:

QVQLVESGGGLVQPGGSLRLSCTVSGSIFGLPGMSWYRQAPGAQRELVADISSDGGRTHYADSVKGRFTISRDNDKKTVYLQMDSL
KPDDTAVYYCNVKFTHHWGQGIQVTVSSEPKTPKPQ (SEQ ID NO:42)

JDQ-F9
Nucleotide sequence:

CAGGTGCAGCTCGTGGAGTCTGGGGGAGGCTTGGTGCAGGATGGGGGGTCTCTGAGGCTCTCCTGCACAACATCTGGAAGTA
TCGACAGTTTCAATGCCATAGAGTGGTACCGCCAGGCTCCAGGGAAGCAGCGCGAATTGGTCGCAAGTATAAGTAGTGATGGT
CGTCGCACAAACTATGCAGACTCCGTGAAGGGCCGATTCACCATCTCCGGAGACAACGCCAAGAACACGGTGTATCTGCAAAT
GAACAGCCTGAAACCTGAGGACACAGCCGTGTATTACTGTCATAGACCTTTTACCCACTACTGGGGCCAGGGGACCCAGGTCA
CCGTCTCCTCAGAACCCAAGACACCAAAACCACAA (SEQ ID NO:43)

amino acid sequence:

QVQLVESGGGLVQDGGSLRLSCTTSGSIDSFNAIEWYRQAPGKQRELVASISSDGRRTNYADSVKGRFTISGDNAKNTVYLQMNSLK
PEDTAVYYCHRPFTHYWGQGTQVTVSSEPKTPKPQ (SEQ ID NO:44)

Fig. 4B

Two nanobodies were identified that bind to BoNT/A holotoxin, H7 and B5. Each was expressed in different formats fused to E-tag and, in some cases, fused to one another E-tag →
nanobody →

H7/E and B5/E,
single-tagged
nanobody
monomers

H7/B5/E,
single-tagged
nanobody
heterodimer

E/H7/B5/E,
double-tagged
nanobody
heterodimer

1000 LD$_{50}$

- E/H7/B5/E + anti-E mAb
- H7/B5/E + anti-E mAb
- H7/E + B5/E + anti-E mAb
- Co

10,000 LD$_{50}$

- E/H7/B5/E + anti-E mAb
- Co

H7/E

ATGAGCGATAAAATTATTCACCTGACTGACGACAGTTTTGACACGGATGTACTCAAAGCGGACGGGGCGATCCTCGTCGATTTCTG
GGCAGAGTGGTGCGGTCCGTGCAAAATGATCGCCCCGATTCTGGATGAAATCGCTGACGAATATCAGGGCAAACTGACCGTTGCAA
AACTGAACATCGATCAAAACCCTGGCACTGCGCCGAAATATGGCATCCGTGGTATCCCGACTCTGCTGCTGTTCAAAAACGGTGAA
GTGGCGGCAACCAAAGTGGGTGCACTGTCTAAAGGTCAGTTGAAAGAGTTCCTCGACGCTAACCTGGCCGGTTCTGGTTCTGGCCA
TATGCACCATCATCATCATCATTCTTCTGGTCTGGTGCCACGCGGTTCTGGTATGAAAGAAACCGCTGCTGCTAAATTCGAACGCC
AGCACATGGACAGCCCAGATCTGGGTACCGACGACGACGACAAGGCCATGGCGATATCGGATCCGAATTCCCAGGTGCAGCTCGTG
GAGTCAGGTGGAGGCTTGGTGCAGGTTGGGGGGTCTCTGAGACTCTCCTGTGTAGTTTCTGGAAGCGACATCAGTGGCATTGCGAT
GGGCTGGTACCGCCAGGCTCCAGGGAAGCGGCGCGAAATGGTCGCAGATATTTTTTCTGGCGGTAGTACAGACTATGCAGGCTCCG
TGAAGGGCCGATTCACCATCTCCAGAGACAACGCCAAGAAGACGAGCTATCTGCAAATGAACAACGTGAAACCTGAGGACACCGGA
GTCTACTACTGTAGGCTGTACGGGAGCGGTGACTACTGGGGCCAGGGGACCCAGGTCACCGTCTCCTCAGCGCACCACAGCGAAGA
CCCCACTAGTGGTGCGCCGGTGCCGTATCCGGATCCGCTGGAACCGCGTTAA(SEQ ID NO:45)

MSDKIIHLTDDSFDTDVLKADGAILVDFWAEWCGPCKMIAPILDEIADEYQGKLTVAKLNIDQNPGTAPKYGIRGIPTLLLFKNGE
VAATKVGALSKGQLKEFLDANLAGSGSGHMHHHHHHSSGLVPRGSGMKETAAAKFERQHMDSPDLGTDDDDKAMAISDPNS*QVQLV*
*ESGGGLVQVGGSLRLSCVVSGSDISGIAMGWYRQAPGKRREMVADIFSGGSTDYAGSVKGRFTISRDNAKKTSYLQMNNVKPEDTG*
*VYYCRLYGSGDYWGQGTQVTVSSAHHSEDP*TSGAPVPYPDPLEPR (SEQ ID NO:46)

ATGAGCGATAAAATTATTCACCTGACTGACGACAGTTTTGACACGGATGTACTCAAAGCGGACGGGGCGATCCTCGTCGATTTCTG
GGCAGAGTGGTGCGGTCCGTGCAAAATGATCGCCCCGATTCTGGATGAAATCGCTGACGAATATCAGGGCAAACTGACCGTTGCAA
AACTGAACATCGATCAAAACCCTGGCACTGCGCCGAAATATGGCATCCGTGGTATCCCGACTCTGCTGCTGTTCAAAAACGGTGAA
GTGGCGGCAACCAAAGTGGGTGCACTGTCTAAAGGTCAGTTGAAAGAGTTCCTCGACGCTAACCTGGCCGGTTCTGGTTCTGGCCA
TATGCACCATCATCATCATCATTCTTCTGGTCTGGTGCCACGCGGTTCTGGTATGAAAGAAACCGCTGCTGCTAAATTCGAACGCC
AGCACATGGACAGCCCAGATCTGGGTACCGACGACGACGACAAGGCCATGGCGATATCGGATCCGAATTCCCAGGTGCAGCTCGTG
GAGTCCGGCGGAGGCTTGGTGCACCCTGGGGGGTCTCTGAGACTCTCTTGTGCACCCTCTGCCAGTCTACCATCAACACCCTTCAA
CCCCTTCAACAATATGGTGGGCTGGTACCGTCAGGCTCCAGGTAAACAGCGCGAAATGGTCGCAAGTATTGGTCTACGAATAAACT
ATGCAGACTCCGTGAAGGGCCGATTCACCATCTCCAGAGACAACGCCAAGAACACGGTGGATCTGCAGATGGACAGCCTGCGACCT
GAGGACTCAGCCACATACTACTGTCATATAGAATACACCCACTACTGGGGCAAAGGGACCCTGGTCACCGTCTCCTCGGAACCCAA
GACACCAAAACCACAAACTAGTGGTGCGCCGGTGCCGTATCCGGATCCGCTGGAACCGCGTTAA(SEQ ID NO:47)

MSDKIIHLTDDSFDTDVLKADGAILVDFWAEWCGPCKMIAPILDEIADEYQGKLTVAKLNIDQNPGTAPKYGIRGIPTLLLFKNGE
VAATKVGALSKGQLKEFLDANLAGSGSGHMHHHHHHSSGLVPRGSGMKETAAAKFERQHMDSPDLGTDDDDKAMAISDPNS*QVQLV*
*ESGGGLVHPGGSLRLSCAPSASLPSTPFNPFNNMVGWYRQAPGKQREMVASIGLRINYADSVKGRFTISRDNAKNTVDLQMDSLRP*
*EDSATYYCHIEYTHYWGKGTLVTVSSEPKTPKPQT*SGAPVPYPDPLEPR (SEQ ID NO:48)

ATGAGCGATAAAATTATTCACCTGACTGACGACAGTTTTGACACGGATGTACTCAAAGCGGACGGGGCGATCCTCGTCGATTTCTG
GGCAGAGTGGTGCGGTCCGTGCAAAATGATCGCCCCGATTCTGGATGAAATCGCTGACGAATATCAGGGCAAACTGACCGTTGCAA
AACTGAACATCGATCAAAACCCTGGCACTGCGCCGAAATATGGCATCCGTGGTATCCCGACTCTGCTGCTGTTCAAAAACGGTGAA
GTGGCGGCAACCAAAGTGGGTGCACTGTCTAAAGGTCAGTTGAAAGAGTTCCTCGACGCTAACCTGGCCGGTTCTGGTTCTGGCCA
TATGCACCATCATCATCATCATTCTTCTGGTCTGGTGCCACGCGGTTCTGGTATGAAAGAAACCGCTGCTGCTAAATTCGAACGCC
AGCACATGGACAGCCCAGATCTGGGTACCGACGACGACGACAAGGCCATGGCGGCCGCTCAGGTGCAGCTCGTGGAGTCAGGTGGA
GGCTTGGTGCAGGTTGGGGGGTCTCTGAGACTCTCCTGTGTAGTTTCTGGAAGCGACATCAGTGGCATTGCGATGGGCTGGTACCG
CCAGGCTCCAGGGAAGCGGCGCGAAATGGTCGCAGATATTTTTTCTGGCGGTAGTACAGACTATGCAGGCTCCGTGAAGGGCCGAT
TCACCATCTCCAGAGACAACGCCAAGAAGACGAGCTATCTGCAAATGAACAACGTGAAACCTGAGGACACCGGAGTCTACTACTGT
AGGCTGTACGGGAGCGGTGACTACTGGGGCCAGGGGACCCAGGTCACCGTCTCCTCAGCGCACCACAGCGAAGACCCCACTAGTGC
GATCGCTGGTGGAGGCGGTTCAGGCGGAGGTGGCTCTGGCGGTGGCGGTTCCCTGCAGGGTCAGTTGCAGCTCGTGGAGTCCGGCG
GAGGCTTGGTGCACCCTGGGGGGTCTCTGAGACTCTCTTGTGCACCCTCTGCCAGTCTACCATCAACACCCTTCAACCCCTTCAAC
AATATGGTGGGCTGGTACCGTCAGGCTCCAGGTAAACAGCGCGAAATGGTCGCAAGTATTGGTCTACGAATAAACTATGCAGACTC
CGTGAAGGGCCGATTCACCATCTCCAGAGACAACGCCAAGAACACGGTGGATCTGCAGATGGACAGCCTGCGACCTGAGGACTCAG
CCACATACTACTGTCATATAGAATACACCCACTACTGGGGCAAAGGGACCCTGGTCACCGTCTCCTCGGAACCCAAGACACCAAAA
CCACAACCGGCGCGCCAGGGTGCGCCGGTGCCGTATCCGGACCCGCTGGAACCGCGTTAA(SEQ ID NO:49)

MSDKIIHLTDDSFDTDVLKADGAILVDFWAEWCGPCKMIAPILDEIADEYQGKLTVAKLNIDQNPGTAPKYGIRGIPTLLLFKNGE
VAATKVGALSKGQLKEFLDANLAGSGSGHMHHHHHHSSGLVPRGSGMKETAAAKFERQHMDSPDLGTDDDDKAMAAA*QVQLVESGG*
*GLVQVGGSLRLSCVVSGSDISGIAMGWYRQAPGKRREMVADIFSGGSTDYAGSVKGRFTISRDNAKKTSYLQMNNVKPEDTGVYYC*
*RLYGSGDYWGQGTQVTVSSAHHSEDPT*SAIAGGGGSGGGGSGGGGSLQG*QLQLVEGGGGLVHPGGSLRLSCAPSASLPSTPFNPFN*
*NMVGWYRQAPGKQREMVASIGLRINYADSVKGRFTISRDNAKNTVDLQMDSLRPEDSATYYCHIEYTHYWGKGTLVTVSSEPKTPK*
*PQ*PARQGAPVPYPDPLEPR (SEQ ID NO:50)

ATGAGCGATAAAATTATTCACCTGACTGACGACAGTTTTGACACGGATGTACTCAAAGCGGACGGGGCGATCCTCGTCGATTTCTGGGCAGAGTGGT
GCGGTCCGTGCAAAATGATCGCCCCGATTCTGGATGAAATCGCTGACGAATATCAGGGCAAACTGACCGTTGCAAAACTGAACATCGATCAAAACCC
TGGCACTGCGCCGAAATATGGCATCCGTGGTATCCCGACTCTGCTGCTGTTCAAAAACGGTGAAGTGGCGGCAACCAAAGTGGGTGCACTGTCTAAA
GGTCAGTTGAAAGAGTTCCTCGACGCTAACCTGGCCGGTTCTGGTTCTGGCCATATGCACCATCATCATCATCATTCTTCTGGTCTGGTGCCACGCG
GTTCTGGTATGAAAGAAACCGCTGCTGCTAAATTCGAACGCCAGCACATGGACAGCCCAGATCTGGGTACCGACGACGACGACAAGGCCATGGCGAT
ATCGGATCCGAATTCTGGCGCACCTGTCCCATACCCAGACCCTCTGGAACCACGAGCGGCCGCTCAGGTGCAGCTCGTGGAGTCAGGTGGAGGCTTG
GTGCAGGTTGGGGGGTCTCTGAGACTCTCCTGTGTAGTTTCTGGAAGCGACATCAGTGGCATTGCGATGGGCTGGTACCGCCAGGCTCCAGGGAAGC
GGCGCGAAATGGTCGCAGATATTTTTTCTGGCGGTAGTACAGACTATGCAGGCTCCGTGAAGGGCCGATTCACCATCTCCAGAGACAACGCCAAGAA
GACGAGCTATCTGCAAATGAACAACGTGAAACCTGAGGACACCGGAGTCTACTACTGTAGGCTGTACGGGAGCGGTGACTACTGGGGCCAGGGGACC
CAGGTCACCGTCTCCTCAGCGCACCACAGCGAAGACCCCACTAGTGCGATCGCTGGTGGAGGCGGTTCAGGCGGAGGTGGCTCTGGCGGTGGCGGTT
CCCTGCAGGGTCAGTTGCAGCTCGTGGAGTCCGGCGGAGGCTTGGTGCACCCTGGGGGGTCTCTGAGACTCTCTTGTGCACCCTCTGCCAGTCTACC
ATCAACACCCTTCAACCCCTTCAACAATATGGTGGGCTGGTACCGTCAGGCTCCAGGTAAACAGCGCGAAATGGTCGCAAGTATTGGTCTACGAATA
AACTATGCAGACTCCGTGAAGGGCCGATTCACCATCTCCAGAGACAACGCCAAGAACACGGTGGATCTGCAGATGGACAGCCTGCGACCTGAGGACT
CAGCCACATACTACTGTCATATAGAATACACCCACTACTGGGGCAAAGGGACCCTGGTCACCGTCTCCTCGGAACCCAAGACACCAAAACCACAACC
GGCGCGCCAGGGTGCGCCGGTGCCGTATCCGGACCCGCTGGAACCGCGTTAA(SEQ ID NO:51)

MSDKIIHLTDDSFDTDVLKADGAILVDFWAEWCGPCKMIAPILDEIADEYQGKLTVAKLNIDQNPGTAPKYGIRGIPTLLLFKNGE
VAATKVGALSKGQLKEFLDANLAGSGSGHMHHHHHHSSGLVPRGSGMKETAAAKFERQHMDSPDLGTDDDDKAMAISDPNSGAPVP
YPDPLEPRAAAQVQLVESGGGLVQVGGSLRLSCVVSGSDISGIAMGWYRQAPGKRREMVADIFSGGSTDYAGSVKGRFTISRDNAK
KTSYLQMNNVKPEDTGVYYCRLYGSGDYWGQGTQVTVSSAHHSEDPTSAIAGGGGSGGGGSGGGGSLQGQLQLVESGGGLVHPGGS
LRLSCAPSASLPSTPFNPFNNMVGWYRQAPGKQREMVASIGLRINYADSVKGRFTISRDNAKNTVDLQMDSLRPEDSATYYCHIEY
THYWGKGTLVTVSSEPKTPKPQPARQGAPVPYPDPLEPR (SEQ ID NO:52)

Fig. 10D

VHH sequences in italics

E-tag underlined

Thioredoxin:

MSDKIIHLTDDSFDTDVLKADGAILVDFWAEWCGPCKMIAPILDEIADEYQGKLTVAKLNIDQNPGTAPKYGIRGIPTLLLFKNGE
VAATKVGALSKGQLKEFLDANLA (SEQ ID NO:53)

Fig. 10E

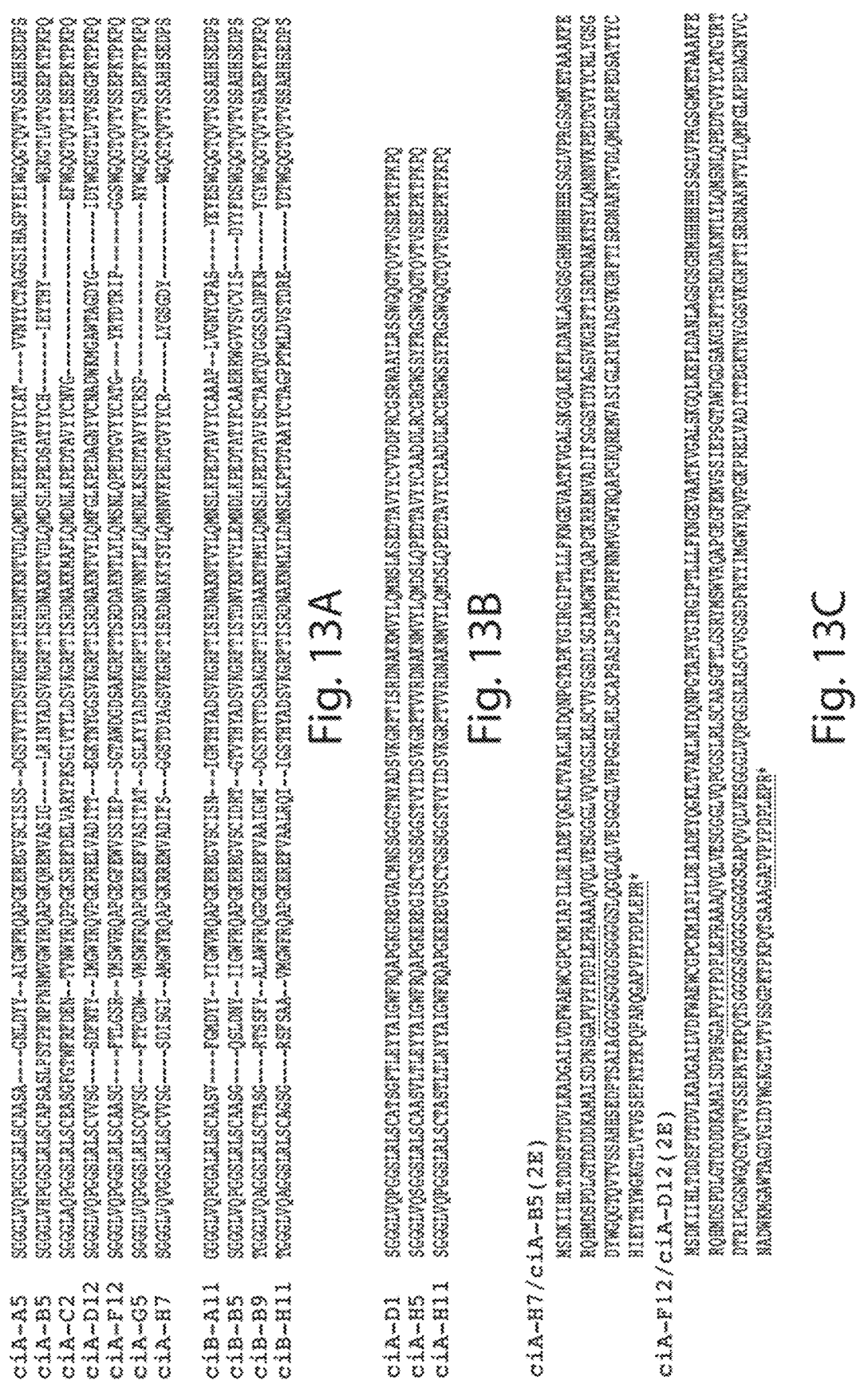

```
ciA-A5   SGGGLVQPGGSLRLSCAASA----GNLDYY--AIGWFRQAPGKEREGVSCISSS--DGSTVYTDSVKGRFTISRDNTKNTVDLQMDNLKPEDTAVYYCAT----VVNYYCTAGGSIHASPYEIWGQGTQVTVSSAHHSEDPS
ciA-B5   SGGGLVHPGGSLRLSCAPSASLPSTPFNPFNNMVGWYRQAPGKQREMVASIG-----LRINYADSVKGRFTISRDNAKNTVDLQMDSLRPEDSATYYCH-------IEYTHY----------WGKGTLVTVSSEPKTPKPQ
ciA-C2   SGGGLAQPGGSLRLSCEASGFGTWFRFDEN--TVNWYRQPPGKSREFDELVARYPKSGIVTYLDSVKGRFTISRDNAKKMAFLQMDNLKPEDTAVYYCNVG------------------EFWGQGTQVTISSEPKTPKPQ
ciA-D12  SGGGLVQPGGSLRLSCVVSG----SDFNTY--IMGWYRQVPGKPRELVADITT---EGKTNYGGSVKGRFTISRDNAKNTVYLQMFGLKPEDAGNYYCNADWKMGAWTAGDYG-------IDYWGKGTLVTVSSGPKTPKPQ
ciA-F12  SGGGLVQPGGSLRLSCAASG----FTLGSR--YMSWVRQAPGEGFEWVSSIEP---SGTAWDGDSAKGRFTTSRDDAKNTLYLQMSNLQPEDTGVYYCATG----YRTDTRIP------GGSWGQGTQVTVSSEPKTPKPQ
ciA-G5   SGGGLVQPGGSLRLSCQVSG----FTFGDW--VMSWFRQAPGKEREFVASITAT--SSLKYYADSVKGRFTISRDNVNNTLFLQMDRLKSEDTAVYYCRSP------------------NYWGQGTQVTVSAEPKTPKPQ
ciA-H7   SGGGLVQVGGSLRLSCVVSG----SDISGI--AMGWYRQAPGKRREMVADIFS---GGSTDYAGSVKGRFTISRDNAKKTSYLQMNNVKPEDTGVYYCR------LYGSGDY----------WGQGTQVTVSSAHHSEDPS

ciB-A11  GGGGLVQPGGALRLSCAASV----FGMDYY--YIGWVRQAPGKEREGVSCISN---IGRTHYADSVKGRFTISRDNAKNTVYLQMNSLKPEDTAVYYCAAAF--LVGNYCPAS-----YEYESWGQGTQVTVSSAHHSEDPS
ciB-B5   SGGGLVQPGGSLRLSCAASG----QSLDNY--IIGWFRQAPGKEREGVSCIDRT--GTVTHYADSVKGRFTISTDNVKNTVYLEMNDLKPEDTATYFCAAERKWGVVSVCVIS----DYYFGSWGQGTQVTVSSAHHSEDPS
ciB-B9   TGGGLVQAGGSLRLSCTASG----RTSSFY--ALAWFRQGPGKEREFVAAIGWI--DGSTRYTDSAKGRFTISRDAAKNTMYLQMNSLKPEDTAVYSCTARTQYGGSSADPKN-------YGYWGQGTQVTVSAEPKTPKPQ
ciB-H11  TGGGLVQAGGSLRLSCAGSG----RSFSAA--VMGWFRQAPGKEREFVAALRQI--IGSTHYADSVKGRFTISRDNAKNMLYLDMNSLKPTDTAAYYCTAGPPTMLDVSTDRE-------YDTWGQGTQVTVSSAHHSEDPS
```

Fig. 13A

```
ciA-D1   SGGGLVQPGGSLRLSCATSGFTLEYYAIGWFRQAPGKGREGVACMNSSGGGTNYADSVKGRFTISRDNAKKMVYLQMNSLKSEDTAVYYCVVDDFRCGSRWAAYLRSSWGQGTQVTVSSEPKTPKPQ
ciA-H5   SGGGLVQSGGSLRLSCAASVLTLEYYAIGWFRQAPGKEREGISCTGSSGGSTVYIDSVKGRFTVVRDNAKNMVYLQMDSLQPEDTAVYYCAADDLRCGRGWSSYFRGSWGQGTQVTVSSEPKTPKPQ
ciA-H11  SGGGLVQPGGSLRLSCTASTLTLNYYAIGWFRQAPGKEREGVSCTGSSGGSTVYIDSVKGRFTVVRDNAKNMVYLQMDSLQPEDTAVYYCAADDLRCGRGWSSYFRGSWGQGTQVTVSSEPKTPKPQ
```

Fig. 13B ciA-H7/ciA-B5(2E)

MSDKIIHLTDDSFDTDVLKADGAILVDFWAEWCGPCKMIAPILDEIADEYQGKLTVAKLNIDQNPGTAPKYGIRGIPTLLLFKNGEVAATKVGALSKGQLKEFLDANLAGSGSGHMHHHHHHSSGLVPRGSGMKETAAAKFE
RQHMDSPDLGTDDDDKAMAISDPNSGAPVPYPDPLEPRAAAQVQLVESGGGLVQVGGSLRLSCVVSGSDISGIAMGWYRQAPGKRREMVADIFSGGSTDYAGSVKGRFTISRDNAKKTSYLQMNNVKPEDTGVYYCRLYGSG
DYWGQGTQVTVSSAHHSEDPTSAIAGGGGSGGGGSGGGGSLQGQLQLVESGGGLVHPGGSLRLSCAPSASLPSTPFNPFNNMVGWYRQAPGKQREMVASIGLRINYADSVKGRFTISRDNAKNTVDLQMDSLRPEDSATYYC
HIEYTHYWGKGTLVTVSSEPKTPKPQPARQGAPVPYPDPLEPR* ciA-F12/ciA-D12(2E)

MSDKIIHLTDDSFDTDVLKADGAILVDFWAEWCGPCKMIAPILDEIADEYQGKLTVAKLNIDQNPGTAPKYGIRGIPTLLLFKNGEVAATKVGALSKGQLKEFLDANLAGSGSGHMHHHHHHSSGLVPRGSGMKETAAAKFE
RQHMDSPDLGTDDDDKAMAISDPNSGAPVPYPDPLEPRAAAQVQLVESGGGLVQPGGSLRLSCAASGFTLGSRYMSWVRQAPGEGFEWVSSIEPSGTAWDGDSAKGRFTTSRDDAKNTLYLQMSNLQPEDTGVYYCATGYRT
DTRIPGGSWGQGTQVTVSSEPKTPKPQTSGGGGSGGGGSGGGGSGAPQVQLVESGGGLVQPGGSLRLSCVVSGSDFNTYIMGWYRQVPGKPRELVADITTEGKTNYGGSVKGRFTISRDNAKNTVYLQMFGLKPEDAGNYYC
NADWKMGAWTAGDYGIDYWGKGTLVTVSSGPKTPKPQTSAAAGAPVPYPDPLEPR*

Fig. 13C

| VHH | SPR Kd (nM) |
|---|---|
| ciA-H7 | 0.06 +/- 0.07 |
| ciA-D1 | 0.71 +/- 0.004 |
| ciA-H4 | 1.54 +/- 0.06 |
| ciA-H11 | 4.3 +/- 0.09 |

METHODS, COMPOSITIONS AND KITS FOR TREATING A SUBJECT USING A RECOMBINANT HETEROMULTIMERIC NEUTRALIZING BINDING PROTEIN

CROSS-REFERENCE TO RELATED APPLICATIONS

This application, filed Jul. 9, 2021, is a continuation of application U.S. Ser. No. 15/475,664, filed Mar. 31, 2017, now U.S. Pat. No. 11,091,563, issued Aug. 17, 2021, which is a continuation of application U.S. Ser. No. 14/665,542, filed Mar. 23, 2015, now U.S. Pat. No. 9,834,616, issued Dec. 5, 2017, which is a divisional of application U.S. Ser. No. 13/566,524, filed Aug. 3, 2012, now U.S. Pat. No. 9,023,352, issued May 5, 2015, which claims benefit of U.S. provisional application No. 61/514,949, filed Aug. 4, 2011, and is a continuation-in-part of application U.S. Ser. No. 12/889,511, filed Sep. 24, 2010, now U.S. Pat. No. 8,349,326, issued Jan. 8, 2013, which is a continuation-in-part of application U.S. Ser. No. 12/032,744, filed Feb. 18, 2008, now U.S. Pat. No. 8,865,169, issued Oct. 21, 2014, which claims benefit of U.S. provisional application No. 60/890,626, filed Feb. 20, 2007, each of which is incorporated by reference herein in its entirety.

GOVERNMENT SUPPORT

This invention was made with government support under grant U54-AI057159 awarded by the National Institutes of Health. The government has certain rights in the invention.

SEQUENCE LISTING

The present application contains a Sequence Listing which has been submitted electronically in ASCII format and is hereby incorporated by reference in its entirety. Said ASCII copy, created on Dec. 8, 2023, is named 167774-011210USCON-Sequence_Listing.txt and is 144,501 bytes in size.

TECHNICAL FIELD

Compositions, methods, and kits using a recombinant heteromultimeric neutralizing binding protein are provided for treating a subject at risk for exposure or exposed to a disease agent.

BACKGROUND

A need exists for generating high affinity binding agents that treat both routine incidents of disease and pandemics, and efforts to discover and produce these agents are underway. The production of antibodies and their storage is a costly and lengthy process. In fact, development of a single antibody therapeutic agent often requires years of clinical study. Yet multiple, different therapeutic antibodies are necessary for the effective treatment of patients exposed to a disease agent, an infection outbreak or a bio-terrorist assault. Developing and producing multiple antibodies that can bind to different targets (e.g. microbial pathogens, viral pathogens, toxins, and cancer cells) is often a difficult task because it involves separately producing, storing and transporting multiple antibodies for each pathogen or toxin. Production and stockpiling a sufficient amount of antibodies to protect large populations is a challenge and currently has not been achieved. The shelf life of antibodies is often relatively short (e.g., weeks or months), and accordingly freshly prepared batches of antibodies have to be produced to replace the expiring antibodies.

Accordingly, there is a need for a cost effective and efficient way to provide alternatives to current therapeutic agents. Further a need exists for alternative therapeutics that are easier to develop and produce, have a longer shelf life, and bind as a single agent to multiple targets on the same disease agent, as well as to different disease agents.

SUMMARY

An aspect of the invention provides a pharmaceutical composition for treating a subject at risk for exposure to or exposed to at least one disease agent, the pharmaceutical composition including: at least one recombinant heteromultimeric neutralizing binding protein containing two or more binding regions, such that the binding regions are not identical and each binding region has affinity to specifically bind a non-overlapping portion of the disease agent, and the binding protein neutralizes the disease agent thereby treating the subject for exposure to the disease agent. In a related embodiment, the binding protein includes at least one tag that is an epitope that is specifically recognized and bound by an antibody. For example, the antibody is selected from: IgA, IgE, IgG, and IgM. In related embodiments, the anti-tag antibody that recognizes and specifically binds to the tag epitope, viz., the anti-tag antibody, is recombinantly produced and administered to the subject. Alternatively, the anti-tag antibody is endogenously produced within the subject.

In various embodiments of the pharmaceutical composition, at least one of the binding regions and/or the binding protein is selected from the group of: a single-chain antibody (scFv); a recombinant camelid heavy-chain-only antibody (VHH); a shark heavy-chain-only antibody (VNAR); a microprotein; a darpin; an anticalin; an adnectin; an aptamer; a Fv; a Fab; a Fab'; and a F(ab')2. In a related embodiment the binding regions specifically bind to a surface, a portion, or an epitope of the disease agent or molecular target. For example, the epitope contains a peptide including an amino acid sequence, or is a carbohydrate side chain of the peptide.

In a related embodiment of the pharmaceutical composition, the binding regions or multimeric components of the heteromultimeric neutralizing binding protein are associated non-covalently or covalently.

The binding protein in a related embodiment of pharmaceutical composition includes a linker that separates the binding regions, such that the linker includes at least one selected from the group of: a peptide, a protein, a sugar, and a nucleic acid. In a related embodiment, the linker includes a carbohydrate. In a related embodiment, the linker does not affect ability of the binding protein to bind to the disease agent or to a plurality of disease agents. For example, the linker includes amino acid sequence GGGGS (SEQ ID NO: 54), GGGGSGGGGSGGGGS (SEQ ID NO: 55), a portion thereof, or substantially identical. The sequence listing material in computer readable form ASCII text file (122 kilobytes) created Mar. 23, 2015 entitled "Sequence_identifications_03232015", containing sequence listings numbers 1-112, has been electronically filed herewith and is incorporated by reference herein in its entirety.

The disease agent in various embodiments is at least one selected from: a virus, a cancer cell, a fungus, a bacterium, a parasite such as a protozoan or a helminth. Alternatively the disease agent is a pathogenic molecule, which is a product of a disease agent, and is selected from the group of: a protein, a lipopolysaccharide, and a toxin. The pathogenic molecule is secreted by or is produced by a disease-causing organism, e.g., a pathogen or infectious agent such as a virus, a bacterium, a prion, or a fungus. For example, the pathogenic molecule results from degradation of a disease-producing organism.

In various embodiments, the toxin is at least one selected from the group consisting of: an aflatoxin, a dinoflagellate toxin, a Botulinum toxin, a *Staphylococcal* α-hemolysin, a *Staphylococcal* leukocidin, an aerolysin cytotoxic enterotoxin, a cholera toxin, a *Bacillus cereus* hemolysis II, an *Helicobacter pylori* vacuolating toxin, a *Bacillus anthracis* toxin, a *cholera* toxin, an *Escherichia coli* serotype O157:H7 toxin, an *Escherichia coli* serotype O104:H7 toxin, a lipopolysaccharide endotoxin, a Shiga toxin, a pertussis toxin, a *Clostridium perfringens* iota toxin, a *Clostridium spiroforme* toxin, a *Clostridium difficile* toxin, *Clostridium difficile* toxin A, *Clostridium difficile* toxin B, *Clostridium septicum* a toxin, and *Clostridium botulinum* C2 toxin.

In various embodiments of the pharmaceutical composition, the at least one disease agent includes a plurality of non-identical disease agents, and the binding protein binds to the plurality of the disease agents, thereby neutralizing the plurality of the non-identical disease agents.

The toxin in various embodiments of the pharmaceutical composition is a *C. botulinum* toxin, such that at least one of the binding regions includes a recombinant camelid heavy-chain-only antibody, and such that the pharmaceutical composition includes an amino acid sequence selected from the group of:

(SEQ ID NO: 56)
LVQVGGSLRLSCVVSGSDISGIAMGWYRQAPGKRREMVADIFSGGSTDYA
GSVKGRFTISRDNAKKTSYLQMNNVKPEDTGVYYCRLYGSGDYWGQGTQV
TVSSAHHSEDP;

(SEQ ID NO: 57)
LVHPGGSLRLSCAPSASLPSTPFNPFNNMVGWYRQAPGKQREMVASIGLR
INYADSVKGRFTISRDNAKNTVDLQMDSLRPEDSATYYCHIEYTHYWGKG
TLVTVSSEPKTPKPQ;
and, (SEQ ID NO: 58)
QVQLVESGGGLVQVGGSLRLSCVVSGSDISGIAMGWYRQAPGKRREMVAD
IFSGGSTDYAGSVKGRFTISRDNAKKTSYLQMNNVKPEDTGVYYCRLYGS
GDYWGQGTQVTVSSAHHSEDPTSAIAGGGGSGGGGSGGGGSLQGQLQLVE
SGGGLVHPGGSLRLSCAPSASLPSTPFNPFNNMVGWYRQAPGKQREMVAS
IGLRINYADSVKGRFTISRDNAKNTVDLQMDSLRPEDSATYYCHIEYTHY
WGKGTLVTVSSEPKTPKPQ.

In a related embodiment of the pharmaceutical composition, the toxin is a *C. difficile* toxin A, such that the binding region includes a recombinant camelid heavy-chain-only antibody having an amino acid sequence selected from the group consisting of:

(SEQ ID NO: 59)
QVQLVETGGLVQPGGSLRLSCAASGFTLDYSSIGWFRQAPGKEREGVSCI
SSSGDSTKYADSVKGRFTTSRDNAKNTVYLQMNSLKPDDTAVYYCAAFRA

-continued

TMCGVFPLSPYGKDDWGKGTLVTVSSEPKTPKPQP;

(SEQ ID NO: 60)
QLQLVETGGGLVQPGGSLRLSCAASGFTFSDYVMTWVRQAPGKGPEWIAT
INTDGSTMRDDSTKGRFTISRDNAKNTLYLQMTSLKPEDTALYYCARGRV
ISASAIRGAVRGPGTQVTVSSEPKTPKPQP;

(SEQ ID NO: 61)
QVQLVESGGGLVQPGGSLRLSCAASGFTLDYYAIGWFRQAPGKEREGVSG
ISSVDGSTYYADSVRGRFTISRDNAKNTVYLQMNSLKPEDTAVYYCAADQ
SPIPIHYSRTYSGPYGMDYWGKGTLVTVSSAHHSEDP;

(SEQ ID NO: 62)
QLQLVESGGGLVQPGGSLRLSCAASGFTLDYYAIGWFRQAPGKEREGVSG
ISFVDGSTYYADSVKGRFAISRGNAKNTVYLQMNSLKPEDTAVYYCAADQ
SSIPMHYSSTYSGPSGMDYWGKGTLVTVSSEPKTPKPQP;

(SEQ ID NO: 63)
QLQLVETGGGLVQAGGSLRLSCAASGRTLSNYPMGWFRQAPGKEREFVAA
IRRIADGTYYADSVKGRFTISRDNAWNTLYLQMNGLKPEDTAVYFCATGP
GAFPGMVVTNPSAYPYWGQGTQVTVSSEPKTPKPQP;

(SEQ ID NO: 64)
QLQLVESGGGLVQPGGSLRLSCAASGFTLDYYAIGWFRQAPGKEREGVSG
ISSSDGSTYYADSVKGRFTISRDNATNTVYLQMNSLKPEDTAVYYCAADQ
AAIPMHYSASYSGPRGMDYWGKGTLVTVSSEPKTPKPQP;

(SEQ ID NO: 87)
MSDKIIHLTDDSFDTDVLKADGAILVDFWAEWCGPCKMIAPILDEIADEY
QGKLTVAKLNIDQNPGTAPKYGIRGIPTLLLFKNGEVAATKVGALSKGQL
KEFLDANLAGSGSGHMHHHHHHSSGLVPRGSGMKETAAAKFERQHMDSPD
LGTDDDDKAMAISDPNSQVQLVESGGGLVQPGGSLRLSCEASGFTLDYYG
IGWFRQPPGKEREAVSYISASARTILYADSVKGRFTISRDNAKNAVYLQM
NSLKREDTAVYYCARRRFSASSVNRWLADDYDVWGRGTQVAVSSEPKTPK
PQTSAIAGGGGSGGGGSGGGGSLQAMAAASQVQLVESGGGLVQTGGSLRL
SCASSGSIAGFETVTWSRQAPGKSLQWVASMTKTNNEIYSDSVKGRFIIS
RDNAKNTVYLQMNSLKPEDTGVYFCKGPELRGQGIQVTVSSEPKTPKPQP
ARR;
and, (SEQ ID NO: 95)
MSDKIIHLTDDSFDTDVLKADGAILVDFWAEWCGPCKMIAPILDEIADEY
QGKLTVAKLNIDQNPGTAPKYGIRGIPTLLLFKNGEVAATKVGALSKGQL
KEFLDANLAGSGSGHMHHHHHHSSGLVPRGSGMKETAAAKFERQHMDSPD
LGTDDDDKAMAISDPNSQVQLVETGGLVQPGGSLRLSCAASGFTLDYSSI
GWFRQAPGKEREGVSCISSSGDSTKYADSVKGRFTTSRDNAKNTVYLQMN
SLKPDDTAVYYCAAFRATMCGVFPLSPYGKDDWGKGTLVTVSSEPKTPKP
QPTSAIAGGGGSGGGGSGGGGSLQAMAAAQLQLVETGGGLVQPGGSLRLS
CAASGFTFSDYVMTWVRQAPGKGPEWIATINTDGSTMRDDSTKGRFTISR
DNAKNTLYLQMTSLKPEDTALYYCARGRVISASAIRGAVRGPGTQVTVSS
EPKTPKPQPARQTSPSTVRLESRVRELEDRLEELRDELERAERRANEMSI -continued

QLDEC.

The toxin in various embodiments of the pharmaceutical composition is a *C. difficile* toxin B, such that at least one of the binding regions of the binding protein includes a recombinant camelid heavy-chain-only antibody having an amino acid sequence selected from the group consisting of:

(SEQ ID NO: 65)
QVQLVESGGGLVQPGGSLRLSCAASGFSLDYYGIGWFRQAPGKERQEVSY
ISASAKTKLYSDSVKGRFTISRDNAKNAVYLEMNSLKREDTAVYYCARRR
FDASASNRWLAADYDYWGQGTQVTVSSEPKTPKPQ;

(SEQ ID NO: 66)
QVQLVESGGGLVQAGGSLRLSCVSSERNPGINAMGWYRQAPGSQRELVAI
WQTGGSLNYADSVKGRFTISRDNLKNTVYLQMNSLKPEDTAVYYCYLKKW
RDQYWGQGTQVTVSSEPKTPKPQ;

(SEQ ID NO: 67)
QVQLVESGGGLVQPGGSLRLSCEASGFTLDYYGIGWFRQPPGKEREAVSY
ISASARTILYADSVKGRFTISRDNAKNAVYLQMNSLKREDTAVYYCARRR
FSASSVNRWLADDYDVWGRGTQVAVSSEPKTPKPQ;

(SEQ ID NO: 68)
QVQLVESGGGLVQTGGSLRLSCASSGSIAGFETVTWSRQAPGKSLQWVAS
MTKTNNEIYSDSVKGRFIISRDNAKNTVYLQMNSLKPEDTGVYFCKGPEL
RGQGIQVTVSSEPKTPKPQ;

(SEQ ID NO: 69)
QVQLVESGGGLVEAGGSLRLSCVVTGSSFSTSTMAWYRQPPGKQREWVAS
FTSGGAIKYTDSVKGRFTMSRDNAKKMTYLQMENLKPEDTAVYYCALHNA
VSGSSWGRGTQVTVSSEPKTPKPQ;

(SEQ ID NO: 70)
VQLVESGGGLVQAGGSLRLSCAASGLMFGAMTMGWYRQAPGKEREMVAYI
TAGGTESYSESVKGRFTISRINANNMVYLQMTNLKVEDTAVYYCNAHNFW
RTSRNWGQGTQVTVSSEPKTPKP;

(SEQ ID NO: 71)
VQLVESGGGLVQAGDSLTLSCAASESTFNTFSMAWFRQAPGKEREYVAAF
SRSGGTTNYADSVKGRATISTDNAKNTVYLHMNSLKPEDTAVYFCAADRP
AGRAYFQSRSYNYWGQGTQVTVSSAHHSEDP;

(SEQ ID NO: 72)
VQLVESGGGSVQIGGSLRLSCVASGFTFSKNIMSWARQAPGKGLEWVSTI
SIGGAATSYADSVKGRFTISRDNANDTLYLQMNNLKPEDTAVYYCSRGPR
TYINTASRGQGTQVTVSSEPKTPKP;

(SEQ ID NO: 73)
VQLVESGGGLVQAGGSLRLSCVGSGRNPGINAMGWYRQAPGSQRELVAVW
QTGGSTNYADSVKGRFTISRDNLKNTVYLQMNSLKPEDTAVYYCYLKKWR
DEYWGQGTQVTVSSAHHSEDP;

(SEQ ID NO: 74)
VQLVESGGGLVQAGESLRLSCVVSESIFRINTMGWYRQTPGKQREVVARI
TLRNSTTYADSVKGRFTISRDDAKNTLYLKMDSLKPEDTAVYYCHRYPLI
FRNSPYWGQGTQVTVSSEPKTPKP;

-continued (SEQ ID NO: 75)
VQLVESGGGLVQAGESLRLSCVVSESIFRINTMGWYRQTPGKQREVVARI
TLRNSTTYADSVKGRFTISRDDAKNTLYLKMDSLKPEDTAVYYCHRYPLI
FRNSPYWGQGTQVTVSSEPKTP;

(SEQ ID NO: 76)
VQLVESGGGLVQAGGSLRLSCAAPGLTFTSYRIVIGWFRQAPGKEREYVA
AITGAGATNYADSAKGRFTISKNNTASTVHLQMNSLKPEDTAVYYCAASN
RAGGYWRASQYDYWGQGTQVTVSSAHHSEDP;
(SEQ ID NO: 87); and, SEQ ID NO: 95.

The toxin is a Shiga toxin in various embodiments of the pharmaceutical composition, such that at least one of the binding regions includes a recombinant camelid heavy-chain-only antibody having an amino acid sequence selected from the group consisting of:

(SEQ ID NO: 77)
QVQLVETGGGLAQAGDSLRLSCVEPGRTLDMYAMGWIRQAPGEEREFVAS
ISGVGGSPRYADSVKGRFTISKDNTKSTIWLQMNSLKPEDTAVYYCAAGG
DIYYGGSPQWRGQGTRVTVSSEPKTPKPQ;

(SEQ ID NO: 78)
QVQLVESGGGLVQAGGSLRLSCAASGRINGDYAMGWFRQAPGEEREFVAV
NSWIGGSTYYTDSVKGRFTLSRDNAKNTLSLQMNSLKPEDTAVYYCAAGH
YTDFPTYFKEYDYWGQGTQVTVSSEPKTPKPQ;

(SEQ ID NO: 79)
QVQLVETGGLVQAGGSLRLSCAASGVPFSDYTMAWFRQAPGKEREVVARI
TWRGGGPYYGNSGNGRFAISRDIAKSMVYLHMDSLKPEDTAVYYCAASRL
RPALASMASDYDYWGQGTQVSVSSEPKTPKPQ;

(SEQ ID NO: 80)
QVQLVESGGGLVQPGESLRLSCVASASTFSTSLMGWVRQAPGKGLESVAE
VRTTGGTFYAKSVAGRFTISRDNAKNTLYLQMNSLKAEDTGVYYCTAGAG
PIATRYRGQGTQVTVSSAHHSEDP;

(SEQ ID NO: 81)
QVQLVESGGGLVQPGGSLKLSCAASGFTLADYVTVWFRQAPGKSREGVSC
ISSSRGTPNYADSVKGRATVSRNNANNTVYLQMNGLKPDDTAIYYCAAIR
PARLRAYRECLSSQAEYDYWGQGTQVTVSSAHHSEDP;

(SEQ ID NO: 82)
QVQLVESGGGLVQPGGSLGLSCAMSGTTQDYSAVGWFRQAPGKEREGVSC
ISRSGRRTNYADSVRGRFTISRDNAKDTVYLQMNSLKPDDTAVYYCAARK
TDMSDPYYVGCNGMDYWGKGTLVTVSSAHHSEDP;

(SEQ ID NO: 83)
QVQLVESGGGLVQPGGSLTLSCTASGFTLNSYKIGWFRQAPGKEREGVSC
INSGGNLRSVEGRFTISRDNTKNTVSLHMDSLKPEDTGVYHCAAAPALNV
FSPCVLAPRYDYWGQGTQVTVSSAHHSEDP;

(SEQ ID NO: 84)
QVQLVESGGGLVQPGGSLRLSCAASGFTLGSYHIGWFRHPPGKEREGTSC
LSSRGDYTKYAEAVKGRFTISRDNTKSTVYLQMNNLKPEDTGIYVCAAIR
PVLSDSHCTLAARYNYWGQGTQVTVSSAHHSEDP;

(SEQ ID NO: 85)

-continued

QVQLVESGGGLVQPGGSLRLSCAALEFTLEDYAIAWFRQAPGKEREGVSC

ISKSGVTKYTDSVKGRFTVARDNAKSTVILQMNNLRPEDTAVYNCAAVRP

VFVDSVCTLATRYTYWGEGTQVTVSSAHHSEDP;

and (SEQ ID NO: 86)

QVQLVETGGGLVQPGGSLKLSCAASEFTLDDYHIGWFRQAPGKEREGVSC

INKRGDYINYKDSVKGRFTISRDGAKSTVFLQMNNLRPEDTAVYYCAAVN

PVFPDSRCTLATRYTHWGQGTQVTVSSAHHSEDP.

The binding protein and/or at least one binding region in various embodiments of the pharmaceutical composition includes an amino acid sequence that is substantially identical to at least one of SEQ ID NOs: 56-87 and 95, wherein substantially identical is having at least 50% identity, 60% identity, at least 65% identity, at least 70% identity, at least 75% identity, at least 80% identity, at least 85% identity, at least 90% identity, or and at least 95% identity to the amino acid sequence of SEQ ID NOs: 56-87 and 95. Alternatively, the binding protein and/or at least one binding region is encoded by at least one nucleotide sequence or the protein includes amino acid sequence selected from the group of SEQ ID NOs: 1-87 and 95, and substantially identical to any of these nucleotide sequences or amino acid sequences.

The pharmaceutical composition in various embodiments further includes a source of the binding protein. For example, the source of the binding protein is selected from the group of: a nucleic acid vector with a gene encoding the binding protein; a viral vector the binding protein; the binding protein; and the binding protein expressed directly from naked nucleic acid. For example the vector encoding the binding protein is at least one selected from an adenovirus, an adeno-associated virus, a herpesvirus, a poxvirus, and a lentivirus.

An aspect of the invention provides a method for treating a subject at risk for exposure to or exposed to at least one disease agent, the method including: contacting the subject with at least one recombinant heteromultimeric neutralizing binding protein including two or more binding regions, such that the binding regions are not identical, and such that each binding region specifically binds a non-overlapping portion of the disease agent, so that the binding protein neutralizes the disease agent thereby treating the subject for the exposure. In a related embodiment, the binding protein includes at least one tag. For example, the tag includes an epitope that synergistically increases neutralization of the disease agent by the binding protein. In a related embodiment, the epitope is specifically recognized and bound by an anti-antibody, for example a phagocytic antibody or a clearance antibody endogenous produced by the subject. Alternatively, the anti-tag antibody is a recombinant antibody administered to the subject.

In various embodiments of the method, at least one binding region and/or the binding protein is selected from the group of: a single-chain antibody (scFv); a recombinant camelid heavy-chain-only antibody (VHH); a shark heavy-chain-only antibody (VNAR); a microprotein; a darpin; an anticalin; an adnectin; an aptamer; a Fv; a Fab; a Fab'; and a F(ab')2. In various embodiments, the two or more binding regions included in the binding protein are non-identical types of binding agents, for example the binding regions include non-identical VHHs, scFvs, VNARs, microproteins; darpins; an anticalins; adnectins; aptamers; Fvs; Fabs; Fab's; a $F(ab')_2$s, or combinations thereof.

The binding protein in various embodiments includes a linker that separates multimeric components of the binding regions. In related embodiments, the linker includes at least one selected from the group of: a peptide, a protein, a sugar, or a nucleic acid. In related embodiments, the linker includes a single amino acid or a plurality of amino acids. In a related embodiment, the linker includes amino acid sequence GGGGS (SEQ ID NO: 54) or a portion thereof. In a related embodiment, the linker includes amino acid sequence GGGGSGGGGSGGGGS (SEQ ID NO: 55) or a portion thereof or multiples thereof. The linker in various embodiments stabilizes the binding protein and does not prevent the respective binding of the binding regions to the disease agent or to a plurality of disease agents.

In various embodiments of the method, the disease agent is at least one selected from a virus, a cancer cell, a fungus, a bacterium, a parasite and a product thereof such as a pathogenic molecule, a protein, a lipopolysaccharide, and a toxin.

The toxin in various embodiments of the method is at least one selected from the group of: *Staphylococcal* α-hemolysin, *Staphylococcal* leukocidin, aerolysin cytotoxic enterotoxin, a *cholera* toxin, *Bacillus cereus* hemolysis II, and *Helicobacter pylori* vacuolating toxin, *Bacillus anthracis, cholera* toxin, *Escherichia coli* serotype O157:H7, *Escherichia coli* serotype O104:H7, lipopolysaccharide endotoxin, Shiga toxin, pertussis toxin, *Clostridium perfringens* iota toxin, *Clostridium spiroforme* toxin, Botulinum neurotoxin, *Clostridium difficile* toxin A, *Clostridium difficile* toxin B, *Clostridium septicum* a toxin, and *Clostridium botulinum* C2 toxin; and the bacterium is selected from the group consisting of: *B. anthracis, B. cereus, C. botulinum, C. difficile, C. perfringens, C. spiroforme*, and *V. cholera.*

The method further includes, prior contacting the subject with the binding protein, engineering the binding regions and/or the binding protein. In certain embodiments of the method, the binding regions of the binding protein are specific to different classes/types of disease agents, such that each of the plurality of binding regions is non-identical and is specific for a different bacteria, virus, fungus, cancer, and/or pathogenic molecule. For example, a binding region is specific for a virus and another binding region is specific for a bacterium.

The method in various embodiments further includes observing and/or detecting neutralization of the disease agent by the binding protein such that the binding protein is effective for treating the subject and ensuring survival of the subject. In a related embodiment, detecting neutralization by the binding protein includes identifying a reduction or remediation in at least one pathology symptom associated with the disease agent. For example detecting and/or identifying neutralization involves measuring an amount or a concentration of disease agent in the subject or a sample from the subject, and comparing a control amount or concentration prior to contacting, such that a decrease in the amount or the concentration of the disease agent after contacting compared to prior to contacting is a positive indication that the subject is treated. For example, the sample is obtained from a cell, a tissue, or a fluid from the subject.

In various embodiments of the method, the disease agent is a plurality of disease agents, and the method involves prior to contacting, engineering the binding protein to bind to different domains of the plurality of the disease agents. For example the plurality of the disease agents include at least two non-identical types of viruses, cancer cells, fungi, bacteria, parasites and products thereof such pathogenic molecules, proteins, lipopolysaccharides, and toxins, and combinations thereof.

The method in a related embodiment further includes, prior to contacting, engineering at least one of the binding regions and/or the binding protein with at least one amino acid sequence selected from the group of SEQ ID NOs: 56-87 and 95, and substantially identical.

In various embodiments of the method, contacting the subject with the binding protein includes administering to the subject a source of expression of the binding protein, such that the source of the expression of the binding protein is a nucleic acid encoding the binding protein, such that the nucleic acid includes at least one selected from the group consisting of: a naked nucleic acid vector, bacterial vector, and a viral vector.

An aspect of the invention provides a kit for treating a subject exposed to or at risk for exposure to a disease agent, the kit including: a pharmaceutical composition for treating a subject at risk for exposure to or exposed to at least one disease agent, the pharmaceutical composition including: at least one recombinant heteromultimeric neutralizing binding protein comprising two or more binding regions, such that the binding regions are not identical and each binding region has affinity to specifically bind a non-overlapping portion of the disease agent, and the binding protein neutralizes the disease agent thereby treating the subject for exposure to the disease agent; a container; and, instructions for use.

In various embodiments of the kit, at least one of the binding regions and/or the binding protein is selected from the group of: a single-chain antibody (scFv); a recombinant camelid heavy-chain-only antibody (VHH); a shark heavy-chain-only antibody (VNAR); a microprotein; a darpin; an anticalin; an adnectin; an aptamer; a Fv; a Fab; a Fab'; and a $F(ab')_2$. In related embodiments, at least one binding region and/or the binding protein includes a tag and/or a linker.

In various embodiments the tag and/or the linker includes at least one selected from the group of: a peptide, a protein, a sugar, and a nucleic acid. In a related embodiment of the kit, the tag includes an amino acid sequence, for example SEQ ID NO:15, or a portion thereof. In related embodiments, the linker includes an amino acid sequence, for example the linker includes GGGGS (SEQ ID NO: 54), GGGGSGGGGSGGGGS (SEQ ID NO: 55), or a portion thereof.

The disease agent in various embodiments of the kit is selected from: a virus, a cancer cell, a fungus, a bacterium, a parasite and a product thereof such as a pathogenic molecule, a protein, a lipopolysaccharide, and a toxin. In a related embodiment of the kit, the disease agent is a plurality of disease agents. For example, the subject is exposed to a plurality of diseases, such as two or more diseases from any of viral, bacterial, fungal, and protozoal diseases. In various embodiments of the kit, the plurality of the disease agents includes two or more of a viral pathogen, and bacterial pathogens such as strains that produce a Botulinum toxin A, a Botulinum toxin B, a *C. difficile* toxin, or a Shiga toxin.

The toxin in various embodiments of the kit is at least one selected from the group of: a Botulinum neurotoxin, *Staphylococcal* α-hemolysin, *Staphylococcal* leukocidin, aerolysin cytotoxic enterotoxin, a *cholera* toxin, *Bacillus cereus* hemolysis II, and *Helicobacter pylori* vacuolating toxin, *Bacillus anthracis, cholera* toxin, *Escherichia coli* serotype O157:H7, *Escherichia coli* serotype O104:H7, lipopolysaccharide endotoxin, Shiga toxin, pertussis toxin, *Clostridium perfringens* iota toxin, *Clostridium spiroforme* toxin, *Clostridium difficile* toxin A, *Clostridium difficile* toxin B, *Clostridium septicum* a toxin, and *Clostridium botulinum* C2 toxin.

The toxin in various embodiments of the kit is a *C. botulinum* toxin, such that at least one binding region of the binding protein includes a recombinant camelid heavy-chain-only antibody, and such that the pharmaceutical composition includes an amino acid sequence selected from the group consisting of: SEQ ID NO: 56, SEQ ID NO: 57, SEQ ID NO: 58, and an amino acid sequence substantially identical to any of SEQ ID NOs: 56-58 and portions thereof.

In a related embodiment of the kit, the toxin is a *C. difficile* toxin A, such that at least one binding region of the binding protein includes a recombinant camelid heavy-chain-only antibody having an amino acid sequence selected from the group consisting of: SEQ ID NO: 59, SEQ ID NO: 60, SEQ ID NO: 61, SEQ ID NO: 62, SEQ ID NO: 63, SEQ ID NO: 64, SEQ ID NO: 87, SEQ ID NO: 95, and an amino acid sequence substantially identical to any of SEQ ID NOs: 59-64, 87 and 95 and portions thereof.

The toxin in various embodiments is a *C. difficile* toxin B, such that at least one binding region of the binding protein includes a recombinant camelid heavy-chain-only antibody having an amino acid sequence selected from the group consisting of: SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 87, SEQ ID NO: 95, and an amino acid sequence substantially identical to any of SEQ ID NOs: 66-76, 87 and 95 and portions thereof.

The toxin in various embodiments of the kit is a Shiga toxin, such that at least one binding region of the binding protein includes a recombinant camelid heavy-chain-only antibody having an amino acid sequence selected from the group consisting of: SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, and an amino acid sequence substantially identical to any of SEQ ID NOs: 77-86 and portions thereof.

An aspect of the invention provides a composition including at least one amino acid sequence selected from the group of: SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86; SEQ ID NO: 87, SEQ ID NO: 95, and substantially identical, wherein substantially identical is an amino acid sequence having at least 50% identity, at least 60% identity, at least 65% identity, at least 70% identity, at least 75% identity, at least 80% identity, at least 85% identity, at least 90% identity, at least 95% identity, or at least 99% identity to any of the amino acid sequence of SEQ ID NOs: 56-87 and 95 and portions thereof.

BRIEF DESCRIPTION OF THE DRAWINGS

FIGS. 1A-1E are nucleotide sequences and amino acid sequences. FIG. 1A shows nucleotide sequences of scFv #2 (SEQ ID NO: 1) and scFv #3 (SEQ ID NO: 3). FIG. 1B shows nucleotide sequences of scFv #7 (SEQ ID NO: 5) and scFv #8 (SEQ ID NO: 7). FIG. 1C shows nucleotide sequences of scFv #21 (SEQ ID NO: 9). and scFv #E (SEQ ID NO: 11). FIG. 1D shows amino acid sequences of scFv #2 (SEQ ID NO: 2), scFv #3 (SEQ ID NO: 4), scFv #7 (SEQ ID NO: 6), scFv #8 (SEQ ID NO: 8), and scFv #21 (SEQ ID NO: 10). FIG. 1E shows amino acid sequence of scFv #E (SEQ ID NO: 12).

FIG. 2 is the nucleotide sequence of scFv #7-2E (SEQ ID NO: 13) and the amino acid sequence of scFv #7-2E (SEQ ID NO: 14).

FIGS. 3A, 3A-1, 3B and 3C are the nucleotide sequences of BoNT/A holotoxin binding VHHs and corresponding amino acid sequences of BoNT/A holotoxin binding VHH. FIGS. 3A and 3A-1 show nucleotide sequences of BoNT/A holotoxin binding VHHs of JDA-D12 (SEQ ID NO: 19), JDQ-A5 (SEQ ID NO: 21), JDQ-B5 (SEQ ID NO: 23), and JDQ-C2 (SEQ ID NO: 25), and corresponding amino acid sequences of JDA-D12 (SEQ ID NO: 20), JDQ-A5 (SEQ ID NO: 22), JDQ-B5 (SEQ ID NO: 24), and JDQ-C2 (SEQ ID NO: 26). FIG. 3B shows nucleotide sequences of BoNT/A holotoxin binding VHHs of JDQ-F12 (SEQ ID NO: 27), JDQ-G5 (SEQ ID NO: 29), and JDQ-H7 (SEQ ID NO: 31), and corresponding amino acid sequences of JDQ-F12 (SEQ ID NO: 28), JDQ-G5 (SEQ ID NO: 30), JDQ-H7 (SEQ ID NO: 32). FIG. 3C shows nucleotide sequences of BoNT/A holotoxin binding VHHs of JEQ-A5 (SEQ ID NO: 33) and JEQ-H11 (SEQ ID NO: 35), and corresponding amino acid sequences of JEQ-A5 (SEQ ID NO: 34) and JEQ-H11 (SEQ ID NO: 36).

FIGS. 4A and 4B: FIG. 4A is a set of three nucleotide sequences of VHHs identified as BoNT/A binders that were experimentally shown to bind to the same epitope, and the set of three corresponding VHH amino acid sequences. The VHH nucleotide sequences are DQ-B5 (SEQ ID NO: 23), JDO-E9 (SEQ ID NO: 37), and JDQ-B2 (SEQ ID NO: 39), and the corresponding VHH amino acid sequences are JDQ-B5 (SEQ ID NO: 24), JDO-E9 (SEQ ID NO: 38), and JDQ-B2 (SEQ ID NO: 40). FIG. 4B is a set of two nucleotide sequences of VHHs identified as BoNT/A binders that were experimentally shown to bind to the same epitope, and the set of two corresponding VHH amino acid sequences. The VHH sequences are JDQ-C5 (SEQ ID NO: 41), and JDQ-F9 (SEQ ID NO: 43), and, the corresponding VHH amino acid sequences are JDQ-C5 (SEQ ID NO: 42), and JDQ-F9 (SEQ ID NO: 44).

FIG. 9A is a Meyer-Kaplan survival plot showing percent (%) of mice surviving over a period of time (days) after receiving 1,000-fold the median lethal dose ($LD_{50}$) of a Botulinum neurotoxin serotype A (BoNT/A) and each of combinations of the following binding agents: H7 and B5 VHH heterodimer with a single epitopic tag (tag or E-tag) and an anti-E-tag mAb (H7/B5/E+anti-E mAb); H7 and B5 VHH monomers each with an E-tag and an anti-E-tag mAb (H7/E+B5/E+anti-E mAb); H7 and B5 VHH heterodimer with two E-tags and an anti-E-tag mAb (E/H7/B5/E+anti-E mAb) and a control (the toxin alone). The data show that administration of heterodimer E/H7/B5/E and anti-E mAb resulted in survival of subjects for seven days. FIG. 9B is a Meyer-Kaplan survival plot showing percent (%) of subjects surviving over a period of time (days) after receiving 10,000-fold the $LD_{50}$ of a Botulinum neurotoxin (BoNT) and H7 and B5 VHH heterodimer with two E-tags and an anti-E-tag mAb (E/H7/B5/E+anti-E mAb) and a control (the toxin alone). Remarkably, 100% of the mice survived a 10,000 $LD_{50}$ challenge of BoNT/A when administered the double-tagged heterodimer and the anti-tag mAb.

FIGS. 10A-10E: FIG. 10A shows a nucleotide sequence of recombinant BoNT/A holotoxin binding VHHs: thioredoxin/JDQ-H7(H7)/E-tag (SEQ ID NO: 45) and a corresponding amino acid sequence of the VHHs for thioredoxin/H7/E-tag (SEQ ID NO: 46). FIG. 10B shows a nucleotide sequence of recombinant BoNT/A holotoxin binding VHHs: thioredoxin/JDQ-B5(B5)/E-tag (SEQ ID NO: 47) and a corresponding amino acid sequence of the VHHs for thioredoxin/B5/E-tag (SEQ ID NO: 48). FIG. 10C shows a nucleotide sequence of recombinant BoNT/A holotoxin binding VHHs: thioredoxin/H7/flexible spacer (fs)/B5/E-tag (SEQ ID NO: 49) and a corresponding amino acid sequence of the VHHs for thioredoxin/H7/fs/B5/E-tag (SEQ ID NO: 50). FIG. 10D shows a nucleotide sequence of recombinant BoNT/A holotoxin binding VHHs: thioredoxin/E-tag/H7/fs/B5/E-tag (SEQ ID NO: 51) and a corresponding amino acid sequence of the VHHs for thioredoxin/E-tag/H7/fs/B5/E-tag (SEQ ID NO: 52). FIG. 10E shows an amino acid sequence of the VHHs for thioredoxin (SEQ ID NO: 53).

FIG. 11A shows percent survival for subjects exposed to ten-fold $LD_{50}$ of BoNT/A then administered 1.5 hours later either a mixture of H7 and B5 monomers; H7/B5 heterodimer; a sheep serum antitoxin; or control toxin only (no agents). FIG. 11B shows percent survival for subjects exposed to ten-fold $LD_{50}$ of BoNT/A then administered three hours later either a mixture of H7 and B5 monomers; H7/B5 heterodimer; a sheep serum antitoxin; or control toxin only (no agents).

FIG. 12A is a line graph showing that VHH monomers neutralized *C. difficile* toxin B (TcdAB) and protected cells from the toxin. The percent CT26 cells affected by TcdB (% affected; ordinate) is shown as a function of concentration (0.003 nM, 0.03 nM, 0.3 nM, 3 nM, 30 nM, 300 nM, or 3000 nM) of administered VHH monomers: 5D (circle), 2D (square), or E3 (light upward facing triangle). Control cells were administered toxin only (TcdB; dark downward facing triangle). Strength of neutralizing VHH activity was observed in the order 5D as strongest followed by E3 and 2D. FIG. 12B is a line graph showing percent of cells affected by TcdB (% affected; ordinate) as a function of concentration of administered mixture of 5D and E3 monomers, 5D/E3 heterodimer (VHH; abscissa), or a toxin only control. It was observed that the 5D/E3 VHH heterodimer (squares) was about tenfold more potent as toxin neutralizing agent than the mixture of 5D monomer and E3 monomer (triangles). FIG. 12C is a Meyer-Kaplan survival plot of a *C. difficile* infection model showing percent mouse survival (ordinate) as a function of time (hours post challenge, abscissa) of subjects co-administered toxin and VHH neutralizing agents. Subjects were co-administered a lethal dose of TcdB with: a mixture of 10 μg of 5D monomers and E3 monomers (5 μg of each monomer per mouse; dashed line, blue); a mixture of 1 μg of 5D monomers and E3 monomers (500 ng of each monomer per mouse; thick solid line, blue), 5D/E3 heterodimer (250 ng per mouse; light solid line, red), or phosphate-buffered saline (PBS; thin solid line, black). Percent survival was calculated for each group of subjects.

FIGS. 13A-13C are amino acid sequences for VHH monomers and VHH heterodimers designed to specifically bind epitopes of botulism toxins serotype A (BoNT/A) and serotype B (BoNT/B). Each VHH was purified from *E. coli* as a thioredoxin fusion protein having a single carboxyl-terminal epitopic tag (tag or E-tag). FIG. 13A is a set of amino acid sequences of VHH monomers that specifically recognize and bind to epitopes on BoNT/A (ciA-A5 (SEQ ID NO: 97), ciA-B5 (SEQ ID NO: 98), ciA-C2 (SEQ ID NO: 99), ciA-D12 (SEQ ID NO: 100), ciA-F12 (SEQ ID NO: 101), ciA-G5 (SEQ ID NO: 102), and ciA-H7 (SEQ ID NO: 103)) and epitopes of BoNT/B (ciB-A11 (SEQ ID NO: 104), ciB-B5 (SEQ ID NO: 105), ciB-B9 (SEQ ID NO: 106), and ciB-H11 (SEQ ID NO: 107)). The sequences are aligned to show homology. Dashed regions of the amino acid sequences are spaces inserted to align the amino acid regions. FIG. 13B is a set of amino acid sequences of VHH monomers (ciA-D1 (SEQ ID NO: 108), ciA-H5 (SEQ ID NO: 109), and ciA-H11 (SEQ ID NO: 110)) that bind specifically to the same epitope of BoNT/B as ciA-H7 (SEQ ID NO: 103). FIG. 13C shows amino acid sequences for double-tagged VHH heterodimers, ciA-H7/ciA-B5(2E) (SEQ ID NO: 111) and ciA-F12/CiA-D12(2E) (SEQ ID NO: 112), that specifically bind BoNT/A.

FIG. 14A shows SDS-PAGE analysis of the tagged (E) VHH monomers ciA-D1, ciA-H4, ciA-H11, ciA-A5, ciA-C2, ciA-D12, ciA-F12, ciA-G5, and ciA-H7. FIG. 14B is a SDS-PAGE analysis of single- or double-tagged VHH heterodimers including: ciA-H7/ciA-B5 singly tagged on ciA-B5 (left channel); double tagged ciA-H7/ciA-B5 having a tag on both ciA/H7 and ciA-B5 (second channel from left), ciA-F12/ciA-D12 singly tagged on ciA-B5 (third channel from the left); double tagged ciA-F12/ciA-D12 having a tag on both ciA/F12 and ciA-D12 (fourth channel from left), double tagged ciA-A11/ciA-B5 having a tag on both ciA/A11 and ciA-B5 (right channel).

FIG. 16A (top) is a drawing of a BoNT/A bound to two different tagged binding protein monomers that are each specifically bound by an anti-tag antibody. FIG. 16A (bottom) is a set of graphs showing percent of survival (% survival, ordinate) as a function of time (days, abscissa) of subjects co-administered 100-fold (FIG. 16 A bottom left graph) or 1,000-fold (FIG. 16 A bottom right graph) the $LD_{50}$ of a BoNT/A and combinations of VHH monomers (ciA-D12 and ciA-F12) with or without anti-tag clearing antibody (+αE and −αE respectively). The mixture of VHH monomer B5, VHH monomer H7 and anti-tag clearing antibody protected subjects from the 100-fold $LD_{50}$ of toxin. FIG. 16B (top) is a drawing of a BoNT/A bound to three different monomeric tagged binding protein each specifically bound by an anti-tag antibody. FIG. 16B (bottom) is a set of graphs showing percent survival on the ordinate as a function of time (days, abscissa) of subjects co-administered 1,000-fold BoNT/A $LD_{50}$ (FIG. 16B bottom left graph) or 10,000-fold BoNT/A $LD_{50}$ (FIG. 16B bottom right graph), and combinations of three VHH monomers with or without anti-tag clearing antibody (+αE and −αE respectively). FIG. 16C (top) is a drawing of a BoNT/A bound to four different tagged binding protein monomers that are each specifically bound by an anti-tag antibody. FIG. 16C (bottom) is a set of graphs showing percent survival, ordinate, of subjects as a function of time (days, abscissa) of subjects co-administered 1,000-fold BoNT/A $LD_{50}$ (FIG. 16C bottom left graph) or 10,000-fold BoNT/A $LD_{50}$ (FIG. 16C bottom right graph), and a mixture of ciA-B5, ciA-H7, ciA-D12 and ciA-F12 VHH monomers with (+αE) or without (−αE) anti-tag clearing antibody.

FIG. 18A is a table showing binding affinities (Kd) determined by surface plasmon resonance (SPR) analysis of each of VHH monomers ciA-H7, ciA-D1, ciA-H4, and ciA-H11. SPR analysis was used to determine the binding affinities to epitope A1 of BoNT/A for each VHH monomer. H7 has the greatest affinity and H11 the least affinity. FIG. 18B is a set of graphs showing percent survival on the ordinate of subjects as a function of time (days, abscissa) following co-administration of BoNT/A at 100-fold (FIG. 18B left graph) or 1,000-fold (FIG. 18B right graph) the $LD_{50}$, and a mixture of two VHH monomers (B5+C2) or a mixture of three VHH monomers with anti-tag clearing antibody: B5+C2+H11; B5+C2+H7; B5+C2+D1; or B5+C2+H2.

FIG. 19A (top) is a drawing of a BoNT/A bound to two different tagged heterodimer binding proteins that are each specifically bound by an anti-tag antibody. FIG. 19A (bottom) is a set of graphs showing percent survival on the ordinate of subjects as a function of time (days, abscissa) after co-administration of 1,000-fold (FIG. 19A bottom left graph) or 10,000-fold (FIG. 19A bottom right graph) the BoNT/A $LD_{50}$, and a VHH heterodimer composition with (+αE) or without (−αE) anti-tag clearing antibody. The tagged VHH heterodimer composition was either composed of neutralizing VHHs ciA-H7 and ciA-B5 (H7/B5), or of non-neutralizing VHHs ciA-D12 and ciA-F12 (D12/F12). Data show that subjects administered the heterodimer composition containing neutralizing VHHs ciA-B5 and ciA-H7 survived longer than subjects administered the heterodimer composition containing non-neutralizing VHHs ciA-D12 and ciA-F12. Subjects administered clearing anti-tag antibodies generally survived longer than subjects not administered clearing-tag antibodies. FIG. 19B (top) is a drawing of a BoNT/A bound to two different double-tagged heterodimer binding proteins that are each specifically bound by two anti-tag antibodies. FIG. 19B (bottom) is a set of graphs showing percent survival, ordinate, of subjects as a function of time (days, abscissa) after co-administration of an amount of BoNT/A 1,000-fold (FIG. 19B bottom left graph) or 10,000-fold (FIG. 19B bottom right graph) the $LD_{50}$, and double tagged VHH heterodimers with (+αE) or without (−αE) anti-tag clearing antibody. Subjects administered neutralizing ciA-B5/ciA-H7 heterodimer survived longer than subjects administered non-neutralizing ciA-D12/ciA-F12 heterodimer. Data show that all subjects administered double-tagged ciA-B5/ciA-H7 heterodimers and anti-tag clearing antibody survived exposure to 1,000-fold (FIG. 19B bottom left graph) or 10,000-fold the $LD_{50}$ of BoNT/A (FIG. 19B bottom right graph).

FIG. 23A is a set of graphs showing percent survival of subjects as a function administration of: double tagged ciA-D12/ciA-F12 heterodimer with anti-tag clearing antibody (+αE), double tagged ciA-D12/ciA-F12 heterodimer without anti-tag clearing antibody (−αE), a sheep serum antitoxin, or toxin only control (no agents). Prior to administration of heterodimer, subjects were exposed 1.5 hours (FIG. 23A left graph) or three hours (FIG. 23A right graph) to ten-fold BoNT/A $LD_{50}$. Data show 100% survival of subjects administered ciA-D12/ciA-F12 heterodimer and anti-tag antibody after 1.5 hours. Survival of subjects administered ciA-D12/ciA-F12 heterodimer was comparable to that in subjects administered sheep serum antitoxin. FIG. 23B is a set of graphs showing percent survival of subjects as a function administration of: double tagged ciA-B5 and ciA-H7 heterodimer with anti-tag clearing antibody (+αE), or with double tagged ciA-B5/ciA-H7 heterodimer without anti-tag clearing antibody (−αE), or with a sheep serum antitoxin, or toxin only control (no agents). Prior to treatment with heterodimer, subjects were exposed to ten-fold BoNT/A $LD_{50}$ either 1.5 hours (FIG. 23B left graph) or three hours (FIG. 23B right graph). Data show that subjects administered ciA-B5/ciA-H7 heterodimer with or without anti-E tag antibody survived longer than subjects administered sheep serum antitoxin. Survival of subjects administered ciA-B5/ciA-H7 heterodimer was greater than subjects administered sheep serum antitoxin.

FIG. 24A is a graph showing survival on the ordinate as a function of time (days, abscissa) co-administration of 1,000-fold (FIG. 24A left graph) or 10,000-fold (FIG. 24A right graph) BoNT/B $LD_{50}$ and a combination of ciB-A11 and ciB-B5 heterodimer with (+αE) or without (−αE) anti-tag clearing antibody, or toxin only control (no agents). Data show that subjects administered ciA-A11/ciA-B5 heterodimer and anti-E-tag clearing antibody survived and were protected longer from BoNT/A than control subjects administered no agents and no anti-E tag antibody. FIG. 24B is a set of graphs showing subject survival (ordinate) as a function of time, abscissa, after administration of: double tagged ciB-A11 and ciB-B5 heterodimer and anti-tag clearing antibody (+αE), or double tagged ciB-A11 and ciB-B5 heterodimer without anti-tag clearing antibody (−αE), a sheep serum antitoxin, or toxin only control. Following 1.5 hours (FIG. 24B left graph) or three hours (FIG. 24B right graph) exposure to ten-fold BoNT/B $LD_{50}$, the subjects were administered the heterodimer. A greater percentage of subjects administered ciB-A11 and ciB-B5 heterodimer survived exposure to BoNT/B than subjects administered sheep serum antitoxin.

FIG. 28A is a protocol for a clinically relevant murine *C. difficile* infection model. Administration of VHH is given after a spore challenge. FIG. 28B shows percent survival (ordinate) as a function of time following spore challenge (abscissa) for subjects administered 5D/AA6 heterodimer as described in FIG. 28A. Data show that after the spore challenge, 90% of 5D/AA6 heterodimer contacted-subjects survived, and all control subjects not administered 5D/AA6 heterodimer or other agent died within two days. FIG. 28C shows percent diarrhea (ordinate) as a function of time following spore challenge (abscissa) for subjects administered 5D/AA6 heterodimer (5D/AA6 TrxA; left bar), or control PBS (right bar) as described in FIG. 28A. Data show that 5D/AA6 heterodimer administered-subjects were five-fold less likely to display symptoms of diarrhea than control untreated subjects.

DETAILED DESCRIPTION

Figure 5:
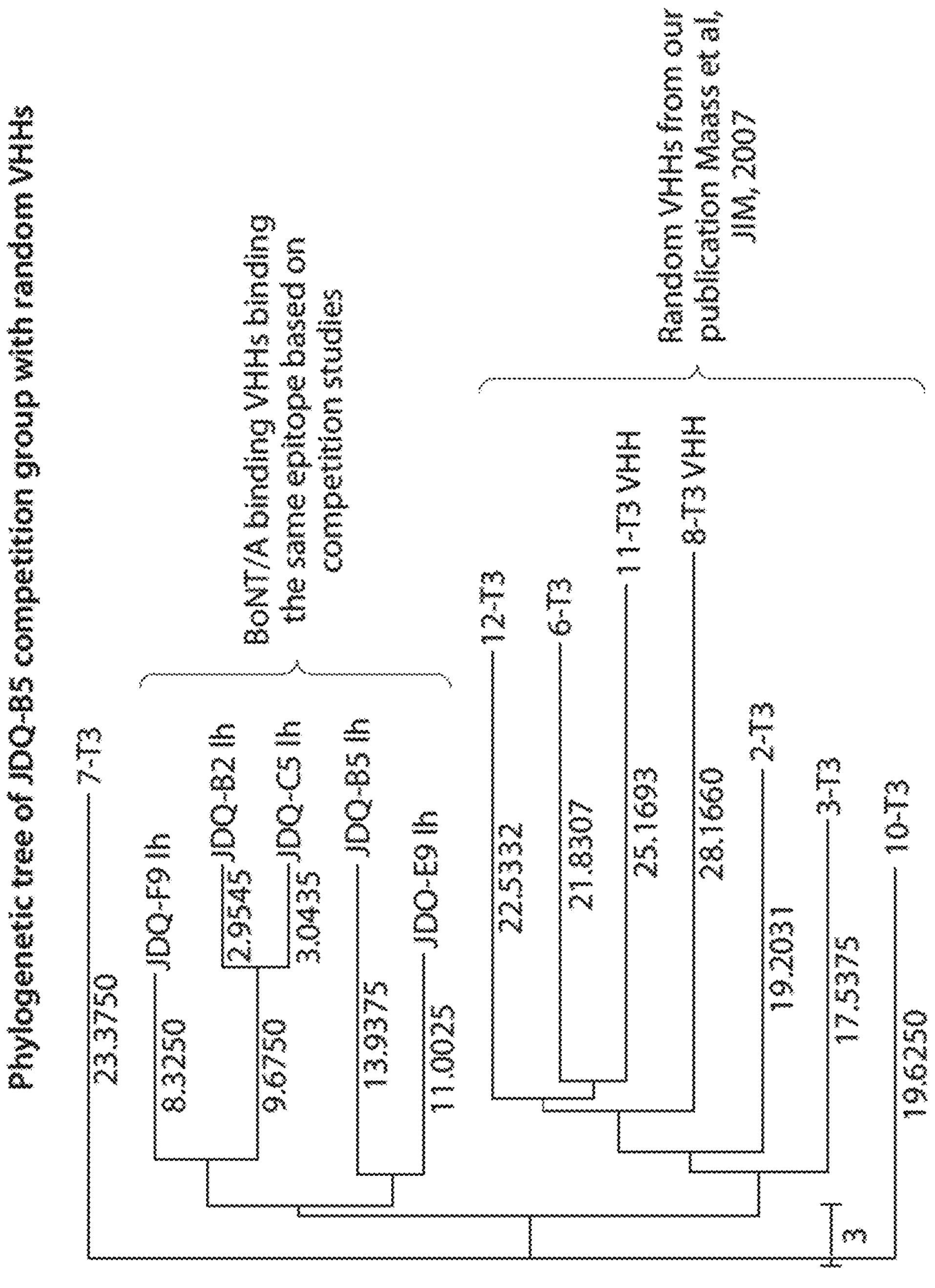
FIG. 5 is a schematic drawing of a phylogenetic tree comparing the homology between BoNT/A binding VHHs within the JDQ-B5 competition group (which compete for binding, thus bind the same epitope) in comparison to control alpaca VHHs.

The presence of toxins in the circulation is the cause of a wide variety of human and animal illnesses. Antitoxins are therapeutic agents that prevent toxin infection or reduce further development of negative symptoms in patients that have been exposed to a toxin (a process referred to as "intoxication"). Typically, antitoxins are antisera obtained from large animals (e.g., sheep, horse, and pig) that were immunized with inactivated or non-functional toxin. More recently, antitoxin therapies have been developed using combinations of antitoxin monoclonal antibodies including yeast-displayed single-chain variable fragment antibodies generated from vaccinated humans or mice. See, Nowakowski et al. 2002, *Proc Natl Acad Sci USA* 99: 11346-11350; Mukherjee et al. 2002, *Infect Immun* 70: 612-619; Mohamed et al. 2005, *Infect Immun* 73: 795-802; Walker, K. 2010 Interscience Conference on Antimicrobial Agents and Chemotherapy—50th Annual Meeting—Research on Promising New Agents: Part 1. IDrugs 13: 743-745. Antisera and monoclonal antibodies can be difficult to produce economically at scale, usually requiring long development times and resulting in problematic quality control, shelf-life and safety issues. New therapeutic strategies to develop and prepare antitoxins are needed.

Antitoxins function through two key mechanisms neutralization of toxin function and clearance of the toxin from the body. Toxin neutralization occurs through biochemical processes including inhibition of enzymatic activity and prevention of binding to cellular receptors. Antibody mediated serum clearance occurs subsequent to the binding of multiple antibodies to the target antigen (Daeron M. 1997, *Annu Rev Immunol* 15: 203-234; Davies et al. 2002, *Arthritis Rheum* 46: 1028-1038; Johansson et al. 1996, *Hepatology* 24: 169-175; and Lovdal et al. 2000, *J Cell Sci* 113 (Pt 18): 3255-3266). Multimeric antibody decoration of the target is necessary to permit binding to low affinity Fc receptors (Davies et al. 2002, *Arthritis Rheum* 46: 1028-1038 and Lovdal et al. 2000, *J Cell Sci* 113 (Pt 18): 3255-3266). Without being limited by any particular theory or mechanism of action, it is here envisioned that an ideal antitoxin therapeutic would both promote toxin neutralization to immediately block further toxin activity and also accelerate toxin clearance to eliminate future pathology if neutralization becomes reversed.

Effective clearance of botulinum neurotoxin (BoNT), a National Institute of Allergy and Infectious Diseases (NIAID) Category A priority pathogen, is believed by some researchers to require three or more antibodies bound to the toxin. Nowakowski et al. 2002. (*Proc Natl Acad Sci USA* 99: 11346-11350) determined that effective protection of mice against high dose challenge of BoNT serotype A (BoNT/A) required co-administration of three antitoxin monoclonal antibodies, and that all three antibodies presumably promoted clearance. Data have shown that administration of a pool of three or more small binding agents, each produced with a common epitopic tag, reduced serum levels of a toxin when co-administered with an anti-tag monoclonal antibody (Shoemaker et al. U.S. published application 2010/0278830

A1 published Nov. 4, 2010 and Sepulveda et al. 2009 Infect Immun 78: 756-763, each of which is incorporated herein in its entirety). The tagged binding agents directed the binding of anti-tag monoclonal antibody to multiple sites on the toxin, thus indirectly decorating the toxin with antibody Fc domains and leading to its clearance through the liver.

Pools of scFv domain binding agents with specificity for BoNT/A and each containing a common epitopic tag (E-tag), had been shown to be effective for decorating the botulinum toxin with multiple anti-tag antibodies (Shoemaker et al. U.S. utility patent publication number 2010/0278830 published Nov. 4, 2010 and U.S. continuation-in-part patent publication number 2011/0129474 published Jun. 2, 2011, each of which is incorporated herein by reference in its entirety). Data showed that the administration of binding agents and clearance antibodies to subjects resulted in clearance via the liver with an efficacy in mouse assays equivalent to conventional polyclonal antitoxin sera. Ibid. and Sepulveda et al. 2009 Infect Immun 78: 756-763. The tagged scFvs toxin targeting agents and the anti-tag monoclonal antibodies were effective for treating subjects at risk for or having been contacted with a disease agent.

The use of small binding agents to direct the decoration of toxin with antibody permits new strategies for the development of agents with improved therapeutic and commercial properties. Examples herein show that a single recombinant heterodimeric binding protein/agent including two or more high-affinity BoNT binding agents (camelid heavy-chain-only Ab VH (VHH) domains) and two epitopic tags, co-administered with an anti-tag mAb, protected subjects from botulism caused negative symptoms and lethality. Further the binding protein resulted in antitoxin efficacy equivalent to and greater than conventional BoNT antitoxin serum in two different in vivo assays. Examples herein compare neutralizing or non-neutralizing binding agents administered with or without clearing antibody, and show the relative contributions of toxin neutralization and toxin clearance to antitoxin efficacy. Examples herein show that both toxin neutralization and toxin clearance contribute significantly to antitoxin efficacy in subjects. Toxin neutralization or toxin clearance using heterodimer binding protein antitoxins sufficiently protected subjects from BoNT lethality in a therapeutically relevant, post-intoxication assay. Methods in Examples herein optionally further include a clearing antibody for example a monoclonal anti-E-tag antibody.

It was observed in Examples herein that VHH binding agents that neutralized toxin function significantly improved the antitoxin efficacy and even obviated the need for clearing antibody in a clinically relevant post-intoxication BoNT/A assay. The methods, compositions and kits using the multimeric binding proteins described herein have widespread application in antitoxin development and other therapies in which neutralization and/or accelerated clearance of a target molecule benefits a patient. For example, the target molecule is an exogenous disease agent that infects or is at risk to infect a patient. Exogenous disease agent for example is a virus, a cancer cell, a fungus, a bacterium, a parasite and a product thereof such as a pathogenic molecule, a protein, a lipopolysaccharide, or a toxin. Alternatively, the molecule is an endogenous (body produced) molecule that is produced in the patient and that causes or produces harmful effects on the patient. For example, the molecule is a hormone or a protein that is associated with a disease or condition, e.g., inflammation, cancer, transplant rejection, kidney failure, or a defect in blood clotting such as hemophilia and thrombophilia. In various embodiments, the disease agent is a toxin of *C. difficile*.

*C. difficile* is a gram-positive, spore forming, anaerobic bacterium that is the leading cause of antibiotic-associated diarrhea, the severity of which ranges from mild diarrhea to life threatening pseudomembranous colitis (Bartlett J G. 2002, *N Engl J Med* 346:334-9 and Feng et al. PCT/US10/58701 filed Dec. 2, 2010, each of which is incorporated by reference in its entirety). Pathogenic *C. difficile* strains excrete exotoxins A (TcdA) and B (TcdB) that have been intimately linked to its pathogenicity. Both TcdA and TcdB are enterotoxic, capable of inducing intestinal epithelial damage and increasing mucosal permeability, and hence are thought to be responsible for the pathogenesis of *C. difficile*-associated colitis (Kelly C P et al. 1998, *Annu Rev Med* 49:375-90). *C. difficile* has emerged as a leading cause of hospital-acquired enteric infections with rapidly escalating annual health care costs in the United States (Kyne L et al. 2002, *Clin Infect Dis* 34:346-353). The severity of *C. difficile*-associated infections ranges from mild diarrhea to life threatening pseudomembranous colitis (Bartlett J G et al. 2002, *N Engl J Med* 346:334-339; Borriello S P 1998, *Antimicrob Chemother* 41 Suppl C:13-19). Several hospital outbreaks of *C. difficile*-associated diarrhea (CDAD), with high morbidity and mortality in the past few years in North America, have been attributed to the widespread use of broad-spectrum antibiotics.

The emergence of more virulent *C. difficile* strains contributes also to the increased incidence and severity of the disease (Loo V G et al. 2005, *N Engl J Med* 353:2442-2449; McDonald L C et al. 2005, *N Engl J Med* 353:2433-2441). Antibiotic usage results in a reduction of commensal microflora in the gut, which permits *C. difficile* to proliferate more extensively, leading to the further production of toxins (Owens J R et al. 2008, *Clinical Infectious Diseases* 46(s1): S19-S31). *C. difficile* infection (CDI) includes a range of symptoms varying from mild diarrhea to severe fulminate lethal disease (Kuijper E J et al. 2007, *Curr Opin Infect Dis* 20(4):376-383). Recent outbreaks of highly virulent *C. difficile* strains (McDonald L C et al. 2005, *N Engl J Med* 353(23):2433-2441; Loo V G et al. 2005, *N Engl J Med* 353(23):2442-2449) have increased the urgency to devote greater resources towards the understanding of the molecular, genetic, and biochemical basis for the pathogenesis, with a view to use such information to develop novel preventive and treatment modalities.

A cell-based immunocytotoxicity assay for detecting *C. difficile* toxins described in Feng et al. (PCT/US2009/003055 published Nov. 19, 2009 as WO 2009/139919) uses an anti-*C. difficile* toxin A (TcdA) monoclonal antibody, named A1H3, which substantially enhanced the activity of TcdA on Fc gamma receptor I (FcγRI)-expressing cells (He X, Sun X, Wang J, et al. Antibody-enhanced, Fc{gamma}R-mediated endocytosis of *C. difficile* toxin A. Infect Immun 2009). Feng et al. shows use of A1H3 enhancing antibody, in combination with an electronic sensing system to develop a real-time and ultrasensitive assay for the detection of biological activity of *C. difficile* toxins.

Toxin A (TcdA) and toxin B (TcdB) are the major virulence factors contributing to pathogenic *C. difficile* strains. These strains are enterotoxic, inducing intestinal epithelial cell damage, disrupting epithelium tight junctions leading to increased mucosal permeability (Pothoulakis C et al. 2001, *Am J Physiol Gastrointest Liver Physiol* 280:G178-183; Riegler M et al. 1995, *J Clin Invest* 95:2004-2011; Savidge T C et al. 2003, *Gastroenterology* 125:413-420). Moreover, these toxins induce production of immune mediators, leading to subsequent neutrophil infiltration and severe colitis (Kelly C P et al. 1994, *J Clin Invest* 93:1257-1265; Kelly C P et al. 1998, *Annu Rev Med* 49:375-390). TcdA and TcdB are structurally homologous, and contain a putative N-terminal glucosyltransferase and a cysteine proteinase domain, a transmembrane domain, and a C-terminal receptor binding domain (von Eichel-Streiber C et al.1996, *Trends Microbiol* 4:375-382) (Jank T et al. 2008, *Trends Microbiol* 16:222-229; Voth D E et al. 2005, *Clin Microbiol Rev* 18:247-263).

Interaction between the toxin C-terminus and the host cell receptors initiates a receptor-mediated endocytosis (Florin I et al. 1983 Biochim Biophys Acta 763:383-392; Karlsson K A 1995 Curr Opin Struct Biol 5:622-635; Tucker K D et al. 1991 Infect Immun 59:73-78). Although the intracellular mode of action remains unclear, it has been proposed that the toxins undergo conformational change at low pH in the endosomal compartment, leading to membrane insertion and channel formation (Florin I et al. 1986 Microb Pathog 1:373-385; Giesemann T et al. 2006 J Biol Chem 281: 10808-10815; Henriques B et al. 1987 Microb Pathog 2:455-463; Qa'Dan M et al. 2000 Infect Immun 68:2470-2474). A host cofactor is then required to trigger a second structural change which is accompanied by an immediate autocatalytic cleavage and release of the glucosyltransferase domain into cytosol (Pfeifer G et al. 2003 J Biol Chem 278:44535-44541; Reineke J e al. 2007 Nature 446:415-419; Rupnik M et al. 2005 Microbiology 151:199-208). Once the glucosyltransferase domain reaches the cytosol, it inactivates proteins of the Rho/Rac family, leading to alterations of cytoskeleton and ultimately cell death (Just I et al. 1995 Nature 375:500-503; Sehr P et al. 1998 Biochemistry 37:5296-5304).

The clinical manifestation of CDI is highly variable, from asymptomatic carriage, to mild self-limiting diarrhea, to the more severe pseudomembranous colitis. The prevalence of systemic complication and death in CDI has become increasingly common (Siemann M et al. 2000 Intensive care medicine 26:416-421). In life-threatening cases of CDI, systemic complications are observed, including cardiopulmonary arrest (Johnson S et al. 2001 Annals of internal medicine 135:434-438), acute respiratory distress syndrome (Jacob S S et al. 2004 Heart Lung 33:265-268), multiple organ failure (Dobson G et al. 2003 Intensive care medicine 29:1030), renal failure (Cunney R J et al. 1998 Nephrol Dial Transplant 13:2842-2846), and liver damage (Sakurai T et al. 2001 J Infect Dis 33:69-70). The exact reason for these negative complications is unclear, and may be caused by entry of the toxin into the circulation and systemic dissemination (Hamm E E et al. 2006 Proc Natl Acad Sci USA 103:14176-14181).

Standard therapy depends on treatment with vancomycin or metronidazole, neither of which is fully effective (Zar et al. 2007 Clinical Infectious Diseases 45:302-307). Moreover, an estimated 15% to 35% of those infected with *C. difficile* relapse following treatment (Barbut et al. 2000 J Clin Microbiol 38: 2386-2388; Tonna et al: Postgrad Med J 81: 367). Unfortunately, the primary treatment option for recurrent CDI is still metronidazole or vancomycin. Other options, such as probiotics, toxin-absorbing polymer and anion-exchange resins, have limited efficacy (Gerding, D. N., Muto, C. A. & Owens, R. C., Jr. 2008 Clin Infect Dis 46 Suppl 1: S32-42). Therefore, immune-based therapies are the probably the most promising approaches to control the disease. Antibodies specific for both of these toxins, and not against TcdA or TcdB alone, protect against toxigenic *C. difficile* infection in a hamster model (Libby et al, 1982 Infect Immun 36: 822-829; Fernie et al, 1983 Dev Biol Stand 53: 325; and Kim et al, 2006 Infection and immunity 74: 6339). Human serum antibodies specific for both TcdA and TcdB are associated also with protection against symptomatic disease and recurrence. Recent phase II clinical trial led by Merck demonstrated that the systemically administered human IgG monoclonal antibodies against TcdA and TcdB prevents disease relapse in CDI patients (Lowy et al, 2010 The New England journal of medicine 362: 197). However, the treatment involved the injection of a large quantity of two individual antibodies against each toxin.

Examples herein show a new approach to the development of antitoxins that employs a single recombinant protein to promote toxin decoration with multiple copies of a single monoclonal antibody leading to its neutralization and clearance from the body. The methods, compositions, and kits herein are useful for treating a great number of the most common pathogenic biological targets by accelerating neutralization and clearance from the subject or patient.

Examples herein show that camelid VHH binding domains, which have multiple commercial advantages over scFvs due in part to the ease and reduced cost of producing VHHs, were effective as toxin targeting agents both with and without being administered with clearing antibody. An important advantage of VHHs is the ability of medical professionals and scientists to express these binding agents as heterodimers in which each component VHH remains fully functional. The multimeric fusion proteins containing at least two VHH binding regions resulted in the component VHHs binding to different epitopes on the same toxin target. Without being limited by any particular theory or mechanism of action, it is believed that incorporation of two epitope tags on the heterodimers resulted in decoration of the toxin with two clearing antibodies at each epitope, and resulted in a total of four monoclonal clearing antibodies binding to the heterodimers on the toxin. In addition, with certain heterodimers the decoration promoted efficient toxin clearance. Either neutralization or clearance or both are important mechanisms of remediating toxin exposure. As each double-tagged heterodimeric binding agent was bound only to only two monoclonal antibodies, the heterodimeric agent itself may not be effectively cleared by low affinity Fc receptors unless actually bound to the toxin.

The ability of antitoxin antibodies to protect mammalian subjects from the symptoms of toxin exposure is influenced by several factors that are described herein. Examples herein used intoxication models and varied the dose of antitoxin agent and the timing of antitoxin administration relative to exposure to toxin in order to determine whether both the dose and the timing of the antitoxin are factors that influence antitoxin efficacy. In addition, examples herein analyzed the role that affinity of the antibody for the toxin has on the ability of the antibody to bind ($K_{on}$) and remain bound ($K_{off}$) to the toxin and exert its effect. Data show that the ability of the antibody monomer/heterodimer to inhibit the enzymatic activity of the toxin and/or prevent its entry into target cells (i.e. neutralization) is a major factor in effective antitoxin treatment of subjects. Specifically data show that the greater the binding affinity of the binding protein to the target molecule, the greater the potential neutralization and clearance of the binding protein. Examples herein show also that the multimeric binding proteins promoted the clearance of the toxin from the serum and minimized further negative symptoms or lethality by the target molecule or disease agent. A portion of this work was published Jan. 6, 2012 in the Public Library of Science One and was entitled, "A Novel Strategy for Development of Recombinant Antitoxin Therapeutics Tested in a Mouse Botulism", authored by Jean Mukherjee, Jacqueline M. Tremblay, Clinton E. Leysath, Kwasi Ofori, Karen Baldwin, Xiaochuan Feng, Daniela Bedenice, Robert P. Webb, Patrick M. Wright, Leonard A. Smith, Saul Tzipori, and Charles B. Shoemaker (Mukherjee J. et al. 2012, *PLoS One*. 7(1):e29941), which is incorporated by reference herein in its entirety. An aspect of the invention provides a method for treating a subject at risk for exposure to or exposed to a disease agent, the method including: contacting the subject with at least one recombinant heteromultimeric neutralizing binding protein including two or multiple binding regions, such that the binding regions are not identical, and each binding region specifically binds a non-overlapping portion of the disease agent, such that the binding protein neutralizes the disease agent, thereby treating the subject for exposure to the disease agent.

In various embodiments of the method, the binding protein includes at least one tag. For example the tag is a molecule or epitope that is attached or genetically fused to the binding protein and/or binding regions. The tag in various embodiments of the method induces endogenous clearance of the disease agent from the body in vivo. For example the tag includes SEQ ID NO: 15. In a related embodiment, the tag includes an antibody epitope.

In certain embodiments of the method, the binding protein is selected from: a single-chain antibody (scFv); a recombinant camelid heavy-chain-only antibody (VHH); a shark heavy-chain-only antibody (VNAR); a microprotein; a darpin; an anticalin; an adnectin; an aptamer; a Fv; a Fab; a Fab'; and a $F(ab')_2$. In an embodiment, the binding protein is heterodimeric, for example the binding protein has greater potency than each individual monomer. In alternative embodiments, the heteromultimeric neutralizing binding protein is multimeric and the multimeric components are associated non-covalently or covalently.

The binding protein in certain embodiments of the method includes a linker that separates multimeric components of the binding regions. In various embodiments, the linker includes at least one selected from: a peptide, a protein, a sugar, or a nucleotide. For example, the linker includes amino acid sequence GGGGS (SEQ ID NO: 54), or includes amino acid sequence GGGGSGGGGSGGGGS (SEQ ID NO: 55) or a portion thereof. In a related embodiment, the linker is a flexible linker located within subunits/domains of the binding protein, such that the linker does not negatively affect the function of the binding protein to the disease agent. For example the linker includes amino acid sequences/residues including serine and glycine, and in various embodiments is at least about three to five amino acids long, or about five to eight amino acids long, or about eight to fifteen amino acids long.

In certain embodiments, the disease agent is a biological target or biological molecule. For example, the biological target or the biological molecule is naturally occurring within the subject, for example a molecule or compound synthesized by the subject. An example of a biological molecule synthesized by the subject is an IgE that is associated with an allergy or an auto antibody or an MHC protein (e.g., HLA class I antigens A and B and HLA class II antigen DR) associated with an autoimmune disease. For example the autoimmune disease is selected from: lupus erythematosus, Graves' disease, rheumatoid arthritis, Sjögren's syndrome, myasthenia gravis, and Hashimoto's thyroiditis.

The disease agent in various embodiments of the method includes a plurality of non-identical disease agents, for example two or more bacterial toxins, or a viral toxin and a fungal species. In various embodiments, the binding regions of the binding protein are specific to each non-identical disease agent and bind to and neutralize the plurality of disease agents.

In various embodiments of the method, the disease agent is at least one selected from: a virus, a cancer cell, a fungus, a bacterium, a parasite and a product thereof such as a pathogenic molecule, a protein, a lipopolysaccharide, and a toxin. In certain embodiments, the toxin includes a protein, a lipid, a lipopolysaccharide, and a small molecule toxin such as an aflatoxin or a dinoflagellate toxin. The toxin for example is a Botulinum neurotoxin comprising a serotype selected from: A, B, C, D, E, F, and G. In certain embodiments of the method, the toxin is a *Clostridium* exotoxin comprising toxin A (TcdA) and toxin B (TcdB).

In various embodiments of the method, the toxin is at least one selected from: staphylococcal α-hemolysin, staphylococcal leukocidin, aerolysin cytotoxic enterotoxin, a *cholera* toxin, *Bacillus cereus* hemolysis II toxin, a *Helicobacter pylori* vacuolating toxin, a *Bacillus anthracis* toxin, a *cholera* toxin, a *Escherichia coli* serotype O157:H7 toxin, a *Escherichia coli* serotype O104:H7 toxin, a lipopolysaccharide endotoxin, a Shiga toxin, a pertussis toxin, a *Clostridium perfringens* iota toxin, a *Clostridium spiroforme* toxin, a *Clostridium difficile* toxin A, a *Clostridium difficile* toxin B, a *Clostridium septicum* a toxin, and a *Clostridium botulinum* C2 toxin. In a related embodiment of the method, the disease agent is an infectious strain, for example a bacterial strain or a viral strain. In a related embodiment, the disease agent is a Gram-negative strain or a Gram positive strain.

The bacterium in various embodiments of the method is selected from the group consisting of: *B. anthracis, B. cereus, C. botulinum, C. difficile, C. perfringens, C. spiroforme*, and *V cholerae*.

In certain embodiments, the binding regions bind to different disease agents, such that the binding protein is specific for a plurality of disease agents, e.g., a *Clostridium* toxin and an *Escherichia* toxin. For example, the binding protein includes a chimeric fusion protein specific to at least two different disease agents described herein. In certain embodiments of the method, the binding protein is a humanized antibody derived from a non-human species for example a mouse, a rabbit, an alpaca, a llama, or horse.

In a related embodiment, the method further includes observing neutralizing of the disease agent by the binding protein and/or survival of the subject. In certain embodiments of the method, observing further includes measuring an amount of the disease agent or a disease agent product in a sample from the subject. In various embodiments, the sample is selected from: a cell, a fluid, and a tissue. For example, the fluid is at least one selected from: blood, serum, plasma, mucosal fluid, saliva, cerebrospinal fluid, semen, tears, and urine. In certain embodiments of the method, the cell or the tissue is at least one selected from: fecal; vascular; epithelial; endothelial; dermal; dental; connective; muscular; neuronal; facial; cranial; soft tissue including cartilage and collagen; brain; bone; bone marrow; joint tissue; and articular joints. For example, the method includes collecting the fluid, the cell, or the tissue from a biopsy. In certain embodiments, the method includes collecting the fluid, the cell, or the tissue from an ex vivo sample or aliquot. Alternatively, the method includes collecting from fluid, cell, or tissue that is in vivo or in situ.

The method further includes in a related embodiment observing a reduction or a remediation in at least one pathology symptom associated with the disease agent. In various embodiments, the method further includes prior to contacting the subject with the binding protein, observing and/or detecting in the subject an indicium of the exposure to the disease agent selected from: diarrhea, vomiting, breathing difficulty, fever, inflammation, bleeding, pain, numbness, loss of consciousness, tissue necrosis, or organ failure. For example, the subject is a transplant recipient or an immunosuppressed patient.

In a related embodiment, the method further includes contacting the subject with the binding protein at a period of time such as seconds, minutes, or hours after observing the indicium. Alternatively, the method further includes contacting the subject with the binding protein seconds, minutes, hours, or days prior to an event that is associated with the risk for the exposure. For example, the method includes contacting the subject prior to or after the subject's entering a potentially hazardous or dangerous environment such as biohazard facility, a combat zone, or a hazardous waste site.

The method in related embodiments includes contacting the subject with the binding protein by injecting a solution including the binding protein into the subject. In various embodiments, injecting involves at least one selected from: subcutaneous, intravenous, intramuscular, intraperitoneal, intradermal, intramedullary, transcutaneous, and intravitreal. In various embodiments of the method, contacting the subject with binding protein includes at least one technique selected from: topically, ocularly, nasally, bucally, orally, rectally, parenterally, intracisternally, intravaginally, or intraperitoneally. In a related embodiment, contacting the subject involves using an applicator, for example the applicator is a syringe, a needle, a sprayer, a sponge, a gel, a strip, a tape, a bandage, a tray, a string, or a device used to apply a solution to a cell or a tissue.

In a related embodiment of the method, contacting the subject with the binding protein includes administering to the subject a source of expression of the binding protein. In various embodiments of the method, the source of expression of the binding protein is a nucleotide sequence encoding the binding protein, such that the source of the expression includes at least one selected from the group consisting of: a naked nucleic acid vector, bacterial vector, and a viral vector. For example, the bacterial vector is derived from at least one selected from the group consisting of: *E. coli, Bacillus* spp, *Clostridium* spp, *Lactobacillus* spp, and *Lactococcus* spp.

In a related embodiment of the method, contacting further includes administering the vector, for example the naked nucleic acid vector, the bacterial vector, or the viral vector.

In a related embodiment, the nucleotide acid sequence further includes an operably linked signal for promoting expression of the binding protein. For example, the signal includes a mammalian promoter or a non-viral promoter. In a related embodiment, the method involves engineering the binding protein or the source of expression of the binding protein (e.g., viral vector or bacterial vector) using a dimerizer sequence for example having an amino acid sequence including SEQ ID NO: 94 or a portion or homolog thereof. For example, the dimerizer sequences forms a covalent bond or disulfide linkage between at least two amino acid sequences to form a homodimer, a heterodimer, or a multimer. The method in various embodiments includes, prior to contacting, engineering the binding protein using an agent that multimerizes at least one binding region or a multimer, e.g., a heterodimer, a heterotrimer, and a heterotetramer, to form the binding protein.

In a related embodiment of the method, the viral vector is derived from at least one selected from: an adenovirus, an adeno-associated virus, a herpesvirus, and a lentivirus. The method in various embodiments further includes contacting the subject with a gene delivery vehicle selected from at least one of: a liposome, a lipid/polycation (LPD), a peptide, a nanoparticle, a gold particle, and a polymer. For example, the gene delivery vehicle specifically targets a cell or tissue in the body by contacting or binding a receptor located on the cell or tissue.

An aspect of the invention provides a pharmaceutical composition for treating a subject at risk for exposure to or exposed to a disease agent, the pharmaceutical composition including: at least one recombinant heteromultimeric neutralizing binding protein including two or more binding regions, such that the binding regions are not identical, and each binding region specifically binds a non-overlapping portion of the disease agent, such that the binding protein neutralizes the disease agent, thereby treating the subject for exposure to the disease agent.

In a related embodiment, the composition is compounded with a pharmaceutically acceptable buffer or diluent. For example the composition is compounded for parenteral administration such as intravenous, mucosal administration, topical administration, or oral administration.

In various embodiments, the subject is at least one selected from: a human, a dog, a cat, a goat, a cow, a pig, and a horse. For example, the human subject is a: sick child or adult, health-care profession (e.g., doctor and nurse), aid worker, member of the military, or an immunosuppressed patient such as a transplant recipient. In certain embodiments, the pharmaceutical composition is formulated to protect the subject against the exposure, for example that exposure includes a picogram (pg) amount, nanogram (ng) amount, microgram (g) amount, or gram amount of the disease agent or a plurality of disease agents.

The binding protein or binding regions in various embodiments of the composition is selected from the group of: a single-chain antibody (scFv); a recombinant camelid heavy-chain-only antibody (VHH); a shark heavy-chain-only antibody (VNAR); a microprotein; a darpin; an anticalin; an adnectin; an aptamer; a Fv; a Fab; a Fab'; and a $F(ab')_2$. In various embodiments, the binding regions are of a different type, for example, at least one binding region is a VHH and at least other binding region is a scFv, an Fab or any of the types described herein.

The composition in various embodiments further includes at least one agent selected from the group of: an antitoxin, an anti-inflammatory, an anti-tumor, an antiviral, an antibacterial, an anti-mycobacterial, an anti-fungal, an antiproliferative, an anti-apoptotic, an anti-allergy, and an anti-immune suppressant.

In an embodiment, the composition further includes a labeled detectable marker selected from the group consisting of: detectable, fluorescent, colorimetric, enzymatic, radioactive, and the like. For example, the marker is detectable in a sample taken from the subject, the sample exemplified by a cell, a fluid or a tissue. In a related embodiment, the marker includes a peptide, a protein, a carbohydrate, and a polymer.

In an embodiment of the composition, the binding protein includes a linker that separates the binding regions. The linker in a related embodiment separates the binding regions and/or subunits of the multimeric protein. In certain embodiments, the binding protein includes a linker that covalently joins each binding region of the heterodimeric or the multimeric protein. In various embodiments, the linker includes at least one selected from the group of: a peptide, a protein, a sugar, or a nucleic acid. In a related embodiment, the linker includes amino acid sequence GGGGS (SEQ ID NO: 54) or a portion thereof. In a related embodiment, the linker includes amino acid sequence GGGGSGGGGSGGGGS (SEQ ID NO: 55) or a portion thereof or multiples thereof. The linker in various embodiments stabilizes the binding protein and does not prevent the respective binding of the binding regions to the disease agent or to a plurality of disease agents.

In various embodiments of the pharmaceutical composition, the binding protein and/or binding regions include at least one tag that is attached or genetically fused to the binding protein and/or binding regions. The tag for example is a peptide, sugar, or DNA molecule that does not inhibit or prevent binding of the binding protein and/or binding regions to the disease agent. In various embodiments, the tag is at least about: three to five amino acids long, five to eight amino acids long, eight to twelve amino acids long, twelve to fifteen amino acids long, or fifteen to twenty amino acids long. For example, the tag includes SEQ ID NO: 15.

In various embodiments, the disease agent for which the binding protein is specific is at least one selected from: a virus, a cancer cell, a fungus, a bacterium, a parasite and a product thereof such as a pathogenic molecule, a protein, a lipopolysaccharide, or a toxin. In related embodiments of the composition, the toxin includes a protein, a lipid, a lipopolysaccharide, and a small molecule toxin such as an aflatoxin or a dinoflagellate toxin. For example, the toxin is a Botulinum neurotoxin comprising a serotype selected from: A, B, C, D, E, F, and G. In various embodiments of the composition, the toxin is at least one selected from: staphylococcal α-hemolysin, staphylococcal leukocidin, aerolysin cytotoxic enterotoxin, a *cholera* toxin, *Bacillus cereus* hemolysis II toxin, a *Helicobacter pylori* vacuolating toxin, a *Bacillus anthracis* toxin, a *cholera* toxin, a *Escherichia coli* serotype O157:H7 toxin, a *Escherichia coli* serotype O104:H7 toxin, a lipopolysaccharide endotoxin, a Shiga toxin, a pertussis toxin, a *Clostridium perfringens* iota toxin, a *Clostridium spiroforme* toxin, a *Clostridium difficile* toxin A, a *Clostridium difficile* toxin B, a *Clostridium septicum* a toxin, and a *Clostridium botulinum* C2 toxin. In certain embodiments, the disease agent includes a plurality of non-identical disease agents such that the binding regions of the binding protein bind to and neutralize the plurality of disease agents.

In various embodiments of the composition, the bacterium for which the binding protein is specific is selected from: *B. anthracis, B. cereus, C. botulinum, C. difficile, C. perfringens, V cholerae*, and *C. spiroforme*. In a related embodiment, the bacterium is a virulent bacterium or apathogenic bacterium.

The composition in various embodiments is compounded or formulated for a route of delivery selected from the group of: topical, ocular, nasal, bucal, oral, rectal, parenteral, intracisternal, intravaginal, and intraperitoneal.

In various embodiments of the composition, the binding protein is specific for a toxin which is a *C. botulinum* toxin, and the binding regions of the binding protein includes a recombinant camelid heavy-chain-only antibody, and the composition includes an amino acid sequence selected from the group:

```
                                (VHH H7, SEQ ID NO: 56)
LVQVGGSLRLSCVVSGSDISGIAMGWYRQAPGKRREMVADIFSGGSTDYA

GSVKGRFTISRDNAKKTSYLQMNNVKPEDTGVYYCRLYGSGDYWGQGTQV

TVSSAHHSEDP;

                                (VHH B5, SEQ ID NO: 57)
LVHPGGSLRLSCAPSASLPSTPFNPFNNMVGWYRQAPGKQREMVASIGLR

INYADSVKGRFTISRDNAKNTVDLQMDSLRPEDSATYYCHIEYTHYWGKG
```

-continued

```
TLVTVSSEPKTPKPQ;
and

                    (H7/B5 heterodimer, SEQ ID NO: 58)
QVQLVESGGGLVQVGGSLRLSCVVSGSDISGIAMGWYRQAPGKRREMVAD

IFSGGSTDYAGSVKGRFTISRDNAKKTSYLQMNNVKPEDTGVYYCRLYGS

GDYWGQGTQVTVSSAHHSEDPTSAIAGGGGSGGGGSGGGGSLQGQLQLVE

SGGGLVHPGGSLRLSCAPSASLPSTPFNPFNNMVGWYRQAPGKQREMVAS

IGLRINYADSVKGRFTISRDNAKNTVDLQMDSLRPEDSATYYCHIEYTHY

WGKGTLVTVSSEPKTPKPQ.
```

In a related embodiment of the composition, the binding protein is specific for a toxin which is a *C. difficile* toxin A, and the binding region of the binding protein includes a recombinant camelid heavy-chain-only antibody having an amino acid sequence selected from the group of:

```
                                   (AH3, SEQ ID NO: 59)
QVQLVETGGLVQPGGSLRLSCAASGFTLDYSSIGWFRQAPGKEREGVSCI

SSSGDSTKYADSVKGRFTTSRDNAKNTVYLQMNSLKPDDTAVYYCAAFRA

TMCGVFPLSPYGKDDWGKGTLVTVSSEPKTPKPQP;

                                   (AA6, SEQ ID NO: 60)
QLQLVETGGGLVQPGGSLRLSCAASGFTFSDYVMTWVRQAPGKGPEWIAT

INTDGSTMRDDSTKGRFTISRDNAKNTLYLQMTSLKPEDTALYYCARGRV

ISASAIRGAVRGPGTQVTVSSEPKTPKPQP;

                                   (A3H, SEQ ID NO: 61)
QVQLVESGGGLVQPGGSLRLSCAASGFTLDYYAIGWFRQAPGKEREGVSG

ISSVDGSTYYADSVRGRFTISRDNAKNTVYLQMNSLKPEDTAVYYCAADQ

SPIPIHYSRTYSGPYGMDYWGKGTLVTVSSAHHSEDP;

                                   (AC1, SEQ ID NO: 62)
QLQLVESGGGLVQPGGSLRLSCAASGFTLDYYAIGWFRQAPGKEREGVSG

ISFVDGSTYYADSVKGRFAISRGNAKNTVYLQMNSLKPEDTAVYYCAADQ

SSIPMHYSSTYSGPSGMDYWGKGTLVTVSSEPKTPKPQP;

                                  (A11G, SEQ ID NO: 63)
QLQLVETGGGLVQAGGSLRLSCAASGRTLSNYPMGWFRQAPGKEREFVAA

IRRIADGTYYADSVKGRFTISRDNAWNTLYLQMNGLKPEDTAVYFCATGP

GAFPGMVVTNPSAYPYWGQGTQVTVSSEPKTPKPQP;

                                   (AE1, SEQ ID NO: 64)
QLQLVESGGGLVQPGGSLRLSCAASGFTLDYYAIGWFRQAPGKEREGVSG

ISSSDGSTYYADSVKGRFTISRDNATNTVYLQMNSLKPEDTAVYYCAADQ

AAIPMHYSASYSGPRGMDYWGKGTLVTVSSEPKTPKPQP;

                                        (SEQ ID NO: 87)
MSDKIIHLTDDSFDTDVLKADGAILVDFWAEWCGPCKMIAPILDEIADEY

QGKLTVAKLNIDQNPGTAPKYGIRGIPTLLLFKNGEVAATKVGALSKGQL

KEFLDANLAGSGSGHMHHHHHHSSGLVPRGSGMKETAAAKFERQHMDSPD

LGTDDDDKAMAISDPNSQVQLVESGGGLVQPGGSLRLSCEASGFTLDYYG

IGWFRQPPGKEREAVSYISASARTILYADSVKGRFTISRDNAKNAVYLQM

NSLKREDTAVYYCARRRFSASSVNRWLADDYDVWGRGTQVAVSSEPKTPK

PQTSAIAGGGGSGGGGSGGGGSLQAMAAASQVQLVESGGGLVQTGGSLRL
```

-continued

SCASSGSIAGFETVTWSRQAPGKSLQWVASMTKTNNEIYSDSVKGRFIIS
RDNAKNTVYLQMNSLKPEDTGVYFCKGPELRGQGIQVTVSSEPKTPKPQP
ARR;
and, (SEQ ID NO: 95)
MSDKIIHLTDDSFDTDVLKADGAILVDFWAEWCGPCKMIAPILDEIADEY
QGKLTVAKLNIDQNPGTAPKYGIRGIPTLLLFKNGEVAATKVGALSKGQL
KEFLDANLAGSGSGHMHHHHHHSSGLVPRGSGMKETAAAKFERQHMDSPD
LGTDDDDKAMAISDPNSQVQLVETGGLVQPGGSLRLSCAASGFTLDYSSI
GWFRQAPGKEREGVSCISSSGDSTKYADSVKGRFTTSRDNAKNTVYLQMN
SLKPDDTAVYYCAAFRATMCGVFPLSPYGKDDWGKGTLVTVSSEPKTPKP
QPTSAIAGGGGSGGGGSGGGGSLQAMAAAQLQLVETGGGLVQPGGSLRLS
CAASGFTFSDYVMTWVRQAPGKGPEWIATINTDGSTMRDDSTKGRFTISR
DNAKNTLYLQMTSLKPEDTALYYCARGRVISASAIRGAVRGPGTQVTVSS
EPKTPKPQPARQTSPSTVRLESRVRELEDRLEELRDELERAERRANEMSI
QLDEC.

In certain embodiments of the composition, the binding protein is specific for a toxin which is a *C. difficile* toxin B, and the binding region of the binding protein includes a recombinant camelid heavy-chain-only antibody having an amino acid sequence selected from the group consisting of:

(2D, SEQ ID NO: 65)
QVQLVESGGGLVQPGGSLRLSCAASGFSLDYYGIGWFRQAPGKERQEVSY
ISASAKTKLYSDSVKGRFTISRDNAKNAVYLEMNSLKREDTAVYYCARRR
FDASASNRWLAADYDYWGQGTQVTVSSEPKTPKPQ;

(2Ds, SEQ ID NO: 66)
QVQLVESGGGLVQAGGSLRLSCVSSERNPGINAMGWYRQAPGSQRELVAI
WQTGGSLNYADSVKGRFTISRDNLKNTVYLQMNSLKPEDTAVYYCYLKKW
RDQYWGQGTQVTVSSEPKTPKPQ;

(5D, SEQ ID NO: 67)
QVQLVESGGGLVQPGGSLRLSCEASGFTLDYYGIGWFRQPPGKEREAVSY
ISASARTILYADSVKGRFTISRDNAKNAVYLQMNSLKREDTAVYYCARRR
FSASSVNRWLADDYDVWGRGTQVAVSSEPKTPKPQ;

(E3, SEQ ID NO: 68)
QVQLVESGGGLVQTGGSLRLSCASSGSIAGFETVTWSRQAPGKSLQWVAS
MTKTNNEIYSDSVKGRFIISRDNAKNTVYLQMNSLKPEDTGVYFCKGPEL
RGQGIQVTVSSEPKTPKPQ;

(7F, SEQ ID NO: 69)
QVQLVESGGGLVEAGGSLRLSCVVTGSSFSTSTMAWYRQPPGKQREWVAS
FTSGGAIKYTDSVKGRFTMSRDNAKKMTYLQMENLKPEDTAVYYCALHNA
VSGSSWGRGTQVTVSSEPKTPKPQ;

(5E, SEQ ID NO: 70)
VQLVESGGGLVQAGGSLRLSCAASGLMFGAMTMGWYRQAPGKEREMVAYI
TAGGTESYSESVKGRFTISRINANNMVYLQMTNLKVEDTAVYYCNAHNFW
RTSRNWGQGTQVTVSSEPKTPKP;

-continued (B12, SEQ ID NO: 71)
VQLVESGGGLVQAGDSLTLSCAASESTFNTFSMAWFRQAPGKEREYVAAF
SRSGGTTNYADSVKGRATISTDNAKNTVYLHMNSLKPEDTAVYFCAADRP
AGRAYFQSRSYNYWGQGTQVTVSSAHHSEDP;

(A11, SEQ ID NO: 72)
VQLVESGGGSVQIGGSLRLSCVASGFTFSKNIMSWARQAPGKGLEWVSTI
SIGGAATSYADSVKGRFTISRDNANDTLYLQMNNLKPEDTAVYYCSRGPR
TYINTASRGQGTQVTVSSEPKTPKP;

(AB8, SEQ ID NO: 73)
VQLVESGGGLVQAGGSLRLSCVGSGRNPGINAMGWYRQAPGSQRELVAVW
QTGGSTNYADSVKGRFTISRDNLKNTVYLQMNSLKPEDTAVYYCYLKKWR
DEYWGQGTQVTVSSAHHSEDP;

(C6, SEQ ID NO: 74)
VQLVESGGGLVQAGESLRLSCVVSESIFRINTMGWYRQTPGKQREVVARI
TLRNSTTYADSVKGRFTISRDDAKNTLYLKMDSLKPEDTAVYYCHRYPLI
FRNSPYWGQGTQVTVSSEPKTPKP;

(C12, SEQ ID NO: 75)
VQLVESGGGLVQAGESLRLSCVVSESIFRINTMGWYRQTPGKQREVVARI
TLRNSTTYADSVKGRFTISRDDAKNTLYLKMDSLKPEDTAVYYCHRYPLI
FRNSPYWGQGTQVTVSSEPKTP;

(A1, SEQ ID NO: 76)
VQLVESGGGLVQAGGSLRLSCAAPGLTFTSYRMGWFRQAPGKEREYVAAI
TGAGATNYADSAKGRFTISKNNTASTVHLQMNSLKPEDTAVYYCAASNRA
GGYWRASQYDYWGQGTQVTVSSAHHSEDP;
SEQ ID NO: 87; and SEQ ID NO: 95.

In related embodiments of the composition, the binding protein is specific for a toxin which is a Shiga toxin, and the binding region of the binding protein includes a recombinant camelid heavy-chain-only antibody having an amino acid sequence selected from the group:

(JET-A9, SEQ ID NO: 77)
QVQLVETGGGLAQAGDSLRLSCVEPGRTLDMYAMGWIRQAPGEEREFVAS
ISGVGGSPRYADSVKGRFTISKDNTKSTIWLQMNSLKPEDTAVYYCAAGG
DIYYGGSPQWRGQGTRVTVSSEPKTPKPQ;

(JGG-D4, SEQ ID NO: 78)
QVQLVESGGGLVQAGGSLRLSCAASGRINGDYAMGWFRQAPGEEREFVAV
NSWIGGSTYYTDSVKGRFTLSRDNAKNTLSLQMNSLKPEDTAVYYCAAGH
YTDFPTYFKEYDYWGQGTQVTVSSEPKTPKPQ;

(JEN-D10, SEQ ID NO: 79)
QVQLVETGGLVQAGGSLRLSCAASGVPFSDYTMAWFRQAPGKEREVVARI
TWRGGGPYYGNSGNGRFAISRDIAKSMVYLHMDSLKPEDTAVYYCAASRL
RPALASMASDYDYWGQGTQVSVSSEPKTPKPQ;

(JGH-G1, SEQ ID NO: 80)
QVQLVESGGGLVQPGESLRLSCVASASTFSTSLMGWVRQAPGKGLESVAE
VRTTGGTFYAKSVAGRFTISRDNAKNTLYLQMNSLKAEDTGVYYCTAGAG
PIATRYRGQGTQVTVSSAHHSEDP;

-continued (JEU-A6, SEQ ID NO: 81)
QVQLVESGGGLVQPGGSLKLSCAASGFTLADYVTVWFRQAPGKSREGVSC

ISSSRGTPNYADSVKGRATVSRNNANNTVYLQMNGLKPDDTAIYYCAAIR

PARLRAYRECLSSQAEYDYWGQGTQVTVSSAHHSEDP;

(JEU-D2, SEQ ID NO: 82)
QVQLVESGGGLVQPGGSLGLSCAMSGTTQDYSAVGWFRQAPGKEREGVSC

ISRSGRRTNYADSVRGRFTISRDNAKDTVYLQMNSLKPDDTAVYYCAARK

TDMSDPYYVGCNGMDYWGKGTLVTVSSAHHSEDP;

(JGH-G9, SEQ ID NO: 83)
QVQLVESGGGLVQPGGSLTLSCTASGFTLNSYKIGWFRQAPGKEREGVSC

INSGGNLRSVEGRFTISRDNTKNTVSLHMDSLKPEDTGVYHCAAAPALNV

FSPCVLAPRYDYWGQGTQVTVSSAHHSEDP;

(JFD-A4, SEQ ID NO: 84)
QVQLVESGGGLVQPGGSLRLSCAASGFTLGSYHIGWFRHPPGKEREGTSC

LSSRGDYTKYAEAVKGRFTISRDNTKSTVYLQMNNLKPEDTGIYVCAAIR

PVLSDSHCTLAARYNYWGQGTQVTVSSAHHSEDP;

(JFD-A5, SEQ ID NO: 85)
QVQLVESGGGLVQPGGSLRLSCAALEFTLEDYAIAWFRQAPGKEREGVSC

ISKSGVTKYTDSVKGRFTVARDNAKSTVILQMNNLRPEDTAVYNCAAVRP

VFVDSVCTLATRYTYWGEGTQVTVSSAHHSEDP;
and (JGG-G6, SEQ ID NO: 86)
QVQLVETGGGLVQPGGSLKLSCAASEFTLDDYHIGWFRQAPGKEREGVSC

INKRGDYINYKDSVKGRFTISRDGAKSTVFLQMNNLRPEDTAVYYCAAVN

PVFPDSRCTLATRYTHWGQGTQVTVSSAHHSEDP.

In various embodiments, the amino acid sequence of the composition further includes an amino acid analog, an amino acid derivative, or a conservative substitution of an amino acid residue. The binding protein in various embodiments includes an amino acid sequence that is substantially identical to the amino acid sequence of SEQ ID NOs: 56-87 and 95. In related embodiments, substantially identical means that the amino acid sequence of the binding protein has at least about 50% identity, at least about 60% identity, at least about 65% identity, at least about 70% identity, at least about 75% identity, at least about 80% identity, at least about 85% identity, at least about 90% identity, at least about 95% identity, at least about 97% identity, at least about 98% identity, or at least about 99% identity to the amino acid sequence of SEQ ID NOs: 56-87 and 95. Alternatively, the binding protein is encoded by at least one nucleotide sequence or the protein includes amino acid sequence selected from the group of SEQ ID NOs: 1-87 and 95, and substantially identical to any of these sequences.

The composition in various embodiments further includes the binding protein or a source of expression of the binding protein selected from the group of: a purified binding protein preparation; a nucleic acid vector with a gene encoding the binding protein; a viral vector encoding the binding protein; and a naked nucleic acid encoding the binding protein which is expressed from the DNA. In related embodiments, the viral vector is derived from a genetically engineered genome of at least one virus selected from: an adenovirus, an adeno-associated virus, a herpes virus, and a lentivirus.

In a related embodiment of the composition, the binding protein is heterodimeric. In various embodiments, the heterodimeric binding protein includes a first binding region and a second binding region. For example the first binding region and the second binding region include VHHs, and the first binding region binds specifically to a *C. difficile* TcdA and the second binding region binds specifically to a *C. difficile* TcdB.

An aspect of the invention provides a kit for treating a subject exposed to or at risk for exposure to a disease agent including: a pharmaceutical composition for treating a subject at risk for exposure to or exposed to a disease agent, the pharmaceutical composition including: at least one recombinant heteromultimeric neutralizing binding protein comprising a plurality binding regions, such that the binding regions are not identical, and each binding region specifically binds a non-overlapping portion of the disease agent, such that the binding protein neutralizes the disease agent, thereby treating the subject for exposure to the disease agent; a container; and, instructions for use. In various embodiments, the instructions for use include instructions for a method for treating a subject at risk for exposure to or exposed to a disease agent using the pharmaceutical composition.

In various embodiments of the kit, the binding protein is selected from the group of: a single-chain antibody (scFv); a recombinant camelid heavy-chain-only antibody (VHH); a shark heavy-chain-only antibody (VNAR); a microprotein; a darpin; an anticalin; an adnectin; an aptamer; a Fv; a Fab; a Fab'; and a $F(ab')_2$.

In a related embodiment of the kit, the binding protein includes a linker. In various embodiments, the linker includes at least one selected from: a peptide, a protein, a sugar, or a nucleic acid. For example, the linker includes amino acid sequence GGGGS (SEQ ID NO: 54), or GGGGSGGGGSGGGGS (SEQ ID NO: 55), or a portion thereof. Alternatively, the linker includes a single amino acid or a plurality of amino acids.

In related embodiments of the kit, the disease agent for which the binding protein and binding regions are specific is selected from: a virus, a cancer cell, a fungus, a bacterium, a parasite, and a product of one of those such as a pathogenic molecule, a protein, a lipopolysaccharide, or a toxin. In related embodiments, the toxin for which the binding protein is specific is a Botulinum neurotoxin including a serotype selected from: A, B, C, D, E, F, and G. In various embodiments of the kit, the toxin for which the binding protein is specific is at least one selected from the group of: staphylococcal α-hemolysin, staphylococcal leukocidin, aerolysin cytotoxic enterotoxin, a *cholera* toxin, a *Bacillus cereus* hemolysis II toxin, a *Helicobacter pylori* vacuolating toxin, a *Bacillus anthracisi* toxin, a *cholera* toxin, an *Escherichia coli* serotype O157:H7 toxin, an *Escherichia coli* serotype O104:H7 toxin, a lipopolysaccharide endotoxin, a Shiga toxin, a pertussis toxin, a *Clostridium perfringens* iota toxin, a *Clostridium spiroforme* toxin, a *Clostridium difficile* toxin A, a *Clostridium difficile* toxin B, a *Clostridium septicum* a toxin, and a *Clostridium botulinum* C2 toxin. In certain embodiments, the binding regions of the binding protein are specific to different classes of disease agents, e.g., each of the plurality of binding regions is different and is specific for an agent from bacteria, virus, fungus, cancer, and a pathogenic molecule. For example a binding region is specific for a virus and another binding region is specific for a bacterium.

In a related embodiment of the kit, the binding protein is specific for a toxin which is a *C. botulinum* toxin, and the binding region includes a recombinant camelid heavy-chain-only antibody, such that the pharmaceutical composition includes the binding protein that has an amino acid sequence selected from the group consisting of: SEQ ID NO: 56, SEQ ID NO: 57, SEQ ID NO: 58, or a portion thereof.

In a related embodiment of the kit, the binding region of the binding protein is specific for a toxin which is a *C. difficile* toxin A, such that the binding region of the binding protein includes a recombinant camelid heavy-chain-only antibody having an amino acid sequence selected from the group of: SEQ ID NO: 59, SEQ ID NO: 60, SEQ ID NO: 61, SEQ ID NO: 62, SEQ ID NO: 63, SEQ ID NO: 64, SEQ ID NO: 87, SEQ ID NO: 95, and a portion thereof.

In a related embodiment of the kit, the toxin for which the binding protein is specific is a *C. difficile* toxin B, and the binding region of the binding protein includes a recombinant camelid heavy-chain-only antibody having an amino acid sequence selected from: SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 87, SEQ ID NO: 95, and a portion thereof. In certain embodiments, the binding protein and/or binding regions are encoded by a nucleotide sequence or the binding protein and/or regions include an amino acid sequence selected from the group of SEQ ID NOs: 1-87 and 95, or are substantially identical to these sequences.

In a related embodiment, the binding protein is specific for a Shiga toxin, and the binding region of the binding protein includes a recombinant camelid heavy-chain-only antibody having an amino acid sequence selected from: SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, and SEQ ID NO: 86.

An aspect of the invention provides a composition including at least one amino acid sequence selected from the group of: SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 94, SEQ ID NO: 95 or a portion thereof. The composition in various embodiments includes an amino acid sequence that is substantially identical to the amino acid sequence of SEQ ID NOs: 59-86. In related embodiments, substantially identical means an amino acid sequence that has at least 60% identity, at least 65% identity, at least 70% identity, at least 75% identity, at least 80% identity, at least 85% identity, at least 90% identity, at least 95% identity, at least about 97% identity, at least about 98% identity, or at least 99% identity to an amino acid sequence of any of SEQ ID NOs: 56-87 and 95.

An aspect of the invention provides a method for treating a subject at risk for exposure to or exposed to a plurality of disease agents, the method including: contacting the subject with at least one recombinant heteromultimeric neutralizing binding protein including two or more binding regions, such that the binding protein neutralizes at least two (plurality) of disease agents, thereby treating the subject for exposure to the plurality of disease agents.

In a related embodiment of the method, the at least two of the binding regions are identical. Alternatively, the at least two binding regions include at least two non-identical binding regions. In related embodiments of the method, the binding protein is at least one selected from the group of: a heterodimer, a trimer, a tetramer, a pentamer, and a hexamer. In various embodiments, the tetramer includes a homodimer of a heterodimer, for example a heterodimer of AH3 and AA6 as is shown in SEQ ID NO: 95.

In various embodiments, the plurality from which the exemplary disease agents are selected from a virus, a cancer cell, a fungus, a bacterium, a parasite and a product thereof such as a pathogenic molecule, a protein, a lipopolysaccharide, or a toxin. For example the disease agents include toxins such as TcdA and TcdB.

In related embodiments of the method, the binding protein includes at least one selected from the group of SEQ ID NOs: 56-87 and 95 or a portion or a homologue.

In related embodiments of the method, the binding protein is selected from the group of: a single-chain antibody (scFv); a recombinant camelid heavy-chain-only antibody (VHH); a shark heavy-chain-only antibody (VNAR); a microprotein; a darpin; an anticalin; an adnectin; an aptamer; a Fv; a Fab; a Fab'; and a $F(ab')_2$. In a related embodiment of the method, the binding protein includes a linker located between each of the multimeric components of the binding regions. In various embodiments, the linker is at least one selected from the group of: a peptide, a protein, a sugar, or a nucleic acid. For example, the linker comprises amino acid sequence GGGGS (SEQ ID NO: 54) or amino acid sequence GGGGSGGGGSGGGGS (SEQ ID NO: 55).

In a related embodiment, the method further includes prior to contacting, engineering the binding protein using a dimerization agent. In a related embodiment, the dimerization agent includes amino acid sequence TSPSTVRLESRVRELEDRLEELRDELERAERRANEMSIQLDEC (SEQ ID NO: 94), or a portion thereof.

In various embodiments of the method, the plurality of disease agents is at least two selected from the group of: *Staphylococcal* α-hemolysin, *Staphylococcal* leukocidin, aerolysin cytotoxic enterotoxin, a *cholera* toxin, *Bacillus cereus* hemolysis II, and *Helicobacter pylori* vacuolating toxin, *Bacillus anthracis, cholera* toxin, *Escherichia coli* serotype O157:H7, *Escherichia coli* serotype O104:H7, lipopolysaccharide endotoxin, Shiga toxin, pertussis toxin, *Clostridium perfringens* iota toxin, *Clostridium spiroforme* toxin, *Clostridium difficile* toxin A, *Clostridium difficile* toxin B, *Clostridium septicum* a toxin, and *Clostridium botulinum* C2 toxin. In related embodiments of the method, the binding protein includes at least one selected from the group of: SEQ ID NOs: 56-87 and 95.

Binding Agent

The binding agent or binding protein is in one embodiment, a molecule that binds to a portion of a target molecule, disease agent, or disease agent target. The binding protein treats the subject by any or all of several mechanisms, including promoting clearance, phagocytosis, neutralization, inhibition, and activation of the immune response. The term "binding agent" or "binding protein", includes in addition to full-length antibodies, molecules such as antibody fragments (e.g., single chain antibodies, and VHHs), microproteins (also referred to as cysteine knot proteins or knottins), darpins, anticalins, adnectins, peptide mimetic molecules, aptamers, synthetic molecules, and refers to any composition that binds to a target and/or disease agent and elicits an immune effector activity against the molecule target and/or disease agent. In certain embodiments, the binding protein is a recombinant multimeric neutralizing binding protein including two or more binding regions, such that the binding regions are not identical, and each and/or disease agent. Alternatively, the binding protein includes binding regions that bind specifically to different types of disease agents such as different types of pathogenic molecules such as bacteria, viruses, fungi, allergens, and toxins. For example at least one binding region of the binding protein binds to a virus surface protein, and at least one different binding region binds to a bacterial toxin.

The multimeric neutralizing binding protein herein in certain embodiments includes one or a plurality of epitopic tags. In certain embodiments, the binding protein includes a linker that covalently connects each binding region of the heterodimer. For example, the linker is a single amino acid or a sequence of a plurality of amino acids that does not affect or reduce the stability, orientation, binding, neutralization, and/or clearance characteristics of the binding regions and binding protein. In certain embodiments, each binding region is specific to a non-identical disease agent. For example the binding protein in certain embodiments includes a binding region specific to a bacterium or bacterial toxin, and at least one other binding region is specific to a virus, fungus, allergen, or to a non-identical bacterium or bacterial toxin. For example, a multimeric binding protein in certain embodiments has binding regions specific to a TcdA and to a TcdA or to a Shiga toxin, or the respective binding regions are specific to each of a Botulinum toxin and a virus.

In certain embodiments, the binding protein neutralizes or inhibits the molecule target and/or disease agent for example by preventing the disease agent entry into cells. In certain embodiments, the binding protein upon being administered to the subject neutralizes the toxin and/or triggers an antibody mediated effector activity in the subject.

The binding protein is in certain embodiments a monomer (e.g., a single unit), or includes a covalently bound protein including a plurality of monomers such as for example a dimer, a trimer, a tetramer, a pentamer, an octamer, a 10-mer, a 15-mer, a 20-mer, or any multimer. In certain embodiments, the binding protein is a monomer and the binding protein has one binding region that binds to an epitope of the molecule target and/or disease agent. Alternatively, the binding protein in certain embodiments has two or more connected or joined monomers each with a binding region and each binding to an epitope of a disease agent or to a plurality of epitopes of disease agents. The multimeric binding protein in certain embodiments includes the same monomer. Alternatively, the multimeric binding protein includes monomers or binding regions or a combination thereof (i.e., heteromultimeric). Accordingly, the multimers can be homogeneous such that each includes two or more monomers having a binding region that binds to the same site of a disease agent. Alternatively, the multimers are heterogeneous and include two or more monomers having a binding region that binds to two or more different sites of one or more disease agents. The heterogeneous multimers (heteromultimers) bind non-overlapping portions of the molecule target and/or disease agent. In various embodiments, the binding protein is a homodimer of a heterodimer or a heterotrimer. In a related embodiment, the heteromultimers bind a plurality of non-identical epitopes on a plurality of disease agents.

In certain embodiments the binding protein includes a single tag, multiple tags, for example each multimeric binding protein includes two or more tags on each component binding region (i.e., monomer). Alternatively, the heterodimer comprises no tag attached to the monomers and/or linker. In certain embodiments, presence of the tag on or operably fused to the binding protein and/or binding region synergistically induces clearance of the disease agent from the body. For example, the tag attached to the binding protein induces an immune response from a patient or subject contacted with a pharmaceutical composition containing the tagged-binding protein. In certain embodiments the tag includes a portion (e.g., conserved, unique, inactivated, and non-functional) of a pathogenic molecule. In certain embodiments, the tag is an adjuvant. See Gerber et al. U.S. Pat. No. 7,879,333 issued Feb. 1, 2011 which is incorporated by reference herein in its entirety. For example, the tag is a peptide, carbohydrate, polymer, or nucleic acid that is effective for enhancing neutralization and/or clearance of the disease agent or plurality of disease agents.

The multimeric binding protein in certain embodiments is a heterodimer having two tags, one tag attached to each monomer, or alternatively, the heterodimer includes one tag on each monomer or one tag total on one of the two monomers. The term “heterodimer” includes a single protein having two different monomers are joined by a linker. Data herein shows that heterodimers having two E-tags effectively protected animals exposed to hundreds-fold and/or thousands-fold the lethal dose of a single disease agent such as a *C. difficile* toxin A. Examples herein show that recombinant multimeric binding proteins, having two or more non-identical binding regions, administered to subjects either before or after contact with a disease agent resulted in comparable and better antitoxin efficacy than serum-based polyclonal antitoxins.

The binding agents/proteins described herein include binding agent/protein portions, regions, and fragments. For example, the binding protein is an antibody and, in certain embodiments the binding protein includes antibody fragments. The term “antibody fragment” refers to portion of an immunoglobulin having specificity to an molecule target and/or disease agent, or a molecule involved in the interaction or binding of the molecule target and/or disease agent. The term “antibody fragment” encompasses fragments from binding protein, for example both polyclonal and monoclonal antibodies including transgenically produced antibodies, single-chain antibodies (scFvs), recombinant Fabs, and recombinant heavy-chain-only antibodies (VHHs), e.g., from any organism producing VHH antibody such as a camelid, a shark, or a designed VHH.

VHHs are antibody-derived therapeutic proteins that contain the unique structural and functional properties of naturally-occurring heavy-chain antibodies. VHH technology is based on fully functional antibodies from camelids that lack light chains. These heavy-chain antibodies contain a single variable domain (VHH) and two constant domains ($CH_2$ and $CH_3$). The cloned and isolated VHH domain is a stable polypeptide harboring the antigen-binding capacity of the original heavy-chain antibody. See, Casterman et al. U.S. Pat. No. 5,840,526, issued Nov. 24, 1998; and Casterman et al. U.S. Pat. No. 6,015,695, issued Jan. 18, 2000, each of which is incorporated by reference herein in its entirety. The variable region of immunoglobulins of the invention, comprises frameworks (FW) and complementarity determining regions (CDR), especially 4 frameworks and 3 complementarity regions. It is distinguished from the four-chain immunoglobulins especially by the fact that this variable region can itself contain an antigen binding site or several, without contribution of the variable region of a light chain which is absent. (See, Casterman, U.S. Pat. No. 6,015,695, Col. 6, lines 33-41). VHHs are commercially available from Ablynx Inc. (Ghent, Belgium) under the trademark of NANOBODIES™.

Suitable methods of producing or isolating antibody fragments having the requisite binding specificity and affinity are described herein and include for example, methods which select recombinant antibody from a library, by PCR (See Ladner U.S. Pat. No. 5,455,030 issued Oct. 3, 1995 and Devy et al. U.S. Pat. No. 7,745,587 issued Jun. 29, 2010, each of which is incorporated by reference herein in its entirety).

Functional fragments of antibodies, including fragments of chimeric, humanized, primatized, veneered or single chain antibodies, can also be produced. Functional fragments or portions of the foregoing antibodies include those which are reactive with the disease agent. For example, antibody fragments capable of binding to the disease agent or portion thereof, including, but not limited to scFvs, Fabs, VHHs, Fv, Fab, Fab' and $F(ab')_2$ are encompassed by the invention. Such fragments can be produced by enzymatic cleavage or by recombinant techniques. For instance, papain or pepsin cleavage are used generate Fab or $F(ab')_2$ fragments, respectively. Antibody fragments are produced in a variety of truncated forms using antibody genes in which one or more stop codons has been introduced upstream of the natural stop site. For example, a chimeric gene encoding a $F(ab')_2$ heavy chain peptide portion can be designed to include DNA sequences encoding the $CH_1$ peptide domain and hinge region of the heavy chain. Accordingly, the present invention encompasses a polynucleic acid that encodes the binding protein described herein (e.g., a binding fragment with a tag). Binding proteins in certain embodiments are made as part of a multimeric protein, the monomer or single binding region (e.g., antibody fragments, microproteins, darpins, anticalins, adnectins, peptide mimetic molecules, aptamers, synthetic molecules, etc) can be linked. Any combination of binding protein or binding region types can be linked. In an embodiment, the monomer or binding region of a multimeric binding protein can be linked covalently. In another embodiment, a monomer binding protein can be modified, for example, by attachment (directly or indirectly (e.g., via a linker or spacer)) to another monomer binding protein. A monomer in various embodiments is attached or genetically fused to another monomer e.g., by recombinant protein that is engineered to contain extra amino acid sequences that constitute the monomers. Thus, the DNA encoding one monomer is joined (in reading frame) with the DNA encoding the second monomer, and so on. Additional amino acids in certain embodiments are encoded between the monomers that produce an unstructured region separating the different monomers to better promote the independent folding of each monomer into its active conformation or shape. Commercially available techniques for fusing proteins are used in various embodiments to join the monomers into a multimeric binding protein of the present invention.

The term "antagonist" as used herein includes proteins or polypeptides that bind to the disease agent, inhibit function of the disease agent, and are included in certain embodiments to the binding region of the binding protein.

A binding protein includes any amino acid sequence that binds to the disease agent or target including molecules that have scaffolds. Examples of binding proteins having scaffolds are DARPins, Anticalins, and AdNectins. DARPins are derived from natural ankyrin repeat proteins and bind to proteins including e.g., human receptors, cytokines, kinases, human proteases, viruses and membrane proteins (Molecular Partners AG Zurich Switzerland). Anticalins are derived from lipocalins, and comprise a hypervariable loops supported by a conserved β-sheet framework, which acts as a binding protein. (Pieris AG, Germany). The scaffold for anticalins are lipocalins. AdNectins are derived from human fibronectin (e.g., the scaffold), and bind to targets of various medical conditions and are commercially available from Adnexus (Waltham, Massachusetts). See also Alexandru et al. U.S. Pat. No. 7,867,724 issued Jan. 11, 2011, which is incorporated by reference herein in its entirety. In certain embodiments, the binding protein having the scaffold is encoded by a nucleotide sequence or the binding protein includes an amino acid sequence that is substantially identical or homologous to the sequences described herein, for example SEQ ID NO: 1-87 and 95.Recombinant multimeric binding proteins herein include amino acid sequences from a binding protein sequence having conservative sequence modifications. As used herein, the term "conservative sequence modifications" refers to amino acid modifications that do not significantly affect or alter the characteristics (e.g., neutralization, clearance, binding, stability, and orientation) of the binding protein, i.e., amino acid sequences of binding protein that present these side chains at the same relative positions will function in a manner similar to the binding protein. Such conservative modifications include amino acid substitutions, additions and deletions. Modification of the amino acid sequence of recombinant multimeric binding protein is achieved using any known technique in the art e.g., site-directed mutagenesis or PCR based mutagenesis. Such techniques are described in Sambrook et al., *Molecular Cloning: A Laboratory Manual*, Cold Spring Harbor Press, Plainview, N Y, 1989 and Ausubel et al., *Current Protocols in Molecular Biology*, John Wiley & Sons, New York, NY, 1989. Conservative amino acid substitutions are modifications in which the amino acid residue is replaced with an amino acid residue having a similar side chain such as replacing a small amino acid with a different small amino acid, a hydrophilic amino acid with a different hydrophilic amino acid, etc.

Examples herein show that a molecule target and/or disease agent is bound by a binding protein, the molecule target and/or disease agent exemplified by a bacterial toxin released by the pathogen, for example a botulinum toxin. Botulinum toxin serotypes A to G are synthesized by organisms including *Clostridium botulinum, Clostridium baratii*, and *Clostridium butyricum*. Simpson, L. L 2004, *Annu. Rev. Pharmacol. Toxicol.* 44: 167-193. *C. botulinum* produces serotypes A to G, *C. baratii* produces serotype F, and *C. butyricum* produces serotype E only. The structures and substrates for each of the botulism toxin serotypes as well as the serotype specific cleavage sites have been determined, and the mechanism of toxin killing has been elucidated. The botulinum toxin acts preferentially on peripheral cholinergic nerve endings to block acetylcholine release, and causes disease (i.e., botulism) and can be used to treat disease (e.g., dystonia). Ibid., Abstract. The toxigenicity of botulinum toxin depends on penetration of the toxin through cellular and intracellular membranes. Thus, toxin that is ingested or inhaled binds to epithelial cells and is transported to the general vascular circulation. Toxin that reaches peripheral nerve endings binds to the cell surface then penetrates the plasma membrane by receptor-mediated endocytosis and the endosome membrane by pH-induced translocation. Ibid., Abstract. Internalized toxin acts in the cytosol as a metalloendoprotease to cleave polypeptides that are essential for exocytosis.

Examples herein show binding proteins/agents that specifically bind each of a variety of distinct serotypes of a microbial neurotoxin that causes botulism, BoNT/A and BoNT/B. The amino acid sequence of the binding agents include scFvs and VHHs for example SEQ ID NOs: 2, 4, 6, 8, 10, 12, 14, 20, 22, 24, 26, 28, 30, 32, 34, 36, 38, 40, 42, 44, 46, 48, 50, 52 or combinations or portions thereof. The corresponding nucleic acid sequences of binding agents are shown in SEQ ID NOs: 1, 3, 5, 7, 9, 11, 13, 19, 21, 23, 25, 27, 29, 31, 33, 35, 37, 39, 41, 43, 45, 47, 49, 51 or a combination thereof. In various embodiments the amino acid sequence of the binding agents includes VHHs for example SEQ ID NO: 56-87 or 95 or combinations or portions thereof. In certain embodiments, the binding agent includes a tag that was engineered as a portion of the binding agent, for example the tag has amino acid sequence of SEQ ID NO: 15, and is genetically fused to the carboxyl end of the binding agents. In certain embodiments, the tag enhances ability of the binding protein to neutralize and/or clear the disease agent from the subject. FIG. 5 shows a phylogenetic tree of JDQ-B5 (SEQ ID NO: 24), a VHH binding agent that specifically binds to BoNT/A and other VHHs that compete with JDQ-B5 for binding to BoNT/A. The length of the branches in the tree represents the relatedness of the sequences with the shorter branches indicating greater relatedness (i.e., homology) and the longer branches indicating less homology of the amino acid sequences.

The present invention provides a number of different binding proteins, each having binding regions with specificity and affinity to target different areas of one or more disease agents. In an embodiment, two or three binding proteins specific to different epitopes of a disease agent are used. In a disease having a number of disease agents involved in causing the disease or condition, such as botulism, multiple disease agents are targeted by the compositions and methods herein. In the case of botulism, since any one of at least seven neurotoxin serotypes are involved, a pool/mixture of binding proteins is prepared containing binding proteins for a plurality of known serotypes that cause the disease in humans. Botulism is often caused by exposure to a single BoNT serotype, and it is generally difficult to quickly determine which serotype is the cause. Thus, the standard of care in treating botulism includes administration of a number of antibodies to protect against most if not all of the serotypes that cause the disease in human. Hence, it is appropriate to protect subjects from botulism, to stockpile binding proteins that bind to several or preferably all known serotypes that cause botulism.

The present invention in various embodiments further encompasses compositions that are multimeric binding proteins having two or more monomers in which a monomer is exemplified by a VHH amino sequence herein. In various embodiments, the composition includes at least one selected from the group of SEQ ID NOs: 56-87 and 95. Compositions further include nucleic acid sequences that encode the amino acids sequences herein, for example SEQ ID NO: 56-87 and 95. In certain embodiments, the monomer or binding region includes at least one sequence described herein, for example SEQ ID NOs: 1-87 and 95. An embodiment of a multimeric binding protein includes two or more of the VHH sequences herein expressed as a single protein. Any combination of two or more of the VHH sequences forms a multimeric binding protein of the present invention. In a particular embodiment, the present invention relates to a heterodimer, i.e., protein, in which any two different VHH sequences herein are expressed as a single protein, i.e., linked and expressed as a genetic fusion.

The binding protein in certain embodiments is a multimeric fusion protein engineered and produced using a multimerization agent to form a complex that effectively binds to and neutralizes a disease agent or plurality of disease agents. In certain embodiments, the multimerization agent includes a dimerization sequence for example including an amino acid sequence shown in SEQ ID NO: 94. For example the dimerzation agent complexes peptide fragments each containing at least: about five to 25 amino acids, about 25 to 50 amino acids, about 50 to 100 amino acids, about 100 to 150 amino acids, and about 150 amino acids to about 200 amino acids. Multimerization agents and methods of using the agents for forming multimeric binding proteins are shown herein in Example 21. See also Moore et al. U.S. Pat. No. 7,763,445 issued Jul. 24, 2012 and Carter et al. U.S. Pat. No. 8,216,865 issued Jul. 10, 2012, each of which is incorporated by reference herein in its entirety.

The disease agent target is any from different classes of pathogens, infectious agents or other unwanted material. A multi-target approach is within the scope of the methods and compositions herein, exemplified by a binding protein that binds to a viral disease agent, a bacterial disease agent, a parasite disease agent, a cancer cell, and a protein produced therefrom and any combination thereof. In various embodiments, a binding protein neutralizes a plurality of pathogens or unwanted material. Examples herein show a VHH heterodimer that binds to and neutralizes both TcdA and TcdB.

The disease agent, pathogen or infectious agent that is neutralized by the binding agent is any molecule, virus, or bacterium that infects a mammal (e.g., human, horse, dog, goat, and cow) or a mammalian cell. In certain embodiments, the disease agent is a bacterium selected from *Actinobacillus, Bacillus, Borrelia, Brucella, Campylobacter, Chlamydia, Clostridium, Coxiella, Enterococcus, Escherichia, Francisella, Hemophilus, Legionella, Mycobacterium, Neisseria, Pasteurella, Pneumophila, Pseudomonas, Rickettsia, Salmonella, Shigella, Staphylococcus, Streptococcus, Treponema*, and *Yersinia*. Alternatively, the disease agent is a virus including for example human immunodeficiency virus, foot-and-mouth disease virus, avian influenza virus, and sheep pox virus.

The binding agent in various embodiments binds to and neutralizes an infectious agent and/or a disease agent associated with a pathology resulting from overexpression of a self protein in the subject such as an immunoglobulin, a leukocyte, a cytokine, and a growth factor. For example, the overexpression is of an inflammatory agent such as a tumor necrosis factor (e.g., TnFα) or an interleukin (IL) such as IL-1 beta, or IL-6. Alternatively, an infectious agent and/or a disease agent is associated with expression of a mutated or modified molecule such as a protein, a sugar, a glycoprotein, or expression of a cell carrying a nucleotide sequence encoding the disease agent.

The binding agent in various embodiments binds to a cancer cell and/or cancer marker. For example, the cancer cell includes a melanoma; a carcinoma (e.g., colon carcinoma); a pancreatic cancer; a sarcoma; a lymphoma; a leukemia; a brain tumor such as glioma; a lung cancer; an esophageal cancer; a mammary (breast) cancer; a bladder cancer; a prostate cancer; a head and neck cancer; an ovarian cancer; a kidney cancer; or a liver cancer.

The binding agents described herein are used in certain embodiments to treat symptoms of an autoimmune disease, a class of disorder which includes Hashimoto's thyroiditis; idiopathic myxedema, a severe hypothyroidism; multiple sclerosis, a demyelinating disease marked by patches or hardened tissue in the brain or the spinal cord; myasthenia gravis which is a disease having progressive weakness of muscles caused by autoimmune attack on acetylcholine receptors at neuromuscular junctions; Guillain-Barre syndrome, a polyneuritis; systemic lupus erythematosis; uveitis; autoimmune oophoritis; chronic immune thrombocytopenic purpura; colitis; diabetes; Grave's disease, which is a form of hypothyroidism; psoriasis; pemphigus vulgaris; and rheumatoid arthritis (RA).

Molecule Target and Disease Agent Target

A molecule target and/or disease agent target is any target which is biological (e.g., protein, sugar, carbohydrate, DNA, RNA) or chemical to which the binding protein binds, and is any target associated with a disease, defect or negative condition. The molecule target or disease agent target is any molecule capable of being bound, or whose activity is altered (e.g., neutralized, reduced or ceased), or that can be recognized by immune effectors and leads for example to clearance, opsonization, killing, and phagocytosis. For example, the disease agent target in certain embodiments is a portion of a pathogen or a molecule released or secreted by the pathogen (e.g. toxin). A pathogen is an agent that causes a disease or condition, and includes a virus, cancer cell, bacterium, parasite or pathogenic protein. The disease agent target includes a pathogenic protein that is derived from normal cells, such as prions. The pathogenic protein or other molecule that is disease agent target is either independent of the pathogen or is associated with or produced by the pathogen.

A virus is a microscopic particle that infects the cells of a biological organism and replicates in the host cell. In various embodiments, viral antigens including viral proteins, are targeted by the binding protein. Binding proteins bind to molecules or receptors on the virus, and are neutralized and/or cleared using the methods described herein. Examples of viruses that are neutralized and/or cleared by the binding protein herein include Influenza, Rhinovirus, Rubeola, Rubella, Herpes, Smallpox, Chickenpox, Human Papilloma, Rabies, and Human Immunodeficiency viruses.

A parasite is an organism that lives on or in a different organism. Parasites have or express molecules that are used as a target by the binding agent. Types of parasites include endoparasites (e.g., parasites that live inside the body of the host) and ectoparasites (e.g., parasites that live on the outside of the host's body). Examples of parasites that are treated by the methods, compositions, and kits herein are shown in Horvitz et al. U.S. patent publication 20110010782 published Jan. 13, 2011. Exemplary parasites include a protozoan (e.g., a *plasmodium*, a *cryptosporidium*, a microsporidium, and *isospora*), a tick, a louse and a parasitic worm.

Molecules on cancer cells also are targets of the binding agent. In related embodiments, the target is a protein on the cancer cell such as a cancer marker. Examples of proteins or receptors associated with cancer cells include CD33, HER2/neu, CA 125 (MUC16), prostate-specific antigen (PSA), and CD44.

The disease agent target in certain embodiments includes bacteria including Gram negative and Gram positive bacteria. Examples of pathogenic bacteria bound by the binding protein include *Clostridium, Staphylococcus, Neisseria, Streptococcus, Moraxella, Listeria*, any of the Enterobacteriaceae, *Escherichia coli, Corynebacterium, Klebsiella, Salmonella, Shigella, Proteus, Pseudomonas, Haemophilus, Bordetella, Legionella, Campylobacter, Helicobacter*, and *Bacteroides*.

Enterohemorrhagic *Escherichia coli* (EHEC) is an emerging food- and water-borne pathogen that colonizes the distal ileum and colon and produces potent cytotoxins (Donnenberg, "Infections due to *Escherichia coli* and other enteric gram-negative bacilli," in ACP Medicine, WebMD Professional Publishing, Danbury CT, Chapter 7, pp. 8-1 to 8-18, 2005). After ingestion of contaminated food, humans develop symptoms ranging from mild diarrhea to the severe, and at times life-threatening, hemolytic uremic syndrome (HUS). Currently, EHEC is the most common cause of pediatric renal failure in the United States (Mead et al, *Emerg Infect Dis,* 5:607-625, 1999). Several EHEC serotypes cause disease, but the 0157 serotype is by far the most common cause of EHEC-related disease in North America, Europe and Japan (Feng, "*Escherichia coli*" in Garcia (ed.) Guide to Foodborne Pathogens. John Wiley and Sons, Inc., pp. 143-162, 2001). See also Waldor et al., U.S. patent publication number 2010/0092511 A1 published Apr. 15, 2012, which is incorporated by reference herein in its entirety.

Shiga toxins are a family of related toxins with two major groups, Stx1 and Stx2 (Friedman et al., 2001 Curr Opin Microbiol 4 (2): 201-7). The toxins are named for Kiyoshi Shiga, who first described the bacterial origin of dysentery caused by *Shigella dysenteriae*. The most common sources for Shiga toxin are the bacteria *S. dysenteriae* and the Shigatoxigenic group of *Escherichia coli* (STEC), which includes serotypes O157:H7, 0104:H4, and other enterohemorrhagic *E. coli*, EHEC (Spears et al. 2006, *FEMS Microbiology Letter* 187-202; Sandvig et al. 2000, *EMBO J* 19 (22): 5943-5950; and Krautz-Peterson et al. 2008, *Infection and Immunity* 76(5) 1931-1939; and Vermeij U.S. Pat. No. 7,807,184 issued Oct. 5, 2010, each of which is incorporated by reference herein in its entirety. Symptoms associated with Shiga toxin-exposure caused infection by EHEC include watery stool followed by severe abdominal pain and bloody stool. Exposed persons develop complications leading to HUS, encephalopathy, and even death (Masuda et al., U.S. Pat. No. 7,345,161 issued Mar. 18, 2008).

Methods for ascertaining the target molecule or disease agent are described herein and depend on the type of molecule being inhibited. For example, in a case in which a class or group of bacteria are to be inhibited, conserved regions of bacteria are targeted, and binding agents that bind to these targets are constructed. Methods for targeting a conserved region or polymorphic region of a nucleotide sequence that encodes the target molecule, or the target molecule having an amino acid sequence are shown in Cicciarelli et al., U.S. patent publication number 2005/0287129 A1 published Dec. 29, 2005 which is incorporated by reference herein in its entirety. In other embodiments, if a specific disease agent such as a bacterium is to be inhibited, a non-conserved region of the disease agent is targeted with the binding agents. The binding of the agents are determined and/or measured for example using standard assays, for example an enzyme-linked immunosorbent assay (ELISA), western blot and radioimmunoassay.

A molecule target or a disease agent target includes pathogenic molecules including polypeptides or toxins to which the binding protein described herein binds, neutralizes and/or clears. The term "pathogenic protein" refers to a protein that can cause, directly or indirectly, a disease, or condition in an individual. A pathogenic protein is for example a protein or a toxin produced by a bacterium, a virus, or a cancer cell. A recombinant multimeric binding protein described herein binds non-overlapping areas of the disease agent target (e.g., a toxin produced by a bacterium) and protects the subject from the pathology of the disease agent target by neutralizing and/or clearing the target. The binding protein protects subjects from negative symptoms caused by exposure to the disease agent target, and the risk of negative symptoms caused by a potential exposure to the target.

Anti-tag antibody described herein is used in various embodiments to effect or facilitate effector functions. The anti-tag antibody includes for example an immunoglobulin such as IgA, IgD, IgE, IgG, and IgM, and subtypes thereof. In addition to monoclonal antibodies, polyclonal antibodies specific to the tag are used in the methods, compositions and kits described herein. Effector functions are performed for example immune molecules interaction with the Fc portion of the immunoglobulin. Depending on the type of immunoglobulin chosen, the effector functions results in clearance of the disease agent (e.g., excretion, degradation, lysis or phagocytosis).

Mammalian antibody types IgA, IgD, IgE, IgG, and IgM, and antibody subtypes are classified according to differences in their heavy chain constant domains. Each immunoglobulin class differs in its biological properties and characteristics. IgA is found for example in areas containing mucus (e.g. in the gut, respiratory tract, and urogenital tract) and prevents the colonization of mucosal areas by pathogens. IgD functions as a disease agent receptor on B cells. IgE binds to allergens and triggers histamine release from mast cells and also provides protection against helminths (worms). IgG, in four forms, provides the majority of antibody-based immunity against invading pathogens. IgM has a very high affinity for eliminating pathogens in the early stages of B cell mediated immunity, and is expressed on the surface of B cells and also in a secreted form.

Leukocytes such as mast cells and phagocytes have specific receptors on the cell surface for binding antibodies. These Fc receptors interact with the Fc region of classes of antibodies (e.g. IgA, IgG, IgE). The engagement of a particular antibody with the Fc receptor on a particular cell triggers the effector function of that cell. For example, phagocytes function to perform phagocytosis, and mast cells function to degranulate. Effector functions generally result in destruction of an invading microbe. In various embodiments, the type of immunoglobulin is chosen specifically for a type of desired effector function.

The present invention includes methods of administering one or more recombinant multimeric binding proteins to a subject (e.g., human, cow, horse, pig, mouse, dog, and cat). The binding protein is administered in certain embodiments as a monomer, or as a multimeric binding protein comprising a plurality of monomers having different binding regions. The methods and compositions herein involve administration of one or more multimeric binding agents that include monomers that each has a binding region that is specific to the disease agent. The binding agent for example includes one or more tags. The binding agent/protein binds to the target region on the disease protein. Administration of two or more binding proteins (e.g., monomer binding proteins or multimeric binding proteins), in various embodiments, increased the effectiveness of the antibody therapy, and reduced the severity of one or more negative symptoms of exposure of the disease protein target. The binding protein is administered in various embodiments as a single monomer, a mixture of multiple (e.g., two or more) monomers, a multimeric binding protein including a plurality of monomers that are same or different, a mixture of multiple (e.g., two or more) multimeric binding proteins comprising more than one monomer, or any combination thereof. Examples herein show that administration of a binding protein containing more than one copy of the tag resulted in increased protection against a disease agent target, e.g., botulinum toxin serotype A. A single anti-tag antibody type in certain embodiments binds to all binding proteins having a tag. In certain embodiments in which the binding proteins have multiple copies (e.g., two or more) of the same tag, the anti-tag antibody binds to each copy of the tag on the binding protein. The phrase, "antibody therapeutic proteins" or "antibody therapeutic preparation" refers to one or more compositions that include at least one binding protein and optionally at least one anti-tag antibody. The multimeric binding protein preparation in certain embodiments contains additional elements including carriers as described herein.

The administration of the one or more binding proteins and/or anti-tag antibody is performed in related embodiments simultaneously or sequentially in time. The binding protein in certain embodiments is administered before, after or at the same time as another binding protein or the anti-tag antibody, providing that the binding proteins and/or the anti-tag antibodies are administered close enough in time to have the desired effect (e.g., before the binding proteins have been cleared by the body). Thus, the term "co-administration" is used herein to mean that the binding proteins and another binding protein or the anti-tag antibody are administered at time points to achieve effective treatment of the disease, and reduction in the level of the pathogen (e.g., virus, bacteria, cancer cell, proteins associated therewith, or combination thereof) and symptoms associated with it. The methods of the present invention are not limited by the amount of time in between which the binding proteins and/or anti-tag antibody are administered; providing that the compositions are administered close enough in time to produce the desired effect. In certain embodiment, the binding proteins is administered only, alternatively the binding protein and/or anti-tag antibody are premixed and administered together. The binding proteins and/or anti-tag antibody are in certain embodiments co-administered with other medications or compositions suitable to treating the disease agent.

The binding protein in certain embodiments is administered prior to the potential risk of exposure to the disease target agent to protect the subjects from symptoms of the disease agent target. For example, the binding protein and/or clearing antibody is administered minutes, hours or days prior to the risk of exposure. Alternatively, the binding protein is administered contemporaneously to the risk of exposure to the disease agent target, or slightly after the risk of exposure. For example, the binding protein is administered to a subject at the moment the subjects contacts, enters or passes through an environment (e.g., room, hallway, building, and field) containing the risk of exposure to the disease agent.

The methods of the present invention include treating a bacterial disease, a parasitic infection, a viral disease, a cancer, small unwanted molecule, a protein or a toxin associated therewith. This is accomplished by administering the binding proteins and anti-tag antibodies described herein to the affected individual or individual at risk. Administration ameliorates or reduces the severity of one or more the symptoms of the disease or condition. The presence, absence or severity of symptoms is measured for example using tests and diagnostic procedures known in the art. Presence, absence and/or level of the disease agent are measured in certain embodiments using methods known in the art. Symptoms or levels of the disease agent can be measured at one or more time points (e.g., before, during and after treatment, or any combination thereof) during the course of treatment to determine if the treatment is effective. A decrease or no change in the level of the disease agent, or severity of symptoms associated therewith indicates that treatment is working, and an increase in the level of the disease agent, or severity of symptoms indicates that treatment is not working. Symptoms and levels of disease agents are measured in various embodiments using methods known in the art. Symptoms that are monitored in certain embodiments include fever, plain including headache, joint pain, muscular pain, difficulty breathing, lethargy, and impaired mobility, appetite and unresponsiveness. Toxin protection is assessed as increased survival and reduction or prevention of symptoms. Methods, compositions and kits using the binding protein decrease and alleviate the symptoms of the disease target agent and also improve survival from exposure to the agent.

The antibody therapeutic agents including one or more binding proteins or agents, and/or an anti-tag antibody are administered in various embodiments with one or more pharmaceutical carriers. The terms "pharmaceutically acceptable carrier" and a "carrier" refer to any generally acceptable excipient or drug delivery device that is relatively inert and non-toxic. The binding agents and anti-tag antibody are administered with or without a carrier. Exemplary carriers include calcium carbonate, sucrose, dextrose, mannose, albumin, starch, cellulose, silica gel, polyethylene glycol (PEG), dried skim milk, rice flour, magnesium stearate, and the like. Suitable formulations and additional carriers are described in Remington's Pharmaceutical Sciences, (17th Ed., Mack Pub. Co., Easton, Pa.), the teachings of which are incorporated herein by reference in their entirety. The binding agents and anti-tag antibody are administered systemically or locally (e.g., by injection or diffusion).

Suitable carriers (e.g., pharmaceutical carriers) include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. The binding protein preparations are sterilized and, if desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. The binding protein preparations in certain embodiments are combined where desired with other active substances, e.g., enzyme inhibitors, to reduce metabolic degradation. A carrier (e.g., a pharmaceutically acceptable carrier) is used optionally in certain embodiments to administer one or more binding agents and an anti-tag antibody.

The binding agents and anti-tag antibodies in certain embodiments are administered topically (as by powders, ointments, or drops), orally, rectally, mucosally, sublingually, parenterally, intracisternally, intravaginally, intraperitoneally, bucally, ocularly, or intranasally, depending on preventive or therapeutic objectives and the severity and nature of a exposure or risk of exposure to the disease agent target. The composition in various embodiments is administered in a single dose or in more than one dose over a period of time to confer the desired effect.

An effective amount of compositions of the present invention varies according to choice of the binding agent, the particular composition formulated, the mode of administration and the age, weight and condition of the patient, for example. As used herein, an effective amount of the binding agents and/or anti-tag antibody is an amount which is capable of reducing one or more symptoms of the disease or conditions caused by the molecule target or disease agent target. Dosages for a particular patient are determined by one of ordinary skill in the art using conventional considerations, (e.g. by means of an appropriate, conventional pharmacological protocol).

A composition in certain embodiments includes one or more nucleotide sequences described herein that encode the binding protein. In various embodiments, a nucleotide sequence is either present as a mixture or in the form of a DNA molecule a multimer. A various embodiments, the composition includes a plurality of nucleotide sequences each encoding the binding protein including a monomer or polypeptide, or any combination of molecules described herein, such that the binding protein is generated in situ. In such compositions, a nucleotide sequence is administered using any of a variety of delivery systems known to those of ordinary skill in the art, including nucleic acid expression systems, bacterial and viral expression systems. Appropriate nucleic acid expression systems contain appropriate nucleotide sequences operably linked for expression in the patient (such as a suitable promoter and terminating signal). Bacterial delivery systems involve administration of a bacterium (such as *Bacillus*-Calmette-Guerrin) that expresses the polypeptide on its cell surface. In an embodiment, the DNA can be introduced using a viral expression system (e.g., vaccinia or other pox virus, retrovirus, or adenovirus), which uses a non-pathogenic (defective), replication competent virus. Techniques for incorporating DNA into such expression systems are well known to those of ordinary skill in the art. The DNA can also be "naked," as described, for example, in Ulmer et al., Science 259:1745-1749, 1993 and reviewed by Cohen, Science 259:1691-1692, 1993. The uptake of naked DNA can be increased by coating the DNA onto biodegradable beads, which are efficiently transported into recipient cells.

Systems or kits of the present invention include in various embodiments one or more binding agents having a binding region and one or more tags, and an anti-tag antibody having an anti-tag region (e.g., an anti-tag antibody), as described herein.

The methods, compositions and kits described herein in certain embodiments include isolated polypeptide molecules that have been engineered or isolated to act as binding agents or binding proteins. A binding protein composition includes for example an amino acid sequence selected from SEQ ID NOs: 2, 4, 6, 8, 10, 12, 14, 20, 22, 24, 26, 28, 30, 32, 34, 36, 38, 40, 42, 44, 46, 48, 50, 52 or combinations thereof. In various embodiments, a binding protein composition includes a nucleotide sequence that encodes an amino acid sequence, for example the nucleotide sequence is selected from SEQ ID NOs: 1, 3, 5, 7, 9, 11, 13, 19, 21, 23, 25, 27, 29, 31, 33, 35, 37, 39, 41, 43, 45, 47, 49, 51 or combinations thereof. The binding protein composition includes for example a tag, for example a tag having an amino acid sequence of SEQ ID NO: 15.

As used herein, the term "polypeptide" encompasses amino acid chains of any length, including full length proteins (i.e., disease agents), in which the amino acid residues are linked by covalent peptide bonds. A polypeptide comprises a portion of the binding agent, the entire binding agent, or contains additional sequences. The polypeptides of the binding agents of the present invention referred to herein as "isolated" are polypeptides that are separated away and purified from other proteins and cellular material of their source of origin. The compositions and methods of the present invention also encompass variants of the above polypeptides and DNA molecules. A polypeptide "variant," as used herein, is a polypeptide that differs from the recited polypeptide by having one or more conservative substitutions and/or modifications, such that the functional ability of the binding agent to bind to the disease agent target is retained.

The present invention also encompasses proteins and polypeptides, variants thereof, or those having amino acid sequences analogous to the amino acid sequences of binding agents described herein. Such polypeptides are defined herein as analogs (e.g., homologues), or mutants or derivatives. "Analogous" or "homologous" amino acid sequences refer to amino acid sequences with sufficient identity of any one of the amino acid sequences of the present invention so as to possess the biological activity (e.g., the ability to bind to the disease agent target). For example, an analog polypeptide can be produced with "silent" changes in the amino acid sequence wherein one, or more, amino acid residues differ from the amino acid residues of any one of the sequence, yet still possesses the function or biological activity of the polypeptide. The binding protein includes for example an amino acid having at least about 60% (e.g., 65%, 70%, 75%, 80%, 85%, 90% or 95%) identity or similarity with SEQ ID NOs: 2, 4, 6, 8, 10, 12, 14, 20, 22, 24, 26, 28, 30, 32, 34, 36, 38, 40, 42, 44, 46, 48, 50, 52, 56-87, 95 or combination thereof. Percent "identity" refers to the amount of identical nucleotides or amino acids between two nucleotides or amino acid sequences, respectfully. As used herein, "percent similarity" refers to the amount of similar amino acids between two amino acid sequences, i.e., having conservative amino acid changes compared to the original sequences, or to the amount of similar nucleotides between two nucleotide sequences.

Referring to FIGS. 4 and 5, by comparing the B5 (SEQ ID NO: 24) polypeptide sequence to the other polypeptide sequences in the chart, the polypeptide sequence similarity is determined as follows: E-9 (SEQ ID NO: 38) is 74% similar, C5 (SEQ ID NO: 42) is 67% similar, B2 (SEQ ID NO: 40) is 68% similar, and F9 (SEQ ID NO: 44) is 73% similar. The BLAST was done using default parameters on the NCBI website. Since these VHHs have been shown to compete with B5, i.e., for binding to the target, the present invention includes those sequences having a sequence similarity of at least about 65%. In like manner, by comparing the B5 (SEQ ID NO: 23) nucleic acid sequence to the other nucleic acid sequences in the chart, the polypeptide sequence similarity is determined as follows: E-9 (SEQ ID NO: 37) is 81% identical, C5 (SEQ ID NO: 41) is 75% identical, B2 (SEQ ID NO: 39) is 86% identical, and F9 (SEQ ID NO: 43) is 80% identical. The present invention includes those nucleic acid sequences having a sequence identity of at least about 75%.

Homologous polypeptides are determined using methods known to those of skill in the art. Initial homology searches are performed at NCBI by comparison to sequences found in the GenBank, EMBL and SwissProt databases using, for example, the BLAST network service. Altschuler, S. F., et al., J. Mol. Biol., 215:403 (1990), Altschuler, S. F., Nucleic Acids Res., 25:3389-3402 (1998). Computer analysis of nucleotide sequences can be performed using the MOTIFS and the FindPatterns subroutines of the Genetics Computing Group (GCG, version 8.0) software. Protein and/or nucleotide comparisons were performed according to Higgins and Sharp (Higgins, D. G. and Sharp, P. M., Gene, 1998 73:237-244, e.g., using default parameters). In certain embodiments, the recombinant multimeric binding protein acid sequence is an amino acid sequence that is substantially identical to sequences described herein, for example any of SEQ ID NOs: 56-87 and 95. The term "substantially identical" is used herein to refer to a first amino acid sequence that contains a sufficient or minimum number of amino acid residues that are identical to aligned amino acid residues in a second amino acid sequence such that the first and second amino acid sequences can have a common structural domain and/or common functional activity. For example, amino acid sequences that contain a common structural domain having at least about 60% identity, or at least 75%, 85%, 95%, 96%, 98%, or 99% identity.

Calculations of sequence identity between sequences are performed as follows. To determine the percent identity of two amino acid sequences, the sequences are aligned for optimal comparison purposes (e.g., gaps can be introduced in one or both of a first and a second amino acid sequence for optimal alignment). The amino acid residues at corresponding amino acid positions or nucleotide positions are then compared. When a position in the first sequence is occupied by the same amino acid residue or nucleotide as the corresponding position in the second sequence, then the proteins are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences are accomplished using a mathematical algorithm. Percent identity between two amino acid sequences is determined using an alignment software program using the default parameters. Suitable programs include, for example, CLUSTAL W by Thompson et al., *Nuc. Acids Research* 22:4673, 1994 (www.ebi.ac.uk/clustalw), BL2SEQ by Tatusova and Madden, *FEMS Microbiol. Lett.* 174:247, 1999 (www.ncbi.nlm.nih.gov/blast/bl2seq/bl2.html), SAGA by Notredame and Higgins, *Nuc. Acids Research* 24:1515, 1996 (igs-server.cnrs-mrs.fr/~cnotred), and DIALIGN by Morgenstern et al., *Bioinformatics* 14:290, 1998 (bibiserv.techfak.uni-bielefeld.de/dialign).

The methods, compositions and kits described herein in various embodiments include nucleotide sequence or an isolated nucleic acid molecule (encoding the binding protein) having a nucleotide sequence of SEQ ID NOs: 1, 3, 5, 7, 9, 11, 13, 19, 21, 23, 25, 27, 29, 31, 33, 35, 37, 39, 41, 43, 45, 47, 49, 51 or combinations thereof. See FIGS. 1, 3 and 4. As used herein, the terms "DNA molecule" or "nucleic acid molecule" include both sense and anti-sense strands, cDNA, genomic DNA, recombinant DNA, RNA, and wholly or partially synthesized nucleic acid molecules. A nucleotide "variant" is a sequence that differs from the recited nucleotide sequence in having one or more nucleotide deletions, substitutions or additions. Such modifications are readily introduced using standard mutagenesis techniques, such as oligonucleotide-directed site-specific mutagenesis as taught, for example, by Adelman et al. (DNA 2:183, 1983). Nucleotide variants are naturally occurring allelic variants, or non-naturally occurring variants. Variant nucleotide sequences in various embodiments exhibit at least about 70%, more preferably at least about 80% and most preferably at least about 90% homology to the recited sequence. Such variant nucleotide sequences hybridize to the recited nucleotide sequence under stringent conditions. In one embodiment, "stringent conditions" refers to prewashing in a solution of 6×SSC, 0.2% SDS; hybridizing at 65° Celsius, 6×SSC, 0.2% SDS overnight; followed by two washes of 30 minutes each in 1×SSC, 0.1% SDS at 65° C., and two washes of 30 minutes each in 0.2×SSC, 0.1% SDS at 65° C.

The present invention also encompasses isolated nucleic acid sequences that encode the binding agents and in particular, those which encode a polypeptide molecule having an amino acid sequence of SEQ ID NOs: 2, 4, 6, 8, 10, 12, 14, 20, 22, 24, 26, 28, 30, 32, 34, 36, 38, 40, 42, 44, 46, 48, 50, 52, 56-87, 95 or combinations thereof.

As used herein, an "isolated" nucleotide sequence is a sequence that is not flanked by nucleotide sequences which in nature flank the gene or nucleotide sequence (e.g., as in genomic sequences) and/or has been completely or partially purified from other transcribed sequences (e.g., as in a cDNA or RNA library). Thus, an isolated gene or nucleotide sequence can include a gene or nucleotide sequence which is synthesized chemically or by recombinant means. Nucleic acid constructs contained in a vector are included in the definition of "isolated" as used herein. Also, isolated nucleotide sequences include recombinant nucleic acid molecules and heterologous host cells, as well as partially or substantially or purified nucleic acid molecules in solution. The nucleic acid sequences of the binding agents of the present invention include homologous nucleic acid sequences. "Analogous" or "homologous" nucleic acid sequences refer to nucleic acid sequences with sufficient identity of any one of the nucleic acid sequences described herein, such that once encoded into polypeptides, they possess the biological activity of any one of the binding agents described herein. In particular, the present invention is directed to nucleic acid molecules having at least about 70% (e.g., 75%, 80%, 85%, 90% or 95%) identity with SEQ ID NOs: 1, 3, 5, 7, 9, 11, 13, 19, 21, 23, 25, 27, 29, 31, 33, 35, 37, 39, 41, 43, 45, 47, 49, 51 or combinations thereof.

Also encompassed by the present invention are nucleic acid sequences, DNA or RNA, which are substantially complementary to the DNA sequences encoding the polypeptides of the present invention, and which specifically hybridize with their DNA sequences under conditions of stringency known to those of skill in the art. As defined herein, substantially complementary means that the nucleotide sequence of the nucleic acid need not reflect the exact sequence of the encoding original sequences, but must be sufficiently similar in sequence to permit hybridization with nucleic acid sequence under high stringency conditions. For example, non-complementary bases can be interspersed in a nucleotide sequence, or the sequences can be longer or shorter than the nucleic acid sequence, provided that the sequence has a sufficient number of bases complementary to the sequence to allow hybridization therewith. Conditions for stringency are described in e.g., Ausubel, F. M., et al., Current Protocols in Molecular Biology, (Current Protocol, 1994), and Brown, et al., Nature, 366:575 (1993); and further defined in conjunction with certain assays.

The invention also provides vectors, plasmids or viruses containing one or more of the nucleic acid molecules having the sequence of SEQ ID NO:1, 3, 5, 7, 9, 11, 13, 19, 21, 23, 25, 27, 29, 31, 33, 35, 37, 39, 41, 43, 45, 47, 49, 51 or combinations thereof). Suitable vectors for use in eukaryotic and prokaryotic cells are known in the art and are commercially available or readily prepared by a skilled artisan. Additional vectors can also be found, for example, in Ausubel, F. M., et al., Current Protocols in Molecular Biology, (Current Protocol, 1994) and Sambrook et al., "Molecular Cloning: A Laboratory Manual," 2nd ED. (1989).

Any of a variety of expression vectors known to those of ordinary skill in the art can be employed to express recombinant polypeptides of this invention. Expression can be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast, insect cells, or a mammalian cell line such as COS or CHO. The DNA sequences expressed in this manner can encode any of the polypeptides described herein including variants thereof. Uses of plasmids, vectors or viruses containing the nucleic acids of the present invention include generation of mRNA or protein in vitro or in vivo. In related embodiments, the methods, compositions and kits encompass host cells transformed with the plasmids, vectors or viruses described above. Nucleic acid molecules can be inserted into a construct which can, optionally, replicate and/or integrate into a recombinant host cell, by known methods. The host cell can be a eukaryote or prokaryote and includes, for example, yeast (such as *Pichia pastoris* or *Saccharomyces cerevisiae*), bacteria (such as *E. coli*, or *Bacillus subtilis*), animal cells or tissue, insect Sf9 cells (such as baculoviruses infected SF9 cells) or mammalian cells (somatic or embryonic cells, Human Embryonic Kidney (HEK) cells, Chinese hamster ovary cells, HeLa cells, human 293 cells and monkey COS-7 cells). Host cells suitable in the present invention also include a mammalian cell, a bacterial cell, a yeast cell, an insect cell, and a plant cell.

The nucleic acid molecule can be incorporated or inserted into the host cell by known methods. Examples of suitable methods of transfecting or transforming cells include calcium phosphate precipitation, electroporation, microinjection, infection, lipofection and direct uptake. "Transformation" or "transfection" as used herein refers to the acquisition of new or altered genetic features by incorporation of additional nucleic acids, e.g., DNA. "Expression" of the genetic information of a host cell is a term of art which refers to the directed transcription of DNA to generate RNA which is translated into a polypeptide. Methods for preparing such recombinant host cells and incorporating nucleic acids are described in more detail in Sambrook et al., "Molecular Cloning: A Laboratory Manual," Second Edition (1989) and Ausubel, et al. "Current Protocols in Molecular Biology," (1992), for example.

The host cell is maintained under suitable conditions for expression and recovery of the polypeptides of the present invention. In certain embodiments, the cells are maintained in a suitable buffer and/or growth medium or nutrient source for growth of the cells and expression of the gene product(s). The growth media are not critical to the invention, are generally known in the art and include sources of carbon, nitrogen and sulfur. Examples include Luria-Bertani broth, Superbroth, Dulbecco's Modified Eagles Media (DMEM), RPMI-1640, M199 and Grace's insect media. The growth media can contain a buffer, the selection of which is not critical to the invention. The pH of the buffered Media can be selected and is generally one tolerated by or optimal for growth for the host cell.

The host cell is maintained under a suitable temperature and atmosphere. Alternatively, the host cell is aerobic and the host cell is maintained under atmospheric conditions or other suitable conditions for growth. The temperature is selected so that the host cell tolerates the process and is for example, between about 13-40° Celsius.

The invention having now been fully described, it is further illustrated by the following claims and by the examples, which are found in a paper published in the Public Library of Science (PLoS) One and entitled, "A Novel Strategy for Development of Recombinant Antitoxin Therapeutics Tested in a Mouse Botulism Model", co-authored by Jean Mukherjee, Jacqueline M. Tremblay, Clinton E. Leysath, Kwasi Ofori, Karen Baldwin, Xiaochuan Feng, Daniela Bedenice, Robert P. Webb, Patrick M. Wright, Leonard A. Smith, Saul Tzipori, and Charles B. Shoemaker (12 pages; Mukherjee J et al. 2012 PLoS ONE 7(1): e29941. doi:

10.1371/journal.pone.0029941). This published paper is hereby incorporated by reference herein in its entirety.

The following examples and claims are illustrative and are not meant to be further limiting. Those skilled in the art will recognize or be able to ascertain using no more than routine experimentation, numerous equivalents to the specific procedures described herein. Such equivalents are within the scope of the present invention and claims. The contents of all references including issued patents and published patent applications cited in this application are hereby incorporated by reference.

EXAMPLES

Example 1. Toxins and Reagents

Botulinum neurotoxin serotype A1 (BoNT/A) and serotype B (BoNT/B) were obtained from Metabiologics Inc. Each batch of toxin was calibrated to establish the $LD_{50}$ dose in mice and stored in aliquots at −80° C. until use. Purified recombinant BoNT serotype A1 and B holotoxins containing mutations rendering them catalytically inactive (ciBoNTA, ciBoNTB) obtained. Sheep anti-BoNT/A1 antiserum was produced by immunization of sheep with BoNT/A1 toxoid followed by BoNT/A1 holotoxin. Less than 1 μl of this sheep antitoxin serum protects mice from lethality when co-administered with 10,000-fold the $LD_{50}$ of BoNT/A1. Reagents for Western blotting were purchased from KPL (Gaithersburg, Maryland).

*C. difficile* holotoxins TcdA and TcdB were generated by transformation of shuttle vectors pHis1522 (pHis-TcdA and pHis-TcdB respectively) into *B. megaterium* described in Yang et al. 2008, *BMC Microbiology* 8:192. Point mutations were introduced into conserved amino acids that are responsible for binding to the substrate, uridine diphosphoglucose (UDP-Glucose), in order to generate GT-deficient holotoxins. To generate GT-mutant holotoxin A, a unique restriction enzyme (BamHI) site was designed and constructed between sequences encoding GT and CPD domains using overlapping PCR. The primer sets used were:

```
pHis-F (5'- TTTGTTTATCCACCGAACTAAG -3'; SEQ ID NO:
90),
Bam-R (5'- TCTTCAGAAAGGGATCCACCAG-3'; SEQ ID NO:
91),
Bam-F (5'- TGGTGGATCCCTTTCTGAAGAC -3'; SEQ ID NO:
92),
and
Bpu-R (5'- ACTGCTCCAGTTTCCCAC -3'; SEQ ID NO: 93).
```

The final PCR product was digested with BsrGI and Bpu10I, and was used to replace the corresponding sequence in pHis-TcdA. The resulting plasmid was designated pH-TxA-b. Sequences encoding triple mutations (W101A, D287N, and W519A) in the GT were synthesized by Geneart (Regensburg, Germany) and cloned into pH-TxA-b through BsrGI/BamHI digestion. To generate the mutant holotoxin B construct, the sequence between BsrGI and NheI containing two point mutations (W102A and D288N) was synthesized and inserted into pHis-TcdB at the same restriction enzyme sites, leading to a new plasmid pH-aTcdB. The mutant aTcdA and aTcdB were expressed and purified identical to the wild types in *B. megaterium* as described by Yang et al. 2008, *BMC Microbiology* 8:192. The purified aTcdA and aTcdB were used to immunize alpacas.

Example 2. Alpaca Immunization and VHH-Display Library Preparation

Purified, catalytically inactive mutant forms of full-length recombinant BoNT/A (ciBoNTA) and BoNT/B (ciBoNTB) proteins were obtained as described in Webb et al. 2009 Vaccine 27: 4490-4497. Alpacas (two animals per immunization type) were immunized with either ciBoNTA or with ciBoNTB. Additional alpacas were immunized with aTcdA or aTcdB. The immunization regimen employed 100 μg of protein in the primary immunization and 50 μg in three subsequent boosting immunizations at three weekly intervals in aluminum hydroxide gel adjuvant in combination with oligodeoxynucleotides containing unmethylated CpG dinucleotides (alum/CpG; Superfos Biosector; Copenhagen, Denmark) adjuvant. Five days following the final boost immunization, blood from each animal was obtained for lymphocyte preparation and VHH-display phage libraries were prepared from the immunized alpacas as previously described (Maass et al. 2007, *Int J Parasitol* 37: 953-962 and Tremblay et al. 2010, *Toxicon.* 56(6): 990-998). Independent clones (greater than $10^6$ total) were prepared from B cells of alpacas successfully immunized with each of the BoNT immunogens.

Example 3. Anti-BoNT VHH Identification and Preparation

The VHH-display phage libraries were panned for binding to ciBoNTA or ciBoNTB targets that were coated onto each well of a 12-well plate. Coating was performed by overnight incubation at 4° C. with one ml of a 5 μg/ml target solution in PBS, followed by washing with PBS and two hours incubation at 37° C. with blocking agent (4% non-fat dried milk powder in PBS). Panning, phage recovery and clone fingerprinting were performed as previously described (Ibid.). Based on phage ELISA signals, a total of 192 VHH clones were identified as strong candidate clones for binding to BoNT/A, and 142 VHH clones were identified as strong positives for binding to BoNT/B respectively. Of the strong positives, 62 unique DNA fingerprints were identified among the VHHs selected for binding to BoNT/A and 32 unique DNA fingerprints were identified for VHHs selected for binding to BoNT/B. DNA sequences of the VHH coding regions were obtained for each phage clone and compared for identifying homologies. Based on these data, twelve of the anti-BoNT/A VHHs and eleven anti-BoNT/B VHHs were identified as unlikely to have common B cell clonal origins and were selected for protein expression. Expression and purification of VHHs in *E. coli* as recombinant thioredoxin (Trx) fusion proteins containing hexahistidine was performed as previously described in Tremblay et al. 2010 Toxicon. 56(6): 990-998. For heterodimers, DNA encoding two different VHHs were joined in frame downstream of Trx and separated by DNA encoding a fifteen amino acid flexible spacer having the amino acid sequence $(GGGGS)_3$. VHHs were expressed with a carboxyl terminal E-tag epitope. Furthermore, a number of VHH expression constructions were engineered to contain a second copy of the E-tag by introducing the coding DNA in frame between the Trx and VHH domains. An example of a Trx fusion to a VHH heterodimer with two E-tags is ciA-H7/ciA-B5(2E) shown in FIG. 13C.

Example 4. VHH Target Binding Competition Analysis

Phage displaying individual VHHs were prepared and titered by phage dilution ELISA for recognition of ciBoNTA or ciBoNTB using HRP/anti-M13 Ab for detection (Maass et al. 2007 Int J Parasitol 37: 953-962). A dilution was selected for each phage preparation that produced a signal near the top of the linear range of the ELISA signal. The selected phage dilution (100 μl) for each VHH-displayed phage preparation were added to 96 well plate that has been coated with ciBoNTA or ciBoNTB and then pre-incubated for 30 minutes with 100 μl of a 10 μg/ml solution containing a purified Trx/VHH fusion protein test agent or control in PBS. After an hour, the wells were washed and phage binding was detected. Test VHHs that reduced target binding of phage-displayed VHHs by less than two-fold compared to controls were considered to recognize distinct epitopes. Positive controls were prepared in which the Trx/VHH competitor contained the same VHH as displayed on phage and typically reduced the ELISA signal detected by greater than 95%.

Example 5. Characterization of VHH Binding Properties

VHHs were tested for binding to native or atoxic mutant BoNT holotoxins by standard ELISA using plates coated with 100 μl of 1 μg/ml protein. VHHs were also tested for recognition of BoNT subunits by ELISA using plates coated with 5 μg/ml purified recombinant BoNT light chain or 1 μg/ml BoNT heavy chain. See Tremblay et al. 2010 Toxicon. 56(6): 990-998. VHHs were also characterized for recognition of subunits by Western blotting on BoNT holotoxin following SDS-PAGE electrophoresis under reducing conditions. VHHs were detected with HRP-anti-E-tag mAb (GE Healthcare) by standard procedures.

Example 6. Kinetic Analysis by Surface Plasmon Resonance

Assays to assess the kinetic parameters of the VHHs were performed using a ProteOn XPR36 Protein Interaction Array System (Bio-Rad, Hercules, CA) after immobilization of ciBoNT/A by amine coupling chemistry using the manufacturer recommended protocol. Briefly, after activation of a GLH chip surface with a mixture of 0.4 M ethyl (dimethylaminopropyl) carbodiimide (EDC) and 0.1 M N-hydroxysulfosuccinimide (sulfo-NHS) injected for 300 s at 30 μL/min, ciBoNT/A was immobilized by passing a 60 μg/mL solution of the protein at pH 5 over the surface for 180 s at 25 L/min. The surface was deactivated with a 30 μL/min injection of 1 M ethanolamine for 300 s. A concentration series for each VHH (between 2.5 nM and 1000 nM, optimized for each antibody fragment) was passed over the surface at 100 μL/min for 60 s, then dissociation was recorded for 600 s or 1200 s. The surface was then regenerated with a 36 s injection of 10 mM glycine, pH 2.0 at 50 μL/min. The running buffer used for these assays was 10 mM Hepes, pH 7.4, 150 mM NaCl, 0.005% Tween-20. Data was evaluated with ProteOn Manager software (version 2.1.2) using the Langmuir interaction model.

Example 7. BoNT Neutralization Assay Using Primary Neurons

Neuronal granule cells from the pooled cerebella of either 7-8 day old Sprague-Dawley rats or 5-7 day old CD-1 mice were harvested (Skaper et al 1979, *Dev Neurosci* 2: 233-237) and cultured in 24 well plates as described by Eubanks et al 2010 ACS Med Chem Lett 1: 268-272. After at least a week of culture the well volumes were adjusted to 0.5 ml containing various VHH dilutions or buffer controls followed immediately by addition of BoNT/A in 0.5 ml to a final 10 pM. After overnight at 37° C., cells were harvested and the extent of SNAP25 cleavage assessed by Western blot as previously described (Eubanks, L. M. et al. 2007 Proc. Natl. Acad. Sci. USA 104: 2602-2607).

Example 8. Mouse Toxin Lethality Assay

Female CD1 mice (Charles River) about 15-17 g each were received from three to five days prior to use. On the day each assay was initiated, mice were weighed and placed into groups in an effort to minimize inter-group weight variation. Appropriate dilutions of the VHH agents were prepared in PBS. BoNT holotoxins were separately prepared in PBS at the desired doses. Amounts (600 μl) of VHH agent and (600 μl) of the toxin were combined and incubated at room temperature for 30-60 minutes. An amount (200 μl) of each mixture was administered by intravenous injection at time point zero to groups of mice (five mice per group). Mice were monitored at least four times per day and assessed for symptoms of toxin exposure and lethality/survival. Moribund mice were euthanized. Time to onset of symptoms and time to death were established for each mouse.

Example 9. Mouse Toxin Lethality Assay with Agents Administered Post-Intoxication Groups of mice were prepared as described in the description of the mouse toxin lethality assay. Subjects were administered 10 $LD_{50}$ of BoNT/A by intraperitoneal injection. At indicated times post-intoxication, mice were administered 200 μl of material (e.g., VHH monomer or VHH heterodimer) in PBS by intravenous injection. Mice were monitored for symptoms of intoxication and death as described herein.

Example 10. Single-Chain Fvs (scFv) that Recognize and Bind BoNT/A

To improve therapies that involve multiple monoclonal antibodies (mAbs) by using small recombinant peptide, protein or polynucleotide agents that have the same binding specificity as the mAbs, each of the recombinant binding agents is produced containing the same epitopic tag. A single mAb that recognizes the epitopic tag is co-administered to patients with the binding agents. The different agents bind to the same targets as the multiple mAbs and the anti-tag mAb binds to these agents through the epitopic tag. This permits delivery of the same therapeutic effect that is achieved with multiple mAb therapy, but requires only a single mAb. If desired, mAbs of different isotypes, or polyclonal anti-tag antibodies, could be used therapeutically to deliver different immune effector activities.

A number of small recombinant protein agents were generated. They were called single-chain Fvs (scFvs) and were observed to recognize botulinum neurotoxin serotype A (BoNT/A). These scFvs are recombinant proteins that represent the antigen combining region of an immunoglobulin. Several anti-BoNT/A scFvs were produced and were purified. Each scFv contains the amino acid sequence (GAPVPYPDPLEPR; SEQ ID NO: 15) near the carboxyl terminus which is an epitopic tag referred to herein as "E-tag." An scFvs (scFv #2) was shown to neutralize BoNT/A in a cell-based toxin assay (IC50~7 nM). A second scFv (scFv #7) had little or no neutralization activity in the assay, and was found to bind to BoNT/A with high affinity (Kd~1 nM).

The scFvs were tested for their ability to protect mice from the botulinum toxin BoNT/A by intravenous administration of the agents and toxin. The two scFvs were administered individually or together, and were given to mouse subjects with and without anti-E-tag mAb by intravenous administration. Each subject was administered a dose of 10 $LD_{50}$ of BoNT/A (i.e., an amount of BoNT/A ten-fold the $LD_{50}$), five mice per group. The results are shown in Table 1.

TABLE 1 scFv administration with and without anti-tag antibody alleviates toxin morbidity

| Agents Administered (dose) | Survival | Observations |
|---|---|---|
| none | 0% | Death in less than a day |
| scFv#2 (20 μg) | 0% | Death delayed about a day |
| scFv#7 (20 μg) | 0% | Death delayed less than a day |
| scFv#2 (20 μg) + anti-E-tag mAb (25 μg) | 100% | Symptoms severe |
| scFv#7 (20 μg) + anti-E-tag mAb (25 μg) | 0% | Death delayed several days |
| scFv#2 (10 μg) + scFv#7 (10 μg) + anti-E-tag mAb (25 μg) | 100% | No symptoms |

The results shown in Table 1 clearly show that a BoNT/A neutralizing scFv (scFv #2) alone did not significantly protect mice from the toxin. Subjects survived (100%) following co-administration of scFV #2 and mAb that recognizes an epitopic tag (E-tag) on the scFv. More importantly, co-administering two scFvs, each with E-tag, and anti-tag mAb dramatically improved the protective effect.

Subjects were administered 10 $LD_{50}$ and lower doses of the scFvs and the anti-E-tag mAb, and were analyzed for percent survival. Further, two additional non-neutralizing anti-BoNT/A scFvs (scFv #3 and scFv #21) were tested in combination with the neutralizing scFv #2. Whether the anti-E-tag mAb would function upon administration at a different site and time than the toxin was also tested.

The results in Table 2 confirm those data herein and further show that the mAb specific for the epitopic tag does not have to be pre-mixed with the scFv containing the epitopic tag to be effective. In fact, doses were administered at different sites and times. Combinations of two scFvs (each with E-tags) and the single anti-E-tag mAb, provided greater protection than with one scFv alone. This synergistic protective effect occurred using different scFvs and was observed at significantly lower doses of the scFvs or mAb than used in the data observed in Table 1.

TABLE 2

Anti-E-tag mAbs administered separately protected subjects from toxin

| Agents Administered (dose) | Survival | Observations |
|---|---|---|
| none | 0% | Death in about a day |
| scFv#2 (10 μg) | 0% | Death delayed about 2 days |
| scFv#2 (10 μg) + anti-E-tag mAb (10 μg) (mAb administered intraperitoneally) | 100% | Symptoms moderate |
| scFv#2 (10 μg) + anti-E-tag mAb (10 μg) | 100% | Symptoms mild |
| scFv#2 (10 μg) + anti-E-tag mAb (2 μg) | 100% | Symptoms mild |
| scFv#2 (2 μg) + anti-E-tag mAb (2 μg) | 100% | Symptoms moderate |
| scFv#2 (5 μg) + scFv#7 (3 μg) + anti-E-tag mAb (10 μg) | 100% | No symptoms |
| scFv#2 (1 μg) + scFv#7 (1 μg) + anti-E-tag mAb (10 μg) | 100% | No symptoms |
| scFv#2 (5 μg) + scFv#3 (4 μg) + anti-E-tag mAb (10 μg) | 100% | No symptoms |
| scFv#2 (5 μg) + scFv#21 (3 μg) + anti-E-tag mAb (10 μg) | 100% | No symptoms |

Examples herein tested whether combinations of three and four scFvs with anti-tag mAb protect subjects from an amount of BoNT/A 100-fold, 1000-fold, or 10,000-fold the $LD_{50}$, i.e., 100 $LD_{50}$ BoNT/A, 1000 $LD_{50}$ BoNT/A or 10,000 $LD_{50}$ BoNT/A.

The data shown in Table 3 demonstrate the excellent potency of a tagged binding agent as an antitoxin. Specifically, completely protection of subjects from even mild symptoms of intoxication by 1,000 $LD_{50}$ was observed using combinations of three or four scFvs with anti-E-tag mAb. Subjects were protected from lethality from a 10,000 $LD_{50}$ dose with a combination of four scFvs, although moderate symptoms were observed. The ability to protect mice receiving up to 10,000 $LD_{50}$ of BoNT/A is equivalent to the highest level of protection reported with pools of different anti-BoNT/A mAbs (Nowakowski et al, Proc Natl Acad Sci USA, 99:11346-50).

TABLE 3

Combinations of scFv protect from 100, 1000, and 10,000 fold $LD_{50}$ BoNT/A doses in presence of 10 μg of anti-E-tag mAb

| BoNT/A | Additional agents administered (dose) | Survival | Observations |
|---|---|---|---|
| 100 $LD_{50}$ | None | 0% | Death in less than a day |
| 100 $LD_{50}$ | scFv#2 (2 μg) + scFv#3 (2 μg) + scFv#21 (2 μg) | 100% | No symptoms |
| 1,000 $LD_{50}$ | None | 0% | Death in less than a day |
| 1,000 $LD_{50}$ | scFv#2 (2 μg) + scFv#3 (2 μg) + scFv#21 (2 μg) | 100% | No symptoms |
| 1,000 $LD_{50}$ | scFv#2 (2 μg) + scFv#3 (2 μg) + scFv#7 (2 μg) + scFv#21 (2 μg) | 100% | No symptoms |

TABLE 3-continued

Combinations of scFv protect from 100, 1000, and 10,000 fold $LD_{50}$ BoNT/A doses in presence of 10 μg of anti-E-tag mAb

| BoNT/A | Additional agents administered (dose) | Survival | Observations |
|---|---|---|---|
| 10,000 $LD_{50}$ | None | 0% | Death in a few hours |
| 10,000 $LD_{50}$ | scFv#2 (2 μg) + scFv#3 (2 μg) + scFv#21 (2 μg) | 0% | Death delayed one day |
| 10,000 $LD_{50}$ | scFv#2 (2 μg) + scFv#3 (2 μg) + scFv#7 (2 μg) + scFv#21 (2 μg) | 100% | Moderate symptoms |

The next example tested efficacy of a binding agent containing two copies of the epitopic tag. The anti-BoNT/A binding agent, scFv #7, was engineered to contain another copy of the E-tag peptide. The E-tag peptide was present on the carboxyl terminus of each scFv. An altered version of scFv #7 (called scFv #7-2E) was engineered to be identical to scFv #7 and to have an additional copy of the E-tag peptide fused to the amino terminus.

TABLE 4

Protection from BoNT/A using scFvs having multiple tag sequences in presence of 10 μg of anti-E-tag mAb

| BoNT/A $LD_{50}$ | Additional agents administered (1 μg each) | Survival | Observations |
|---|---|---|---|
| 100 | None | 0% | Death in less than 6 hours |
| 100 | scFv#2 + scFv#3 + scFv#7 | 100% | No symptoms |
| 100 | scFv#2 + scFv#3 + scFv#7-2E | 100% | No symptoms |
| 1,000 | None | 0% | Death in less than 2 hours |
| 1,000 | scFv#2 + scFv#3 + scFv#7 | 0% | Death delayed 2 days |
| 1,000 | scFv#2 + scFv#3 + scFv#7-2E | 100% | No symptoms |
| 10,000 | None | 0% | Death in less than 2 hours |
| 10,000 | scFv#2 + scFv#3 + scFv#7 | 0% | Death delayed less than a day |
| 10,000 | scFv#2 + scFv#3 + scFv#7-2E | 20% | Death delayed many days |
| 10,000 | scFv#2 + scFv#3 + scFv #21 + scFv#7 | 0% | Death delayed 2 days |
| 10,000 | scFv#2 + scFv#3 + scFv #21 + scFv#7-2E | 100% | Moderate symptoms |

The results in Table 4 demonstrate that the binding agent with two epitope tags dramatically improved the in vivo antitoxin efficacy of the tagged binding agent. With a combination of three scFvs, including scFvs #2, scFvs #3 and scFvs #7 or scFvs #7-2E, clearly the use of scFvs #7-2E was substantially superior in protection of mice to the use of scFvs #7 with only one E-tag. The improvement by presence of two copies of tag was particularly evident in the groups of mice challenged with 1,000 $LD_{50}$. In these groups, the triple combination of scFv #2+scFv #3+scFv #7 was insufficient to allow survival of the mice. When scFv #7 was replaced with scFv #7-2E, all the mice survived without symptoms. Furthermore, use of a pool of scFv #2+scFv #3+scFv #7-2E permitted the survival of one of five mice challenged with 10,000 $LD_{50}$ and delayed the death of the other mice by several days. The equivalent pool with scFv #7 having only one E-tag only delayed death for one day in mice challenged with 10,000 $LD_{50}$. Finally, an identical combination of four scFvs (#2, #3, #21 and #7) in which the efficacy using scFv #7 was compared with scFv #7-2E. Administering only one g of each scFv, the presence of scFv #7 did not result in survival of mice challenged with 10,000 $LD_{50}$, and the same combination the scFv #7-2E was protective. These data show that mice were effectively protected from high doses of toxin by administering a smaller number high affinity binding agents, each containing two or more epitope tags together with an anti-tag mAb.

The method herein improves therapeutic agent flexibility, provides highly stable binding agents with long shelf life, substantially reduces the cost of production, and permits commercially feasible therapeutic applications that involve multiple target agents. Furthermore, the strategy herein will permit much more rapid development of new antitoxins. The binding agents are much more quickly developed to commercialization than mAbs. The single anti-tag mAb needed for co-administration is the same for therapies requiring different tagged binding agents and thus can be pre-selected for its commercial scale up properties and stockpiled in advance of the development of the binding agents.

An immediate application is in anti-toxin therapy, an area of high interest because of bioterrorist threats. For example, it is now thought that effective prevention of botulinum intoxication using toxin neutralizing mAbs will require administration of three different mAbs each targeting the same toxin. Since there are at least seven different botulinum toxins, this suggests that 21 different mAbs (or more) may need to be stockpiled for use in the event of a major botulism outbreak as might occur through bioterror. Monoclonal antibodies are very expensive to produce and have relatively short shelf lives. Methods and compositions herein would make it possible to produce 21 different recombinant binding agents, each having longer shelf-life and lower production costs, and then stockpile only a single mAb. It is possible that this approach could open up many other mAb therapeutic strategies that involve multiple binding targets, but which have not been pursued because of prohibitive development and production costs and poor product shelf life. Methods and compositions herein permit the use of mAbs of different antibody isotypes to be used with the same binding agents to provide greater therapeutic flexibility.

Example 11: BoNT/a VHHs Binding Agents

VHH binding agents were identified, produced and purified that were specific to each of botulinum neurotoxin serotype A (BoNT/A) and serotype B (BoNT/B). The VHHs made herein included nine amino acids at the amino coding end and which are associated with the forward PCR primer sequence. See FIGS. 3A, 3A-1, 3B and 3C for the sequences. These sequences derive from 'framework 1' and include minor variants of the original coding sequence. The most common amino acid sequence is QVQLVESGG (SEQ ID NO: 16) and which is the amino acid sequence used in assays shown in FIGS. 3A, 3A-1, 3B and 3C.

At the carboxyl coding end of the VHHs either amino sequence, AHHSEDPS (SEQ ID NO: 17), or the amino sequence, EPKTPKPQ (SEQ ID NO: 18) is located, present in the VHHs sequence as shown in FIGS. 3A, 3A-1, 3B and 3C, and these were observed to be interchangeable without loss of function. Identical clones were identified from alpacas that vary only in the hinge sequence and retain virtually the same target binding function. See also, D. R. Maass et al. 2007 Journal of Immunological Methods 324: 13-25.

As a result of the altered splicing, the amino acid sequence that joins the VH domain to the $CH_2$ domain in heavy chain IgGs is called the "hinge" region, and is unique to this class of camelid antibodies (See D. R. Maass et al. 2007 Journal of Immunological Methods 324:13-25 which is incorporated by reference in its entirety). The two distinct hinge sequence types found in camels and llamas are referred to as the "short" hinge and the "long" hinge respectively. SEQ ID NO: 17 is a short hinge sequence derived from a camel, and SEQ ID NO: 18 is a long hinge sequence derived from a llama.

During screening for VHH binding agents, different coding sequences are identified that display significant homology among randomly identified clones. VHH sequences that are homologous are predicted to be related and thus to recognize the same epitope on the target to which they have been shown to bind. Examples herein experimentally demonstrate epitope recognition by methods for binding competition. These findings demonstrate that significant variation is permitted in VHH amino acid sequences without loss of target binding. An example of the extent of variation permitted is shown in FIG. 4A-B. Each VHH identified in FIGS. 4A-4B as a BoNT/A binder was experimentally observed to bind to the same epitope as JDQ-B5 based on binding competition assays.

FIG. 5 shows a phylogenetic tree that compares the homology among BoNT/A binding VHHs within the JDQ-B5 competition group to random alpaca VHHs. The homology comparison uses the unique amino acids that are present between the forward PCR primer sequences and the hinge region (above). The distance of the lines is a measure of homology; the shorter the distance separating two VHHs, the more homologous. Four VHHs that bind to the same epitope as JDQ-B5 cluster within a group that is distinct from the random VHHs as shown, strong evidence of relatedness of these clones. The results show that substantial variation in the VHH sequence is tolerated without loss of the target binding capability.

Figure 6:
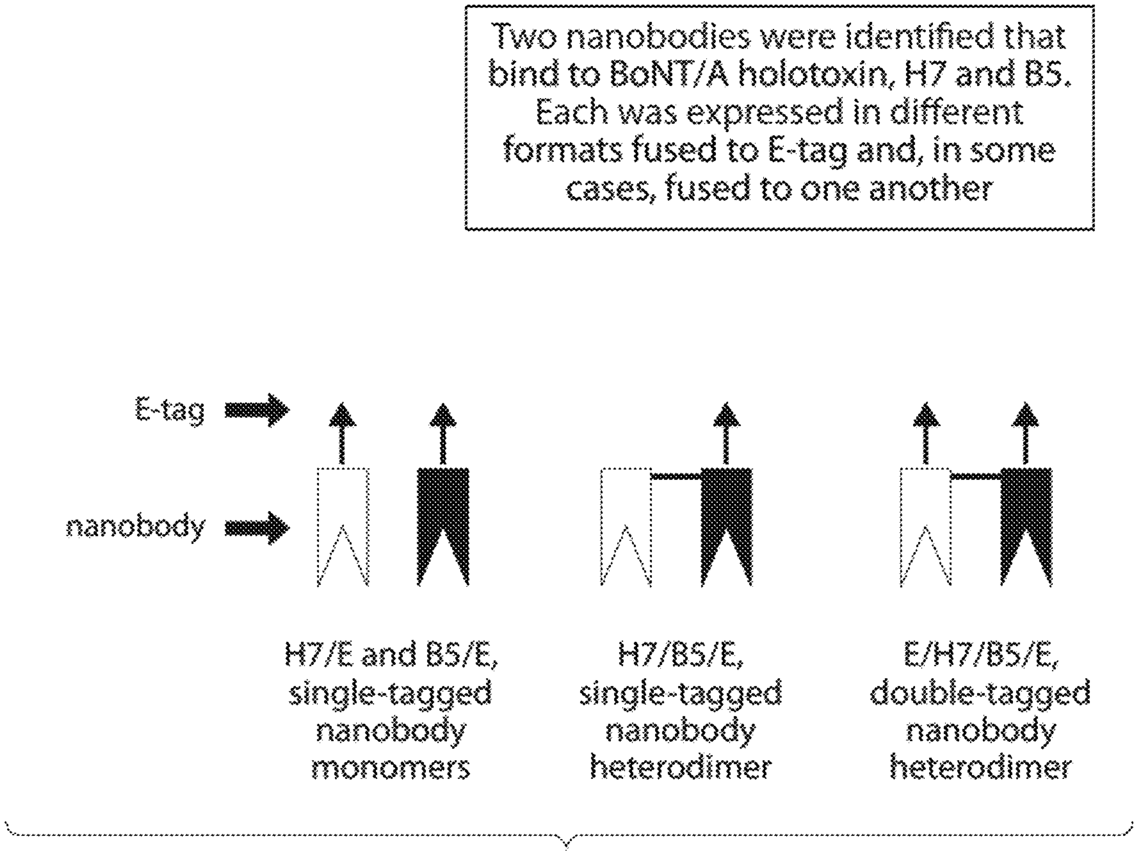
FIG. 6 is a schematic drawing of binding agent VHHs that are produced in different formats including formats in which the binding agents are fused to one or more E-tags or as fusion proteins.

The coding DNAs for two different VHH monomers were cloned in an *E. coli* expression vector in several different ways to produce different recombinant proteins. To produce single VHH monomers, the VHH coding DNA was inserted into the plasmid pET32b to fuse the VHH in frame with an amino terminal bacterial thioredoxin and a carboxyl terminal epitopic tag (E-tag GAPVPYPDPLEPR; SEQ ID NO: 15). Additional coding DNA deriving from the pET32b expression vector DNA was also present between the thioredoxin and VHH coding sequences, the DNA encoding six histidines (to facilitate purification) and an enterokinase cleavage site, DDDDK (SEQ ID NO: 96) to permit enzymatic separation of thioredoxin from the VHH. The resulting expression vectors were used for expression of VHH monomers. VHH monomers JDQ-H7 (SEQ ID NO: 32, referred to as "H7) and JDQ-B5 (SEQ ID NO: 24, referred to as "B5") were expressed using this system (FIG. 6). A representation of the two monomer VHH proteins produced by these expression vectors, labeled H7/E and B5/E, is shown in FIG. 10A.

Expression vectors were prepared in pET32b in which DNA encoding two iterations of the VHH monomer (e.g., SEQ ID NOs: 46 and 48) was present, and the monomers joined in frame to yield heterodimers. For these constructions, the two nucleic acid sequences encoding the VHHs were separated by a nucleotide sequence encoding a 15 amino acid linker, SEQ ID NO: 55, which provides a flexible spacer (fs) between the expressed VHH proteins to separate the domains and facilitate independent folding. The E-tag coding DNA followed the second VHH coding DNA (SEQ ID NO: 49) in frame to obtain a single-tagged VHH heterodimer H7B5/E (SEQ ID NO: 50), the expression of which is shown in FIG. 10B. A second copy of the E-tag coding DNA (e.g., SEQ ID NO: 51) was included upstream of the first VHH (at the amino coding end) for expression of a double-tagged VHH heterodimer E/H7/B5/E (SEQ ID NO: 52) shown in FIG. 10B.

The thioredoxin fusion partner was included to improve expression and folding of the VHHs, and was observed as not necessary for VHH function. The activity of the VHH agents to protect mice from BoNT/A intoxication in mouse lethality assays was tested using VHH agents in which thioredoxin was cleaved (by enterokinase) from the VHH. It was observed that absence of thioredoxin caused no significant reduction in activity.

Figure 7:
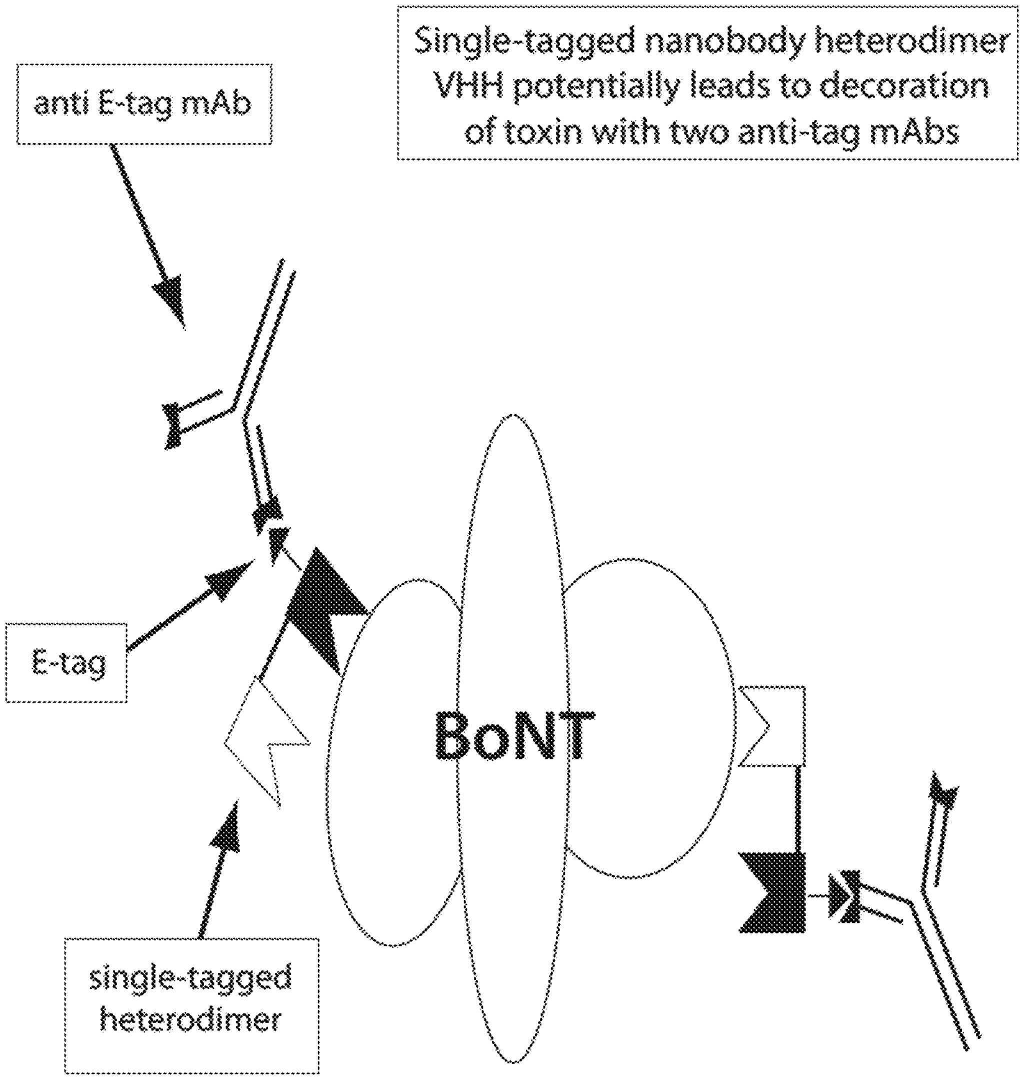
FIG. 7 is a drawing of a single-tagged heterodimeric binding protein (exemplary VHHs) binding to the disease agent, a toxin, and leading to decoration of the toxin with two anti-tag monoclonal antibodies (mAbs).
Figure 8:
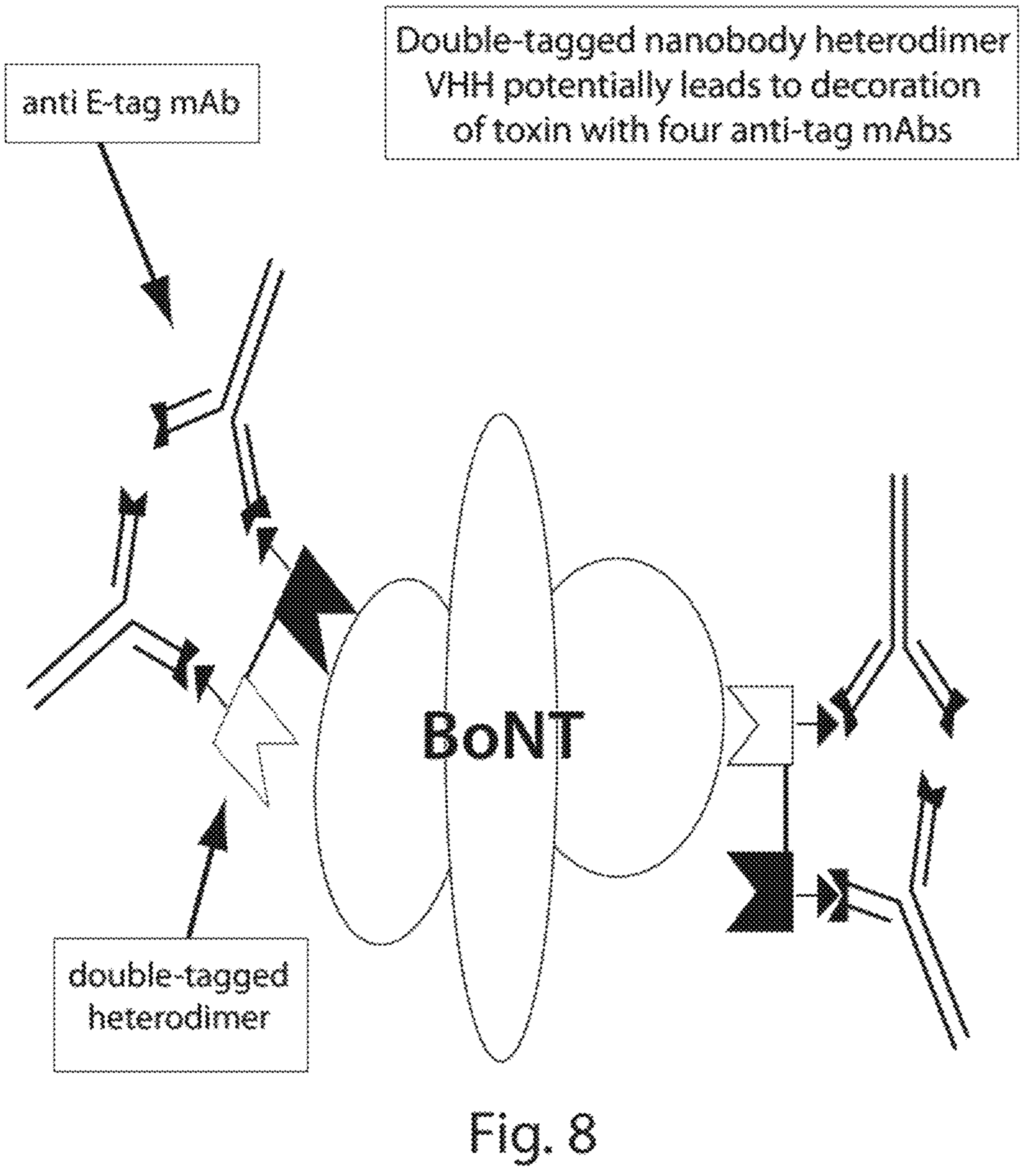
FIG. 8 is a drawing of a double-tagged binding protein (here shown are VHHs) a heterodimeric binding to the disease agent, toxin, and leading to decoration of the toxin with four anti-tag mAbs.

A single-tagged heterodimer VHH was predicted to lead to decoration of the BoNT toxin by the anti E-Tag mAb in a ratio of 1:1. Accordingly, a single-tagged heterodimer was expected to bind at two sites on the toxin and lead to decoration of the toxin with two anti E-tag antibodies (see FIG. 7). A double-tagged heterodimer provides for binding of the anti E-tag antibody in a ratio of 2:1 and thus should bind at two sites on the toxin and lead to decoration of the toxin with four anti-tag antibodies (see FIG. 8). These agents were tested for their ability to protect mice from BoNT/A toxin.

For these examples, the VHH agents and the toxin were pre-mixed and then intravenously administered to groups of five subjects (mice) per group. The subjects were monitored and the time to death was noted for those that succumbed to the toxin. In the results shown in FIG. 9A, a pool of two VHH monomers, H7/E and B5/E (1 μg of each monomer per subject), in the presence of anti-E-tag mAb (Phadia, Sweden) (5 μg/mouse) delayed death only about one day in mice exposed to 1,000 $LD_{50}$ of BoNT/A. The single-tagged VHH heterodimer, H7/B5/E (2 μg/mouse) in the presence of anti-E-tag mAb (5 μg/mouse) delayed death by about a day and a half in mice exposed to 1,000 $LD_{50}$ of BoNT/A.

Figure 9B:
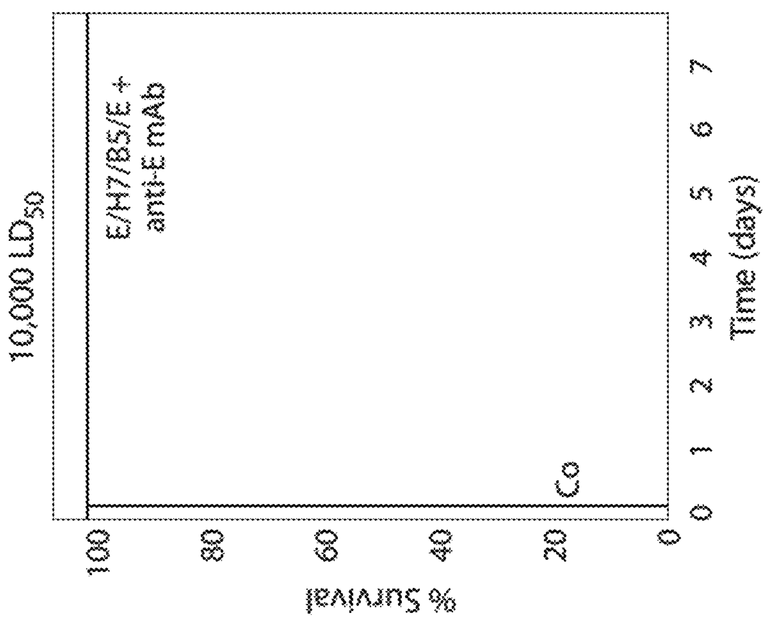
FIGS. 9A-9B are a set of Meyer-Kaplan survival plots that double-tagged heterodimer E/H7/B5/E and the anti-tag mAb completely protected subjects from 1,000-fold and 1,000-fold the median lethal dose of a Botulinum neurotoxin serotype A toxin.
Figure 9A:
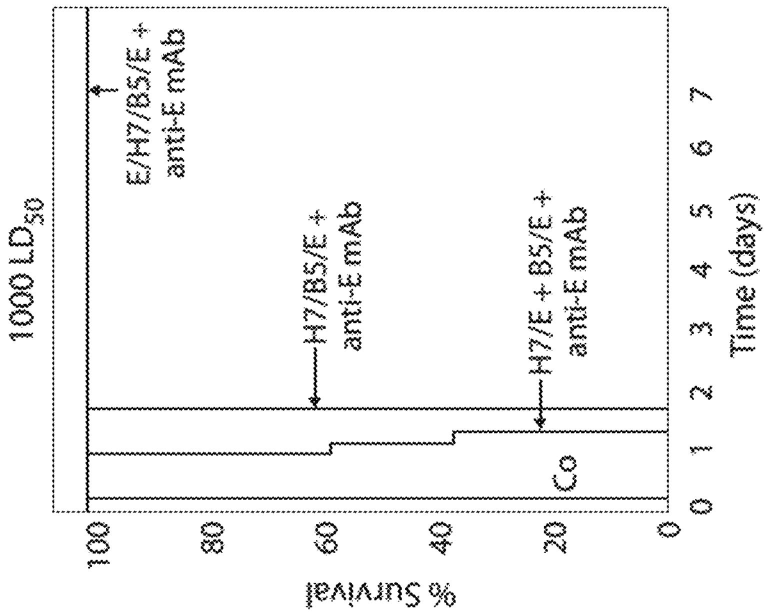

In contrast, it was observed that the double-tagged heterodimer, E/H7/B5/E (2 μg/mouse) administered with anti-E-tag mAb resulted in full survival of mice exposed to 1,000 $LD_{50}$ and even 10,000 $LD_{50}$ of BoNT/A (FIG. 9B). Mice given the double-tagged VHH heterodimer, E/H7/B5/E, in the absence of co-administered anti-E-tag mAb, did not survive a 1,000 $LD_{50}$ amount of BoNT/E, showing that the anti-tag mAb was necessary for full efficacy. The ability of the double-tagged VHH heterodimer, E/H7/B5/E, administered with anti-E-tag mAb to protect mice against 10,000 $LD_{50}$ demonstrates that this treatment achieved a level of efficacy similar to that obtained with a commercial polyclonal antitoxin sera.

In other examples, the BoNT/A-binding VHH heterodimer agents were tested for their ability to prevent death in subjects previously exposed to BoNT/A. In these examples, groups of five subjects were first exposed to 10 $LD_{50}$ BoNT/A. Then, after 1.5 or three hours from exposure, mice were treated either with the E/H7/B5/E heterodimer agent (2 μg/subject) administered with anti-E-tag mAb (5 μg/subject), or with a dose of potent polyclonal anti-BoNT/A sera that had been prepared in sheep. This sera had been previously shown to protect subjects against 10,000 $LD_{50}$ of BoNT/A when it was co-administered with the toxin (assays performed as in previous paragraph). All subjects were monitored and the time to death was determined for non-survivors. Control subjects (2 groups of five each) died within about a day. All subjects treated with polyclonal antisera 1.5 hour post-intoxication (five) survived, and four of five subjects treated three hours post-exposure both 1.5 hours and three hours post-intoxication survived. Five out of five subjects treated with the VHH heterodimer and anti-E-tag mAb both 1.5 hours and three hours post-exposure survived. Thus the VHH heterodimer and anti-E-tag treatment was at least as effective as conventional polyclonal antitoxins at protecting subjects from BoNT exposure in the more clinically relevant post-exposure challenge model.

Example 12. Neutralization of Botulinum Neurotoxin Using VHH Binding Proteins Examples herein show that scFv antitoxin compositions prevent development of disease symptoms in subjects exposed to a botulinum toxin. These antitoxin agents were antibodies that bound the toxin and neutralized the activity of the toxin and/or promoted rapid clearance from the body. Data show that effective neutralization was achieved using a mixture of two high-affinity toxin VHH binding agents, each of which strongly neutralized toxin in cell-based assays. Administration of a multimeric composition was much more effective at protecting subjects from toxin than a pool of two neutralizing monomer binding agents only.

Camelid heavy chain only Vh domain (VHH) binding agents with high affinity for Botulinum neurotoxin serotype A (BoNT/A) were produced including H7 (SEQ ID NO: 56), B5 (SEQ ID NO: 57). Methods of generating VHH binding agents are shown in Shoemaker et al., Application U.S. Ser. No. 12/032,744, published as US Application No. 2010/0278830 A1 on Nov. 4, 2010, and Shoemaker et al., Application U.S. Ser. No. 12/899,511, published as US Application No. 2011/0129474 A1 on Jun. 2, 2011, each of which is incorporated herein by reference in its entirety.

Figures 11A, 11B:
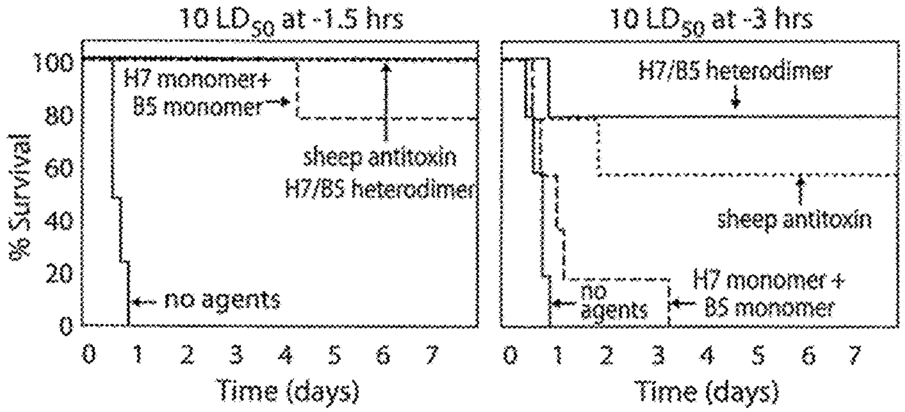
FIGS. 11A-11B are Meyer-Kaplan survival plots showing percent survival (% survival, ordinate) of subjects as a function of time in days (abscissa) following contact with BoNT/A and administration of VHH binding/neutralizing agents at a later time (1.5 hours or three hours later). Subjects (five per group) were intravenously exposed to 10 $LD_{50}$ (ten-fold $LD_{50}$) of BoNT/A, and then later administered either: a mixture of 1 μg ciA-H7 monomer (SEQ ID NO: 32) and 1 μg of ciA-B5 monomer (SEQ ID NO: 24); H7/B5 heterodimeric protein (SEQ ID NO: 58); a sheep antitoxin serum; or control (no binding agent). Data show that the H7/B5 heterodimer was effective as an antitoxin neutralizing agent and protected subjects from the lethal challenge of BoNT/A.

VHHs (H7, B5 and C2) displayed potent BoNT/A neutralization activity in assays of exposure or intoxication of primary neurons in culture. The H7 VHH and B5 VHH monomers were expressed in *E. coli* and a single heterodimeric polypeptide (H7/B5) was constructed and expressed with the H7 and B5 VHH domains/subunits separated by a fifteen amino acid flexible spacer having three repeats of amino acid sequence GGGGS (SEQ ID NO: 55). A combination of the H7 monomer binding agent and B5 monomer binding, and a H7/B5 single chain heterodimer binding agent were tested to determine ability to protect mouse subjects from death caused by BoNT/A. The subjects received ten-fold the lethal dose of BoNT/A that causes death in 50% of mice (10 $LD_{50}$), and either 1.5 hours or three hours later were administered either: 1 micrograms (pg) of H7 binding agent; a sheep antitoxin serum produced against BoNT/A; 1 μg of B5 monomer binding agent; or 2 μg of H7/B5 single chain heterodimer binding agent (FIGS. 11A-11B). The amount of sheep antitoxin serum administered was equivalent to the amount of commercial antitoxin serum generally administered.

Data show that subjects administered a combination of monomeric H7 and B5 binding agents died within three days. Control subjects administered no therapeutic agent died within one day (FIGS. 11A-11B). Subjects administered the sheep antitoxin serum survived at 80%. Most important, subjects administered H7/B5 single chain heterodimer binding agent survived additional days compared to the control subjects, with 80% of subjects administered H7/B5 heterodimer binding agent surviving for seven days.

Figure 12A:
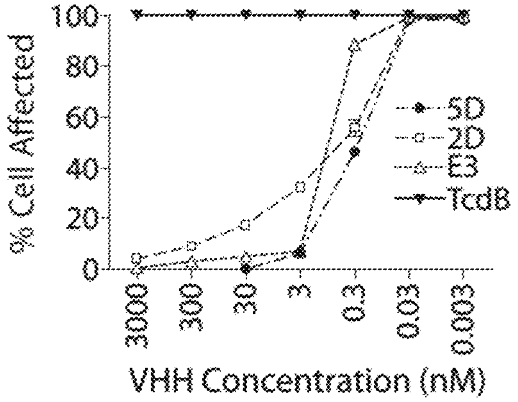
FIGS. 12A-12C are line graphs showing that VHH monomers and VHH heterodimers neutralized *C. difficile* toxin b (TcdB) and protected subjects from death caused by exposure to TcdB.

Example 13. Neutralization of *C. difficile* Toxins Using Heteromultimer Binding Agents A set of VHH binding agents that bind *Clostridium difficile* toxin B (TcdB) was obtained and shown in Examples herein to inhibit the ability of the toxin to intoxicate or infect cells (FIG. 12A). Potent anti-TcdB neutralizing VHHs were selected, identified by codes names 5D and E3, and were expressed as separate monomers or as a heterodimer. A pool/mixture of VHH monomers, 5D and E3, was compared in for ability to prevent TcdB lethality to cells to the 5D/E3 heterodimer.

CT26 cells were exposed to TcdB (100 picograms/ml) in the presence of different concentrations (0.03 nM, 0.1 nM, 0.3 nM, 1 nM, 3 nM, 10 nM, or 30 nM) of: a mixture of 5D VHH monomer (SEQ ID NO: 67) and E3 VHH monomer (SEQ ID NO: 68), or a 5D/E3 heterodimer (SEQ ID NO: 87). Control cells were not administered neutralizing agents. Cell rounding caused by TcdB was monitored using a phase-contrast microscope.

Culture media from expressing cells were administered with either the mixture of 5D and E3 VHH monomers, or the 5D/E3 VHH heterodimer were found to be effective in protecting the cells from TcdB associated cell rounding. Control cells (100%) showed cell rounding and negative indicia of TcdB following toxin exposure.

Figure 12B:
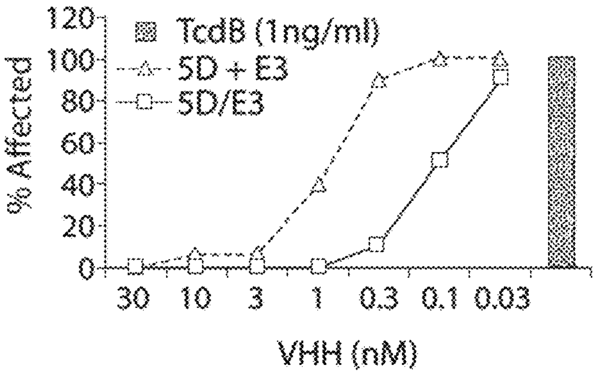

It was observed that administering 0.1 nM 5D/E3 heterodimer to subjects prior to TcdB exposure resulted in 50% cell rounding (i.e., 50% TcdB infection; FIG. 12B). The same level of cell rounding protection (50%), was achieved with 1 nM of the mixture of 5D and E3 monomers. Thus, the 5D/E3 VHH heterodimer was observed to be about ten-fold more potent as a toxin neutralizing agent than a pool containing the same two VHHs as monomers (FIG. 12B).

The improved antitoxin and protective potency 5D/E3 heterodimer was further analyzed using an in vivo toxin challenge mouse model. Subjects were co-administered a lethal dose of TcdB (1 ng/mL) with either a mixture of 500 nanograms (ng) of 5D monomer and 500 ng E3 VHH monomer; or with 250 ng of 5D/E3 VHH heterodimer; or with phosphate buffered saline, PBS. See FIG. 12C. Data show that each of the VHH binding agents was a more effective TcdB neutralizing agent for subjects than the PBS control. Survival was observed at 100% for subjects administered 5D/E3 VHH heterodimer (250 ng) and at about 40% for subjects administered a mixture of 5D and E3 VHH monomers. Control subjects receiving PBS survived at a rate of 20%.

Figure 12C:
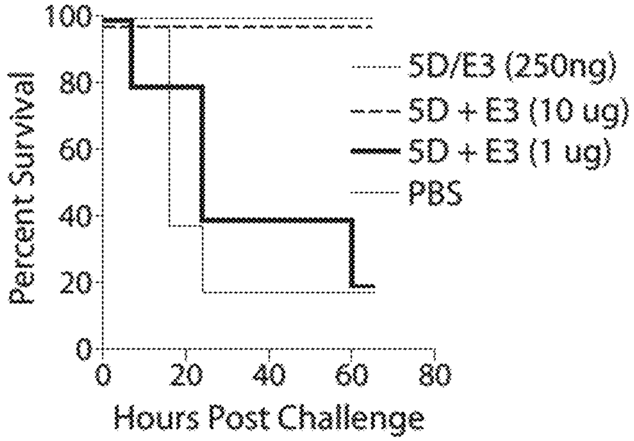

Data show that subjects administered a mixture of 5D and E3 monomers survived for fewer days and were less protected from a lethal TcdB challenge than subjects administered the 5D/E3 heterodimer (FIG. 12C). Most important, the improved protection and neutralizing ability of the 5D/E3 heterodimers was observed even if the amount of heterodimer administered was 75% less than the amount of the mixture of 5D and E3 monomers. Further analysis was performed in Examples below to determine the relative factors for VHH monomers and heterodimers to effectively neutralize and clear disease agent targets from the body (FIGS. 12A-12C).

Example 14. Identification and Characterization of Anti-BoNT VHHs

Serum clearance of Botulinum neurotoxin serotype A (BoNT/A) was dramatically accelerated by administering a pool of different epitopically-tagged single-chain Ig variable fragment (scFv) domain binding agents with an anti-tag monoclonal antibody (Shoemaker et al., Application U.S. Ser. No. 12/032,744, published as Application No. 2010/0278830 A1 on Nov. 4, 2010; Shoemaker et al., Application U.S. Ser. No. 12/899,511, published as Application No. 2011/0129474 A1 on Jun. 2, 2011; Sepulveda et al. 2009 Infect Immun 78: 756-763, and Tremblay et al. 2010 Toxicon. 56(6): 990-998, each of which is incorporated herein in its entirety).

To determine whether a more commercially and clinically acceptable binding agent than scFvs could be identified, a panel of camelid heavy-chain-only Vh (VHH) binding agents having high affinity for epitopes of BoNT/A holotoxin was produced. VHHs were obtained that bound to an epitope of a distinct BoNT serotype, BoNT/B holotoxin, and these VHHs were tested for antitoxin efficacy. Competition ELISAs were performed to identify the VHHs with the highest affinity for unique epitopes on BoNT/A and BoNT/B. VHHs specific for each of BoNT/A (FIG. 13A) and for BoNT/B (FIG. 13B) were identified.

The VHHs in FIG. 13A-13B include amino acid sequence QLQLVE (SEQ ID NO: 88) and QVQLVE (SEQ ID NO: 89) at the amino terminus region. The sequence was encoded by the PCR primer used to generate the VHH-display library (Maass et al. 2007 Int J Parasitol 37: 953-962). The eight amino acids shown at the carboxy-terminus end were encoded by the short hinge or long hinge PCR primers that were used to generate the VHH library.

The amino acid sequences for double-tagged VHH heterodimer antitoxins that specifically bind BoNT/A: ciA-H7/ciA-B5(2E) and ciA-F12/ciA-D12(2E) are shown in FIG. 13C. Each heterodimer included two VHH monomers and two epitopic tags. The amino acid sequences of the tags within the amino acid sequences of the heterodimers are underlined (FIG. 13C). The amino acid sequence preceding the first E-tag in each VHH protein contained the thioredoxin fusion partner and hexahistidine encoded by the pET32b expression vector. The VHH sequences were flanked by the two E-tag peptides and were separated by the unstructured spacer having amino acid sequence $(GGGGS)_3$, SEQ ID NO: 55.

Figure 14A:
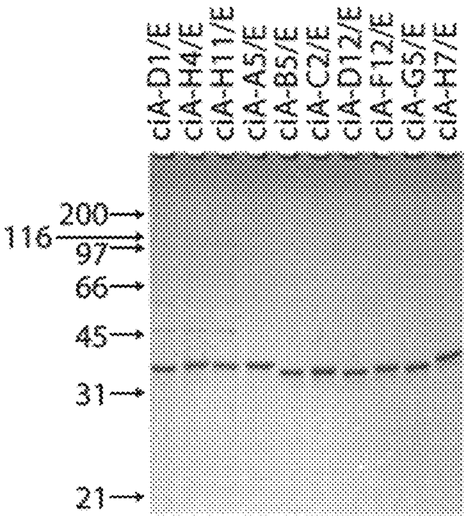
FIGS. 14A and 14B are photographs of sodium dodecyl sulfate polyacrylamide gel electrophoresis (SDS-PAGE) analyses of VHH monomers and VHH heterodimers.
Figure 14B:
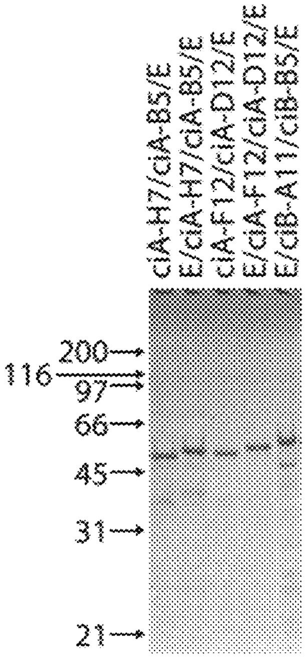

Each VHH was purified from *E. coli* as a thioredoxin fusion protein containing a single carboxyl-terminal epitopic tag (E-tag). Sodium dodecyl sulfate polyacrylamide gel electrophoresis (SDS-PAGE) analyses of VHH monomers and VHH heterodimers was performed (FIG. 14A-14B). The channels were loaded with one microgram (pg) of each VHH monomer or heterodimer. Molecular weight markers (12, 31, 45, 66, 97, 116 and 200 kilodaltons) are shown on the border of each gel. FIG. 14A shows SDS-PAGE analysis of the tagged (E) VHH monomers: ciA-D1, ciA-H4, ciA-H11, ciA-A5, ciA-C2, ciA-D12, ciA-F12, ciA-G5, and ciA-H7. Dark bands were observed at approximately 35-38 kilodalton molecular weight for all single tagged VHH monomers. Channels loaded with ciA-D1, ciA-H4, ciA-H11, and ciA-B5 showed light bands at about 45-46 kilodaltons (kDa), and at about 59 kDa to about 62 kDa molecular weight. SDS-PAGE analysis was performed also on single- or double-tagged VHH heterodimers: ciA-H7/ciA-B5 singly tagged on ciA-B5; double tagged ciA-H7/ciA-B5 having a tag on both ciA/H7 and ciA-B5, ciA-F12/ciA-D12 singly tagged on ciA-B5; double tagged ciA-F12/ciA-D12 having a tag on both ciA/F12 and ciA-D12, double tagged ciA-A11/ciA-B5 having a tag on both ciA/A11 and ciA-B5 (FIG. 14B). Strong dark bands at about 48 kDa to about 58 kDa molecular weight were observed for each heterodimer (FIG. 14B).

The unique BoNT/A binding VHHs were further characterized and analyzed for ability to affinity target BoNT/A using surface plasmon resonance (SPR) in which a lower Kd indicates stronger binding/affinity between the VHH and the toxin target. Analysis was performed also to determine the ability of the BoNT/A binding VHHs to prevent intoxication of primary neurons in culture (FIG. 15 and Table 5).

Neuronal granule cells from pooled cerebella of seven day old to eight day old Sprague-Dawley rats or five day old to seven day old CD-1 mice were harvested as described by Skaper et al 1979, *Dev Neurosci* 2:233-237. The cells were then cultured in 24-well plates as described by Eubanks et al 2010, *ACS Med Chem Lett* 1: 268-272. After a week or more of culture, each culture well was adjusted to a volume of 0.5 ml with dilutions of VHHs (ciA-H7, ciA-B5, ciA-C2, ciA-D12, ciA-F12, ciA-A5 or ciA-G5) or a buffer control, and BoNT/A (ten picomoles) was added. After overnight incubation at 37° C., cells were harvested and the extent of synaptosomal-associated protein 25 (SNAP25) cleavage was determined by Western blot using commercially available rabbit anti-SNAP25 (Sigma). See FIG. 15. SNAP-25 is a membrane bound protein anchored to the cytosolic face of membranes by palmitoyl side chains within the molecule that is involved in the regulation of neurotransmitter release. Botulinum toxin serotypes including serotypes A, C and E function to cleave SNAP-25, resulting in paralysis and clinically developed botulism.

Figure 15:
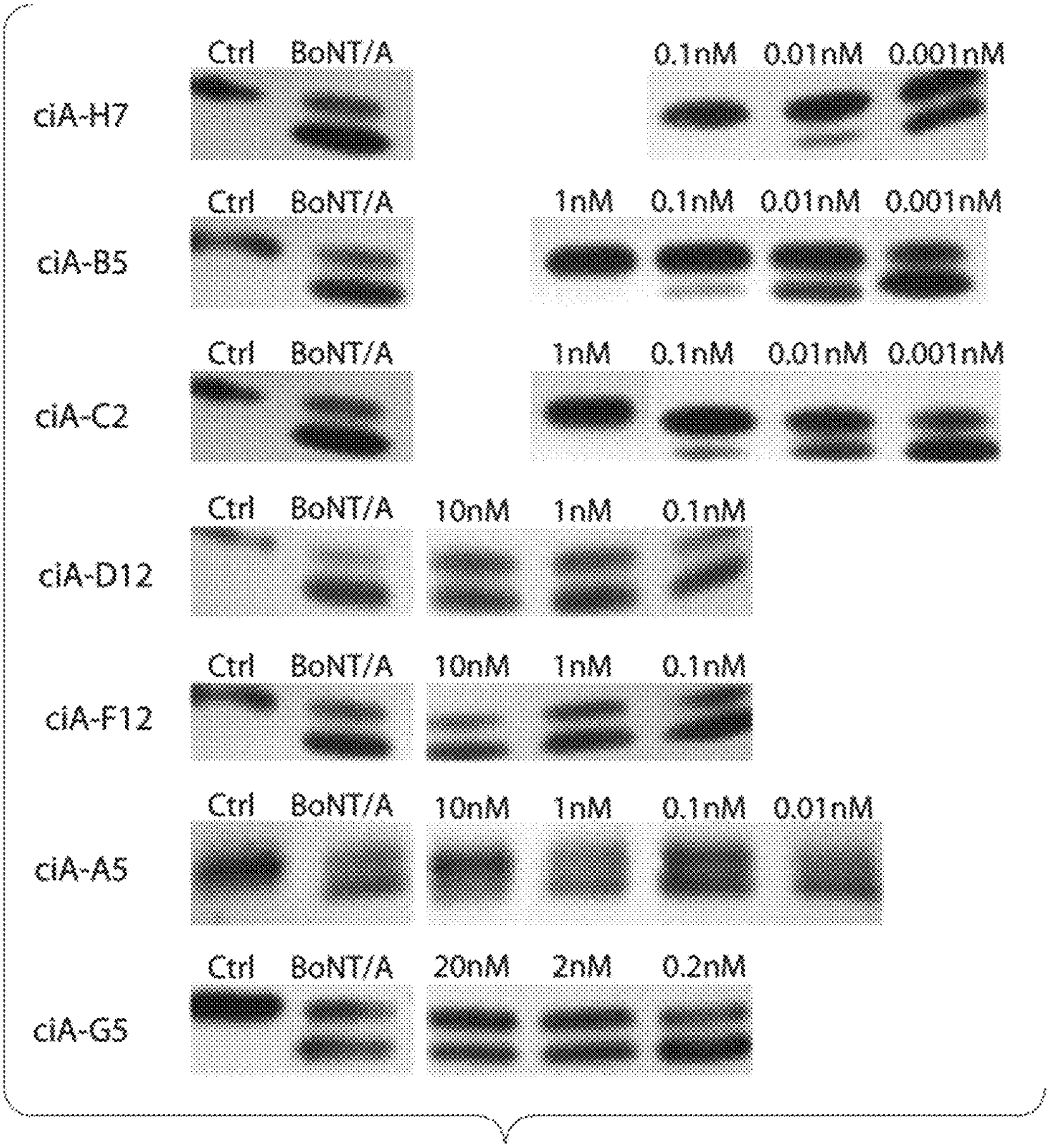
FIG. 15 presents photographs of Western blots showing ability of VHH monomers to prevent BoNT/A from cleaving synaptosomal-associated protein 25 (SNAP25) in primary neurons in culture.

The upper band shown in the Western blot photographs is uncleaved SNAP25, and the lower band indicates cleaved SNAP25 (FIG. 15). SNAP25 cleavage (i.e., presence of a lower band) resulting from exposure to botulinum toxin was observed. VHHs were identified by the criterion that at concentrations of less than 0.1 nanomoles (nM) were observed to inhibit BoNT/A cleavage of SNAP25 (i.e., no lower band), are strong neutralizing agents. Weak neutralizing VHHs were identified as VHHs that required greater than 1 nM to inhibit BoNT/A cleavage of SNAP25. VHHs that required greater than 10 nM to prevent SNAP25 cleavage were identified as having no toxin neutralizing ability (FIG. 15).

It was observed that about equimolar amounts of ciA-B5, ciA-C2 and ciA-H7 VHHs prevented intoxication of neurons with 10 picomoles of BoNT/A. Two VHHs (ciA-D12 and ciA-F12) were observed to have no or negligible toxin neutralizing activity even at 1,000-fold excess VHH to toxin. Two VHHs (ciA-A5 and G5) displayed intermediate neutralizing activity compared to ciA-B5, ciA-C2 and ciA-H7, the strongly neutralizing VHHs, and ciA-D12 and ciA-F12, the non-neutralizing VHHs (FIG. 15 and Table 5).

Thus, ciA-B5, ciA-C2 and ciA-H7 were determined to be strong neutralizing VHHs. Other isolates including ciA-D12 and ciA-F12 were observed to be non-neutralizing VHHs that produced no detectable toxin neutralization.

Example 15. Protection from BoNT/a Lethality Using Monomeric Anti-BoNT/a VHHs Epitopically tagged anti-BoNT/A VHH compositions were shown in the Example herein to prevent toxin induced lethality in the presence or absence of the clearing anti-tag mAb. Methods of testing VHHs are shown in Sepulveda et al., 2009 Infect Immun 78:756-763, and Tremblay et al. 2010 Toxicon. 56(6): 990-998. Pools/mixtures of two, three, four or six different anti-BoNT/A VHH monomers with or without anti-E-tag clearing antibody were co-administered to subjects with an amount (1000 $LD_{50}$ or 10,000 $LD_{50}$) of BoNT/A holotoxin. Subjects were then monitored for symptoms of toxin lethality and were observed for time to death.

Figure 16A:
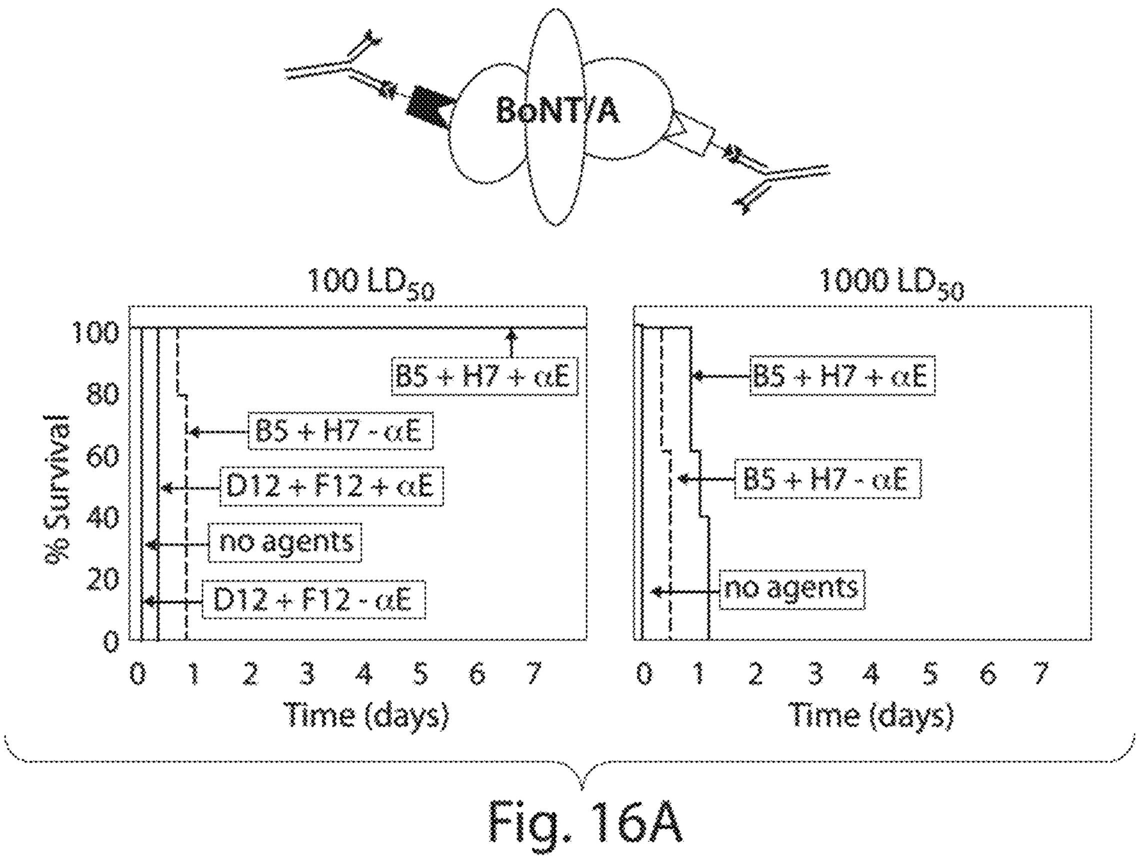
FIGS. 16A-16C show a set of drawings and Meyer-Kaplan survival plots showing that mouse subjects administered each of a set of mixtures of VHH monomers in combination with anti-tag clearing antibody were protected from BoNT/A.

The subjects were co-administered BoNT/A with either a mixture of ciA-H7 and ciA-B5 monomers, or a mixture of ciA-D12 and ciA-F12 monomers (FIG. 16A bottom graphs). Each mixture was administered with (+αE) or without (−αE) anti-E-tag clearing antibody that specifically bound the epitopic tags located on the VHHs. Control subjects were administered toxin only. Unless indicated otherwise, a dashed line in FIGS. 16-24 indicates that no anti-E-tag antibody was administered to the subjects. Each monomeric VHH was used at a total dose of two micrograms (2 μg) per mouse to ensure that the only the complexity and/or identity of the VHH mixtures was varied among groups and was the cause of observed antitoxin efficacy.

Results obtained show that subjects administered ciA-D12 and ciA-F12, two anti-BoNT/A VHH monomers previously determined not to neutralize BoNT/A in cell assays, did not survive toxin challenge for any greater time than did control subjects administered toxin only (FIG. 16A bottom graphs). Administration of 5 μg amounts of anti-E-tag clearing antibody (αE) to subjects only slightly prolonged time before death. Data show that subjects administered neutralizing VHH monomers ciA-H7 and ciA-B5 with anti-E-tag clearing antibody were slightly protected against BoNT/A compared to subjects administered ciA-D12 and ciA-F12, and anti-E-tag clearing antibodies. Thus, the decoration of BoNT/A with two clearing antibodies provided little or no therapeutic benefit to the subjects.

Administration to subjects of a mixture of ciA-B5, and ciA-H7 monomers absent clearing antibody only delayed time to death. Data show that subjects challenged with 100-fold the $LD_{50}$ of BoNT/A (approximately 5 nanograms total) survived longer following administration of a mixture of neutralizing ciA-B5 and ciA-H7 compared to control subjects administered no VHHs. Most important, it was observed that co-administration of clearing antibody and the neutralizing VHHs resulted in 100% survival of subjects challenged with 100-fold the $LD_{50}$ of BoNT/A (FIG. 16A bottom left graph). At a challenge of 1,000-fold the $LD_{50}$ of BoNT/A, death was delayed about one additional day for subjects co-administered a mixture of ciA-B5 and ciA-H7 and anti-E-tag clearing antibody compared to subjects administered VHHs alone or control subjects (FIG. 16A bottom right graph). Thus, it was observed that administering a mixture of toxin neutralization VHH monomers with clearing antibody provided greater therapeutic benefit and protection against BoNT/A than administering VHHs absent the clearing antibody. Relative affinity of each VHH influences the therapeutic effect of the VHH, likewise for VHHs having similar sub-nanomolar affinities (See Table 5).

Figure 16B:
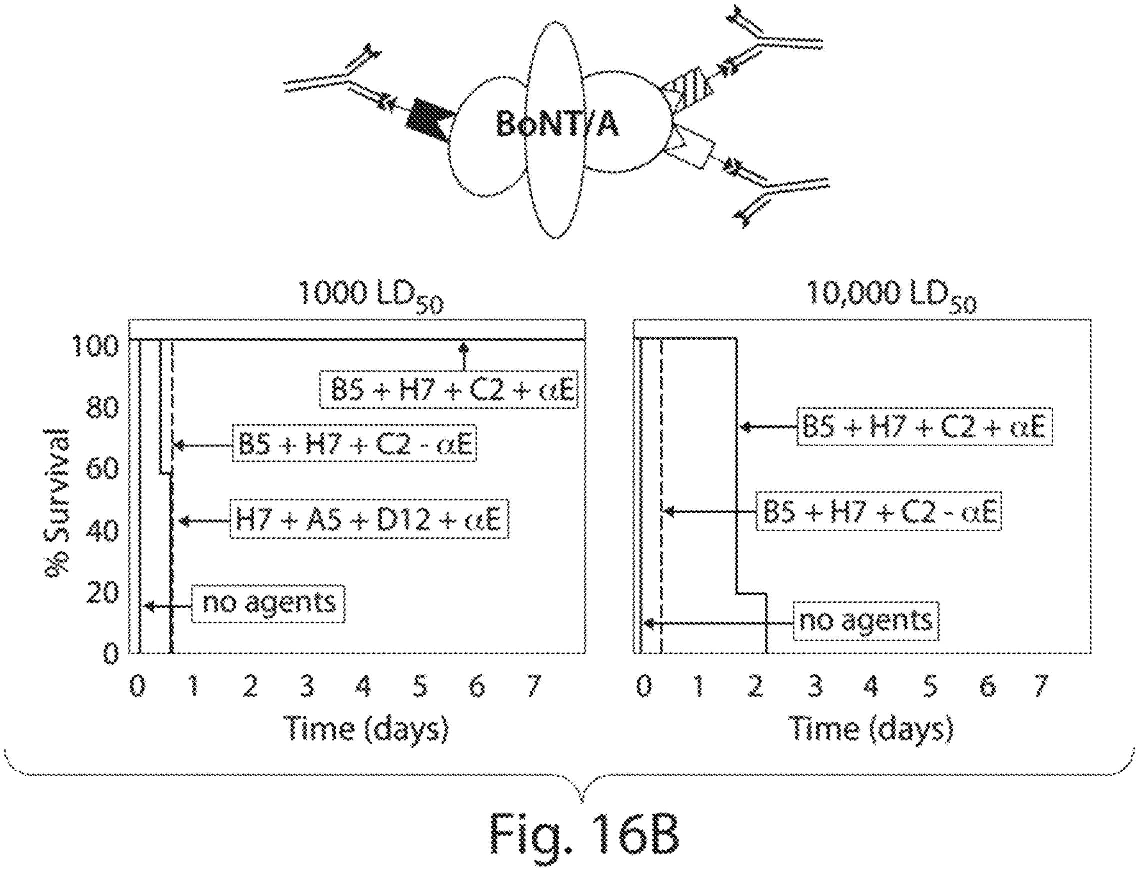

Whether mixtures of VHH monomers containing both neutralizing VHHs and non-neutralizing VHHs were effective antitoxin agents was further tested. Subjects were co-administered 1,000-fold or 10,000-fold BoNT/A $LD_{50}$ and one VHH monomer mixture of either a mixture of ciA-B5, ciA-H7, and ciA-C2; or a mixture of ciA-H7, ciA-A5 and ciA-D12 with (+αE) or without (−αE) an anti-E-tag clearing antibody preparation that specifically binds the epitopic tags located on the VHHs (FIG. 16B bottom graphs). Control subjects were administered toxin only.

Administration of a mixture of ciA-B5, ciA-H7, ciA-C2 monomers, each capable of potent toxin neutralization, delayed death less than a day in mice exposed to 1000-fold the $LD_{50}$ of BoNT/A (FIG. 16B bottom left graph). Subjects were completely protected (100% survival) at 1000-fold the $LD_{50}$ of BoNT/A following administration mixture of ciA-B5, ciA-H7, and ciA-C2 monomers and clearing antibody. Co-administration of 10,000-fold the $LD_{50}$ of BoNT/A (a total amount of 0.5 μg), a mixture of ciA-B5, ciA-H7, ciA-C2 monomers and clearing antibody delayed death more than two days in subjects (See FIG. 16B bottom right graph) compared to control subjects.

TABLE 5

SPR binding data for VHH monomers and heterodimers

| clone | protein | epitope# | neutralization* | SPR Kd (nM) | subunit^ | Genbank |
|---|---|---|---|---|---|---|
| JDY-33 | ciA-H7 | A1 | strong | 0.06 +/− 0.07 | Lc | HQ700708 |
| JDT-2 | ciA-D1 | A1 | strong | 0.71 +/− 0.004 | Lc | |
| JEC-3 | ciA-H4 | A1 | not done | 1.54 +/− 0.06 | Lc | |
| JEC-11 | ciA-H11 | A1 | not done | 4.3 +/− 0.09 | Lc | |
| JDY-46 | ciA-C2 | A2 | strong | 2.7 +/− 3.1 | Lc | HQ700705 |
| JDY-9 | ciA-B5 | A3 | strong | 0.17 +/− 0.06 | Hc | HQ700704 |
| JED-27 | ciA-F12 | A4 | none | 0.24 +/− 0.03 | Lc | HQ700706 |
| JDU-26 | ciA-D12 | A5 | none | 0.21 +/− 0.1 | Lc | HQ700702 |
| JDY-2 | ciA-A5 | A6 | weak | 1.05 +/− 0.05 | none | HQ700703 |
| JDY-59 | ciA-G5 | A7 | weak | 0.32 +/− 0.03 | none | HQ700707 |
| JFA-10 | ciB-H11 | B1 | not done | 0.26 +/− 0.01 | none | |
| JFX-30 | ciB-A11 | B2 | not done | 0.84 +/− 0.68 | none | |
| JFV-48 | ciB-B5 | B3 | not done | 0.97 +/− 0.04 | none | |
| JFV-40 | ciB-B9 | B4 | not done | 23 +/− 5.8 | none | |
| JEZ-2 | ciA-H7/B5 | A1/A3 | strong | 0.014 +/− 0.007 | not done | |
| JFK-21 | ciA-F12/D12 | A4/A5 | not done | 0.097 +/− 0.38 | not done | |
| JGA-3 | ciB-A11/B5 | B2/B3 | not done | 5.3 +/− 1.5 | not done | |

It was observed that administration of a mixture of ciA-H7, ciA-A5, and ciA-D12 in which two VHH monomers (ciA-A5 and ciA-D12) in the mixture of monomers were weak toxin neutralizers, resulted in subjects surviving much less after exposure to an amount of BoNT/A 1,000-fold BoNT/A $LD_{50}$ (FIG. 16B bottom left graph).

Thus, administration of the mixture of ciA-B5, ciA-H7, and ciA-C2 tagged monomers, each of which are strong neutralizing VHHs, to subjects provided greater protection against BoNT/A than the mixture of ciA-H7, ciA-A5 and ciA-D12, in which two of the three VHH monomers do not neutralize BoNT/A. Data show that 100% of subjects administered the mixture of ciA-B5, ciA-H7, and ciA-C2 with the anti-tag clearing antibody survived a dose of BoNT/A that was 1,000-fold the $LD_{50}$ of a BoNT/A (FIG. 16B bottom left graph), and survived additional days following administration of 10,000-fold the $LD_{50}$ of a BoNT/A (FIG. 16B bottom left graph).

Figure 16C:
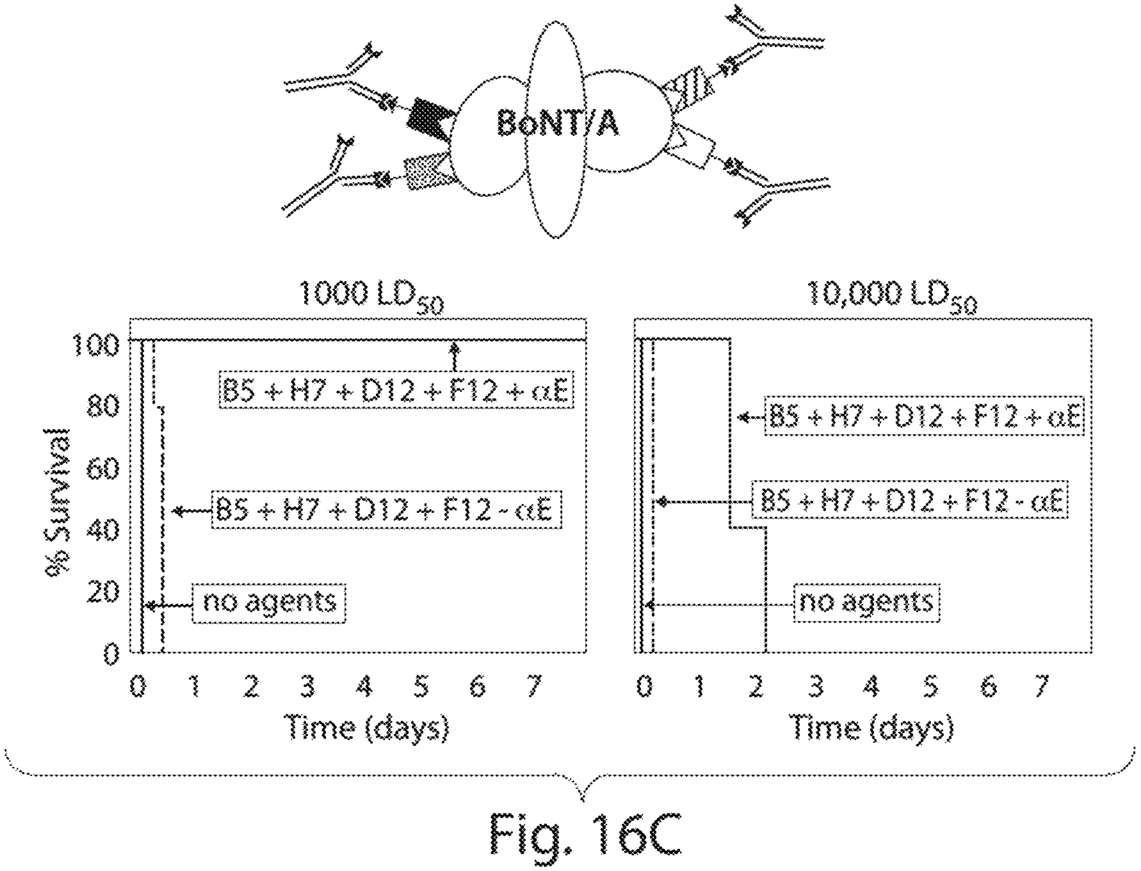

Complete survival (100%) was observed for subjects administered a mixture of ciA-B5, ciA-H7, ciA-D12 and ciA-F12 tagged monomers and anti-tag clearing antibodies of the challenge with an amount of BoNT/A that was 1,000-fold the $LD_{50}$ (FIG. 16C bottom left graph). Administering a pool of anti-BoNT/A VHHs (ciA-B5, ciA-H7, ciA-D12 and ciA-F12) in which only two VHHs (ciA-B5, ciA-H7) were strong toxin neutralizers only slightly delayed death in subjects exposed to 1000-fold the $LD_{50}$ of BoNT/A (FIG. 16C bottom left graph). At 10,000-fold the $LD_{50}$ of a BoNT/A, subjects co-administered the mixture of four VHH tagged monomers and anti-tag clearing antibody survived additional days compared to control subjects (FIG. 16C bottom left graph).

Figure 17:
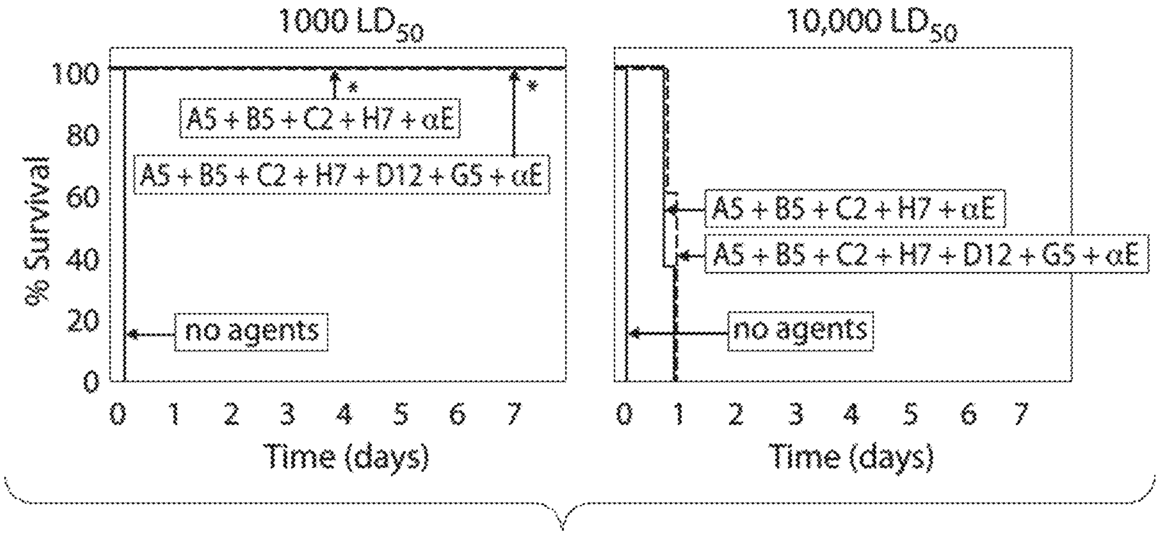
FIG. 17 presents graphs showing percent survival, ordinate, of subjects as a function of time (days, abscissa) of subjects co-administered 1,000-fold BoNT/A $LD_{50}$ (FIG. 17 left graph) or 10,000-fold BoNT/A $LD_{50}$ (FIG. 17 right graph), and mixtures of VHH monomers and anti-tag clearing antibody (αE). Control subjects received toxin only. Unless indicated otherwise, an asterisk (*) in FIGS. 17-24 indicates that the subjects administered the VHH monomer or multimer displayed no symptoms of toxin exposure.

The antitoxin efficacy of a pool of four anti-BoNT/A VHHs tagged monomers (ciA-A5, ciA-B5, ciA-C2 and ciA-H7) was compared to a pool of six different VHH tagged monomers (ciA-A5, ciA-B5, ciA-C2, ciA-H7, ciA-D12, and ciA-G5). The pool of six VHH monomers contained the same VHHs as the pool of four VHHs and further included two VHHs (ciA-D12, and ciA-G5) that were weak neutralizers of BoNT/A (FIG. 17 and Table 5). The different pools of VHH monomers were each administered in the presence of clearing anti-tag antibody. It was observed that 100% of subjects administered either the pool of four VHH tagged monomers or the pool of six VHHs tagged monomers with anti-tag clearing antibody survived challenge with 1000-fold the $LD_{50}$ of BoNT/A (FIG. 17 left graph). Subjects challenged with 10,000-fold the $LD_{50}$ of BoNT/A survived longer following co-administration of either the pool of four VHH monomers or the pool of six VHH monomers with clearing anti-tag antibody, than control subjects administered only toxin (FIG. 17 right graph). These results show that decoration of BoNT/A with a greater number of VHH antibodies, four or more VHHs, greatly improved antitoxin efficacy. Administering a pool of four VHH monomers or a pool of six VHH monomers to the subjects provided additional antitoxin efficacy compared to administering three or fewer VHH monomers.

These data clearly show that toxin clearance was rendered much more effective under conditions in which BoNT is decorated by at least three VHH antibodies and at least about three clearing antibodies. It was observed also that mixtures of monomers having greater number or percentage of toxin neutralization VHHs greatly contributed to percent survival of subjects co-administered a vast excess of the lethal dose of BoNT/A.

Example 16. VHH Affinity and Antitoxin Efficacy

Toxin neutralization and clearance mechanisms were observed herein to depend on affinity of antitoxin binding to the toxin. Without being limited by a particular theory or mechanism of action, the kinetics of toxin binding ($K_{on}$) and release ($K_{off}$) by the antitoxin binding agents contribute to the antitoxin efficacy.

To determine the relationship of toxin affinity to antitoxin efficacy and the role of each, assays were performed for identification of multiple VHHs recognizing the same epitope. In the course of anti-BoNT/A VHH screening and based on competition ELISA analysis, several VHHs (ciA-D1, ciA-H4 and ciA-H11) were identified that recognized the same epitope as ciA-H7. SPR analysis showed that each VHH monomer recognized and bound the ciA-H7 epitope with a different affinity. The dissociation constant (Kd) identifies the strength of binding or affinity between a ligand and a receptor, between the VHH antibody and the toxin.

Figures 18A, 18B:
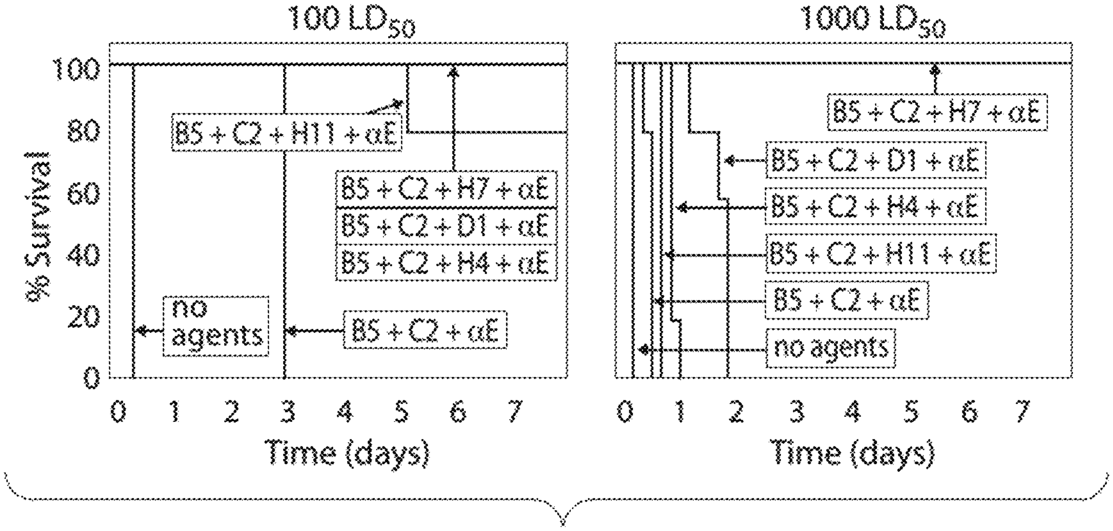
FIGS. 18A and 18B present a table showing affinity binding data for VHHs and a set of line graphs showing improved protection of subjects from very large doses of BoNT/A following administration of each of sets of mixtures of VHH monomers with strong affinity for BoNT/A and clearing antibody.

The VHH Kd values for the VHHs having the stronger binding to BoNT/A were determined to be 0.06±0.07 nM for ciA-H7, 0.71±0.004 for ciA-D1, and the VHH Kd values for the VHHs having the weakest binding to BoNT/A were determined to be the 1.54±0.06 for ciA-H4, and 4.3±0.09 for ciA-H11 respectively (FIG. 18A). These four VHHs were tested with anti-tag clearing antibody for their efficacy as antitoxin VHHs in combination with the two VHHs (ciA-B5, ciA-C2) that recognize distinct, non-overlapping epitopes of BoNT/A (FIG. 18B left and right graphs).

Subjects (five mice per group) were co-administered BoNT/A and one of four mixtures containing three VHH monomers: ciA-H7, ciA-B5 and ciA-C2; ciA-D1, ciA-B5 and ciA-C2; ciA-H4, ciA-B5 and ciA-C2; or ciA-H11, ciA-B5 and ciA-C2. Each mixture included two strong neutralizing VHH monomers (ciA-B5 and ciA-C2), and one VHH of ciA-H7, ciA-D1, ciA-H4, or ciA-H11. Control subjects received toxin only.

Data show that 100% of subjects survived following co-administration of 100 BoNT/A $LD_{50}$ and VHH mixtures containing ciA-B5 and ciA-C2 and either ciA-H7, ciA-D1 or ciA-H4. Subjects administered the VHH mixture of ciA-B5, ciA-C2 and ciA-H11 survived the 100 $LD_{50}$ of BoNT/A at 80% (FIG. 18B left graph). Among subjects challenged with 1,000-fold the $LD_{50}$ of a BoNT/A (FIG. 18B right graph), the level of protection was a function of the relative binding affinity or Kd of the VHH to BoNT/A shown in FIG. 18A. Specifically, the greatest protection at 1,000-fold BoNT/A $LD_{50}$ was observed in subjects administered the VHH mixture containing ciA-B5, ciA-C2, and ciA-H7, which had the strongest BoNT/A affinity (i.e., lowest Kd value of 0.06±0.07; FIG. 18A and FIG. 18B right graph). The least extent of protection was observed in subjects administered the VHH mixture containing ciA-B5, ciA-C2, and ciA-H11 (weakest BoNT/A affinity and highest Kd value of 4.3±0.09; FIG. 18A and FIG. 18B right graph), the survival of which was comparable to control subjects not administered VHH monomers.

Correlating the Kd values with antitoxin-toxin binding and affinities, it was observed that the lower the Kd value the greater the respective toxin affinity and the greater the antitoxin efficacy of the VHH. VHH ciA-H7 was observed to have the lowest Kd and the strongest binding affinity to BoNT/A, and was determined to have greater antitoxin efficacy than other VHH compositions identified in FIG. 18A. Thus, sub-nanomolar affinities or Kd values for the tagged toxin binding agents is an important factor in identifying the VHH with greatest antitoxin efficacy and most effective ability to protect subjects from toxin-associated infection and death.

Example 17. Antitoxin VHHs Heterodimers

By engineering and expressing two anti-BoNT/A VHHs as a heterodimer, a resulting multimeric binding protein molecule was obtained, and this composition was found to bind to two different sites on the toxin and yield an improved toxin affinity. Examples herein analyzed the role of epitopic tags on the heterodimer and the role of the amount of the tagging of the heterodimer compared to the clearing antibody with respect to increasing antitoxin efficacy of the heterodimer.

Figure 19A:
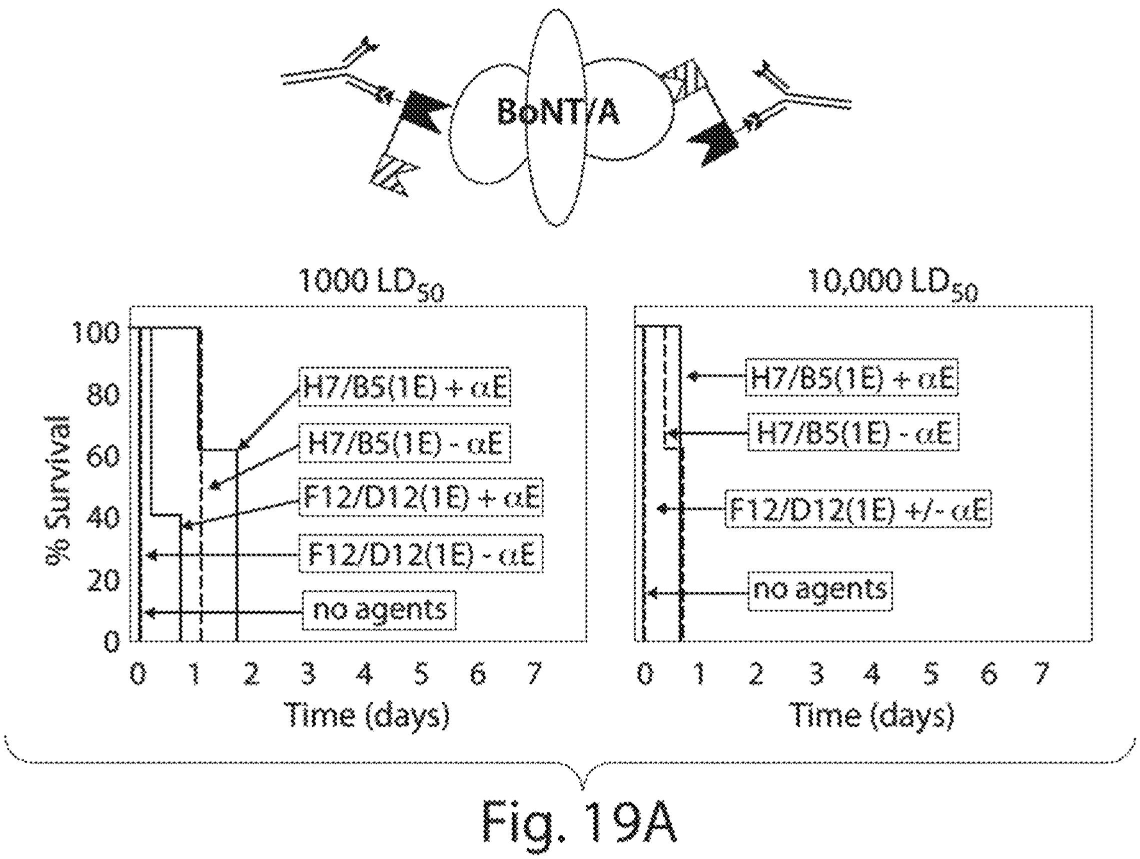
FIGS. 19A and 19B are drawings and graphs showing that administering heterodimers composed of neutralizing VHH components resulted in greater antitoxin efficacy than heterodimers composed of non-neutralizing VHHs, and that presence of two or more E-tags within the VHH heterodimers further increased the antitoxin efficacy.

VHH heterodimers were engineered to contain an epitopic tag for decoration of BoNT/A with two anti-tag clearing antibodies (FIG. 19A top drawing). Survival and protection of subjects was analyzed following challenge with each of 100-fold and 1000-fold the $LD_{50}$ of BoNT/A (FIG. 19A bottom left and right graphs). Data show that administering heterodimer containing two strongly neutralizing VHHs, ciA-B5 and ciA-H7, resulted in greater antitoxin efficacy and longer survival of subjects than administering heterodimers containing two weak or non-neutralizing VHHs, ciA-D12 and ciA-F12 (FIG. 19A bottom left and right graphs).

Figure 19B:
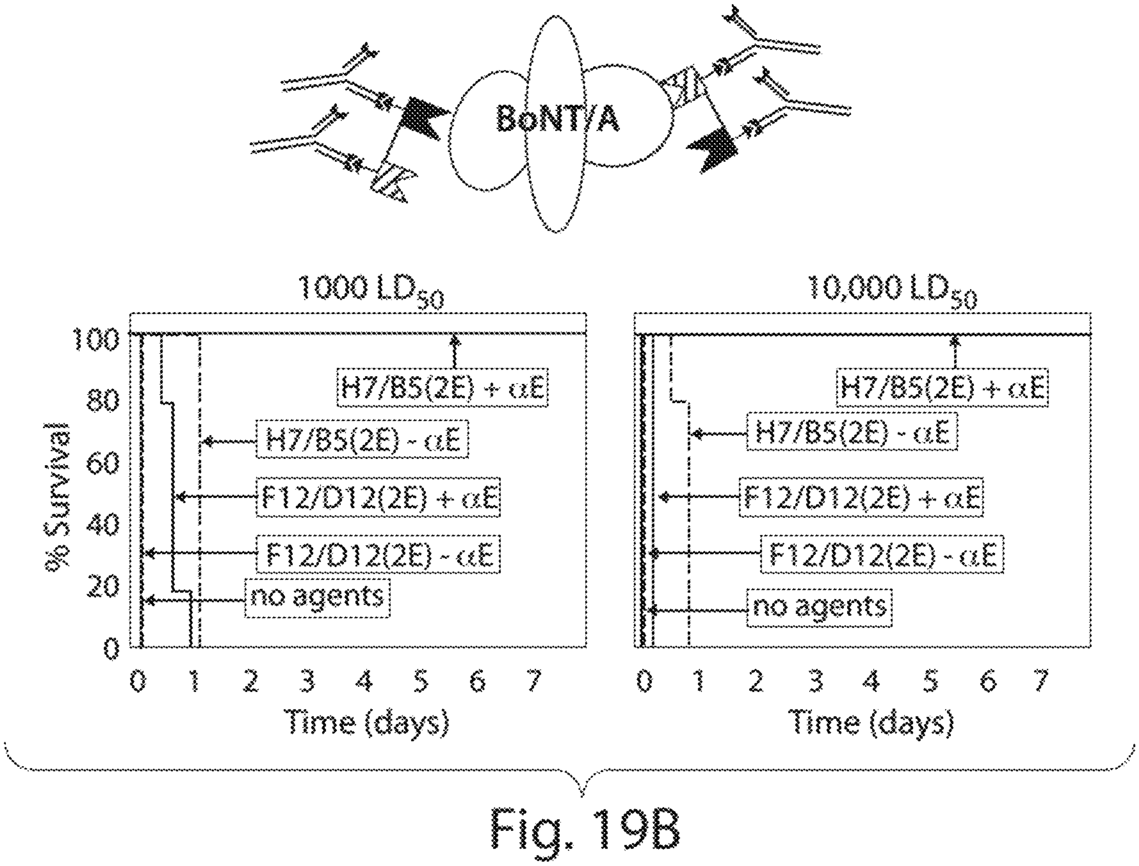

A second copy of the epitopic tag to the heterodimers compared to only one epitopic tag was observed to promote toxin decoration with four clearing antibodies and to yield greater clearing efficacy (FIG. 19B top drawing). All (100%) of subjects survived a challenge with either 1000-fold or 10,000-fold the $LD_{50}$ of BoNT/A and co-administration of ciA-B5/ciA-H7 heterodimer having two epitopic tags and anti-tag clearing antibody (FIG. 19B bottom graphs).

To further analyze whether two or more epitopic tags improved heterodimer antitoxin efficacy, two sets of anti-BoNT/A VHH heterodimers were constructed in which the two VHHs in the heterodimers were either non-neutralizing (ciA-D12/F12) or potent toxin neutralizing agents (ciA-B5/H7). The two different VHH heterodimers were engineered containing either one or two copies of the epitopic tag (E-tag) and were expressed. SPR analysis confirmed that the heterodimer affinities were in the range of 10 picomolar to 100 picomolar which was significantly greater than the affinities of the component monomers (FIG. 15 and Table 5).

The antitoxin efficacies of the single tagged heterodimers administered to mouse subjects after challenge with 1000-fold $LD_{50}$ of BoNT/A (FIG. 19A bottom left graph) were observed to be similar to results obtained from administering a mixture of the two corresponding monomers only (FIG. 16A bottom right graph). Administering the non-neutralizing single-tagged heterodimer, ciA-D12/F12(1E), resulted in no protection from challenge with 1000-fold $LD_{50}$ of BoNT/A in the absence of clearing antibody, and only slightly delayed death in the presence of clearing antibody (FIG. 19A bottom left graph). The toxin neutralizing single-tagged heterodimer, ciA-B5/H7(1E), delayed death in mice exposed to 1000 $LD_{50}$ BoNT/A for one to two days in the absence of clearing antibody and efficacy was only slightly improved by the addition of clearing antibody (FIG. 19A bottom left graph).

Improved antitoxin efficacy was observed in subjects administered a heteromultimeric agent having a second copy of the epitopic tag, with both non-neutralizing and neutralizing anti-BoNT/A VHH heterodimers in which the heterodimer agent was co-administered with clearing antibody. Without being limited by any particular theory or mechanism of action, it is here envisioned that component binding regions in a 'double-tagged heterodimer' bind at two sites on the toxin and each bound heterodimer decorates toxin with two clearing antibodies, resulting in decoration of the toxin with at least four clearing antibodies (FIG. 19B top drawing) which Examples herein show had increased clearance. Administering non-neutralizing double-tagged heterodimer containing ciA-D12/F12(2E) resulted in virtually no antitoxin efficacy in subjects in the absence of clearing antibody at both 1000-fold and 10,000-fold the $LD_{50}$ of BoNT/A (FIG. 19B bottom left and right graphs). In the presence of clearing antibody, ciA-D12/F12(2E) heterodimer fully protected subjects (100% survival) from 100-fold BoNT/A $LD_{50}$ and delayed death about a day in subjects receiving 1000-fold BoNT/A $LD_{50}$ compared to control subjects (FIG. 19B bottom right graph and FIG. 20 left graph). Thus the presence of a second epitopic tag attached to the heterodimer dramatically improved the antitoxin efficacy.

Figure 20:
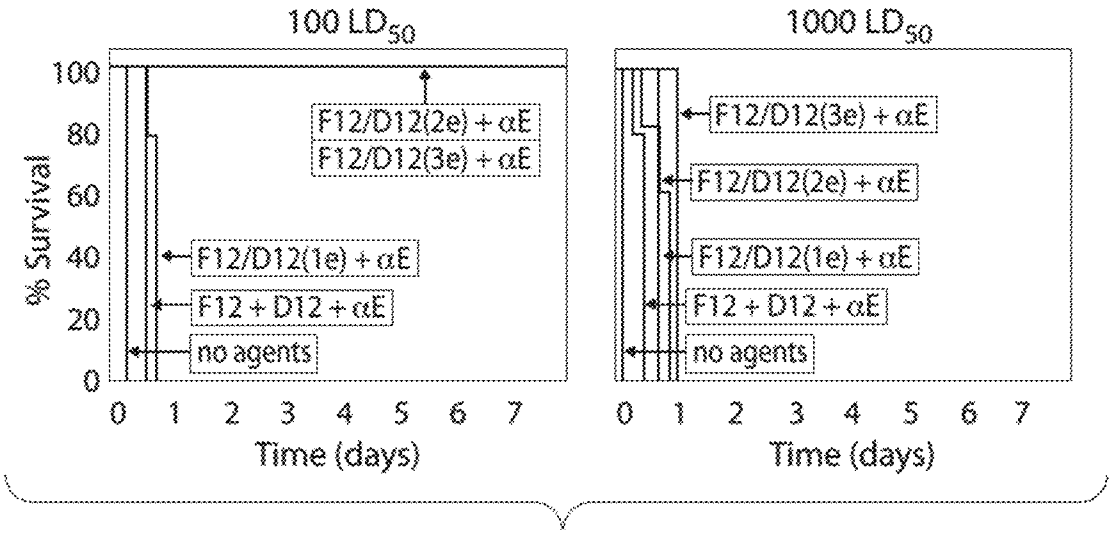
FIG. 20 is a set of graphs showing percent survival on the ordinate of subjects as a function of time (days, abscissa) after co-administration of 100-fold (FIG. 20 left graph) or 1,000-fold (FIG. 20 right graph) BoNT/A $LD_{50}$, and multi-tagged VHH heterodimers with anti-tag clearing antibody. The ciA-D12/ciA-F12 heterodimer protein contained either one tag (1e), two tags (2e), three tags (3e), or control no tag. Subjects (five mice per group) were administered 20 μg of the heterodimer composition or the mixture of ciA-D12 and ciA-F12 monomers (20 μg of each monomer). Control subjects were administered neither monomer nor heterodimer. Each subject received 60 picomoles of anti-E-tag clearing antibody. Data show that subjects administered ciA-D12/ciA-F12 heterodimers having either one tag or two tags survived (100% survival) the challenge of 100-fold the $LD_{50}$ of BoNT/A (FIG. 20 left graph). Subjects receiving 1,000-fold the $LD_{50}$ of BoNT/A and ciA-D12/ciA-F12 heterodimers with clearing antibody died within one day following challenge with independent of number of tags (FIG. 20 right graph).
Figure 21:
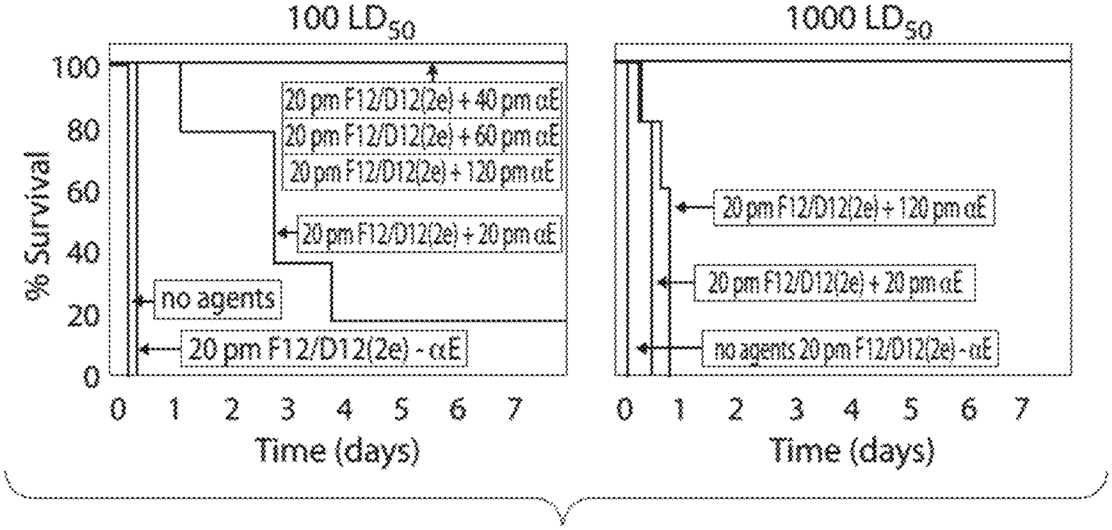
FIG. 21 is a set of graphs showing percent survival, ordinate, of subjects treated with different amounts of anti-tag clearing antibody as a function of time (days, abscissa) after exposure to BoNT/A 100-fold (FIG. 21 left graph) or 1,000-fold (FIG. 21 right graph) the $LD_{50}$ and to double tagged ciA-D12/ciA-F12 heterodimer (20 picomoles). Anti-tag clearing antibody was administered at: 20 picomoles, 40 picomoles, 60 picomoles, 120 picomoles, or control (none). Control subjects received toxin only (no agents). Data show improved antitoxin efficacy in subjects co-administered amounts (40, 60 or 120 picomoles) increased anti-tag clearing antibody compared to 20 picomoles.

Non-neutralizing heterodimer, ciA-D12/F12, with either one, two or three epitopic tags was analyzed for antitoxin efficacy in the presence of clearing antibody (FIG. 20). The single-tagged heterodimer only slightly protected subjects from toxin challenge of 100-fold the $LD_{50}$ of BoNT/A. Subjects challenged with double-tagged heterodimers and triple-tagged heterodimers were fully protected from a challenge of 100-fold the $LD_{50}$ of BoNT/A (FIG. 20 left graph). Only little improvement in antitoxin efficacy was observed with the triple-tagged heterodimers compared to the double-tagged heterodimers, consistent with the observation that near maximal clearance was achieved by decorating the target with four clearing antibodies. A titration of the clearing antibody administered with the double-tagged ciA-D12/F12 heterodimer demonstrated that maximal antitoxin efficacy against both 100-fold and 1,000-fold the $LD_{50}$ of BoNT/A was achieved with the number of clearing antibody molecules (measured in picomoles) administered in an amount approximately equivalent to the number of epitopic tags (FIG. 21 left and right graphs).

An even more dramatic antitoxin effect was observed in cell culture intoxication assays using the double-tagged heterodimer, ciA-B5/H7(2E), in which both of the component anti-BoNT/A VHHs individually possess potent neutralizing activity (FIG. 15). In the absence of clearing antibody, the double-tagged ciA-B5/H7(2E) heterodimer produced the same antitoxin efficacy as the equivalent single-tagged heterodimer (compare FIG. 19A bottom left and right graphs to FIG. 19B bottom left and right graphs). In the presence of clearing antibody, the neutralizing double-tagged heterodimer at 40 picomoles (pmoles) was observed to be a highly potent antitoxin that fully protected cells from lethality when co-administered with 10,000-fold the $LD_{50}$ of BoNT/A, i.e., the total amount was about 3 pmoles.

Figure 22:
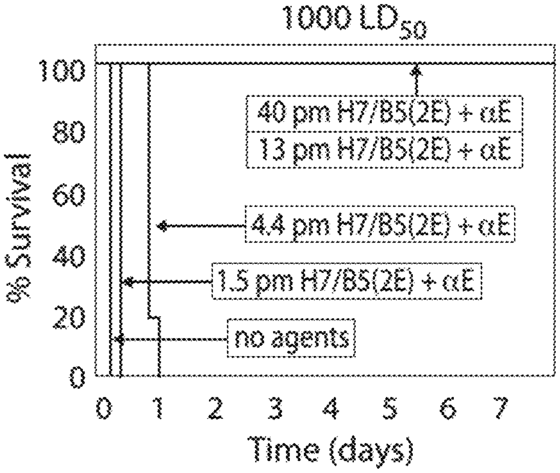
FIG. 22 is a graph showing percent survival, ordinate, of subjects treated with different doses of double tagged neutralizing ciA-B5/ciA-H7 heterodimers as a function of time (days, abscissa) for subjects co-administered 1,000-fold BoNT/A $LD_{50}$, and anti-tag clearing antibody. Heterodimer ciA-B5/ciA-H7 was administered in doses of: 1.5 picomoles, 4.4 picomoles, 13 picomoles, or 40 picomoles. Control subjects received toxin only (no agents). Data show complete survival after seven days of subjects receiving amounts of 13 picomoles or 40 picomoles double tagged neutralizing ciA-B5/ciA-H7 heterodimer, such that than 13 picomoles protected subjects fully from 1,000-fold BoNT/A $LD_{50}$, compared to 1.5 picomoles or 4.4 picomoles (no survival after one day).

A dose-response assay was performed in mouse subjects with double-tagged ciA-B5/H7(2E) heterodimer co-administered with 1000-fold the $LD_{50}$ of BoNT/A (FIG. 22). It was observed that both 40 pmoles and 13 pmoles of double-tagged ciA-B5/H7(2E) heterodimer completely protected the subjects against an exposure of 1000-fold the $LD_{50}$ of BoNT/A. A dose of 4 pmoles ciA-B5/H7(2E) heterodimer had the same protective efficacy for 1,000-fold the $LD_{50}$ of BoNT/A as a dose of 40 pmoles did with 10,000-fold the $LD_{50}$ of BoNT/A (FIG. 15B and FIG. 22). These data show that co-administering about a fifteen-fold molar excess of the double-tagged heterodimer binding agent with the clearing antibody was sufficient to effectively neutralize and/or clear substantially all (greater than 99.99%) of the BoNT/A.

Figure 23A:
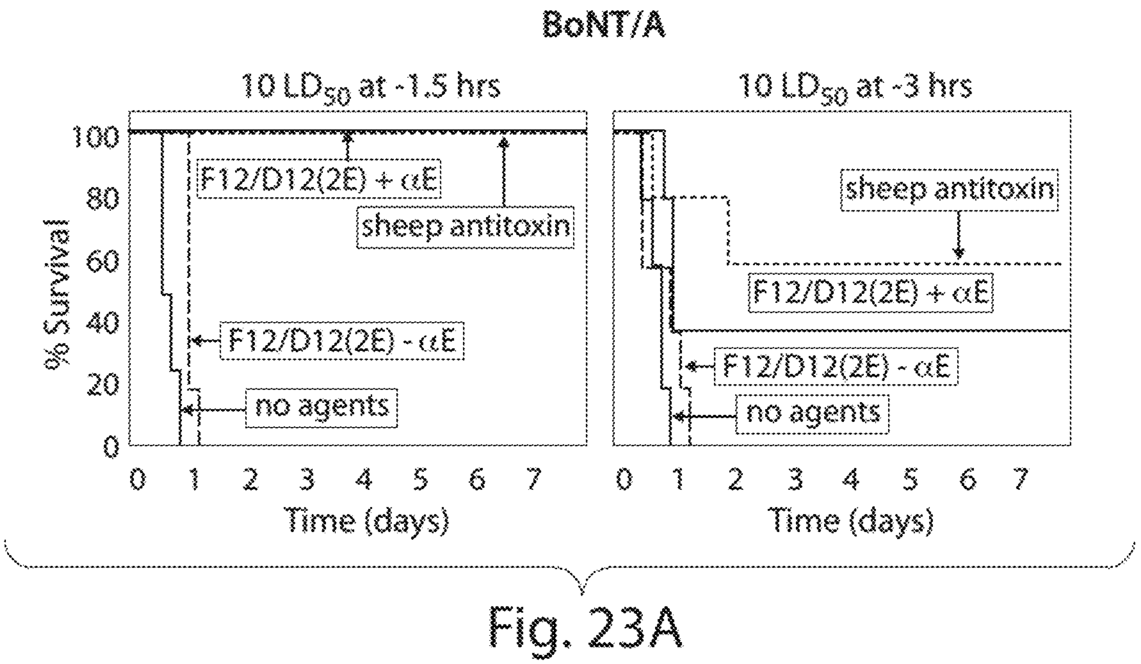
FIGS. 23A and 23B are graphs showing percent survival, ordinate, after subjects were exposed to ten-fold BoNT/A $LD_{50}$ and were administered double-tagged heterodimer and anti-tag clearing antibody of subjects as a function of time (days, abscissa). Administration of heterodimer after toxin exposure was observed to have protected subjects from symptoms and death caused by exposure to ten-fold BoNT/A $LD_{50}$.
Figure 23B:
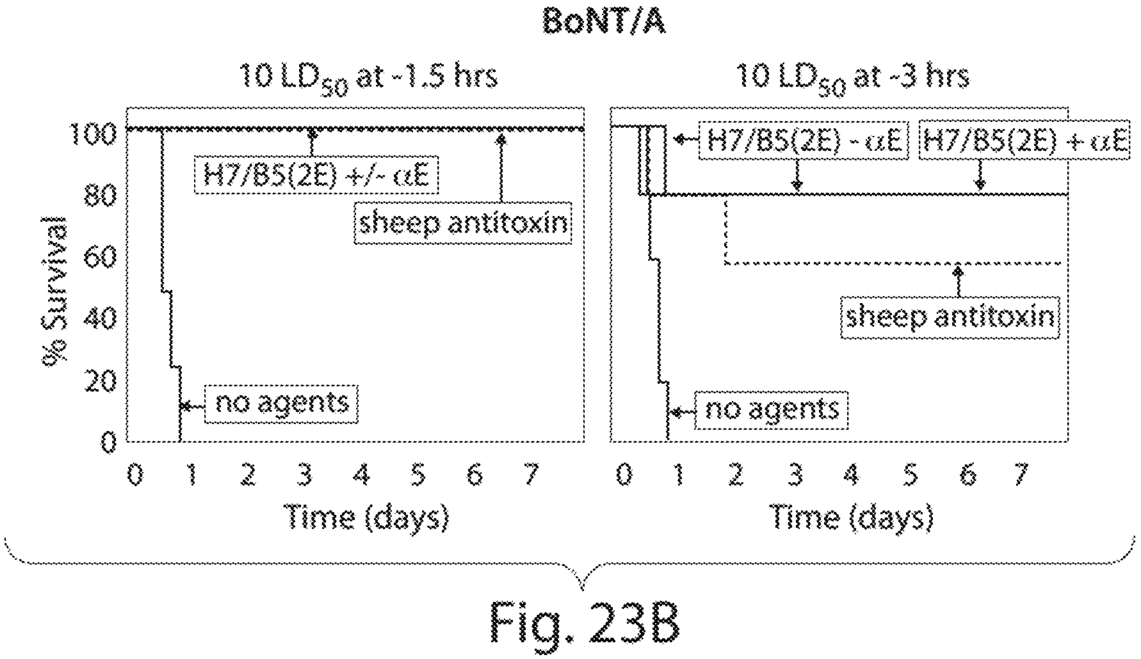

Example 18. Recombinant Antitoxin Efficacy in a Clinically Relevant Post-Intoxication Assay Assays in which varying doses of toxins are co-administered with antitoxin agents were observed to permit sensitive quantification of antitoxin efficacy. To more accurately reflect the typical clinical situation, antitoxin agents were tested in an assay of greater clinical relevance by intraperitoneally administering to mouse subjects ten-fold the $LD_{50}$ of BoNT/A, and at 1.5 hours and three hours afterwards, administering intravenously neutralizing heterodimer antitoxin agents with and without the anti-tag clearing antibody. Different sets of anti-BoNT/A VHH heterodimers were tested: a heterodimer containing non-neutralizing double-tagged ciA-D12/F12(2E), and a heterodimer containing neutralizing double-tagged ciA-H7/B5(2E) heterodimer (FIGS. 23A-B). A potent sheep anti-BoNT/A serum was used as a control in the assay at a dose demonstrated to protect 100% of mice from lethality given 10,000-fold the $LD_{50}$ of BoNT/A.

The non-neutralizing ciA-D12/F12(2E) heterodimer was observed to have little or no antitoxin efficacy in absence of clearing antibody following administration either 1.5 hours or three hours after BoNT/A challenge (FIG. 23A left and right graphs). However, ciA-D12/F12(2E) heterodimer administered with clearing antibody displayed an efficacy nearly equivalent to the positive control sheep antiserum (FIG. 23B left and right graphs). These results show that toxin clearance alone is sufficient to protect mice from a low dose BoNT challenge, even when administered several hours post-exposure to toxin.

Surprisingly, the neutralizing ciA-H7/B5(2E) heterodimer was observed to be as highly effective as an antitoxin in this assay, in the presence or even absence of clearing antibody (FIG. 23B). The double-tagged toxin neutralizing heterodimer administered 1.5 hours after toxin challenge with ten-fold the $LD_{50}$ of BoNT/A resulted in an antitoxin efficacy equivalent to the sheep serum polyclonal antitoxin. It was observed that following challenge at 10 BoNT/A $LD_{50}$ for 1.5 hours, subjects administered ciA-H7/B5(2E) heterodimer absent anti-tag clearing fully survived (100% survival; FIG. 23B left graph). The survival for subjects administered ciA-H7/B5(2E) heterodimer was comparable to subjects administered sheep antitoxin (FIG. 23B left graph).

Data show that three hours after toxin challenge at ten-fold the $LD_{50}$ of BoNT/A, the neutralizing ciA-H7/B5(2E) heterodimer resulted in greater subject survival (80%) than the sheep serum polyclonal antitoxin (60% survival; FIG. 23B right graph). Most important, the survival of subjects using neutralizing ciA-H7/B5(2E) heterodimer was the same with or without clearing antibody (FIG. 23B right graph).

These data clearly show that BoNT neutralization was sufficient for full antitoxin efficacy in a clinically relevant post-intoxication (post-exposure to toxin) assay with low dose toxin challenge. A single recombinant multimeric binding protein with potent toxin neutralization properties was as effective as antitoxin sera in a model of a typical clinical situation involving toxin exposure and subsequent treatment.

Example 19. Antitoxin Efficacy of a Double-Tagged Heterodimer Targeting Botulinum Toxin, BoNT/B Double-tagged VHH heterodimer antitoxins that specifically recognized and bound unique epitopes on BoNT/B holotoxin (FIG. 13B) were identified and expressed. Two of the VHHs, ciB-All and ciA-B5, were observed to be the most effective antitoxins of those obtained from monomer pool assays, and were engineered and expressed as double-tagged heterodimer, ciB-A11/B5(2E).

Figure 24A:
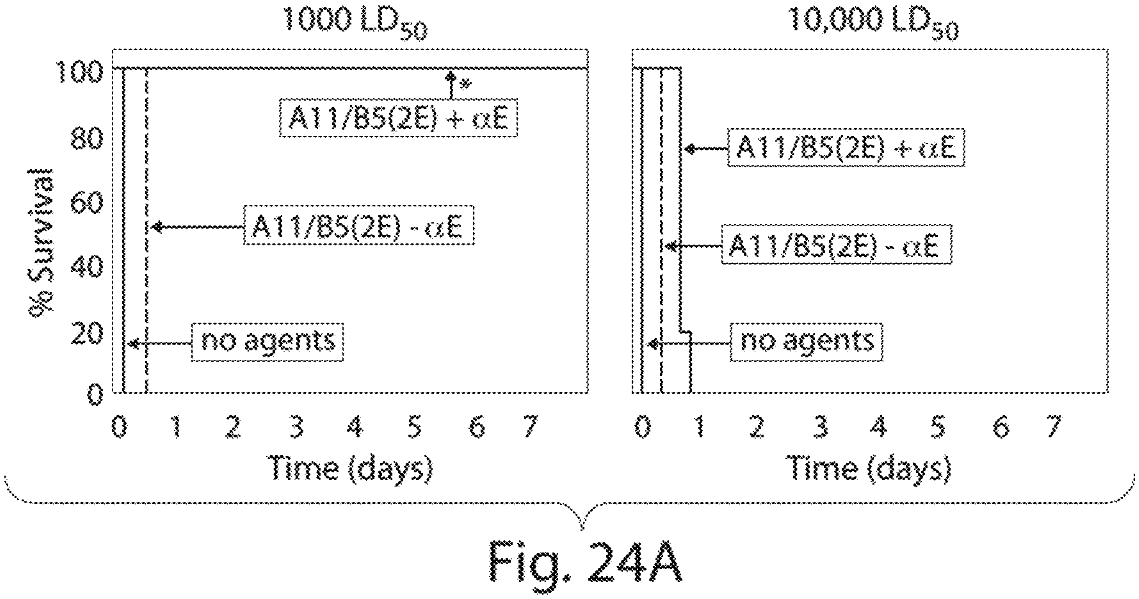
FIGS. 24A and 24B are line graphs showing that subjects administered ciA-A11/ciA-B5 heterodimers with anti-tag clearing antibody were protected from BoNT/B exposure.

Subjects were exposed to either 1,000-fold (FIG. 24A left graph) or 10,000-fold (FIG. 24A right graph) BoNT/B $LD_{50}$, and were administered a ciB-A11 and ciB-B5 heterodimer with (+αE) or without (−αE) anti-tag clearing antibody. Control subjects were exposed only to toxin (no heterodimer binding proteins). Data show that in the presence of clearing antibody the ciB-A11/B5(2E) heterodimer fully protected subjects challenged with 1000-fold the $LD_{50}$ of BoNT/B (FIG. 24A left graph) and extended the life of subjects challenged with 10,000-fold the $LD_{50}$ of BoNT/B (FIG. 24A right graph).

Analysis was performed to determine whether the ciB-A11 and ciA-B5 double tagged heterodimer was effective to treat subjects in a BoNT/B post-exposure in vivo model.

Figure 24B:
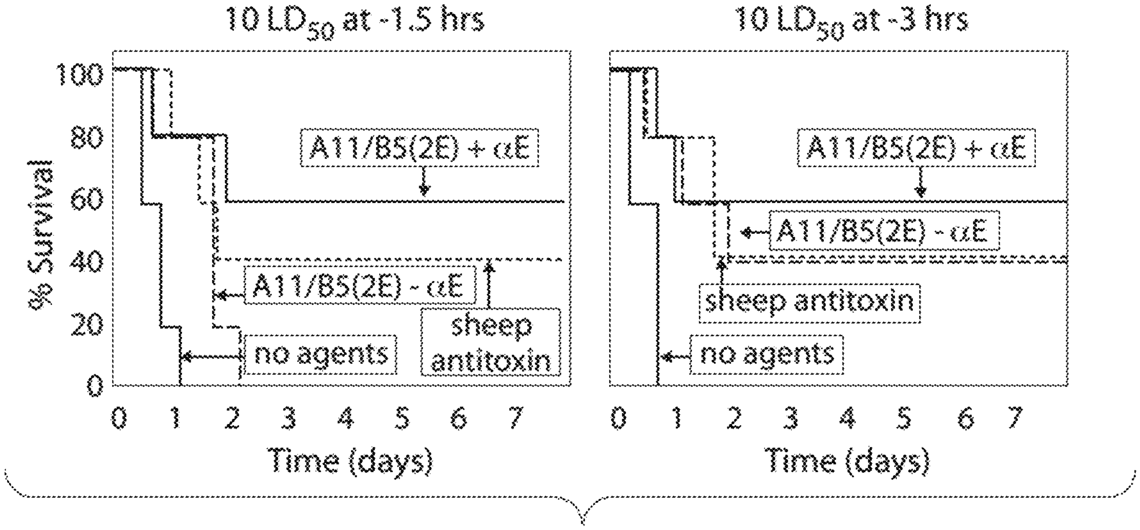

Subjects were intravenously exposed to 10 $LD_{50}$ of BoNT/A, and then were administered 1.5 hours or three hours afterward either: ciB-A11 and ciA-B5 double tagged heterodimeric protein with or without clearing antibody, or a sheep antitoxin serum. Control subjects were only exposed to 10 $LD_{50}$ of BoNT/B (no heterodimeric binding protein was administered). See FIG. 24B left and right graphs. Data show 60% of subjects administered ciB-A1/B5 double tagged heterodimer with anti-tag antibody survived 1.5 hours and three hours after BoNT/B exposure, and further that 20% more subjects survived with ciB-A1/B5 double tagged heterodimer with clearing antibody treatment than with sheep antitoxin at both time points (FIG. 24B left and right graphs). It was observed that three hours after BoNT/B exposure subjects administered A 1/B5 double tagged heterodimer binding protein only (without anti-tag antibody) survived as long as subjects administered sheep antitoxin (FIG. 24B right graph).

Results from these clinically relevant post-intoxication assays herein showed that ciB-A11/B5 heterodimer with or without clearing antibody was as effective as sheep anti-BoNT/B serum in protecting subjects from death caused by BoNT/B holotoxin exposure.

Example 20. VHH Monomers Protect CT26 Cells from TcdA

Cells of murine colorectal cancer cell line CT26 were exposed to TcdA (2 ng/ml) for 24 hours and to a VHH monomer specific to TcdA (A3H, SEQ ID NO 61; A11G, SEQ ID NO:63; AC1, SEQ ID NO: 62; AE1, SEQ ID NO: 64; AH3, SEQ ID NO: 59; or AA6, SEQ ID NO: 60). Controls cells were exposed to TcdA (no VHH monomer was administered). The percentage of cell rounding was monitored using a phase contrast microscope. Control cells administered only TcdA showed extensive cell rounding and distorted cell morphology associated with TcdA toxin exposure.

Figure 25:
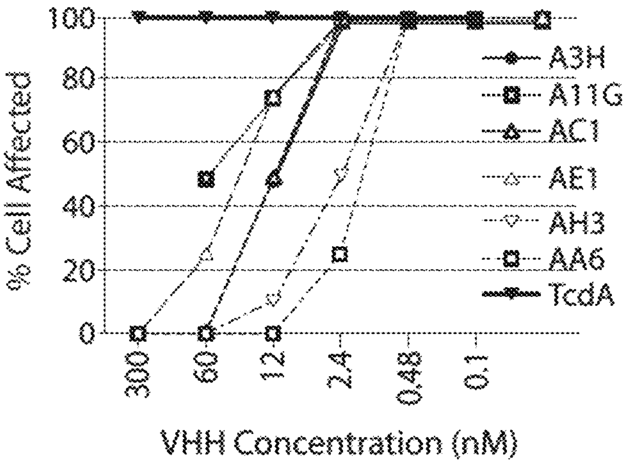
FIG. 25 is a line graph of percent of cells affected by *C. difficile* toxin A (TcdA) and protection of cells from the toxin by VHH monomers. The percent CT26 cells affected by TcdA (% affected; ordinate) is shown as a function of concentration (0.1 nM, 0.48 nM, 2.4 nM, 12 nM, 60 nM, or 300 nM) of each administered VHH monomer: A3H (circle), A11G (light square); AC1 (upward dark empty triangle), AE1 (upward light triangle), AH3 (downward triangle), or AA6 (dark empty square). Control cells were administered toxin only (TcdA; dark downward triangle). Strength of neutralizing VHH activity was observed in the following order: AA6 as strongest, then AH3, AC1, AE1, A11G, and A3H as weakest.

It was observed that each of the VHH monomers reduced the percentage of affected cells and protected the cells from TcdA exposure (FIG. 25). In order of greatest VHH monomer activity to the weakest VHH monomer activity, the greatest activity was observed for AA6, followed AH3, AC1, A3H, AE1, and A116 respectively. It was observed that VHH monomers AA6 and AH3 neutralized TcdA and protected 50% of cells from toxin cytotoxicity at VHH concentrations less than about 10 nM, and thus were considered to have strong TcdA neutralizing activity.

Example 21. Multimeric Binding Proteins Protect Cells from TcdA

CT26 cells were contacted with TcdA (2 ng/ml) and concentrations (0.1 nM, 0.48 nM, 2.4 nM, 12 nM, 60 nM, or 300 nM) of each of VHH monomers: A3H, A11G, AC1, AE1, AH3, or AA6, respectively. Control cells were administered toxin only. The strength of each neutralizing VHH activity was observed by analyzing protection of cells from the toxin by VHH monomers. Percentage of cell rounding (% cell affected) caused by TcdA was monitored using a phase contrast microscope (FIG. 25). Thus, the strongest VHH produced the greatest protection at the lowest concentration. The VHHs were identified in the following order of efficacy: AA6 as the strongest therapeutic agent, followed by AH3, AC1, AE1, A11G, and then A3H as weakest therapeutic agent.

To determine whether VHH monomers or VHH multimers effectively neutralized TcdA, CT26 cells were exposed for 24 hours to TcdA (2 ng/ml) and different concentrations (0.03 ng/mL, 0.1 ng/mL, 1 ng/mL, 3 ng/mL, 10 ng/mL, 30 ng/mL, 100 ng/mL, 300 ng/mL, or 1000 ng/mL) of VHH monomers (AH3 or AA6), VHH heterodimer containing AH3 and AA6, or a homodimer of the heterodimer containing the heterodimer of AH3 and AA6 and fused to an artificial homodimerization domain called oAgB (Ah3/AA6/oAgB; SEQ ID NO: 95). The oAgB domain encodes a peptide having amino acid sequence TSPSTVRLESRVRELEDRLEELRDELERAERRANEMSIQLDEC (SEQ ID NO: 94) that binds to proteins having the same sequence to form homodimers. The cysteine (amino acid abbreviation Cys or C) at the carboxyl end of AgBc becomes oxidized forming a covalent disulfide linkage between the two protein molecules to stabilize the homodimer (dimerizing sequence). Thus the AH3/AA6 heterodimer itself becomes a homodimer containing two copies of AH3/AA6 joined by the oAgBc dimerization domain (SEQ ID NO: 95). Control cells were exposed to toxin only and not to VHH agents. The percentage of cell rounding (% cell affected) was monitored using a phase contrast microscope (FIG. 26).

Figure 26:
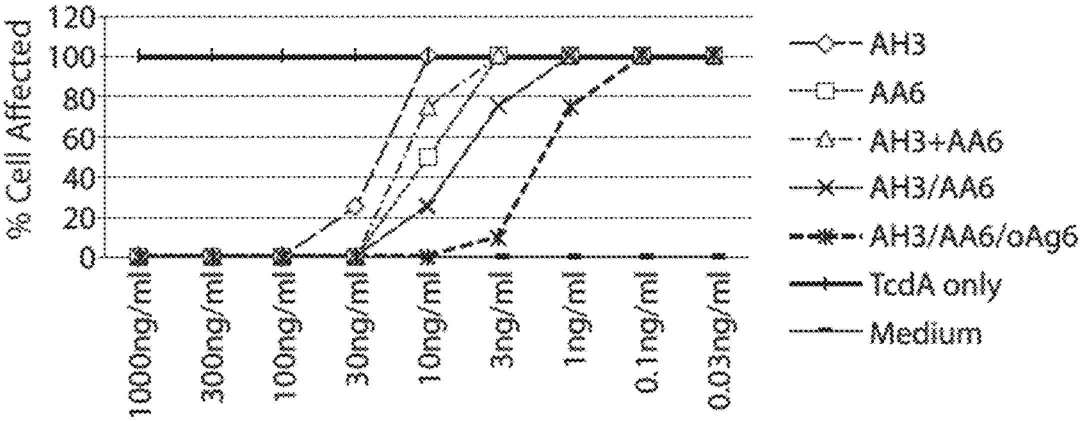
FIG. 26 is a line graph showing percent CT26 cells affected after 24 hours of TcdA exposure (ordinate) as a function of concentration administered (abscissa: 0.03 ng/mL, 0.1 ng/mL, 1 ng/mL, 3 ng/mL, 10 ng/mL, 30 ng/mL, 100 ng/mL, 300 ng/mL, or 1000 ng/mL), or toxin only control (TcdA; vertical line). Agents administered were: VHH monomer AH3 (AH3, diamond), VHH monomer AA6 (AA6, square), a mixture of VHH monomers AH3 and AA6 (AH3+AA6, triangle), VHH heterodimer of AH3 and AA6 (AH3/AA6, -x-); or a homodimer of heterodimer (tetramer) containing AH3 and AA6 using a dimerizer sequence oAgB (AH3/AA6/oAgB, stars; SEQ ID NO: 95). Control cells were treated with medium only. Percent cell rounding was analyzed using a phase contrast microscope. It was observed that the homodimer of the heterodimer containing AH3 and AA6 resulted in the strongest TcdA neutralization.

Data show that control cells contacted with toxin only showed extensive toxin mediated-cell rounding, and that each of the VHH monomers, AH3/AA6 heterodimer and AH3/AA6/oAgB heterodimer/homodimer neutralized TcdA and protected the CT26 cells from the toxin (FIG. 26). The AH3/AA6/oAgB heterodimer/homodimer displayed greatest activity to neutralize and protect cells compared to the AH3/AA6 heterodimer, AH3 monomer, and AA6 monomer respectively. The AH3/AA6/oAgB heterodimer/homodimer displayed about three-fold stronger neutralizing activity for TcdA and protection of the cells than the AH3/AA6 heterodimer alone, and about ten-fold better activity and protection than the VHH monomers (AH3 and AA6 respectively).

Example 22. Heterodimer Binding Proteins Protect Cells from TcdA and TcdB

Figure 27:
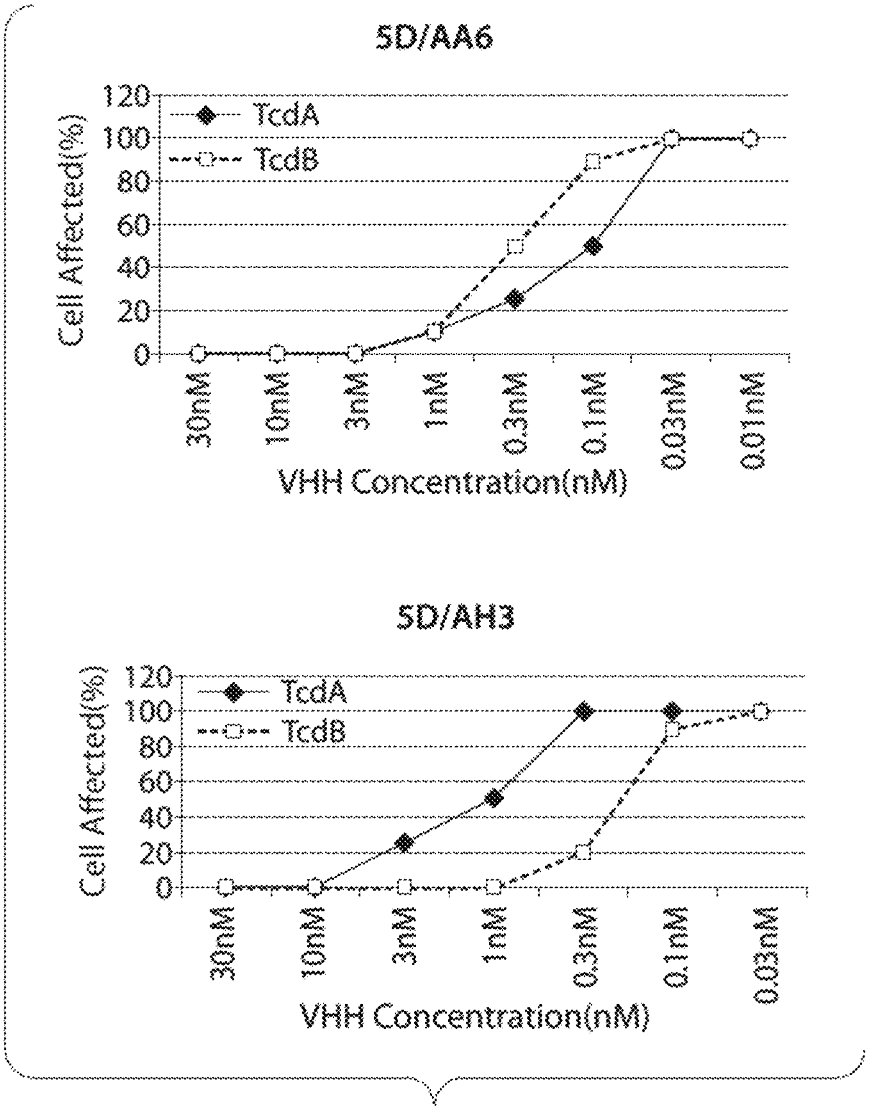
FIG. 27 is a set of line graphs showing percent affected CT26 cells exposed to toxin (ordinate) and then contacted with VHH heterodimer of 5D and AA6 (FIG. 27 top graph) or with heterodimer of 5D and AH3 (FIG. 27 bottom graph) as a function of concentration of VHH (abscissa: 0.01 nM, 0.03 nM, 0.1 nM, 0.3 nM, 1 nM, 3 nM, 10 nM, or 30 nM). CT26 cells were exposed overnight to TcdA (2 ng/mL; diamond) or TcdB (0.1 ng/mL; square), and then treated with either heterodimer 5D/AA6 (FIG. 27 top graph) or heterodimer 5D/AH3 (FIG. 27 bottom graph). Each heterodimer included a VHH monomer (5D) that neutralized TcdB, and a VHH monomer (AA6 or AH3) that neutralized TcdA. Data show that the treatment was effective to protect cells from both toxins.

To determine activity of VHH heterodimers to neutralize both TcdA and TcdB, CT26 cells were exposed overnight to TcdA (2 ng/ml) or TcdB (0.1 ng/ml), and then treated with a heterodimer composition containing VHH 5D and VHH AA6 (FIG. 27 top graph) or with a heterodimer composition containing VHH 5D and VHH AH3 (FIG. 27 bottom graph). Each heterodimer was engineered to contain a VHH (5D) that strongly neutralized TcdB (FIG. 13) and to contain also a VHH (AA6 or AH3) that strongly neutralized TcdA (FIG. 25). The percentage of cell rounding (% cell affected) was monitored using a phase contrast microscope (FIG. 27 top and bottom graphs).

Data show that each of the 5D/AA6 heterodimer and the 5D/AH3 heterodimer neutralized both TcdA and TcdB (FIG. 27 top and bottom graphs). It was observed that 5D/AA6 heterodimer was about five-fold more effective in neutralizing TcdA than the 5D/AH3 heterodimer. Thus, the relative neutralization strength of each heterodimer (FIG. 27) corresponded to the relative neutralization strength of each corresponding AA6 monomer and AH3 monomer shown in FIGS. 25-26.

It was observed that the 5D/AA6 heterodimer was about three-fold or four-fold more effective to neutralize TcdB than the 5D/AH3 heterodimer. Using a concentration of about 0.2 nM of administered 5D/AA6 heterodimer, 50% of cells were protected, compared to about 1 nM of 5D/AH3 heterodimer required for this same level of protection. Without being limited by any particular theory or mechanism of action, it is here envisioned that the relative greater TcdA neutralization ability of the AA6 binding region compared to AH3 binding region resulted in a synergistically greater ability of the respective heterodimer to neutralize a separate toxin TcdB. The increased toxin neutralization for 5D/AA6 for TcdB is presumably caused by amino acid sequences in TcdA and TcdB that are similar and are neutralized effectively by the AA6 component of the heterodimer compared to the AH3 component of the heterodimer.

Figures 28A, 28B, 28C:
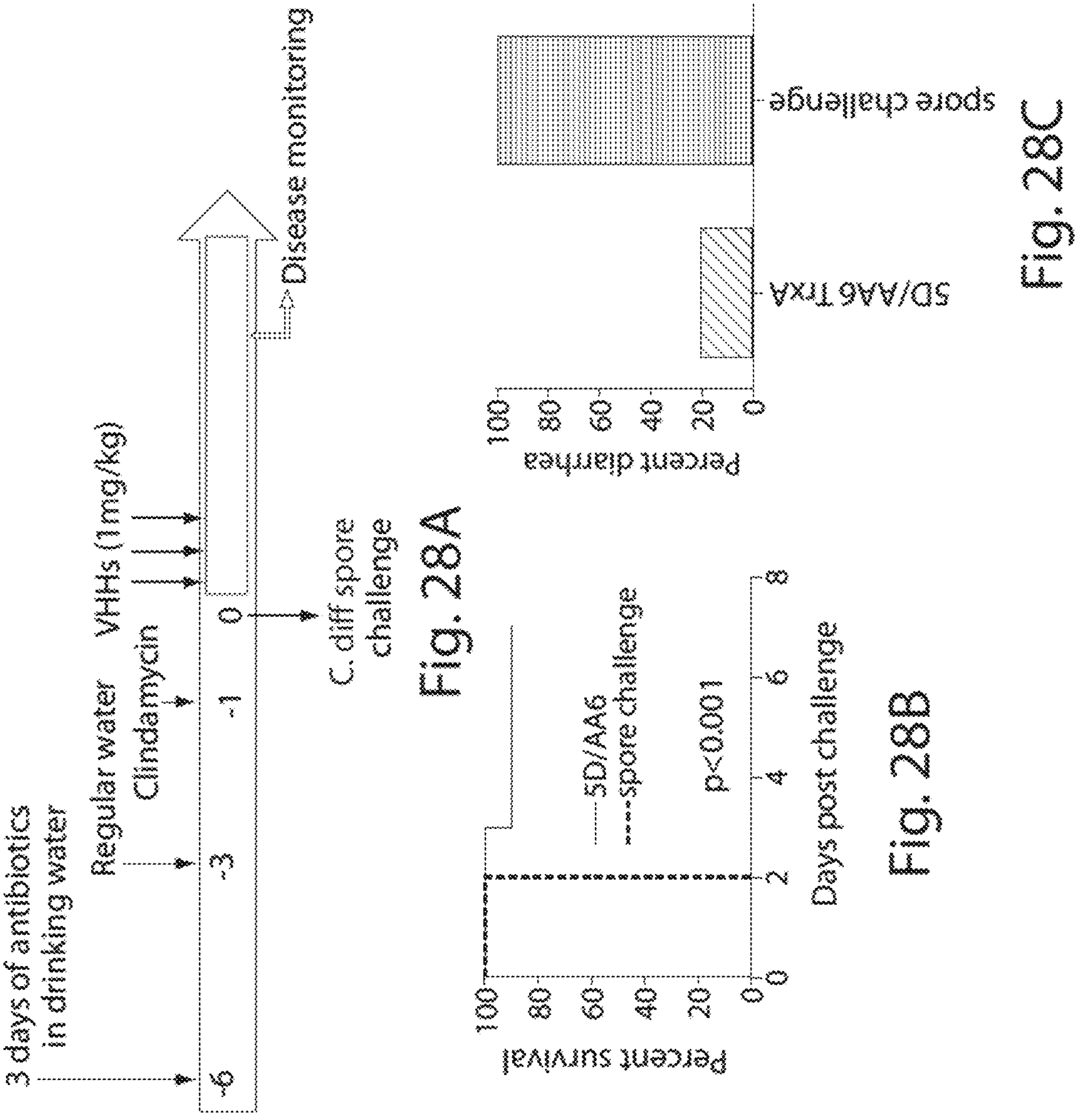
FIGS. 28A-28C are a drawing, a line graph and a bar graph showing that a VHH heterodimer of 5D and AA6 protected mouse subjects from TcdA and TcdB in an oral *C. difficile* spore challenge model.

Example 23. 5D/AA6 Heterodimer Protected Subjects from *C. difficile* Infection To further determine whether a single heterodimer could neutralize both TcdA and TcdB and protect mice from oral *C. difficile* spore challenge, a protocol for a clinically relevant mouse *C. difficile* infection model (Chen et al. 2008 Gastroenterology 135: 1984-1992) was performed as shown in FIG. 28. Groups of mice (ten mice/group) were treated to obtain a model of *C. difficile* associated diarrhea by treatment for three days with antibiotics in drinking water of the subjects, and then two days later by intraperitoneal administration of a single dose of clindamycin before challenge with spores of a *C. difficile* strain expressing both TcdA and TcdB ($10^6$ spores/subject) on day zero (FIG. 28A). To induce more severe and fulminant disease, steroid dexamethasone was supplied to the subjects in drinking water on day −6 (100 mg/mL) until day zero (Sun et al. 2001 Infection and Immunity 79: 2556-2864). Subjects were intraperitoneally injected with VHH heterodimer containing 5D and AA6 (1 mg/kg) three times (six hours, 16 hours, and 24 hours following inoculation/challenge). Control subjects were similarly treated by injection with PBS instead of with the VHH heterodimer. Subjects were monitored hours and days following the VHH injection.

Data show that 100% of control subjects administered toxin died within two days of toxin challenge (FIG. 28B) and suffered diarrhea (FIG. 28C). Only 20% of subjects administered 5D/AA6 heterodimer developed diarrhea and 90% survived (FIGS. 28B and C). Thus, 5D/AA6 heterodimer protected subjects from both TcdA and TcdB spore challenge in a clinically relevant mouse *C. difficile* infection model.

Example 24. Recombinant Multimeric Binding Proteins Neutralize a Plurality of Disease Agents Effectiveness of the antitoxin treatment using multimeric binding proteins are analyzed to determine the ability of the binding proteins to bind to and neutralize a disease agent target.

Recombinant heteromultimeric neutralizing binding protein containing multiple binding regions with or without epitopic tags are produced. The binding regions are not identical and each binding region has affinity to specifically bind a non-overlapping portion of a disease agent: TcdA toxin, TcdB toxin, and a Shiga toxin. The genes encoding proteins are multimerized to form different heteromultimeric binding proteins using the oAgBc dimerization domain (SEQ ID NO: 94) shown in Example 21.

Subjects are exposed to a mixture of disease agents (TcdA toxin, TcdB toxin, Shiga toxin and a norovirus), and then are administered each of the heteromultimeric binding proteins, or a mixture of monoclonal antibodies specific for either TcdA, TcdB, Shiga Toxin 1, and the norovirus. Control subjects are administered the mixture of disease agents only (no multimeric binding proteins). Subjects are monitored for indicia of exposure to the pathogenic molecules such as diarrhea, fever, tachycardia, respiratory distress, and death.

Meyer-Kaplan plots quantifying survival of subjects are prepared and weeks later remaining subjects are sacrificed to analyze tissue and cell morphology. A surprising synergistic protective effect is observed for subjects administered the multimeric binding proteins with or without epitopic tags. Data show that subjects administered the multimeric binding proteins survive longer and have little or no indicia of exposure to the mixture of disease agents compared results for subjects administered monoclonal antibodies to each disease agent and for control subjects administered only disease agents. Subjects administered heteromultimeric binding proteins specific for disease agents do not experience diarrhea, fever or other indicia of exposure to the disease agents. Tissues from subjects administered multimeric binding proteins show normal cell appearance without signs of cell rounding or cell lysis caused by either TcdA, TcdB, Shiga Toxin 1, and the norovirus. The multimeric binding proteins neutralize each of these disease agents. Control subjects have diarrhea, and tissues excised from the intestinal systems show indicia of colitis and extensive internal bleeding.

The multimeric binding protein specific for a mixture of bacterial toxins and a viral infectious agent neutralize each of the disease agents and protected the cells from the subjects from cytotoxicity and cell lysis.

What is claimed is:

1. A composition comprising at least one VHH polypeptide or at least one functional binding fragment thereof, wherein the at least one VHH polypeptide or the at least one functional binding fragment thereof binds to *Clostridium difficile* toxin B and wherein the at least one VHH polypeptide comprises:

(a) an amino acid sequence comprising SEQ ID NO: 67, wherein the amino acid sequence of SEQ ID NO: 67 comprises SEQ ID NO: 16 at its amino terminus and SEQ ID NO: 18 at its carboxy terminus;

(b) an amino acid sequence comprising SEQ ID NO: 68, wherein the amino acid sequence of SEQ ID NO: 68 comprises SEQ ID NO: 16 at its amino terminus and SEQ ID NO: 18 at its carboxy terminus; or (c) an amino acid sequence comprising SEQ ID NO: 69, wherein the amino acid sequence of SEQ ID NO: 69 comprises SEQ ID NO: 16 at its amino terminus and SEQ ID NO: 18 at its carboxy terminus.

2. The composition of claim 1 comprising at least two of the VHH polypeptides or the functional binding fragments thereof.

3. The composition of claim 2, wherein the at least two of the VHH polypeptides or the functional binding fragments thereof are present as a multimer.

4. The composition of claim 3, wherein the multimer is a dimer.

5. The composition of claim 3, wherein the multimer is a trimer.

6. The composition of claim 3, wherein the multimer is formed with a scaffold.

7. The composition of claim 3, wherein the multimer is homodimeric.

8. The composition of claim 3, wherein the multimer is heterodimeric.

9. The composition of claim 1, further comprising an additional therapeutic agent.

10. The composition of claim 9, wherein the additional therapeutic agent is selected from the group consisting of an an antitoxin, an ant-inflammatory agent, an anti-tumor agent, an antiviral agent, an antibacterial agent, an anti-mycobacterial agent, an anti-fungal agent, an anti-proliferative agent, an anti-apoptotic agent, an anti-allergy agent, and an anti-immune suppressant agent.

11. A composition comprising:

(a) an amino acid sequence comprising SEQ ID NO: 67 or a functional binding fragment thereof which binds to *Clostridium difficile* toxin B and wherein SEQ ID NO: 67 comprises SEQ ID NO: 16 at its amino terminus and SEQ ID NO: 18 at its carboxy terminus;

(b) an amino acid sequence comprising SEQ ID NO: 68 or a functional binding fragment thereof which binds to *Clostridium difficile* toxin B and wherein SEQ ID NO: 68 comprises SEQ ID NO: 16 at its amino terminus and SEQ ID NO: 18 at its carboxy terminus; or (c) an amino acid sequence of SEQ ID NO: 69 or a functional binding fragment thereof which binds to *Clostridium difficile* toxin B and wherein SEQ ID NO:

69 comprises SEQ ID NO: 16 at its amino terminus and SEQ ID NO: 18 at its carboxy terminus; and an antibacterial agent.

12. The composition of claim 11, comprising at least two of the VHH polypeptides or the functional binding fragments thereof.

13. The composition of claim 12, wherein the at least two of the VHH polypeptides or the functional binding fragments thereof are present as a multimer.

14. The composition of claim 13, wherein the multimer is a dimer.

15. The composition of claim 13, wherein the multimer is a trimer.

16. The composition of claim 13, wherein the multimer is homodimeric.

17. The composition of claim 13, wherein the multimer is heterodimeric.

18. A composition comprising:

(a) an amino acid sequence comprising SEQ ID NO: 67 or a functional binding fragment thereof which binds to *Clostridium difficile* toxin B;

(b) an amino acid sequence comprising SEQ ID NO: 68 or a functional binding fragment thereof which binds to *Clostridium difficile* toxin B; or (c) an amino acid sequence of SEQ ID NO: 69 or a functional binding fragment thereof which binds to *Clostridium difficile* toxin B; and an antibacterial agent.

19. The composition of claim 1, further comprising a pharmaceutically acceptable carrier, diluent, or excipient.

20. The composition of claim 11, further comprising a pharmaceutically acceptable carrier, diluent, or excipient.

21. The composition of claim 18, further comprising a pharmaceutically acceptable carrier, diluent, or excipient.

22. The composition of claim 1, wherein the at least one VHH polypeptide comprises four framework regions and three complementarity determining regions (CDRs).

23. The composition of claim 11, wherein the at least one VHH polypeptide comprises four framework regions and three complementarity determining regions (CDRs).

24. The composition of claim 18, wherein the at least one VHH polypeptide comprises four framework regions and three complementarity determining regions (CDRs).

* * * * *

SEQUENCE LISTING

```
<160> NUMBER OF SEQ ID NOS: 112

<210> SEQ ID NO 1
<211> LENGTH: 816
<212> TYPE: DNA
<213> ORGANISM: Artificial Sequence
<220> FEATURE:
<223> OTHER INFORMATION: scFv#2 single chain antibody
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 1

caggctgtgc tgactcagcc gtcctccgtg tccgggtccc cgggccnnan ggtctccatc      60

acctgctctg gaagcaggag taacgttggc acatatggtg taggttggtt ccaacagctc     120

ccaggatcgg gcctcagaac catcatctat tataatgaca aacgaccctc aggggtcccc     180

gaccgattct ctgcctccaa atcgggcaac acagccaccc tgatcatcag ctcgctccag     240

gctgaggatg aggccgatta tttctgtgga agtgccgacg gtagtagtta tggtattttc     300

ggcagtggga ccagactgac cgtcctgggt cagcccgcgg ccgctggtgg aggcggttca     360

ggcggaggtg gctctggcgg tggcggatcg gcgcgccagg tggggctgca ggagtcggga     420

cccagcctgg tgaagccctc acagaccctc tccctcacct gcacggtctc tggattctca     480

ttgtccaaca gtgttgtagg ctgggtccgc caggctccag gaaaggtgcc ggagtggctt     540

ggtagtatag acagtggtgg ttacacagtc gctgacccgg ccctgaaatc ccgactcagc     600

atcacaaggg acacttccaa gagccaagtc tccctgtcac tgaacagcgt gacaactgag     660

gacacggccg tgtactactg tacaagggct tatagtatta cttattatgc gtatcccccc     720

tatatcgact actggggccc aggactcctg gtcaccgtct cctcaactag tggtgcgccg     780

gtgccgtatc cggatccgct ggaaccgcgt gccgca                               816

<210> SEQ ID NO 2
<211> LENGTH: 272
<212> TYPE: PRT
<213> ORGANISM: Artificial Sequence
```

```
<220> FEATURE:
<223> OTHER INFORMATION: scFv#2 single chain antibody
<220> FEATURE:
<221> NAME/KEY: misc_feature
<222> LOCATION: (16)..(17)
<223> OTHER INFORMATION: Xaa can be any naturally occurring amino acid

<400> SEQUENCE: 2

Gln Ala Val Leu Thr Gln Pro Ser Ser Val Ser Gly Ser Pro Gly Xaa
1               5                   10                  15

Xaa Val Ser Ile Thr Cys Ser Gly Ser Arg Ser Asn Val Gly Thr Tyr
            20                  25                  30

Gly Val Gly Trp Phe Gln Gln Leu Pro Gly Ser Gly Leu Arg Thr Ile
        35                  40                  45

Ile Tyr Tyr Asn Asp Lys Arg Pro Ser Gly Val Pro Asp Arg Phe Ser
    50                  55                  60

Ala Ser Lys Ser Gly Asn Thr Ala Thr Leu Ile Ile Ser Ser Leu Gln
65                  70                  75                  80

Ala Glu Asp Glu Ala Asp Tyr Phe Cys Gly Ser Ala Asp Gly Ser Ser
                85                  90                  95

Tyr Gly Ile Phe Gly Ser Gly Thr Arg Leu Thr Val Leu Gly Gln Pro
            100                 105                 110

Ala Ala Ala Gly Gly Gly Gly Ser Gly Gly Gly Gly Ser Gly Gly Gly
        115                 120                 125

Gly Ser Ala Arg Gln Val Gly Leu Gln Glu Ser Gly Pro Ser Leu Val
    130                 135                 140

Lys Pro Ser Gln Thr Leu Ser Leu Thr Cys Thr Val Ser Gly Phe Ser
145                 150                 155                 160

Leu Ser Asn Ser Val Val Gly Trp Val Arg Gln Ala Pro Gly Lys Val
                165                 170                 175

Pro Glu Trp Leu Gly Ser Ile Asp Ser Gly Gly Tyr Thr Val Ala Asp
            180                 185                 190

Pro Ala Leu Lys Ser Arg Leu Ser Ile Thr Arg Asp Thr Ser Lys Ser
        195                 200                 205

Gln Val Ser Leu Ser Leu Asn Ser Val Thr Thr Glu Asp Thr Ala Val
    210                 215                 220

Tyr Tyr Cys Thr Arg Ala Tyr Ser Ile Thr Tyr Tyr Ala Tyr Pro Pro
225                 230                 235                 240

Tyr Ile Asp Tyr Trp Gly Pro Gly Leu Leu Val Thr Val Ser Ser Thr
                245                 250                 255

Ser Gly Ala Pro Val Pro Tyr Pro Asp Pro Leu Glu Pro Arg Ala Ala
            260                 265                 270


<210> SEQ ID NO 3
<211> LENGTH: 826
<212> TYPE: DNA
<213> ORGANISM: Artificial Sequence
<220> FEATURE:
<223> OTHER INFORMATION: scFv#3 Single Chain Antibody

<400> SEQUENCE: 3

caggctgtgc tgactcagcc gtcctccgtg tccaggtccc tgggccagag tgtctccatc      60

acctgctctg gaagcagcag caacgttgga tatggtgatt atgtgggctg gttccaacgg     120

gtcccaggat cagcccccaa actcctcatc tatggtgcaa ccactcgagc ctcgggggtc     180

cccgaccgat tctccggctc caggtctggc aacacagcga ctctgaccat cagctcgctc     240

caggctgagg acgaggccga ttattactgt tcatcttacg acagtagtca ctatagtatt     300
```

-continued

```
ttcggcagtg ggaccagcct gaccgtcctg ggtcagcccg cggccgctgg tggaggcggt    360

tcaggcggag gtggctctgg cggtggcgga tcggcgcgcc aggtggagct gcaggagtcg    420

ggacccagcc tggtgaagcc ctcacagacc ctctccctca cctgcacggt ctctggattc    480

tcattaagta gcaatgctgt aggctgggtc cgccaggctc caggaaaggc gccggagtgg    540

gttggtggta tagatataga tggaaggccg gtctataaac caggccttaa gtcccggctc    600

agcatcacca gggacacctc caacgctcaa gtctccctgt cactgagcag cgtgacaact    660

gaggacacgg ccgtgtactt ctgtgcaagt tattatggtg gttatcttta taattatgcc    720

cctggggcat atatcgagca cttgagccca ggactcctga tcaccgtctc ctcaactagt    780

ggtgcgccgg tgccgtatcc ggatccgctg gaaaccgcgt gccgca                   826
```

```
<210> SEQ ID NO 4
<211> LENGTH: 275
<212> TYPE: PRT
<213> ORGANISM: Artificial Sequence
<220> FEATURE:
<223> OTHER INFORMATION: scFv#3 single chain antibody

<400> SEQUENCE: 4

Gln Ala Val Leu Thr Gln Pro Ser Ser Val Ser Arg Ser Leu Gly Gln
1               5                   10                  15

Ser Val Ser Ile Thr Cys Ser Gly Ser Ser Ser Asn Val Gly Tyr Gly
            20                  25                  30

Asp Tyr Val Gly Trp Phe Gln Arg Val Pro Gly Ser Ala Pro Lys Leu
        35                  40                  45

Leu Ile Tyr Gly Ala Thr Thr Arg Ala Ser Gly Val Pro Asp Arg Phe
    50                  55                  60

Ser Gly Ser Arg Ser Gly Asn Thr Ala Thr Leu Thr Ile Ser Ser Leu
65                  70                  75                  80

Gln Ala Glu Asp Glu Ala Asp Tyr Tyr Cys Ser Ser Tyr Asp Ser Ser
                85                  90                  95

His Tyr Ser Ile Phe Gly Ser Gly Thr Ser Leu Thr Val Leu Gly Gln
            100                 105                 110

Pro Ala Ala Ala Gly Gly Gly Gly Ser Gly Gly Gly Gly Ser Gly Gly
        115                 120                 125

Gly Gly Ser Ala Arg Gln Val Glu Leu Gln Glu Ser Gly Pro Ser Leu
    130                 135                 140

Val Lys Pro Ser Gln Thr Leu Ser Leu Thr Cys Thr Val Ser Gly Phe
145                 150                 155                 160

Ser Leu Ser Ser Asn Ala Val Gly Trp Val Arg Gln Ala Pro Gly Lys
                165                 170                 175

Ala Pro Glu Trp Val Gly Gly Ile Asp Ile Asp Gly Arg Pro Val Tyr
            180                 185                 190

Lys Pro Gly Leu Lys Ser Arg Leu Ser Ile Thr Arg Asp Thr Ser Asn
        195                 200                 205

Ala Gln Val Ser Leu Ser Leu Ser Ser Val Thr Thr Glu Asp Thr Ala
    210                 215                 220

Val Tyr Phe Cys Ala Ser Tyr Tyr Gly Gly Tyr Leu Tyr Asn Tyr Ala
225                 230                 235                 240

Pro Gly Ala Tyr Ile Glu His Leu Ser Pro Gly Leu Leu Ile Thr Val
                245                 250                 255

Ser Ser Thr Ser Gly Ala Pro Val Pro Tyr Pro Asp Pro Leu Glu Pro
            260                 265                 270
```

-continued

```
Arg Ala Ala
        275


<210> SEQ ID NO 5
<211> LENGTH: 816
<212> TYPE: DNA
<213> ORGANISM: Artificial Sequence
<220> FEATURE:
<223> OTHER INFORMATION: scFv#7 Single Chain Antibody

<400> SEQUENCE: 5

tcctatgaac tgacccagcc gccttcaatg tcggtggcct tgggacagac ggccaaggtc      60

acctgccagg gagacaactt agaaaacttt tatgttcagt ggcaccagca gaagccgggc     120

caggcccctg tgacggtcat tttcaggat aataagaggc cctcggggat ccctgaccgg      180

ttctctggct ccaactcggg gaacacggcc accctgacca tcagcggggc ccggaccgag     240

gacgaggccg actattactg tcagtcaggc cacagcagta tcggtggtgt tttcggcagc     300

gggaccagcc tgaccgtcct gggtcagccc gcggccgctg gtggaggcgg ttcaggcgga     360

ggtggctctg gcggtggcgg atcggcgcgc caggtgcagc tgcaggagtc gggacccagc     420

ctggtgaagc cctcacagac cctctccctc acctgcacgg tctctggctt ctcattaacg     480

ggaaattctg taacctgggt ccgccaggct ccaggaaacg tgccggagtg gcttggtggt     540

ataagccgcg gtggacgcac atactatgat acggccctga agtcccggct cagcatcacc     600

agggacacct ccaagaggca agtctcccta tcactgagca gcgtgacgac tgaggacacg     660

gccatgtact tctgtgcaag atcggcatat agtactcttt atgattatga gtatgccgct     720

gatatctacg actggggccc aggactcctg gtcaccgtct cctcaactag tggtgcgccg     780

gtgccgtatc cggatccgct ggaaccgcgt gccgca                               816


<210> SEQ ID NO 6
<211> LENGTH: 272
<212> TYPE: PRT
<213> ORGANISM: Artificial Sequence
<220> FEATURE:
<223> OTHER INFORMATION: scFv#7 Single Chain Antibody

<400> SEQUENCE: 6

Ser Tyr Glu Leu Thr Gln Pro Pro Ser Met Ser Val Ala Leu Gly Gln
1               5                   10                  15

Thr Ala Lys Val Thr Cys Gln Gly Asp Asn Leu Glu Asn Phe Tyr Val
            20                  25                  30

Gln Trp His Gln Gln Lys Pro Gly Gln Ala Pro Val Thr Val Ile Phe
        35                  40                  45

Gln Asp Asn Lys Arg Pro Ser Gly Ile Pro Asp Arg Phe Ser Gly Ser
    50                  55                  60

Asn Ser Gly Asn Thr Ala Thr Leu Thr Ile Ser Gly Ala Arg Thr Glu
65                  70                  75                  80

Asp Glu Ala Asp Tyr Tyr Cys Gln Ser Gly His Ser Ser Ile Gly Gly
                85                  90                  95

Val Phe Gly Ser Gly Thr Ser Leu Thr Val Leu Gly Gln Pro Ala Ala
            100                 105                 110

Ala Gly Gly Gly Gly Ser Gly Gly Gly Gly Ser Gly Gly Gly Gly Ser
        115                 120                 125

Ala Arg Gln Val Gln Leu Gln Glu Ser Gly Pro Ser Leu Val Lys Pro
    130                 135                 140
```

```
Ser Gln Thr Leu Ser Leu Thr Cys Thr Val Ser Gly Phe Ser Leu Thr
145                 150                 155                 160

Gly Asn Ser Val Thr Trp Val Arg Gln Ala Pro Gly Asn Val Pro Glu
                165                 170                 175

Trp Leu Gly Gly Ile Ser Arg Gly Gly Arg Thr Tyr Tyr Asp Thr Ala
            180                 185                 190

Leu Lys Ser Arg Leu Ser Ile Thr Arg Asp Thr Ser Lys Arg Gln Val
        195                 200                 205

Ser Leu Ser Leu Ser Ser Val Thr Thr Glu Asp Thr Ala Met Tyr Phe
    210                 215                 220

Cys Ala Arg Ser Ala Tyr Ser Thr Leu Tyr Asp Tyr Glu Tyr Ala Ala
225                 230                 235                 240

Asp Ile Tyr Asp Trp Gly Pro Gly Leu Leu Val Thr Val Ser Ser Thr
                245                 250                 255

Ser Gly Ala Pro Val Pro Tyr Pro Asp Pro Leu Glu Pro Arg Ala Ala
            260                 265                 270
```

<210> SEQ ID NO 7
<211> LENGTH: 795
<212> TYPE: DNA
<213> ORGANISM: Artificial Sequence
<220> FEATURE:
<223> OTHER INFORMATION: scFv#8 Single Chain Antibody
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 7

```
tcctatgaac tgacccagcc gccttcagtg tcggtggttt ggggncngan ggccgagatc      60

acctgccagg gagacctact ggataaaaaa tatacagctt ggtaccagca gaagccgggc     120

caggctccta tgaaaatcat taataaagac agtgagcggc cttcagggat ccgggaccgg     180

ttctcgggct ccagctcagg caaaacagcc accctaacca tcaacggggc ccggcctgag     240

gacgaggccg actattactg tttatcaggt gacagcaata ataatggtgt cttcggcagc     300

gggaccagcc tgaccgtcct gggtcagccc gcggccgctg gtggaggcgg ttcaggcgga     360

ggtggctctg gcggtggcgg atcggcgcgc caggtggagc tgcaggggtc gggacccagc     420

ctggtgaagc cctcgcagac cctctccctc acctgcacgg tctctggatt ctcatggccc     480

aacaatgctg tggattgggt ccgccaggct ccaggaaagg cgccggagtg gcttggtggt     540

attgccgata atggaagaac aaactacaac acggccctaa aagcccggct cagcatcact     600

agggacaccg ccaagagcca tgtctcccta tcgctgagca gcgtgacagc tgaggatacg     660

gccgtttact attgtacagc gggggttatg gtcatgcacg ccactgacta ctggggcccg     720

ggactcctgg tcaccgtctc ctcaactagt ggtgcgccgg tgccgtatcc ggatccgctg     780

gaaccgcgtg ccgca                                                      795
```

<210> SEQ ID NO 8
<211> LENGTH: 265
<212> TYPE: PRT
<213> ORGANISM: Artificial Sequence
<220> FEATURE:
<223> OTHER INFORMATION: scFv#8 Single Chain Antibody
<220> FEATURE:
<221> NAME/KEY: misc_feature
<222> LOCATION: (16)..(17)
<223> OTHER INFORMATION: Xaa can be any naturally occurring amino acid

<400> SEQUENCE: 8

```
Ser Tyr Glu Leu Thr Gln Pro Pro Ser Val Ser Val Val Trp Gly Xaa
1               5                   10                  15

Xaa Ala Glu Ile Thr Cys Gln Gly Asp Leu Leu Asp Lys Lys Tyr Thr
            20                  25                  30

Ala Trp Tyr Gln Gln Lys Pro Gly Gln Ala Pro Met Lys Ile Ile Asn
        35                  40                  45

Lys Asp Ser Glu Arg Pro Ser Gly Ile Arg Asp Arg Phe Ser Gly Ser
    50                  55                  60

Ser Ser Gly Lys Thr Ala Thr Leu Thr Ile Asn Gly Ala Arg Pro Glu
65                  70                  75                  80

Asp Glu Ala Asp Tyr Tyr Cys Leu Ser Gly Asp Ser Asn Asn Asn Gly
                85                  90                  95

Val Phe Gly Ser Gly Thr Ser Leu Thr Val Leu Gly Gln Pro Ala Ala
            100                 105                 110

Ala Gly Gly Gly Gly Ser Gly Gly Gly Gly Ser Gly Gly Gly Gly Ser
        115                 120                 125

Ala Arg Gln Val Glu Leu Gln Gly Ser Gly Pro Ser Leu Val Lys Pro
    130                 135                 140

Ser Gln Thr Leu Ser Leu Thr Cys Thr Val Ser Gly Phe Ser Trp Pro
145                 150                 155                 160

Asn Asn Ala Val Asp Trp Val Arg Gln Ala Pro Gly Lys Ala Pro Glu
                165                 170                 175

Trp Leu Gly Gly Ile Ala Asp Asn Gly Arg Thr Asn Tyr Asn Thr Ala
            180                 185                 190

Leu Lys Ala Arg Leu Ser Ile Thr Arg Asp Thr Ala Lys Ser His Val
        195                 200                 205

Ser Leu Ser Leu Ser Ser Val Thr Ala Glu Asp Thr Ala Val Tyr Tyr
    210                 215                 220

Cys Thr Ala Gly Val Met Val Met His Ala Thr Asp Tyr Trp Gly Pro
225                 230                 235                 240

Gly Leu Leu Val Thr Val Ser Ser Thr Ser Gly Ala Pro Val Pro Tyr
                245                 250                 255

Pro Asp Pro Leu Glu Pro Arg Ala Ala
            260                 265
```

<210> SEQ ID NO 9
<211> LENGTH: 810
<212> TYPE: DNA
<213> ORGANISM: Artificial Sequence
<220> FEATURE:
<223> OTHER INFORMATION: scFv#21 Single Chain Antibody
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 9

```
caggctgtgg tgactcagcc gtcctccgtg tccgggtccc cgggccnnan agtctccatc     60
```

-continued

```
acctgctctg gaagcagcag caacgttggt agatatgctg taggctggtt ccaacagctc    120

ccaggatcgg gcctcagaac cgtcatctat tataatagca atcgaccctc aggggtcccc    180

gaccgattct ctggctccaa atcgggcaac acagccaccc tgaccatcag ctcgctccag    240

gctgaggatg aggccgatta tttctgtgga agttatgaca gtagtatcta tggtgttttc    300

ggcagcggga ccaggctgac cgtcctgggt cagcccgcgg ccgctggtgg aggcggttca    360

ggcggaggtg gctctggcgg tggcggatcg gcgcgccagg tgcagctgca ggagtcggga    420

cccagcctgg tgaggccctc acagaccctc tccctcacct gcacgatctc tggattctct    480

ttaagagagt atggtgtagg ttgggtccgc caggctccag gaaaggcgtt ggagtggctt    540

gggcgaatag atgattctgg atacacatta cataatcctg cccttaagtc ccggctcacc    600

ataactaggg acatctccaa gagccaagtc tccctgtcac tgagcagcgt gacacttgag    660

gacacggccg aatattactg cgtatatgct agtcgtggta ctgcttggtt gggagacatc    720

gatgtctggg gcccaggact cctgctcact gtctcctcaa ctagtggtgc gccggtgccg    780

tatccggatc cgctggaacc gcgtgccgca                                     810
```

```
<210> SEQ ID NO 10
<211> LENGTH: 270
<212> TYPE: PRT
<213> ORGANISM: Artificial Sequence
<220> FEATURE:
<223> OTHER INFORMATION: scFv#21 Single Chain Antibody
<220> FEATURE:
<221> NAME/KEY: misc_feature
<222> LOCATION: (16)..(17)
<223> OTHER INFORMATION: Xaa can be any naturally occurring amino acid

<400> SEQUENCE: 10

Gln Ala Val Val Thr Gln Pro Ser Ser Val Ser Gly Ser Pro Gly Xaa
1               5                   10                  15

Xaa Val Ser Ile Thr Cys Ser Gly Ser Ser Ser Asn Val Gly Arg Tyr
            20                  25                  30

Ala Val Gly Trp Phe Gln Gln Leu Pro Gly Ser Gly Leu Arg Thr Val
        35                  40                  45

Ile Tyr Tyr Asn Ser Asn Arg Pro Ser Gly Val Pro Asp Arg Phe Ser
    50                  55                  60

Gly Ser Lys Ser Gly Asn Thr Ala Thr Leu Thr Ile Ser Ser Leu Gln
65                  70                  75                  80

Ala Glu Asp Glu Ala Asp Tyr Phe Cys Gly Ser Tyr Asp Ser Ser Ile
                85                  90                  95

Tyr Gly Val Phe Gly Ser Gly Thr Arg Leu Thr Val Leu Gly Gln Pro
            100                 105                 110

Ala Ala Ala Gly Gly Gly Gly Ser Gly Gly Gly Gly Ser Gly Gly Gly
        115                 120                 125

Gly Ser Ala Arg Gln Val Gln Leu Gln Glu Ser Gly Pro Ser Leu Val
    130                 135                 140

Arg Pro Ser Gln Thr Leu Ser Leu Thr Cys Thr Ile Ser Gly Phe Ser
145                 150                 155                 160

Leu Arg Glu Tyr Gly Val Gly Trp Val Arg Gln Ala Pro Gly Lys Ala
                165                 170                 175

Leu Glu Trp Leu Gly Arg Ile Asp Asp Ser Gly Tyr Thr Leu His Asn
            180                 185                 190

Pro Ala Leu Lys Ser Arg Leu Thr Ile Thr Arg Asp Ile Ser Lys Ser
        195                 200                 205
```

-continued

Gln Val Ser Leu Ser Leu Ser Ser Val Thr Leu Glu Asp Thr Ala Glu
    210                 215                 220

Tyr Tyr Cys Val Tyr Ala Ser Arg Gly Thr Ala Trp Leu Gly Asp Ile
225                 230                 235                 240

Asp Val Trp Gly Pro Gly Leu Leu Leu Thr Val Ser Ser Thr Ser Gly
                245                 250                 255

Ala Pro Val Pro Tyr Pro Asp Pro Leu Glu Pro Arg Ala Ala
            260                 265                 270

<210> SEQ ID NO 11
<211> LENGTH: 816
<212> TYPE: DNA
<213> ORGANISM: Artificial Sequence
<220> FEATURE:
<223> OTHER INFORMATION: scFv#E Single Chain Antibody
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 11
caggctgtgc tgactcagcc gtcctccgtg tccaggtccc tgggccnnan tgtctcgatc 60
acctgctctg gaggcagcag caacgttgga caaggtgatt atgtggcctg gttccaacag 120
gtcccaggat cagcccccaa actcctcatc tatgatgcga cgaatcgagc ctcgggggtc 180
cccgaccgat tcgtcggctc cagatatggc aactcagcga ctctgatcat cacctcggtc 240
caggctgagg acgaggccga ttattattgt gcatcttatg acagtagtat gtatacgatt 300
ttcggcagcg ggaccagcct gaccgtcctg ggtcagcccg cggccgctgg tggaggcggt 360
tcaggcggag gtggctctgg cggtggcgga tcggcgcgcc aggtggagct gcaggggtcg 420
ggacccagcc aggtgaagcc ctcacagacc ctctccctca tctgcacgat ctctggattc 480
tcattaacca gcaataatgt agcctgggtc cgccaggctc caggaaaggg actggagtgg 540
gttggtgtca taagtgatgg tggaactcca tactataact cggccctgaa atcccggctc 600
agcatcacca gggacacctc caagagccag gtctccctgt cactgagcag cgtgacaact 660
gaggacacgg ccgtgtacta ctgtgcacgg acgttggatt atagtcatat ttggttgtac 720
tccgccgacc aatggggccc aggactcctg gtcaccgtct cctcaactag tggtgcgccg 780
gtgccgtatc cggatccgct ggaaccgcgt gccgca 816

<210> SEQ ID NO 12
<211> LENGTH: 272
<212> TYPE: PRT
<213> ORGANISM: Artificial Sequence
<220> FEATURE:
<223> OTHER INFORMATION: scFv#E Single Chain Antibody
<220> FEATURE:
<221> NAME/KEY: misc_feature
<222> LOCATION: (16)..(17)
<223> OTHER INFORMATION: Xaa can be any naturally occurring amino acid

<400> SEQUENCE: 12

Gln Ala Val Leu Thr Gln Pro Ser Ser Val Ser Arg Ser Leu Gly Xaa
1               5                   10                  15

Xaa Val Ser Ile Thr Cys Ser Gly Gly Ser Ser Asn Val Gly Gln Gly
            20                  25                  30

-continued

```
Asp Tyr Val Ala Trp Phe Gln Gln Val Pro Gly Ser Ala Pro Lys Leu
        35                  40                  45

Leu Ile Tyr Asp Ala Thr Asn Arg Ala Ser Gly Val Pro Asp Arg Phe
    50                  55                  60

Val Gly Ser Arg Tyr Gly Asn Ser Ala Thr Leu Ile Ile Thr Ser Val
65                  70                  75                  80

Gln Ala Glu Asp Glu Ala Asp Tyr Tyr Cys Ala Ser Tyr Asp Ser Ser
                85                  90                  95

Met Tyr Thr Ile Phe Gly Ser Gly Thr Ser Leu Thr Val Leu Gly Gln
            100                 105                 110

Pro Ala Ala Ala Gly Gly Gly Gly Ser Gly Gly Gly Gly Ser Gly Gly
        115                 120                 125

Gly Gly Ser Ala Arg Gln Val Glu Leu Gln Gly Ser Gly Pro Ser Gln
    130                 135                 140

Val Lys Pro Ser Gln Thr Leu Ser Leu Ile Cys Thr Ile Ser Gly Phe
145                 150                 155                 160

Ser Leu Thr Ser Asn Asn Val Ala Trp Val Arg Gln Ala Pro Gly Lys
                165                 170                 175

Gly Leu Glu Trp Val Gly Val Ile Ser Asp Gly Gly Thr Pro Tyr Tyr
            180                 185                 190

Asn Ser Ala Leu Lys Ser Arg Leu Ser Ile Thr Arg Asp Thr Ser Lys
        195                 200                 205

Ser Gln Val Ser Leu Ser Leu Ser Ser Val Thr Thr Glu Asp Thr Ala
    210                 215                 220

Val Tyr Tyr Cys Ala Arg Thr Leu Asp Tyr Ser His Ile Trp Leu Tyr
225                 230                 235                 240

Ser Ala Asp Gln Trp Gly Pro Gly Leu Leu Val Thr Val Ser Ser Thr
                245                 250                 255

Ser Gly Ala Pro Val Pro Tyr Pro Asp Pro Leu Glu Pro Arg Ala Ala
            260                 265                 270


<210> SEQ ID NO 13
<211> LENGTH: 861
<212> TYPE: DNA
<213> ORGANISM: Artificial Sequence
<220> FEATURE:
<223> OTHER INFORMATION: scFv#7-2E Single Chain Antibody

<400> SEQUENCE: 13

ggtgcgccgg tgccgtatcc ggatccgctc gagccgcgtg ccggctccta tgaactgacc      60

cagccgcctt caatgtcggt ggccttggga cagacggcca aggtcacctg ccagggagac     120

aacttagaaa acttttatgt tcagtggcac cagcagaagc cgggccaggc ccctgtgacg     180

gtcatttttc aggataataa gaggccctcg gggatccctg accggttctc tggctccaac     240

tcggggaaca cggccaccct gaccatcagc ggggcccgga ccgaggacga ggccgactat     300

tactgtcagt caggccacag cagtatcggt ggtgttttcg gcagcgggac cagcctgacc     360

gtcctgggtc agcccgcggc cgctggtgga ggcggttcag gcggaggtgg ctctggcggt     420

ggcggatcgg cgcgccaggt gcagctgcag gagtcgggac ccagcctggt gaagccctca     480

cagaccctct ccctcacctg cacggtctct ggcttctcat taacgggaaa ttctgtaacc     540

tgggtccgcc aggctccagg aaacgtgccg gagtggcttg gtggtataag ccgcggtgga     600

cgcacatact atgatacggc cctgaagtcc cggctcagca tcaccaggga cacctccaag     660

aggcaagtct ccctatcact gagcagcgtg acgactgagg acacggccat gtacttctgt     720
```

-continued

```
gcaagatcgg catatagtac tctttatgat tatgagtatg ccgctgatat ctacgactgg    780

ggcccaggac tcctggtcac cgtctcctca actagtggtg cgccggtgcc gtatccggat    840

ccgctggaac cgcgtgccgc a                                              861


<210> SEQ ID NO 14
<211> LENGTH: 287
<212> TYPE: PRT
<213> ORGANISM: Artificial Sequence
<220> FEATURE:
<223> OTHER INFORMATION: scFv#7-2E Single Chain Antibody

<400> SEQUENCE: 14

Gly Ala Pro Val Pro Tyr Pro Asp Pro Leu Glu Pro Arg Ala Gly Ser
1               5                   10                  15

Tyr Glu Leu Thr Gln Pro Pro Ser Met Ser Val Ala Leu Gly Gln Thr
            20                  25                  30

Ala Lys Val Thr Cys Gln Gly Asp Asn Leu Glu Asn Phe Tyr Val Gln
        35                  40                  45

Trp His Gln Gln Lys Pro Gly Gln Ala Pro Val Thr Val Ile Phe Gln
    50                  55                  60

Asp Asn Lys Arg Pro Ser Gly Ile Pro Asp Arg Phe Ser Gly Ser Asn
65                  70                  75                  80

Ser Gly Asn Thr Ala Thr Leu Thr Ile Ser Gly Ala Arg Thr Glu Asp
                85                  90                  95

Glu Ala Asp Tyr Tyr Cys Gln Ser Gly His Ser Ser Ile Gly Gly Val
            100                 105                 110

Phe Gly Ser Gly Thr Ser Leu Thr Val Leu Gly Gln Pro Ala Ala Ala
        115                 120                 125

Gly Gly Gly Gly Ser Gly Gly Gly Gly Ser Gly Gly Gly Gly Ser Ala
    130                 135                 140

Arg Gln Val Gln Leu Gln Glu Ser Gly Pro Ser Leu Val Lys Pro Ser
145                 150                 155                 160

Gln Thr Leu Ser Leu Thr Cys Thr Val Ser Gly Phe Ser Leu Thr Gly
                165                 170                 175

Asn Ser Val Thr Trp Val Arg Gln Ala Pro Gly Asn Val Pro Glu Trp
            180                 185                 190

Leu Gly Gly Ile Ser Arg Gly Gly Arg Thr Tyr Tyr Asp Thr Ala Leu
        195                 200                 205

Lys Ser Arg Leu Ser Ile Thr Arg Asp Thr Ser Lys Arg Gln Val Ser
    210                 215                 220

Leu Ser Leu Ser Ser Val Thr Thr Glu Asp Thr Ala Met Tyr Phe Cys
225                 230                 235                 240

Ala Arg Ser Ala Tyr Ser Thr Leu Tyr Asp Tyr Glu Tyr Ala Ala Asp
                245                 250                 255

Ile Tyr Asp Trp Gly Pro Gly Leu Leu Val Thr Val Ser Ser Thr Ser
            260                 265                 270

Gly Ala Pro Val Pro Tyr Pro Asp Pro Leu Glu Pro Arg Ala Ala
        275                 280                 285


<210> SEQ ID NO 15
<211> LENGTH: 13
<212> TYPE: PRT
<213> ORGANISM: Artificial Sequence
<220> FEATURE:
<223> OTHER INFORMATION: Epitope Tag

<400> SEQUENCE: 15
```

Gly Ala Pro Val Pro Tyr Pro Asp Pro Leu Glu Pro Arg
1 5 10

<210> SEQ ID NO 16
<211> LENGTH: 9
<212> TYPE: PRT
<213> ORGANISM: Artificial Sequence
<220> FEATURE:
<223> OTHER INFORMATION: VHH binding agents

<400> SEQUENCE: 16

Gln Val Gln Leu Val Glu Ser Gly Gly
1 5

<210> SEQ ID NO 17
<211> LENGTH: 8
<212> TYPE: PRT
<213> ORGANISM: Artificial Sequence
<220> FEATURE:
<223> OTHER INFORMATION: VHH binding agents

<400> SEQUENCE: 17

Ala His His Ser Glu Asp Pro Ser
1 5

<210> SEQ ID NO 18
<211> LENGTH: 8
<212> TYPE: PRT
<213> ORGANISM: Artificial Sequence
<220> FEATURE:
<223> OTHER INFORMATION: VHH binding agents

<400> SEQUENCE: 18

Glu Pro Lys Thr Pro Lys Pro Gln
1 5

<210> SEQ ID NO 19
<211> LENGTH: 396
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 19
caggtgcagc tcgtggagtc aggaggaggc ttggtgcagc ctgggggatc tctgagactc 60
tcgtgtgtag tctctggaag tgacttcaat acctatatca tgggctggta ccgccaggtt 120
ccagggaagc cgcgcgagtt ggtcgcagat attactactg aaggaaaaac aaactatggc 180
ggctccgtaa agggacgatt caccatctcc agagacaacg ccaaaaacac ggtgtatctg 240
caaatgttcg gcctgaaacc tgaggacgcg ggtaattatg tctgtaacgc agactggaag 300
atgggtgcat ggaccgcggg ggactacggt atcgactact ggggcaaagg gaccctggtc 360
accgtctcct cagaacccaa gacaccaaaa ccacaa 396

<210> SEQ ID NO 20
<211> LENGTH: 132
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 20

Gln Val Gln Leu Val Glu Ser Gly Gly Gly Leu Val Gln Pro Gly Gly
1 5 10 15

```
Ser Leu Arg Leu Ser Cys Val Val Ser Gly Ser Asp Phe Asn Thr Tyr
            20                  25                  30

Ile Met Gly Trp Tyr Arg Gln Val Pro Gly Lys Pro Arg Glu Leu Val
        35                  40                  45

Ala Asp Ile Thr Thr Glu Gly Lys Thr Asn Tyr Gly Gly Ser Val Lys
    50                  55                  60

Gly Arg Phe Thr Ile Ser Arg Asp Asn Ala Lys Asn Thr Val Tyr Leu
65                  70                  75                  80

Gln Met Phe Gly Leu Lys Pro Glu Asp Ala Gly Asn Tyr Val Cys Asn
                85                  90                  95

Ala Asp Trp Lys Met Gly Ala Trp Thr Ala Gly Asp Tyr Gly Ile Asp
            100                 105                 110

Tyr Trp Gly Lys Gly Thr Leu Val Thr Val Ser Ser Glu Pro Lys Thr
        115                 120                 125

Pro Lys Pro Gln
    130


<210> SEQ ID NO 21
<211> LENGTH: 408
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 21

caggtgcagc tcgtggagtc cggtggaggc ttggtgcagc ctgggggtc tctgagactc      60

tcctgtgcag cctctgcagg caatctggat tattatgcca taggctggtt ccgccaggcc    120

ccagggaagg agcgcgaggg ggtctcatgt attagtagta gtgatggtag cactgtctat    180

acagactccg tgaagggccg attcaccatc tccagagaca ataccaagaa cacggtagat    240

ctgcaaatgg acaatttgaa acctgaggac acggccgttt attactgtgc gacagtcgtt    300

aactactact gcacagccgg tgggtccatt cacgcgagcc cgtatgaaat ctggggccag    360

gggacccagg tcaccgtctc ctcagcgcac cacagcgaag acccctcg                 408


<210> SEQ ID NO 22
<211> LENGTH: 136
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 22

Gln Val Gln Leu Val Glu Ser Gly Gly Gly Leu Val Gln Pro Gly Gly
1               5                   10                  15

Ser Leu Arg Leu Ser Cys Ala Ala Ser Ala Gly Asn Leu Asp Tyr Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Asp Gly Ser Thr Val Tyr Thr Asp Ser Val
    50                  55                  60

Lys Gly Arg Phe Thr Ile Ser Arg Asp Asn Thr Lys Asn Thr Val Asp
65                  70                  75                  80

Leu Gln Met Asp Asn Leu Lys Pro Glu Asp Thr Ala Val Tyr Tyr Cys
                85                  90                  95

Ala Thr Val Val Asn Tyr Tyr Cys Thr Ala Gly Gly Ser Ile His Ala
            100                 105                 110
```

```
Ser Pro Tyr Glu Ile Trp Gly Gln Gly Thr Gln Val Thr Val Ser Ser
        115                 120                 125

Ala His His Ser Glu Asp Pro Ser
        130                 135

<210> SEQ ID NO 23
<211> LENGTH: 375
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 23

caggtgcagc tcgtggagtc cggcggaggc ttggtgcacc ctggggggtc tctgagactc      60

tcttgtgcac cctctgccag tctaccatca cacccttca accccttcaa caatatggtg     120

ggctggtacc gtcaggctcc aggtaaacag cgcgaaatgg tcgcaagtat tggtctacga     180

ataaactatg cagactccgt gaagggccga ttcaccatct ccagagacaa cgccaagaac     240

acggtggatc tgcagatgga cagcctgcga cctgaggact cagccacata ctactgtcat     300

atagaataca cccactactg gggcaaaggg accctggtca ccgtctcctc ggaacccaag     360

acaccaaaac cacaa                                                     375

<210> SEQ ID NO 24
<211> LENGTH: 133
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 24

Gln Val Gln Leu Val Glu Ser Gly Gly Gly Leu Val His Pro Gly Gly
1               5                  10                  15

Ser Leu Arg Leu Ser Cys Ala Pro Ser Ala Ser Leu Pro Ser Thr Pro
            20                  25                  30

Phe Asn Pro Phe Asn Asn Met Val Gly Trp Tyr Arg Gln Ala Pro Gly
        35                  40                  45

Lys Gln Arg Glu Met Val Ala Ser Ile Gly Leu Arg Ile Asn Tyr Ala
    50                  55                  60

Asp Ser Val Lys Gly Arg Phe Thr Ile Ser Arg Asp Asn Ala Lys Asn
65                  70                  75                  80

Thr Val Asp Leu Gln Met Asp Ser Leu Arg Pro Glu Asp Ser Ala Thr
                85                  90                  95

Tyr Tyr Cys His Ile Glu Tyr Thr His Tyr Trp Gly Lys Gly Thr Leu
            100                 105                 110

Val Thr Val Ser Ser Glu Pro Lys Thr Pro Lys Pro Gln Glu Pro Lys
        115                 120                 125

Thr Pro Lys Pro Gln
    130

<210> SEQ ID NO 25
<211> LENGTH: 378
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 25

caggtgcagc tcgtggagtc tggtggaggc ttggcgcagc ctggggggtc tctgagactc      60
```

```
tcctgtgaag cgtctggttt tgggacatgg ttcaggttcg atgagaacac cgtgaactgg    120

taccgccagc ctccaggaaa gtcgcgcgag ttcgacgagt tggtcgctcg ttacccaaaa    180

agtggcatcg taacctattt agactccgtg aagggccgat tcacgatctc cagagacaac    240

gccaaaaaaa tggcgtttct gcaaatggac aacctgaaac ctgaggacac ggccgtctat    300

tattgcaatg tcggtgaatt ttggggccag gggacccagg tcacgatctc ctcagaaccc    360

aagacaccaa aaccacaa                                                  378
```

<210> SEQ ID NO 26
<211> LENGTH: 126
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 26

```
Gln Val Gln Leu Val Glu Ser Gly Gly Gly Leu Ala Gln Pro Gly Gly
1               5                   10                  15

Ser Leu Arg Leu Ser Cys Glu Ala Ser Gly Phe Gly Thr Trp Phe Arg
            20                  25                  30

Phe Asp Glu Asn Thr Val Asn Trp Tyr Arg Gln Pro Pro Gly Lys Ser
        35                  40                  45

Arg Glu Phe Asp Glu Leu Val Ala Arg Tyr Pro Lys Ser Gly Ile Val
    50                  55                  60

Thr Tyr Leu Asp Ser Val Lys Gly Arg Phe Thr Ile Ser Arg Asp Asn
65                  70                  75                  80

Ala Lys Lys Met Ala Phe Leu Gln Met Asp Asn Leu Lys Pro Glu Asp
                85                  90                  95

Thr Ala Val Tyr Tyr Cys Asn Val Gly Glu Phe Trp Gly Gln Gly Thr
            100                 105                 110

Gln Val Thr Ile Ser Ser Glu Pro Lys Thr Pro Lys Pro Gln
        115                 120                 125
```

<210> SEQ ID NO 27
<211> LENGTH: 384
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 27

```
caggtgcagc tcgtggagtc gggggggaggc ttggtgcagc ctgggggggtc tctgagactc     60

tcctgtgcag cctctggatt caccctaggg tcgcgttaca tgagctgggt ccgccaggct    120

ccaggagagg ggttcgagtg ggtctcaagt attgaaccct ctggtaccgc atgggatgga    180

gactccgcga agggacgatt caccacttcc agagacgacg ccaagaacac gctttatctg    240

caaatgagca acctgcaacc cgaggacacg ggtgtttatt actgtgcaac agggtatcgg    300

acggacacga ggattccggg tggctcgtgg ggccagggga cccaggtcac cgtctcctca    360

gaacccaaga caccaaaacc acaa                                           384
```

<210> SEQ ID NO 28
<211> LENGTH: 128
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 28

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Gly Ser Arg
            20                  25                  30

Tyr Met Ser Trp Val Arg Gln Ala Pro Gly Glu Gly Phe Glu Trp Val
        35                  40                  45

Ser Ser Ile Glu Pro Ser Gly Thr Ala Trp Asp Gly Asp Ser Ala Lys
    50                  55                  60

Gly Arg Phe Thr Thr Ser Arg Asp Asp Ala Lys Asn Thr Leu Tyr Leu
65                  70                  75                  80

Gln Met Ser Asn Leu Gln Pro Glu Asp Thr Gly Val Tyr Tyr Cys Ala
                85                  90                  95

Thr Gly Tyr Arg Thr Asp Thr Arg Ile Pro Gly Gly Ser Trp Gly Gln
            100                 105                 110

Gly Thr Gln Val Thr Val Ser Ser Glu Pro Lys Thr Pro Lys Pro Gln
        115                 120                 125

<210> SEQ ID NO 29
<211> LENGTH: 360
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 29
caggtgcagc tcgtggagtc tggaggaggc ttggtgcagc ctggggggtc tctgagactc 60
tcctgtcaag tctctggatt caccttcggt gactgggtca tgagctggtt ccgccaggct 120
ccggggaagg agcgcgaatt cgtcgcaagt attacggcta ctagtagtct aaagtattat 180
gcagactccg tgaagggccg attcaccatc tccagagaca atgtcaacaa cacactgttt 240
ctgcaaatgg atcgcctgaa atctgaggac acggccgttt attactgtcg gtcccccaac 300
tactggggcc aggggaccca ggtcaccgtc tccgccgaac ccaagacacc aaaaccacaa 360

<210> SEQ ID NO 30
<211> LENGTH: 120
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 30

Gln Val Gln Leu Val Glu Ser Gly Gly Gly Leu Val Gln Pro Gly Gly
1               5                   10                  15

Ser Leu Arg Leu Ser Cys Gln Val Ser Gly Phe Thr Phe Gly Asp Trp
            20                  25                  30

Val Met Ser Trp Phe Arg Gln Ala Pro Gly Lys Glu Arg Glu Phe Val
        35                  40                  45

Ala Ser Ile Thr Ala Thr Ser Ser Leu Lys Tyr Tyr Ala Asp Ser Val
    50                  55                  60

Lys Gly Arg Phe Thr Ile Ser Arg Asp Asn Val Asn Asn Thr Leu Phe
65                  70                  75                  80

Leu Gln Met Asp Arg Leu Lys Ser Glu Asp Thr Ala Val Tyr Tyr Cys
                85                  90                  95

Arg Ser Pro Asn Tyr Trp Gly Gln Gly Thr Gln Val Thr Val Ser Ala
            100                 105                 110

Glu Pro Lys Thr Pro Lys Pro Gln
115 120

<210> SEQ ID NO 31
<211> LENGTH: 366
<212> TYPE: DNA
<213> ORGANISM: Artificial Sequence
<220> FEATURE:
<223> OTHER INFORMATION: VHH binding agents specific to BoNT/A holotoxin

<400> SEQUENCE: 31
caggtgcagc tcgtggagtc aggtggaggc ttggtgcagg ttgggggtc tctgagactc 60 tcctgtgtag tttctggaag cgacatcagt ggcattgcga tgggctggta ccgccaggct 120
ccagggaagc ggcgcgaaat ggtcgcagat attttttctg gcggtagtac agactatgca 180
ggctccgtga agggccgatt caccatctcc agagacaacg ccaagaagac gagctatctg 240
caaatgaaca acgtgaaacc tgaggacacc ggagtctact actgtaggct gtacgggagc 300
ggtgactact ggggccaggg gacccaggtc accgtctcct cagcgcacca cagcgaagac 360
ccctcg 366

<210> SEQ ID NO 32
<211> LENGTH: 122
<212> TYPE: PRT
<213> ORGANISM: Artificial Sequence
<220> FEATURE:
<223> OTHER INFORMATION: VHH binding agents specific to BoNT/A holotoxin

<400> SEQUENCE: 32

Gln Val Gln Leu Val Glu Ser Gly Gly Gly Leu Val Gln Val Gly Gly
1 5 10 15

Ser Leu Arg Leu Ser Cys Val Val Ser Gly Ser Asp Ile Ser Gly Ile
20 25 30

Ala Met Gly Trp Tyr Arg Gln Ala Pro Gly Lys Arg Arg Glu Met Val
35 40 45

Ala Asp Ile Phe Ser Gly Gly Ser Thr Asp Tyr Ala Gly Ser Val Lys
50 55 60

Gly Arg Phe Thr Ile Ser Arg Asp Asn Ala Lys Lys Thr Ser Tyr Leu
65 70 75 80

Gln Met Asn Asn Val Lys Pro Glu Asp Thr Gly Val Tyr Tyr Cys Arg
85 90 95

Leu Tyr Gly Ser Gly Asp Tyr Trp Gly Gln Gly Thr Gln Val Thr Val
100 105 110

Ser Ser Ala His His Ser Glu Asp Pro Ser
115 120

<210> SEQ ID NO 33
<211> LENGTH: 411
<212> TYPE: DNA
<213> ORGANISM: Artificial Sequence
<220> FEATURE:
<223> OTHER INFORMATION: VHH binding agents specific to BoNT/B holotoxin

<400> SEQUENCE: 33
caggtgcagc tcgtggagtc aggcggaggc ttggtgcagc ctgggggtc tctgaaactc 60 tcctgtgcag cctctggatt cactttggga caccatcgcg ttggctggtt ccgccaggcc 120
ccaggaaaga agcgtgaggg ggtcgcgtgt attagcgcca ctggtcttag cacacactat 180
tcagactccg tgaccggccg atttaccgtc tccagagaca acctcaacaa cgtggcgtat 240

```
ctgcagctga acagcctgaa acctgaggac gcaggtgttt attactgtgc aagcagattc    300

tcccttaatt cggtcgatgc gaatatgtgc ctttcagagc ctcagtatga caactggggc    360

caggggaccc aggtcagaat ctcctcagaa cccaagacac caaaaccaca a             411
```

<210> SEQ ID NO 34
<211> LENGTH: 137
<212> TYPE: PRT
<213> ORGANISM: Artificial Sequence
<220> FEATURE:
<223> OTHER INFORMATION: VHH binding agents specific to BoNT/B holotoxin

<400> SEQUENCE: 34

```
Gln Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Leu Gly His His
            20                  25                  30

Arg Val Gly Trp Phe Arg Gln Ala Pro Gly Lys Lys Arg Glu Gly Val
        35                  40                  45

Ala Cys Ile Ser Ala Thr Gly Leu Ser Thr His Tyr Ser Asp Ser Val
    50                  55                  60

Thr Gly Arg Phe Thr Val Ser Arg Asp Asn Leu Asn Asn Val Ala Tyr
65                  70                  75                  80

Leu Gln Leu Asn Ser Leu Lys Pro Glu Asp Ala Gly Val Tyr Tyr Cys
                85                  90                  95

Ala Ser Arg Phe Ser Leu Asn Ser Val Asp Ala Asn Met Cys Leu Ser
            100                 105                 110

Glu Pro Gln Tyr Asp Asn Trp Gly Gln Gly Thr Gln Val Arg Ile Ser
        115                 120                 125

Ser Glu Pro Lys Thr Pro Lys Pro Gln
    130                 135
```

<210> SEQ ID NO 35
<211> LENGTH: 399
<212> TYPE: DNA
<213> ORGANISM: Artificial Sequence
<220> FEATURE:
<223> OTHER INFORMATION: VHH binding agents specific to BoNT/B holotoxin

<400> SEQUENCE: 35

```
caggtgcagc tcgtggagac gggtggagga ttggtgcagg ccgggggctc tctgagactc     60

tcctgcgcag gctctggacg ctccttcagc gccgctgtca tgggctggtt ccgccaggcg    120

ccagggaagg agcgagaatt cgtagcagca cttagacaaa ttattggtag cacacactat    180

gcagactccg tgaagggccg attcaccatc tccagagaca acgccaagaa catgttgtat    240

ctcgacatga acagcctgaa acctacggac acggccgcgt attactgcac agcgggacct    300

ccgactatgc tggacgtttc taccgaccgg gagtatgaca cctggggtca ggggactcag    360

gtcaccgtct cctcagcgca ccacagcgaa gacccctcg                           399
```

<210> SEQ ID NO 36
<211> LENGTH: 133
<212> TYPE: PRT
<213> ORGANISM: Artificial Sequence
<220> FEATURE:
<223> OTHER INFORMATION: VHH binding agents specific to BoNT/B holotoxin

<400> SEQUENCE: 36

```
Gln Val Gln Leu Val Glu Ser Gly Gly Gly Leu Val Gln Ala Gly Gly
1               5                   10                  15
```

```
Ser Leu Arg Leu Ser Cys Ala Gly Ser Gly Arg Ser Phe Ser Ala Ala
            20                  25                  30

Val Met Gly Trp Phe Arg Gln Ala Pro Gly Lys Glu Arg Glu Phe Val
        35                  40                  45

Ala Ala Leu Arg Gln Ile Ile Gly Ser Thr His Tyr Ala Asp Ser Val
    50                  55                  60

Lys Gly Arg Phe Thr Ile Ser Arg Asp Asn Ala Lys Asn Met Leu Tyr
65                  70                  75                  80

Leu Asp Met Asn Ser Leu Lys Pro Thr Asp Thr Ala Ala Tyr Tyr Cys
                85                  90                  95

Thr Ala Gly Pro Pro Thr Met Leu Asp Val Ser Thr Asp Arg Glu Tyr
            100                 105                 110

Asp Thr Trp Gly Gln Gly Thr Gln Val Thr Val Ser Ser Ala His His
        115                 120                 125

Ser Glu Asp Pro Ser
    130
```

<210> SEQ ID NO 37
<211> LENGTH: 363
<212> TYPE: DNA
<213> ORGANISM: Artificial Sequence
<220> FEATURE:
<223> OTHER INFORMATION: VHH binding agent

<400> SEQUENCE: 37

```
caggtgcagc tcgtggagtc cggaggaggc ttggtgcgac ctggggggtc tctgagactc     60

tcttgtgtag tctctggatt cgcctacgaa atgcccatga tgggctggta ccgccaggct    120

ccagggaatc agcgcgagtt ggtcgcaact attggtacag gtggtaggat gaactatgca    180

gactccgtga agggccgatt caccatctcc agagacaacg ccaagaacac ggtgtatctg    240

caaatgaaca gcctgaaacc tgaggacaca gccgcctatt actgtaaaat cgagtttaca    300

aattactggg gccaggggac ccaagtcacc gtctcctcag aacccaagac accaaaacca    360

caa                                                                  363
```

<210> SEQ ID NO 38
<211> LENGTH: 121
<212> TYPE: PRT
<213> ORGANISM: Artificial Sequence
<220> FEATURE:
<223> OTHER INFORMATION: VHH binding agent

<400> SEQUENCE: 38

```
Gln Val Gln Leu Val Glu Ser Gly Gly Gly Leu Val Arg Pro Gly Gly
1               5                   10                  15

Ser Leu Arg Leu Ser Cys Val Val Ser Gly Phe Ala Tyr Glu Met Pro
            20                  25                  30

Met Met Gly Trp Tyr Arg Gln Ala Pro Gly Asn Gln Arg Glu Leu Val
        35                  40                  45

Ala Thr Ile Gly Thr Gly Gly Arg Met Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Ala Tyr Tyr Cys Lys
                85                  90                  95

Ile Glu Phe Thr Asn Tyr Trp Gly Gln Gly Thr Gln Val Thr Val Ser
            100                 105                 110
```

```
Ser Glu Pro Lys Thr Pro Lys Pro Gln
        115                 120


<210> SEQ ID NO 39
<211> LENGTH: 366
<212> TYPE: DNA
<213> ORGANISM: Artificial Sequence
<220> FEATURE:
<223> OTHER INFORMATION: VHH binding agent

<400> SEQUENCE: 39

caggtgcagc tcgtggagtc aggtggaggc ttggtgcagc cgggggggatc tctgagactg      60

tcctgtacag tctctggaag catcttcgat ctacctggaa tgaactggta tcgccaggct     120

ccaggggcgc agcgcgagtt ggtcgcagat attagtagtg atggtaggag gacaaactat     180

gcagactccg tgaagggccg attcaccatg tccagagaca atgccaagaa aacggtgtat     240

ctgcaaatgg acagcctgaa acctgacgac acggccgtct attactgtaa tgtgaaattt     300

actcaccact ggggccaggg gatccaggtc accgtctcct cagaacccaa gacaccaaaa     360

ccacaa                                                                366


<210> SEQ ID NO 40
<211> LENGTH: 122
<212> TYPE: PRT
<213> ORGANISM: Artificial Sequence
<220> FEATURE:
<223> OTHER INFORMATION: VHH binding agent

<400> SEQUENCE: 40

Gln Val Gln Leu Val Glu Ser Gly Gly Gly Leu Val Gln Pro Gly Gly
1               5                   10                  15

Ser Leu Arg Leu Ser Cys Thr Val Ser Gly Ser Ile Phe Asp Leu Pro
            20                  25                  30

Gly Met Asn Trp Tyr Arg Gln Ala Pro Gly Ala Gln Arg Glu Leu Val
        35                  40                  45

Ala Asp Ile Ser Ser Asp Gly Arg Arg Thr Asn Tyr Ala Asp Ser Val
    50                  55                  60

Lys Gly Arg Phe Thr Met Ser Arg Asp Asn Ala Lys Lys Thr Val Tyr
65                  70                  75                  80

Leu Gln Met Asp Ser Leu Lys Pro Asp Asp Thr Ala Val Tyr Tyr Cys
                85                  90                  95

Asn Val Lys Phe Thr His His Trp Gly Gln Gly Ile Gln Val Thr Val
            100                 105                 110

Ser Ser Glu Pro Lys Thr Pro Lys Pro Gln
        115                 120


<210> SEQ ID NO 41
<211> LENGTH: 366
<212> TYPE: DNA
<213> ORGANISM: Artificial Sequence
<220> FEATURE:
<223> OTHER INFORMATION: VHH binding agent

<400> SEQUENCE: 41

caggtgcagc tcgtggagtc aggcggaggc ttggtgcagc cgggggggatc tctgaggctg      60

tcctgtacgg tctctggaag catcttcggc ctacctggca tgagctggta tcgccaggct     120

ccaggggcgc agcgcgagtt ggtcgcagat attagtagtg atggtgggag gacgcactat     180

gcagactccg tgaagggccg cttcaccatc tccagagaca atgacaagaa aacggtgtat     240
```

```
ctgcagatgg acagcctgaa acctgacgac acggccgtct attactgtaa tgtgaaattt    300

actcaccact ggggccaggg gatccaggtc accgtctcct cagaacccaa gacaccaaaa    360

ccacaa                                                               366


<210> SEQ ID NO 42
<211> LENGTH: 122
<212> TYPE: PRT
<213> ORGANISM: Artificial Sequence
<220> FEATURE:
<223> OTHER INFORMATION: VHH binding agent

<400> SEQUENCE: 42

Gln Val Gln Leu Val Glu Ser Gly Gly Gly Leu Val Gln Pro Gly Gly
1               5                   10                  15

Ser Leu Arg Leu Ser Cys Thr Val Ser Gly Ser Ile Phe Gly Leu Pro
            20                  25                  30

Gly Met Ser Trp Tyr Arg Gln Ala Pro Gly Ala Gln Arg Glu Leu Val
        35                  40                  45

Ala Asp Ile Ser Ser Asp Gly Gly Arg Thr His Tyr Ala Asp Ser Val
    50                  55                  60

Lys Gly Arg Phe Thr Ile Ser Arg Asp Asn Asp Lys Lys Thr Val Tyr
65                  70                  75                  80

Leu Gln Met Asp Ser Leu Lys Pro Asp Asp Thr Ala Val Tyr Tyr Cys
                85                  90                  95

Asn Val Lys Phe Thr His His Trp Gly Gln Gly Ile Gln Val Thr Val
            100                 105                 110

Ser Ser Glu Pro Lys Thr Pro Lys Pro Gln
        115                 120


<210> SEQ ID NO 43
<211> LENGTH: 366
<212> TYPE: DNA
<213> ORGANISM: Artificial Sequence
<220> FEATURE:
<223> OTHER INFORMATION: VHH binding agent

<400> SEQUENCE: 43

caggtgcagc tcgtggagtc tgggggaggc ttggtgcagg atggggggtc tctgaggctc     60

tcctgcacaa catctggaag tatcgacagt ttcaatgcca tagagtggta ccgccaggct    120

ccagggaagc agcgcgaatt ggtcgcaagt ataagtagtg atggtcgtcg cacaaactat    180

gcagactccg tgaagggccg attcaccatc tccggagaca acgccaagaa cacggtgtat    240

ctgcaaatga acagcctgaa acctgaggac acagccgtgt attactgtca tagacctttt    300

acccactact ggggccaggg gacccaggtc accgtctcct cagaacccaa gacaccaaaa    360

ccacaa                                                               366


<210> SEQ ID NO 44
<211> LENGTH: 122
<212> TYPE: PRT
<213> ORGANISM: Artificial Sequence
<220> FEATURE:
<223> OTHER INFORMATION: VHH binding agent

<400> SEQUENCE: 44

Gln Val Gln Leu Val Glu Ser Gly Gly Gly Leu Val Gln Asp Gly Gly
1               5                   10                  15

Ser Leu Arg Leu Ser Cys Thr Thr Ser Gly Ser Ile Asp Ser Phe Asn
```

```
            20                  25                  30

Ala Ile Glu Trp Tyr Arg Gln Ala Pro Gly Lys Gln Arg Glu Leu Val
        35                  40                  45

Ala Ser Ile Ser Ser Asp Gly Arg Arg Thr Asn Tyr Ala Asp Ser Val
    50                  55                  60

Lys Gly Arg Phe Thr Ile Ser Gly Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

His Arg Pro Phe Thr His Tyr Trp Gly Gln Gly Thr Gln Val Thr Val
            100                 105                 110

Ser Ser Glu Pro Lys Thr Pro Lys Pro Gln
        115                 120


<210> SEQ ID NO 45
<211> LENGTH: 912
<212> TYPE: DNA
<213> ORGANISM: Artificial Sequence
<220> FEATURE:
<223> OTHER INFORMATION: VHH binding agent with tag

<400> SEQUENCE: 45

atgagcgata aaattattca cctgactgac gacagttttg acacggatgt actcaaagcg      60

gacggggcga tcctcgtcga tttctgggca gagtggtgcg gtccgtgcaa aatgatcgcc     120

ccgattctgg atgaaatcgc tgacgaatat cagggcaaac tgaccgttgc aaaactgaac     180

atcgatcaaa accctggcac tgcgccgaaa tatggcatcc gtggtatccc gactctgctg     240

ctgttcaaaa acggtgaagt ggcggcaacc aaagtgggtg cactgtctaa aggtcagttg     300

aaagagttcc tcgacgctaa cctggccggt tctggttctg gccatatgca ccatcatcat     360

catcattctt ctggtctggt gccacgcggt tctggtatga aagaaaccgc tgctgctaaa     420

ttcgaacgcc agcacatgga cagcccagat ctgggtaccg acgacgacga caaggccatg     480

gcgatatcgg atccgaattc ccaggtgcag ctcgtggagt caggtggagg cttggtgcag     540

gttggggggt ctctgagact ctcctgtgta gtttctggaa gcgacatcag tggcattgcg     600

atgggctggt accgccaggc tccagggaag cggcgcgaaa tggtcgcaga tatttttttct     660

ggcggtagta cagactatgc aggctccgtg aagggccgat tcaccatctc cagagacaac     720

gccaagaaga cgagctatct gcaaatgaac aacgtgaaac ctgaggacac cggagtctac     780

tactgtaggc tgtacgggag cggtgactac tggggccagg ggacccaggt caccgtctcc     840

tcagcgcacc acagcgaaga ccccactagt ggtgcgccgg tgccgtatcc ggatccgctg     900

gaaccgcgtt aa                                                         912


<210> SEQ ID NO 46
<211> LENGTH: 303
<212> TYPE: PRT
<213> ORGANISM: Artificial Sequence
<220> FEATURE:
<223> OTHER INFORMATION: VHH binding agent with tag

<400> SEQUENCE: 46

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
```

```
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Asp Lys Ala Met
145                 150                 155                 160

Ala Ile Ser Asp Pro Asn Ser Gln Val Gln Leu Val Glu Ser Gly Gly
                165                 170                 175

Gly Leu Val Gln Val Gly Gly Ser Leu Arg Leu Ser Cys Val Val Ser
            180                 185                 190

Gly Ser Asp Ile Ser Gly Ile Ala Met Gly Trp Tyr Arg Gln Ala Pro
        195                 200                 205

Gly Lys Arg Arg Glu Met Val Ala Asp Ile Phe Ser Gly Gly Ser Thr
    210                 215                 220

Asp Tyr Ala Gly Ser Val Lys Gly Arg Phe Thr Ile Ser Arg Asp Asn
225                 230                 235                 240

Ala Lys Lys Thr Ser Tyr Leu Gln Met Asn Asn Val Lys Pro Glu Asp
                245                 250                 255

Thr Gly Val Tyr Tyr Cys Arg Leu Tyr Gly Ser Gly Asp Tyr Trp Gly
            260                 265                 270

Gln Gly Thr Gln Val Thr Val Ser Ser Ala His His Ser Glu Asp Pro
        275                 280                 285

Thr Ser Gly Ala Pro Val Pro Tyr Pro Asp Pro Leu Glu Pro Arg
    290                 295                 300
```

<210> SEQ ID NO 47
<211> LENGTH: 924
<212> TYPE: DNA
<213> ORGANISM: Artificial Sequence
<220> FEATURE:
<223> OTHER INFORMATION: VHH binding agent with tag

<400> SEQUENCE: 47

```
atgagcgata aaattattca cctgactgac gacagttttg acacggatgt actcaaagcg     60

gacggggcga tcctcgtcga tttctgggca gagtggtgcg gtccgtgcaa aatgatcgcc    120

ccgattctgg atgaaatcgc tgacgaatat cagggcaaac tgaccgttgc aaaactgaac    180

atcgatcaaa accctggcac tgcgccgaaa tatggcatcc gtggtatccc gactctgctg    240

ctgttcaaaa acggtgaagt ggcggcaacc aaagtgggtg cactgtctaa aggtcagttg    300

aaagagttcc tcgacgctaa cctggccggt tctggttctg gccatatgca ccatcatcat    360

catcattctt ctggtctggt gccacgcggt tctggtatga aagaaaccgc tgctgctaaa    420

ttcgaacgcc agcacatgga cagcccagat ctgggtaccg acgacgacga caaggccatg    480

gcgatatcgg atccgaattc ccaggtgcag ctcgtggagt ccggcggagg cttggtgcac    540

cctgggggt ctctgagact ctcttgtgca ccctctgcca gtctaccatc aacacccttc    600
```

aaccccttca acaatatggt gggctggtac cgtcaggctc caggtaaaca gcgcgaaatg 660
gtcgcaagta ttggtctacg aataaactat gcagactccg tgaagggccg attcaccatc 720
tccagagaca acgccaagaa cacggtggat ctgcagatgg acagcctgcg acctgaggac 780
tcagccacat actactgtca tatagaatac acccactact ggggcaaagg gaccctggtc 840
accgtctcct cggaacccaa gacaccaaaa ccacaaacta gtggtgcgcc ggtgccgtat 900
ccggatccgc tggaaccgcg ttaa 924

<210> SEQ ID NO 48
<211> LENGTH: 307
<212> TYPE: PRT
<213> ORGANISM: Artificial Sequence
<220> FEATURE:
<223> OTHER INFORMATION: VHH binding agent with tag

<400> SEQUENCE: 48

Met Ser Asp Lys Ile Ile His Leu Thr Asp Asp Ser Phe Asp Thr Asp
1 5 10 15

Val Leu Lys Ala Asp Gly Ala Ile Leu Val Asp Phe Trp Ala Glu Trp
20 25 30

Cys Gly Pro Cys Lys Met Ile Ala Pro Ile Leu Asp Glu Ile Ala Asp
35 40 45

Glu Tyr Gln Gly Lys Leu Thr Val Ala Lys Leu Asn Ile Asp Gln Asn
50 55 60

Pro Gly Thr Ala Pro Lys Tyr Gly Ile Arg Gly Ile Pro Thr Leu Leu
65 70 75 80

Leu Phe Lys Asn Gly Glu Val Ala Ala Thr Lys Val Gly Ala Leu Ser
85 90 95

Lys Gly Gln Leu Lys Glu Phe Leu Asp Ala Asn Leu Ala Gly Ser Gly
100 105 110

Ser Gly His Met His His His His His His Ser Ser Gly Leu Val Pro
115 120 125

Arg Gly Ser Gly Met Lys Glu Thr Ala Ala Ala Lys Phe Glu Arg Gln
130 135 140

His Met Asp Ser Pro Asp Leu Gly Thr Asp Asp Asp Asp Lys Ala Met
145 150 155 160

Ala Ile Ser Asp Pro Asn Ser Gln Val Gln Leu Val Glu Ser Gly Gly
165 170 175

Gly Leu Val His Pro Gly Gly Ser Leu Arg Leu Ser Cys Ala Pro Ser
180 185 190

Ala Ser Leu Pro Ser Thr Pro Phe Asn Pro Phe Asn Asn Met Val Gly
195 200 205

Trp Tyr Arg Gln Ala Pro Gly Lys Gln Arg Glu Met Val Ala Ser Ile
210 215 220

Gly Leu Arg Ile Asn Tyr Ala Asp Ser Val Lys Gly Arg Phe Thr Ile
225 230 235 240

Ser Arg Asp Asn Ala Lys Asn Thr Val Asp Leu Gln Met Asp Ser Leu
245 250 255

Arg Pro Glu Asp Ser Ala Thr Tyr Tyr Cys His Ile Glu Tyr Thr His
260 265 270

Tyr Trp Gly Lys Gly Thr Leu Val Thr Val Ser Ser Glu Pro Lys Thr
275 280 285

Pro Lys Pro Gln Thr Ser Gly Ala Pro Val Pro Tyr Pro Asp Pro Leu
290 295 300

Glu Pro Arg
305

<210> SEQ ID NO 49
<211> LENGTH: 1350
<212> TYPE: DNA
<213> ORGANISM: Artificial Sequence
<220> FEATURE:
<223> OTHER INFORMATION: VHH dimer binding agent with tag

<400> SEQUENCE: 49
atgagcgata aaattattca cctgactgac gacagttttg acacggatgt actcaaagcg 60
gacggggcga tcctcgtcga tttctgggca gagtggtgcg gtccgtgcaa aatgatcgcc 120
ccgattctgg atgaaatcgc tgacgaatat cagggcaaac tgaccgttgc aaaactgaac 180
atcgatcaaa accctggcac tgcgccgaaa tatggcatcc gtggtatccc gactctgctg 240
ctgttcaaaa acggtgaagt ggcggcaacc aaagtgggtg cactgtctaa aggtcagttg 300
aaagagttcc tcgacgctaa cctggccggt tctggttctg gccatatgca ccatcatcat 360
catcattctt ctggtctggt gccacgcggt tctggtatga aagaaaccgc tgctgctaaa 420
ttcgaacgcc agcacatgga cagcccagat ctgggtaccg acgacgacga caaggccatg 480
gcggccgctc aggtgcagct cgtggagtca ggtggaggct tggtgcaggt tggggggtct 540
ctgagactct cctgtgtagt ttctggaagc gacatcagtg gcattgcgat gggctggtac 600
cgccaggctc cagggaagcg gcgcgaaatg gtcgcagata ttttttctgg cggtagtaca 660
gactatgcag gctccgtgaa gggccgattc accatctcca gagacaacgc caagaagacg 720
agctatctgc aaatgaacaa cgtgaaacct gaggacaccg gagtctacta ctgtaggctg 780
tacgggagcg gtgactactg gggccagggg acccaggtca ccgtctcctc agcgcaccac 840
agcgaagacc ccactagtgc gatcgctggt ggaggcggtt caggcggagg tggctctggc 900
ggtggcggtt ccctgcaggg tcagttgcag ctcgtggagt ccggcggagg cttggtgcac 960
cctggggggt ctctgagact ctcttgtgca ccctctgcca gtctaccatc aacacccttc 1020
aaccccttca acaatatggt gggctggtac cgtcaggctc caggtaaaca gcgcgaaatg 1080
gtcgcaagta ttggtctacg aataaactat gcagactccg tgaagggccg attcaccatc 1140
tccagagaca acgccaagaa cacggtggat ctgcagatgg acagcctgcg acctgaggac 1200
tcagccacat actactgtca tatagaatac acccactact ggggcaaagg gaccctggtc 1260
accgtctcct cggaacccaa gacaccaaaa ccacaaccgg cgcgccaggg tgcgccggtg 1320
ccgtatccgg acccgctgga accgcgttaa 1350

<210> SEQ ID NO 50
<211> LENGTH: 449
<212> TYPE: PRT
<213> ORGANISM: Artificial Sequence
<220> FEATURE:
<223> OTHER INFORMATION: VHH dimer binding agent with tag

<400> SEQUENCE: 50

Met Ser Asp Lys Ile Ile His Leu Thr Asp Asp Ser Phe Asp Thr Asp
1 5 10 15

Val Leu Lys Ala Asp Gly Ala Ile Leu Val Asp Phe Trp Ala Glu Trp
20 25 30

Cys Gly Pro Cys Lys Met Ile Ala Pro Ile Leu Asp Glu Ile Ala Asp
35 40 45

```
Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Asp Lys Ala Met
145                 150                 155                 160

Ala Ala Ala Gln Val Gln Leu Val Glu Ser Gly Gly Gly Leu Val Gln
                165                 170                 175

Val Gly Gly Ser Leu Arg Leu Ser Cys Val Val Ser Gly Ser Asp Ile
            180                 185                 190

Ser Gly Ile Ala Met Gly Trp Tyr Arg Gln Ala Pro Gly Lys Arg Arg
        195                 200                 205

Glu Met Val Ala Asp Ile Phe Ser Gly Gly Ser Thr Asp Tyr Ala Gly
    210                 215                 220

Ser Val Lys Gly Arg Phe Thr Ile Ser Arg Asp Asn Ala Lys Lys Thr
225                 230                 235                 240

Ser Tyr Leu Gln Met Asn Asn Val Lys Pro Glu Asp Thr Gly Val Tyr
                245                 250                 255

Tyr Cys Arg Leu Tyr Gly Ser Gly Asp Tyr Trp Gly Gln Gly Thr Gln
            260                 265                 270

Val Thr Val Ser Ser Ala His His Ser Glu Asp Pro Thr Ser Ala Ile
        275                 280                 285

Ala Gly Gly Gly Gly Ser Gly Gly Gly Gly Ser Gly Gly Gly Gly Ser
    290                 295                 300

Leu Gln Gly Gln Leu Gln Leu Val Glu Ser Gly Gly Gly Leu Val His
305                 310                 315                 320

Pro Gly Gly Ser Leu Arg Leu Ser Cys Ala Pro Ser Ala Ser Leu Pro
                325                 330                 335

Ser Thr Pro Phe Asn Pro Phe Asn Asn Met Val Gly Trp Tyr Arg Gln
            340                 345                 350

Ala Pro Gly Lys Gln Arg Glu Met Val Ala Ser Ile Gly Leu Arg Ile
        355                 360                 365

Asn Tyr Ala Asp Ser Val Lys Gly Arg Phe Thr Ile Ser Arg Asp Asn
    370                 375                 380

Ala Lys Asn Thr Val Asp Leu Gln Met Asp Ser Leu Arg Pro Glu Asp
385                 390                 395                 400

Ser Ala Thr Tyr Tyr Cys His Ile Glu Tyr Thr His Tyr Trp Gly Lys
                405                 410                 415

Gly Thr Leu Val Thr Val Ser Ser Glu Pro Lys Thr Pro Lys Pro Gln
            420                 425                 430

Pro Ala Arg Gln Gly Ala Pro Val Pro Tyr Pro Asp Pro Leu Glu Pro
        435                 440                 445

Arg
```

<210> SEQ ID NO 51

<211> LENGTH: 1410
<212> TYPE: DNA
<213> ORGANISM: Artificial Sequence
<220> FEATURE:
<223> OTHER INFORMATION: VHH dimer binding agent with two tags

<400> SEQUENCE: 51

```
atgagcgata aaattattca cctgactgac gacagttttg acacggatgt actcaaagcg     60

gacggggcga tcctcgtcga tttctgggca gagtggtgcg gtccgtgcaa aatgatcgcc    120

ccgattctgg atgaaatcgc tgacgaatat cagggcaaac tgaccgttgc aaaactgaac    180

atcgatcaaa accctggcac tgcgccgaaa tatggcatcc gtggtatccc gactctgctg    240

ctgttcaaaa acggtgaagt ggcggcaacc aaagtgggtg cactgtctaa aggtcagttg    300

aaagagttcc tcgacgctaa cctggccggt tctggttctg gccatatgca ccatcatcat    360

catcattctt ctggtctggt gccacgcggt tctggtatga aagaaaccgc tgctgctaaa    420

ttcgaacgcc agcacatgga cagcccagat ctgggtaccg acgacgacga caaggccatg    480

gcgatatcgg atccgaattc tggcgcacct gtcccatacc cagaccctct ggaaccacga    540

gcggccgctc aggtgcagct cgtggagtca ggtggaggct tggtgcaggt tggggggtct    600

ctgagactct cctgtgtagt ttctggaagc gacatcagtg gcattgcgat gggctggtac    660

cgccaggctc cagggaagcg gcgcgaaatg gtcgcagata tttttctgg cggtagtaca    720

gactatgcag gctccgtgaa gggccgattc accatctcca gagacaacgc caagaagacg    780

agctatctgc aaatgaacaa cgtgaaacct gaggacaccg gagtctacta ctgtaggctg    840

tacgggagcg gtgactactg gggccagggg acccaggtca ccgtctcctc agcgcaccac    900

agcgaagacc ccactagtgc gatcgctggt ggaggcggtt caggcggagg tggctctggc    960

ggtggcggtt ccctgcaggg tcagttgcag ctcgtggagt ccggcggagg cttggtgcac   1020

cctgggggt ctctgagact ctcttgtgca ccctctgcca gtctaccatc aacacccttc   1080

aaccccttca acaatatggt gggctggtac cgtcaggctc caggtaaaca gcgcgaaatg   1140

gtcgcaagta ttggtctacg aataaactat gcagactccg tgaagggccg attcaccatc   1200

tccagagaca acgccaagaa cacggtggat ctgcagatgg acagcctgcg acctgaggac   1260

tcagccacat actactgtca tatagaatac acccactact ggggcaaagg gaccctggtc   1320

accgtctcct cggaacccaa gacaccaaaa ccacaaccgg cgcgccaggg tgcgccggtg   1380

ccgtatccgg acccgctgga accgcgttaa                                    1410
```

<210> SEQ ID NO 52
<211> LENGTH: 469
<212> TYPE: PRT
<213> ORGANISM: Artificial Sequence
<220> FEATURE:
<223> OTHER INFORMATION: VHH dimer binding agent with two tags

<400> SEQUENCE: 52

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
```

```
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Asp Lys Ala Met
145                 150                 155                 160

Ala Ile Ser Asp Pro Asn Ser Gly Ala Pro Val Pro Tyr Pro Asp Pro
                165                 170                 175

Leu Glu Pro Arg Ala Ala Ala Gln Val Gln Leu Val Glu Ser Gly Gly
            180                 185                 190

Gly Leu Val Gln Val Gly Gly Ser Leu Arg Leu Ser Cys Val Val Ser
        195                 200                 205

Gly Ser Asp Ile Ser Gly Ile Ala Met Gly Trp Tyr Arg Gln Ala Pro
    210                 215                 220

Gly Lys Arg Arg Glu Met Val Ala Asp Ile Phe Ser Gly Gly Ser Thr
225                 230                 235                 240

Asp Tyr Ala Gly Ser Val Lys Gly Arg Phe Thr Ile Ser Arg Asp Asn
                245                 250                 255

Ala Lys Lys Thr Ser Tyr Leu Gln Met Asn Asn Val Lys Pro Glu Asp
            260                 265                 270

Thr Gly Val Tyr Tyr Cys Arg Leu Tyr Gly Ser Gly Asp Tyr Trp Gly
        275                 280                 285

Gln Gly Thr Gln Val Thr Val Ser Ser Ala His His Ser Glu Asp Pro
    290                 295                 300

Thr Ser Ala Ile Ala Gly Gly Gly Gly Ser Gly Gly Gly Gly Ser Gly
305                 310                 315                 320

Gly Gly Gly Ser Leu Gln Gly Gln Leu Gln Leu Val Glu Ser Gly Gly
                325                 330                 335

Gly Leu Val His Pro Gly Gly Ser Leu Arg Leu Ser Cys Ala Pro Ser
            340                 345                 350

Ala Ser Leu Pro Ser Thr Pro Phe Asn Pro Phe Asn Asn Met Val Gly
        355                 360                 365

Trp Tyr Arg Gln Ala Pro Gly Lys Gln Arg Glu Met Val Ala Ser Ile
    370                 375                 380

Gly Leu Arg Ile Asn Tyr Ala Asp Ser Val Lys Gly Arg Phe Thr Ile
385                 390                 395                 400

Ser Arg Asp Asn Ala Lys Asn Thr Val Asp Leu Gln Met Asp Ser Leu
                405                 410                 415

Arg Pro Glu Asp Ser Ala Thr Tyr Tyr Cys His Ile Glu Tyr Thr His
            420                 425                 430

Tyr Trp Gly Lys Gly Thr Leu Val Thr Val Ser Ser Glu Pro Lys Thr
        435                 440                 445

Pro Lys Pro Gln Pro Ala Arg Gln Gly Ala Pro Val Pro Tyr Pro Asp
    450                 455                 460

Pro Leu Glu Pro Arg
465
```

<210> SEQ ID NO 53

<211> LENGTH: 109
<212> TYPE: PRT
<213> ORGANISM: Clostridium botulinum

<400> SEQUENCE: 53

Met Ser Asp Lys Ile Ile His Leu Thr Asp Asp Ser Phe Asp Thr Asp
1 5 10 15

Val Leu Lys Ala Asp Gly Ala Ile Leu Val Asp Phe Trp Ala Glu Trp
20 25 30

Cys Gly Pro Cys Lys Met Ile Ala Pro Ile Leu Asp Glu Ile Ala Asp
35 40 45

Glu Tyr Gln Gly Lys Leu Thr Val Ala Lys Leu Asn Ile Asp Gln Asn
50 55 60

Pro Gly Thr Ala Pro Lys Tyr Gly Ile Arg Gly Ile Pro Thr Leu Leu
65 70 75 80

Leu Phe Lys Asn Gly Glu Val Ala Ala Thr Lys Val Gly Ala Leu Ser
85 90 95

Lys Gly Gln Leu Lys Glu Phe Leu Asp Ala Asn Leu Ala
100 105

<210> SEQ ID NO 54
<211> LENGTH: 5
<212> TYPE: PRT
<213> ORGANISM: Artificial Sequence
<220> FEATURE:
<223> OTHER INFORMATION: The sequence has been designed and synthesized

<400> SEQUENCE: 54

Gly Gly Gly Gly Ser
1 5

<210> SEQ ID NO 55
<211> LENGTH: 15
<212> TYPE: PRT
<213> ORGANISM: Artificial Sequence
<220> FEATURE:
<223> OTHER INFORMATION: The sequence has been designed and synthesized

<400> SEQUENCE: 55

Gly Gly Gly Gly Ser Gly Gly Gly Gly Ser Gly Gly Gly Gly Ser
1 5 10 15

<210> SEQ ID NO 56
<211> LENGTH: 111
<212> TYPE: PRT
<213> ORGANISM: Artificial Sequence
<220> FEATURE:
<223> OTHER INFORMATION: The sequence has been designed and synthesized

<400> SEQUENCE: 56

Leu Val Gln Val Gly Gly Ser Leu Arg Leu Ser Cys Val Val Ser Gly
1 5 10 15

Ser Asp Ile Ser Gly Ile Ala Met Gly Trp Tyr Arg Gln Ala Pro Gly
20 25 30

Lys Arg Arg Glu Met Val Ala Asp Ile Phe Ser Gly Gly Ser Thr Asp
35 40 45

Tyr Ala Gly Ser Val Lys Gly Arg Phe Thr Ile Ser Arg Asp Asn Ala
50 55 60

Lys Lys Thr Ser Tyr Leu Gln Met Asn Asn Val Lys Pro Glu Asp Thr
65 70 75 80

Gly Val Tyr Tyr Cys Arg Leu Tyr Gly Ser Gly Asp Tyr Trp Gly Gln

-continued

```
                85                  90                  95

Gly Thr Gln Val Thr Val Ser Ser Ala His His Ser Glu Asp Pro
            100                 105                 110


<210> SEQ ID NO 57
<211> LENGTH: 115
<212> TYPE: PRT
<213> ORGANISM: Artificial Sequence
<220> FEATURE:
<223> OTHER INFORMATION: The sequence has been designed and synthesized

<400> SEQUENCE: 57

Leu Val His Pro Gly Gly Ser Leu Arg Leu Ser Cys Ala Pro Ser Ala
1               5                   10                  15

Ser Leu Pro Ser Thr Pro Phe Asn Pro Phe Asn Asn Met Val Gly Trp
            20                  25                  30

Tyr Arg Gln Ala Pro Gly Lys Gln Arg Glu Met Val Ala Ser Ile Gly
        35                  40                  45

Leu Arg Ile Asn Tyr Ala Asp Ser Val Lys Gly Arg Phe Thr Ile Ser
    50                  55                  60

Arg Asp Asn Ala Lys Asn Thr Val Asp Leu Gln Met Asp Ser Leu Arg
65                  70                  75                  80

Pro Glu Asp Ser Ala Thr Tyr Tyr Cys His Ile Glu Tyr Thr His Tyr
                85                  90                  95

Trp Gly Lys Gly Thr Leu Val Thr Val Ser Ser Glu Pro Lys Thr Pro
            100                 105                 110

Lys Pro Gln
        115


<210> SEQ ID NO 58
<211> LENGTH: 269
<212> TYPE: PRT
<213> ORGANISM: Artificial Sequence
<220> FEATURE:
<223> OTHER INFORMATION: The sequence has been designed and synthesized

<400> SEQUENCE: 58

Gln Val Gln Leu Val Glu Ser Gly Gly Gly Leu Val Gln Val Gly Gly
1               5                   10                  15

Ser Leu Arg Leu Ser Cys Val Val Ser Gly Ser Asp Ile Ser Gly Ile
            20                  25                  30

Ala Met Gly Trp Tyr Arg Gln Ala Pro Gly Lys Arg Arg Glu Met Val
        35                  40                  45

Ala Asp Ile Phe Ser Gly Gly Ser Thr Asp Tyr Ala Gly Ser Val Lys
    50                  55                  60

Gly Arg Phe Thr Ile Ser Arg Asp Asn Ala Lys Lys Thr Ser Tyr Leu
65                  70                  75                  80

Gln Met Asn Asn Val Lys Pro Glu Asp Thr Gly Val Tyr Tyr Cys Arg
                85                  90                  95

Leu Tyr Gly Ser Gly Asp Tyr Trp Gly Gln Gly Thr Gln Val Thr Val
            100                 105                 110

Ser Ser Ala His His Ser Glu Asp Pro Thr Ser Ala Ile Ala Gly Gly
        115                 120                 125

Gly Gly Ser Gly Gly Gly Gly Ser Gly Gly Gly Gly Ser Leu Gln Gly
    130                 135                 140

Gln Leu Gln Leu Val Glu Ser Gly Gly Gly Leu Val His Pro Gly Gly
145                 150                 155                 160
```

-continued

```
Ser Leu Arg Leu Ser Cys Ala Pro Ser Ala Ser Leu Pro Ser Thr Pro
                165                 170                 175

Phe Asn Pro Phe Asn Asn Met Val Gly Trp Tyr Arg Gln Ala Pro Gly
            180                 185                 190

Lys Gln Arg Glu Met Val Ala Ser Ile Gly Leu Arg Ile Asn Tyr Ala
        195                 200                 205

Asp Ser Val Lys Gly Arg Phe Thr Ile Ser Arg Asp Asn Ala Lys Asn
    210                 215                 220

Thr Val Asp Leu Gln Met Asp Ser Leu Arg Pro Glu Asp Ser Ala Thr
225                 230                 235                 240

Tyr Tyr Cys His Ile Glu Tyr Thr His Tyr Trp Gly Lys Gly Thr Leu
                245                 250                 255

Val Thr Val Ser Ser Glu Pro Lys Thr Pro Lys Pro Gln
            260                 265


<210> SEQ ID NO 59
<211> LENGTH: 135
<212> TYPE: PRT
<213> ORGANISM: Artificial Sequence
<220> FEATURE:
<223> OTHER INFORMATION: The sequence has been designed and synthesized

<400> SEQUENCE: 59

Gln Val Gln Leu Val Glu Thr Gly Gly Leu Val Gln Pro Gly Gly Ser
1               5                   10                  15

Leu Arg Leu Ser Cys Ala Ala Ser Gly Phe Thr Leu Asp Tyr Ser Ser
            20                  25                  30

Ile Gly Trp Phe Arg Gln Ala Pro Gly Lys Glu Arg Glu Gly Val Ser
        35                  40                  45

Cys Ile Ser Ser Ser Gly Asp Ser Thr Lys Tyr Ala Asp Ser Val Lys
    50                  55                  60

Gly Arg Phe Thr Thr Ser Arg Asp Asn Ala Lys Asn Thr Val Tyr Leu
65                  70                  75                  80

Gln Met Asn Ser Leu Lys Pro Asp Asp Thr Ala Val Tyr Tyr Cys Ala
                85                  90                  95

Ala Phe Arg Ala Thr Met Cys Gly Val Phe Pro Leu Ser Pro Tyr Gly
            100                 105                 110

Lys Asp Asp Trp Gly Lys Gly Thr Leu Val Thr Val Ser Ser Glu Pro
        115                 120                 125

Lys Thr Pro Lys Pro Gln Pro
    130                 135


<210> SEQ ID NO 60
<211> LENGTH: 130
<212> TYPE: PRT
<213> ORGANISM: Artificial Sequence
<220> FEATURE:
<223> OTHER INFORMATION: The sequence has been designed and synthesized

<400> SEQUENCE: 60

Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60
```

-continued

Gly Arg Phe Thr Ile Ser Arg Asp Asn Ala Lys Asn Thr Leu Tyr Leu
65 70 75 80

Gln Met Thr Ser Leu Lys Pro Glu Asp Thr Ala Leu Tyr Tyr Cys Ala
85 90 95

Arg Gly Arg Val Ile Ser Ala Ser Ala Ile Arg Gly Ala Val Arg Gly
100 105 110

Pro Gly Thr Gln Val Thr Val Ser Ser Glu Pro Lys Thr Pro Lys Pro
115 120 125

Gln Pro
130

<210> SEQ ID NO 61
<211> LENGTH: 137
<212> TYPE: PRT
<213> ORGANISM: Artificial Sequence
<220> FEATURE:
<223> OTHER INFORMATION: The sequence has been designed and synthesized

<400> SEQUENCE: 61

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Asp Tyr Tyr
20 25 30

Ala Ile Gly Trp Phe Arg Gln Ala Pro Gly Lys Glu Arg Glu Gly Val
35 40 45

Ser Gly Ile Ser Ser Val Asp Gly Ser Thr Tyr Tyr Ala Asp Ser Val
50 55 60

Arg Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Asp Gln Ser Pro Ile Pro Ile His Tyr Ser Arg Thr Tyr Ser
100 105 110

Gly Pro Tyr Gly Met Asp Tyr Trp Gly Lys Gly Thr Leu Val Thr Val
115 120 125

Ser Ser Ala His His Ser Glu Asp Pro
130 135

<210> SEQ ID NO 62
<211> LENGTH: 139
<212> TYPE: PRT
<213> ORGANISM: Artificial Sequence
<220> FEATURE:
<223> OTHER INFORMATION: The sequence has been designed and synthesized

<400> SEQUENCE: 62

Gln Leu Gln Leu Val Glu Ser Gly Gly Gly Leu Val Gln Pro Gly Gly
1 5 10 15

Ser Leu Arg Leu Ser Cys Ala Ala Ser Gly Phe Thr Leu Asp Tyr Tyr
20 25 30

Ala Ile Gly Trp Phe Arg Gln Ala Pro Gly Lys Glu Arg Glu Gly Val
35 40 45

Ser Gly Ile Ser Phe Val Asp Gly Ser Thr Tyr Tyr Ala Asp Ser Val
50 55 60

Lys Gly Arg Phe Ala Ile Ser Arg Gly Asn Ala Lys Asn Thr Val Tyr
65 70 75 80

Leu Gln Met Asn Ser Leu Lys Pro Glu Asp Thr Ala Val Tyr Tyr Cys

```
                85                  90                  95

Ala Ala Asp Gln Ser Ser Ile Pro Met His Tyr Ser Ser Thr Tyr Ser
            100                 105                 110

Gly Pro Ser Gly Met Asp Tyr Trp Gly Lys Gly Thr Leu Val Thr Val
        115                 120                 125

Ser Ser Glu Pro Lys Thr Pro Lys Pro Gln Pro
    130                 135


<210> SEQ ID NO 63
<211> LENGTH: 136
<212> TYPE: PRT
<213> ORGANISM: Artificial Sequence
<220> FEATURE:
<223> OTHER INFORMATION: The sequence has been designed and synthesized

<400> SEQUENCE: 63

Gln Leu Gln Leu Val Glu Thr Gly Gly Gly Leu Val Gln Ala Gly Gly
1               5                   10                  15

Ser Leu Arg Leu Ser Cys Ala Ala Ser Gly Arg Thr Leu Ser Asn Tyr
            20                  25                  30

Pro Met Gly Trp Phe Arg Gln Ala Pro Gly Lys Glu Arg Glu Phe Val
        35                  40                  45

Ala Ala Ile Arg Arg Ile Ala Asp Gly Thr Tyr Tyr Ala Asp Ser Val
    50                  55                  60

Lys Gly Arg Phe Thr Ile Ser Arg Asp Asn Ala Trp Asn Thr Leu Tyr
65                  70                  75                  80

Leu Gln Met Asn Gly Leu Lys Pro Glu Asp Thr Ala Val Tyr Phe Cys
                85                  90                  95

Ala Thr Gly Pro Gly Ala Phe Pro Gly Met Val Val Thr Asn Pro Ser
            100                 105                 110

Ala Tyr Pro Tyr Trp Gly Gln Gly Thr Gln Val Thr Val Ser Ser Glu
        115                 120                 125

Pro Lys Thr Pro Lys Pro Gln Pro
    130                 135


<210> SEQ ID NO 64
<211> LENGTH: 139
<212> TYPE: PRT
<213> ORGANISM: Artificial Sequence
<220> FEATURE:
<223> OTHER INFORMATION: The sequence has been designed and synthesized

<400> SEQUENCE: 64

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ser Gly Ile Ser Ser Ser Asp Gly Ser Thr Tyr Tyr Ala Asp Ser Val
    50                  55                  60

Lys Gly Arg Phe Thr Ile Ser Arg Asp Asn Ala Thr Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Gln Ala Ala Ile Pro Met His Tyr Ser Ala Ser Tyr Ser
            100                 105                 110
```

Gly Pro Arg Gly Met Asp Tyr Trp Gly Lys Gly Thr Leu Val Thr Val
115 120 125

Ser Ser Glu Pro Lys Thr Pro Lys Pro Gln Pro
130 135

<210> SEQ ID NO 65
<211> LENGTH: 135
<212> TYPE: PRT
<213> ORGANISM: Artificial Sequence
<220> FEATURE:
<223> OTHER INFORMATION: The sequence has been designed and synthesized

<400> SEQUENCE: 65

Gln Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Asp Tyr Tyr
20 25 30

Gly Ile Gly Trp Phe Arg Gln Ala Pro Gly Lys Glu Arg Gln Glu Val
35 40 45

Ser Tyr Ile Ser Ala Ser Ala Lys Thr Lys Leu Tyr Ser Asp Ser Val
50 55 60

Lys Gly Arg Phe Thr Ile Ser Arg Asp Asn Ala Lys Asn Ala Val Tyr
65 70 75 80

Leu Glu Met Asn Ser Leu Lys Arg Glu Asp Thr Ala Val Tyr Tyr Cys
85 90 95

Ala Arg Arg Arg Phe Asp Ala Ser Ala Ser Asn Arg Trp Leu Ala Ala
100 105 110

Asp Tyr Asp Tyr Trp Gly Gln Gly Thr Gln Val Thr Val Ser Ser Glu
115 120 125

Pro Lys Thr Pro Lys Pro Gln
130 135

<210> SEQ ID NO 66
<211> LENGTH: 123
<212> TYPE: PRT
<213> ORGANISM: Artificial Sequence
<220> FEATURE:
<223> OTHER INFORMATION: The sequence has been designed and synthesized

<400> SEQUENCE: 66

Gln Val Gln Leu Val Glu Ser Gly Gly Gly Leu Val Gln Ala Gly Gly
1 5 10 15

Ser Leu Arg Leu Ser Cys Val Ser Ser Glu Arg Asn Pro Gly Ile Asn
20 25 30

Ala Met Gly Trp Tyr Arg Gln Ala Pro Gly Ser Gln Arg Glu Leu Val
35 40 45

Ala Ile Trp Gln Thr Gly Gly Ser Leu Asn Tyr Ala Asp Ser Val Lys
50 55 60

Gly Arg Phe Thr Ile Ser Arg Asp Asn Leu Lys Asn Thr Val Tyr Leu
65 70 75 80

Gln Met Asn Ser Leu Lys Pro Glu Asp Thr Ala Val Tyr Tyr Cys Tyr
85 90 95

Leu Lys Lys Trp Arg Asp Gln Tyr Trp Gly Gln Gly Thr Gln Val Thr
100 105 110

Val Ser Ser Glu Pro Lys Thr Pro Lys Pro Gln
115 120

<210> SEQ ID NO 67

<211> LENGTH: 135
<212> TYPE: PRT
<213> ORGANISM: Artificial Sequence
<220> FEATURE:
<223> OTHER INFORMATION: The sequence has been designed and synthesized

<400> SEQUENCE: 67

```
Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Gly Ile Gly Trp Phe Arg Gln Pro Pro Gly Lys Glu Arg Glu Ala Val
        35                  40                  45

Ser Tyr Ile Ser Ala Ser Ala Arg Thr Ile Leu Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Arg Glu Asp Thr Ala Val Tyr Tyr Cys
                85                  90                  95

Ala Arg Arg Arg Phe Ser Ala Ser Ser Val Asn Arg Trp Leu Ala Asp
            100                 105                 110

Asp Tyr Asp Val Trp Gly Arg Gly Thr Gln Val Ala Val Ser Ser Glu
        115                 120                 125

Pro Lys Thr Pro Lys Pro Gln
    130                 135
```

<210> SEQ ID NO 68
<211> LENGTH: 119
<212> TYPE: PRT
<213> ORGANISM: Artificial Sequence
<220> FEATURE:
<223> OTHER INFORMATION: The sequence has been designed and synthesized

<400> SEQUENCE: 68

```
Gln Val Gln Leu Val Glu Ser Gly Gly Gly Leu Val Gln Thr Gly Gly
1               5                   10                  15

Ser Leu Arg Leu Ser Cys Ala Ser Ser Gly Ser Ile Ala Gly Phe Glu
            20                  25                  30

Thr Val Thr Trp Ser Arg Gln Ala Pro Gly Lys Ser Leu Gln Trp Val
        35                  40                  45

Ala Ser Met Thr Lys Thr Asn Asn Glu Ile Tyr Ser Asp Ser Val Lys
    50                  55                  60

Gly Arg Phe Ile Ile Ser Arg Asp Asn Ala Lys Asn Thr Val Tyr Leu
65                  70                  75                  80

Gln Met Asn Ser Leu Lys Pro Glu Asp Thr Gly Val Tyr Phe Cys Lys
                85                  90                  95

Gly Pro Glu Leu Arg Gly Gln Gly Ile Gln Val Thr Val Ser Ser Glu
            100                 105                 110

Pro Lys Thr Pro Lys Pro Gln
        115
```

<210> SEQ ID NO 69
<211> LENGTH: 124
<212> TYPE: PRT
<213> ORGANISM: Artificial Sequence
<220> FEATURE:
<223> OTHER INFORMATION: The sequence has been designed and synthesized

<400> SEQUENCE: 69

```
Gln Val Gln Leu Val Glu Ser Gly Gly Gly Leu Val Glu Ala Gly Gly
1               5                   10                  15

Ser Leu Arg Leu Ser Cys Val Val Thr Gly Ser Ser Phe Ser Thr Ser
            20                  25                  30

Thr Met Ala Trp Tyr Arg Gln Pro Pro Gly Lys Gln Arg Glu Trp Val
        35                  40                  45

Ala Ser Phe Thr Ser Gly Gly Ala Ile Lys Tyr Thr Asp Ser Val Lys
    50                  55                  60

Gly Arg Phe Thr Met Ser Arg Asp Asn Ala Lys Lys Met Thr Tyr Leu
65                  70                  75                  80

Gln Met Glu Asn Leu Lys Pro Glu Asp Thr Ala Val Tyr Tyr Cys Ala
                85                  90                  95

Leu His Asn Ala Val Ser Gly Ser Ser Trp Gly Arg Gly Thr Gln Val
            100                 105                 110

Thr Val Ser Ser Glu Pro Lys Thr Pro Lys Pro Gln
        115                 120


<210> SEQ ID NO 70
<211> LENGTH: 123
<212> TYPE: PRT
<213> ORGANISM: Artificial Sequence
<220> FEATURE:
<223> OTHER INFORMATION: The sequence has been designed and synthesized

<400> SEQUENCE: 70

Val Gln Leu Val Glu Ser Gly Gly Gly Leu Val Gln Ala Gly Gly Ser
1               5                   10                  15

Leu Arg Leu Ser Cys Ala Ala Ser Gly Leu Met Phe Gly Ala Met Thr
            20                  25                  30

Met Gly Trp Tyr Arg Gln Ala Pro Gly Lys Glu Arg Glu Met Val Ala
        35                  40                  45

Tyr Ile Thr Ala Gly Gly Thr Glu Ser Tyr Ser Glu Ser Val Lys Gly
    50                  55                  60

Arg Phe Thr Ile Ser Arg Ile Asn Ala Asn Asn Met Val Tyr Leu Gln
65                  70                  75                  80

Met Thr Asn Leu Lys Val Glu Asp Thr Ala Val Tyr Tyr Cys Asn Ala
                85                  90                  95

His Asn Phe Trp Arg Thr Ser Arg Asn Trp Gly Gln Gly Thr Gln Val
            100                 105                 110

Thr Val Ser Ser Glu Pro Lys Thr Pro Lys Pro
        115                 120


<210> SEQ ID NO 71
<211> LENGTH: 131
<212> TYPE: PRT
<213> ORGANISM: Artificial Sequence
<220> FEATURE:
<223> OTHER INFORMATION: The sequence has been designed and synthesized

<400> SEQUENCE: 71

Val Gln Leu Val Glu Ser Gly Gly Gly Leu Val Gln Ala Gly Asp Ser
1               5                   10                  15

Leu Thr Leu Ser Cys Ala Ala Ser Glu Ser Thr Phe Asn Thr Phe Ser
            20                  25                  30

Met Ala Trp Phe Arg Gln Ala Pro Gly Lys Glu Arg Glu Tyr Val Ala
        35                  40                  45

Ala Phe Ser Arg Ser Gly Gly Thr Thr Asn Tyr Ala Asp Ser Val Lys
    50                  55                  60
```

Gly Arg Ala Thr Ile Ser Thr Asp Asn Ala Lys Asn Thr Val Tyr Leu
65 70 75 80

His Met Asn Ser Leu Lys Pro Glu Asp Thr Ala Val Tyr Phe Cys Ala
85 90 95

Ala Asp Arg Pro Ala Gly Arg Ala Tyr Phe Gln Ser Arg Ser Tyr Asn
100 105 110

Tyr Trp Gly Gln Gly Thr Gln Val Thr Val Ser Ser Ala His His Ser
115 120 125

Glu Asp Pro
130

<210> SEQ ID NO 72
<211> LENGTH: 125
<212> TYPE: PRT
<213> ORGANISM: Artificial Sequence
<220> FEATURE:
<223> OTHER INFORMATION: The sequence has been designed and synthesized

<400> SEQUENCE: 72

Val Gln Leu Val Glu Ser Gly Gly Gly Ser Val Gln Ile Gly Gly Ser
1 5 10 15

Leu Arg Leu Ser Cys Val Ala Ser Gly Phe Thr Phe Ser Lys Asn Ile
20 25 30

Met Ser Trp Ala Arg Gln Ala Pro Gly Lys Gly Leu Glu Trp Val Ser
35 40 45

Thr Ile Ser Ile Gly Gly Ala Ala Thr Ser Tyr Ala Asp Ser Val Lys
50 55 60

Gly Arg Phe Thr Ile Ser Arg Asp Asn Ala Asn Asp Thr Leu Tyr Leu
65 70 75 80

Gln Met Asn Asn Leu Lys Pro Glu Asp Thr Ala Val Tyr Tyr Cys Ser
85 90 95

Arg Gly Pro Arg Thr Tyr Ile Asn Thr Ala Ser Arg Gly Gln Gly Thr
100 105 110

Gln Val Thr Val Ser Ser Glu Pro Lys Thr Pro Lys Pro
115 120 125

<210> SEQ ID NO 73
<211> LENGTH: 121
<212> TYPE: PRT
<213> ORGANISM: Artificial Sequence
<220> FEATURE:
<223> OTHER INFORMATION: The sequence has been designed and synthesized

<400> SEQUENCE: 73

Val Gln Leu Val Glu Ser Gly Gly Gly Leu Val Gln Ala Gly Gly Ser
1 5 10 15

Leu Arg Leu Ser Cys Val Gly Ser Gly Arg Asn Pro Gly Ile Asn Ala
20 25 30

Met Gly Trp Tyr Arg Gln Ala Pro Gly Ser Gln Arg Glu Leu Val Ala
35 40 45

Val Trp Gln Thr Gly Gly Ser Thr Asn Tyr Ala Asp Ser Val Lys Gly
50 55 60

Arg Phe Thr Ile Ser Arg Asp Asn Leu Lys Asn Thr Val Tyr Leu Gln
65 70 75 80

Met Asn Ser Leu Lys Pro Glu Asp Thr Ala Val Tyr Tyr Cys Tyr Leu
85 90 95

Lys Lys Trp Arg Asp Glu Tyr Trp Gly Gln Gly Thr Gln Val Thr Val

```
            100                 105                 110

Ser Ser Ala His His Ser Glu Asp Pro
        115                 120


<210> SEQ ID NO 74
<211> LENGTH: 124
<212> TYPE: PRT
<213> ORGANISM: Artificial Sequence
<220> FEATURE:
<223> OTHER INFORMATION: The sequence has been designed and synthesized

<400> SEQUENCE: 74

Val Gln Leu Val Glu Ser Gly Gly Gly Leu Val Gln Ala Gly Glu Ser
1               5                   10                  15

Leu Arg Leu Ser Cys Val Val Ser Glu Ser Ile Phe Arg Ile Asn Thr
            20                  25                  30

Met Gly Trp Tyr Arg Gln Thr Pro Gly Lys Gln Arg Glu Val Val Ala
        35                  40                  45

Arg Ile Thr Leu Arg Asn Ser Thr Thr Tyr Ala Asp Ser Val Lys Gly
    50                  55                  60

Arg Phe Thr Ile Ser Arg Asp Asp Ala Lys Asn Thr Leu Tyr Leu Lys
65                  70                  75                  80

Met Asp Ser Leu Lys Pro Glu Asp Thr Ala Val Tyr Tyr Cys His Arg
                85                  90                  95

Tyr Pro Leu Ile Phe Arg Asn Ser Pro Tyr Trp Gly Gln Gly Thr Gln
            100                 105                 110

Val Thr Val Ser Ser Glu Pro Lys Thr Pro Lys Pro
        115                 120


<210> SEQ ID NO 75
<211> LENGTH: 122
<212> TYPE: PRT
<213> ORGANISM: Artificial Sequence
<220> FEATURE:
<223> OTHER INFORMATION: The sequence has been designed and synthesized

<400> SEQUENCE: 75

Val Gln Leu Val Glu Ser Gly Gly Gly Leu Val Gln Ala Gly Glu Ser
1               5                   10                  15

Leu Arg Leu Ser Cys Val Val Ser Glu Ser Ile Phe Arg Ile Asn Thr
            20                  25                  30

Met Gly Trp Tyr Arg Gln Thr Pro Gly Lys Gln Arg Glu Val Val Ala
        35                  40                  45

Arg Ile Thr Leu Arg Asn Ser Thr Thr Tyr Ala Asp Ser Val Lys Gly
    50                  55                  60

Arg Phe Thr Ile Ser Arg Asp Asp Ala Lys Asn Thr Leu Tyr Leu Lys
65                  70                  75                  80

Met Asp Ser Leu Lys Pro Glu Asp Thr Ala Val Tyr Tyr Cys His Arg
                85                  90                  95

Tyr Pro Leu Ile Phe Arg Asn Ser Pro Tyr Trp Gly Gln Gly Thr Gln
            100                 105                 110

Val Thr Val Ser Ser Glu Pro Lys Thr Pro
        115                 120


<210> SEQ ID NO 76
<211> LENGTH: 129
<212> TYPE: PRT
<213> ORGANISM: Artificial Sequence
<220> FEATURE:
```

<223> OTHER INFORMATION: The sequence has been designed and synthesized

<400> SEQUENCE: 76

Val Gln Leu Val Glu Ser Gly Gly Gly Leu Val Gln Ala Gly Gly Ser
1 5 10 15

Leu Arg Leu Ser Cys Ala Ala Pro Gly Leu Thr Phe Thr Ser Tyr Arg
20 25 30

Met Gly Trp Phe Arg Gln Ala Pro Gly Lys Glu Arg Glu Tyr Val Ala
35 40 45

Ala Ile Thr Gly Ala Gly Ala Thr Asn Tyr Ala Asp Ser Ala Lys Gly
50 55 60

Arg Phe Thr Ile Ser Lys Asn Asn Thr Ala Ser Thr Val His Leu Gln
65 70 75 80

Met Asn Ser Leu Lys Pro Glu Asp Thr Ala Val Tyr Tyr Cys Ala Ala
85 90 95

Ser Asn Arg Ala Gly Gly Tyr Trp Arg Ala Ser Gln Tyr Asp Tyr Trp
100 105 110

Gly Gln Gly Thr Gln Val Thr Val Ser Ser Ala His His Ser Glu Asp
115 120 125

Pro

<210> SEQ ID NO 77
<211> LENGTH: 129
<212> TYPE: PRT
<213> ORGANISM: Artificial Sequence
<220> FEATURE:
<223> OTHER INFORMATION: The sequence has been designed and synthesized

<400> SEQUENCE: 77

Gln Val Gln Leu Val Glu Thr Gly Gly Gly Leu Ala Gln Ala Gly Asp
1 5 10 15

Ser Leu Arg Leu Ser Cys Val Glu Pro Gly Arg Thr Leu Asp Met Tyr
20 25 30

Ala Met Gly Trp Ile Arg Gln Ala Pro Gly Glu Glu Arg Glu Phe Val
35 40 45

Ala Ser Ile Ser Gly Val Gly Gly Ser Pro Arg Tyr Ala Asp Ser Val
50 55 60

Lys Gly Arg Phe Thr Ile Ser Lys Asp Asn Thr Lys Ser Thr Ile Trp
65 70 75 80

Leu Gln Met Asn Ser Leu Lys Pro Glu Asp Thr Ala Val Tyr Tyr Cys
85 90 95

Ala Ala Gly Gly Asp Ile Tyr Tyr Gly Gly Ser Pro Gln Trp Arg Gly
100 105 110

Gln Gly Thr Arg Val Thr Val Ser Ser Glu Pro Lys Thr Pro Lys Pro
115 120 125

Gln

<210> SEQ ID NO 78
<211> LENGTH: 132
<212> TYPE: PRT
<213> ORGANISM: Artificial Sequence
<220> FEATURE:
<223> OTHER INFORMATION: The sequence has been designed and synthesized

<400> SEQUENCE: 78

Gln Val Gln Leu Val Glu Ser Gly Gly Gly Leu Val Gln Ala Gly Gly
1 5 10 15

```
Ser Leu Arg Leu Ser Cys Ala Ala Ser Gly Arg Ile Asn Gly Asp Tyr
            20                  25                  30

Ala Met Gly Trp Phe Arg Gln Ala Pro Gly Glu Glu Arg Glu Phe Val
        35                  40                  45

Ala Val Asn Ser Trp Ile Gly Gly Ser Thr Tyr Tyr Thr Asp Ser Val
    50                  55                  60

Lys Gly Arg Phe Thr Leu Ser Arg Asp Asn Ala Lys Asn Thr Leu Ser
65                  70                  75                  80

Leu Gln Met Asn Ser Leu Lys Pro Glu Asp Thr Ala Val Tyr Tyr Cys
                85                  90                  95

Ala Ala Gly His Tyr Thr Asp Phe Pro Thr Tyr Phe Lys Glu Tyr Asp
            100                 105                 110

Tyr Trp Gly Gln Gly Thr Gln Val Thr Val Ser Ser Glu Pro Lys Thr
        115                 120                 125

Pro Lys Pro Gln
    130


<210> SEQ ID NO 79
<211> LENGTH: 132
<212> TYPE: PRT
<213> ORGANISM: Artificial Sequence
<220> FEATURE:
<223> OTHER INFORMATION: The sequence has been designed and synthesized

<400> SEQUENCE: 79

Gln Val Gln Leu Val Glu Thr Gly Gly Leu Val Gln Ala Gly Gly Ser
1               5                   10                  15

Leu Arg Leu Ser Cys Ala Ala Ser Gly Val Pro Phe Ser Asp Tyr Thr
            20                  25                  30

Met Ala Trp Phe Arg Gln Ala Pro Gly Lys Glu Arg Glu Val Val Ala
        35                  40                  45

Arg Ile Thr Trp Arg Gly Gly Gly Pro Tyr Tyr Gly Asn Ser Gly Asn
    50                  55                  60

Gly Arg Phe Ala Ile Ser Arg Asp Ile Ala Lys Ser Met Val Tyr Leu
65                  70                  75                  80

His Met Asp Ser Leu Lys Pro Glu Asp Thr Ala Val Tyr Tyr Cys Ala
                85                  90                  95

Ala Ser Arg Leu Arg Pro Ala Leu Ala Ser Met Ala Ser Asp Tyr Asp
            100                 105                 110

Tyr Trp Gly Gln Gly Thr Gln Val Ser Val Ser Ser Glu Pro Lys Thr
        115                 120                 125

Pro Lys Pro Gln
    130


<210> SEQ ID NO 80
<211> LENGTH: 124
<212> TYPE: PRT
<213> ORGANISM: Artificial Sequence
<220> FEATURE:
<223> OTHER INFORMATION: The sequence has been designed and synthesized

<400> SEQUENCE: 80

Gln Val Gln Leu Val Glu Ser Gly Gly Gly Leu Val Gln Pro Gly Glu
1               5                   10                  15

Ser Leu Arg Leu Ser Cys Val Ala Ser Ala Ser Thr Phe Ser Thr Ser
            20                  25                  30

Leu Met Gly Trp Val Arg Gln Ala Pro Gly Lys Gly Leu Glu Ser Val
        35                  40                  45
```

Ala Glu Val Arg Thr Thr Gly Gly Thr Phe Tyr Ala Lys Ser Val Ala
    50                  55                  60

Gly Arg Phe Thr Ile Ser Arg Asp Asn Ala Lys Asn Thr Leu Tyr Leu
65                  70                  75                  80

Gln Met Asn Ser Leu Lys Ala Glu Asp Thr Gly Val Tyr Tyr Cys Thr
                85                  90                  95

Ala Gly Ala Gly Pro Ile Ala Thr Arg Tyr Arg Gly Gln Gly Thr Gln
            100                 105                 110

Val Thr Val Ser Ser Ala His His Ser Glu Asp Pro
        115                 120

<210> SEQ ID NO 81
<211> LENGTH: 137
<212> TYPE: PRT
<213> ORGANISM: Artificial Sequence
<220> FEATURE:
<223> OTHER INFORMATION: The sequence has been designed and synthesized

<400> SEQUENCE: 81

Gln Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Leu Ala Asp Tyr
            20                  25                  30

Val Thr Val Trp Phe Arg Gln Ala Pro Gly Lys Ser Arg Glu Gly Val
        35                  40                  45

Ser Cys Ile Ser Ser Ser Arg Gly Thr Pro Asn Tyr Ala Asp Ser Val
    50                  55                  60

Lys Gly Arg Ala Thr Val Ser Arg Asn Asn Ala Asn Asn Thr Val Tyr
65                  70                  75                  80

Leu Gln Met Asn Gly Leu Lys Pro Asp Asp Thr Ala Ile Tyr Tyr Cys
                85                  90                  95

Ala Ala Ile Arg Pro Ala Arg Leu Arg Ala Tyr Arg Glu Cys Leu Ser
            100                 105                 110

Ser Gln Ala Glu Tyr Asp Tyr Trp Gly Gln Gly Thr Gln Val Thr Val
        115                 120                 125

Ser Ser Ala His His Ser Glu Asp Pro
    130                 135

<210> SEQ ID NO 82
<211> LENGTH: 134
<212> TYPE: PRT
<213> ORGANISM: Artificial Sequence
<220> FEATURE:
<223> OTHER INFORMATION: The sequence has been designed and synthesized

<400> SEQUENCE: 82

Gln Val Gln Leu Val Glu Ser Gly Gly Gly Leu Val Gln Pro Gly Gly
1               5                   10                  15

Ser Leu Gly Leu Ser Cys Ala Met Ser Gly Thr Thr Gln Asp Tyr Ser
            20                  25                  30

Ala Val Gly Trp Phe Arg Gln Ala Pro Gly Lys Glu Arg Glu Gly Val
        35                  40                  45

Ser Cys Ile Ser Arg Ser Gly Arg Arg Thr Asn Tyr Ala Asp Ser Val
    50                  55                  60

Arg Gly Arg Phe Thr Ile Ser Arg Asp Asn Ala Lys Asp Thr Val Tyr
65                  70                  75                  80

Leu Gln Met Asn Ser Leu Lys Pro Asp Asp Thr Ala Val Tyr Tyr Cys

```
                85                  90                  95

Ala Ala Arg Lys Thr Asp Met Ser Asp Pro Tyr Tyr Val Gly Cys Asn
            100                 105                 110

Gly Met Asp Tyr Trp Gly Lys Gly Thr Leu Val Thr Val Ser Ser Ala
        115                 120                 125

His His Ser Glu Asp Pro
    130


<210> SEQ ID NO 83
<211> LENGTH: 130
<212> TYPE: PRT
<213> ORGANISM: Artificial Sequence
<220> FEATURE:
<223> OTHER INFORMATION: The sequence has been designed and synthesized

<400> SEQUENCE: 83

Gln Val Gln Leu Val Glu Ser Gly Gly Gly Leu Val Gln Pro Gly Gly
1               5                   10                  15

Ser Leu Thr Leu Ser Cys Thr Ala Ser Gly Phe Thr Leu Asn Ser Tyr
            20                  25                  30

Lys Ile Gly Trp Phe Arg Gln Ala Pro Gly Lys Glu Arg Glu Gly Val
        35                  40                  45

Ser Cys Ile Asn Ser Gly Gly Asn Leu Arg Ser Val Glu Gly Arg Phe
    50                  55                  60

Thr Ile Ser Arg Asp Asn Thr Lys Asn Thr Val Ser Leu His Met Asp
65                  70                  75                  80

Ser Leu Lys Pro Glu Asp Thr Gly Val Tyr His Cys Ala Ala Ala Pro
                85                  90                  95

Ala Leu Asn Val Phe Ser Pro Cys Val Leu Ala Pro Arg Tyr Asp Tyr
            100                 105                 110

Trp Gly Gln Gly Thr Gln Val Thr Val Ser Ser Ala His His Ser Glu
        115                 120                 125

Asp Pro
    130


<210> SEQ ID NO 84
<211> LENGTH: 134
<212> TYPE: PRT
<213> ORGANISM: Artificial Sequence
<220> FEATURE:
<223> OTHER INFORMATION: The sequence has been designed and synthesized

<400> SEQUENCE: 84

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Gly Ser Tyr
            20                  25                  30

His Ile Gly Trp Phe Arg His Pro Pro Gly Lys Glu Arg Glu Gly Thr
        35                  40                  45

Ser Cys Leu Ser Ser Arg Gly Asp Tyr Thr Lys Tyr Ala Glu Ala Val
    50                  55                  60

Lys Gly Arg Phe Thr Ile Ser Arg Asp Asn Thr Lys Ser Thr Val Tyr
65                  70                  75                  80

Leu Gln Met Asn Asn Leu Lys Pro Glu Asp Thr Gly Ile Tyr Val Cys
                85                  90                  95

Ala Ala Ile Arg Pro Val Leu Ser Asp Ser His Cys Thr Leu Ala Ala
            100                 105                 110
```

```
Arg Tyr Asn Tyr Trp Gly Gln Gly Thr Gln Val Thr Val Ser Ser Ala
        115                 120                 125

His His Ser Glu Asp Pro
    130


<210> SEQ ID NO 85
<211> LENGTH: 133
<212> TYPE: PRT
<213> ORGANISM: Artificial Sequence
<220> FEATURE:
<223> OTHER INFORMATION: The sequence has been designed and synthesized

<400> SEQUENCE: 85

Gln Val Gln Leu Val Glu Ser Gly Gly Gly Leu Val Gln Pro Gly Gly
1               5                   10                  15

Ser Leu Arg Leu Ser Cys Ala Ala Leu Glu Phe Thr Leu Glu Asp Tyr
            20                  25                  30

Ala Ile Ala Trp Phe Arg Gln Ala Pro Gly Lys Glu Arg Glu Gly Val
        35                  40                  45

Ser Cys Ile Ser Lys Ser Gly Val Thr Lys Tyr Thr Asp Ser Val Lys
    50                  55                  60

Gly Arg Phe Thr Val Ala Arg Asp Asn Ala Lys Ser Thr Val Ile Leu
65                  70                  75                  80

Gln Met Asn Asn Leu Arg Pro Glu Asp Thr Ala Val Tyr Asn Cys Ala
                85                  90                  95

Ala Val Arg Pro Val Phe Val Asp Ser Val Cys Thr Leu Ala Thr Arg
            100                 105                 110

Tyr Thr Tyr Trp Gly Glu Gly Thr Gln Val Thr Val Ser Ser Ala His
        115                 120                 125

His Ser Glu Asp Pro
    130


<210> SEQ ID NO 86
<211> LENGTH: 134
<212> TYPE: PRT
<213> ORGANISM: Artificial Sequence
<220> FEATURE:
<223> OTHER INFORMATION: The sequence has been designed and synthesized

<400> SEQUENCE: 86

Gln Val Gln Leu Val Glu Thr Gly Gly Gly Leu Val Gln Pro Gly Gly
1               5                   10                  15

Ser Leu Lys Leu Ser Cys Ala Ala Ser Glu Phe Thr Leu Asp Asp Tyr
            20                  25                  30

His Ile Gly Trp Phe Arg Gln Ala Pro Gly Lys Glu Arg Glu Gly Val
        35                  40                  45

Ser Cys Ile Asn Lys Arg Gly Asp Tyr Ile Asn Tyr Lys Asp Ser Val
    50                  55                  60

Lys Gly Arg Phe Thr Ile Ser Arg Asp Gly Ala Lys Ser Thr Val Phe
65                  70                  75                  80

Leu Gln Met Asn Asn Leu Arg Pro Glu Asp Thr Ala Val Tyr Tyr Cys
                85                  90                  95

Ala Ala Val Asn Pro Val Phe Pro Asp Ser Arg Cys Thr Leu Ala Thr
            100                 105                 110

Arg Tyr Thr His Trp Gly Gln Gly Thr Gln Val Thr Val Ser Ser Ala
        115                 120                 125

His His Ser Glu Asp Pro
    130
```

<210> SEQ ID NO 87
<211> LENGTH: 453
<212> TYPE: PRT
<213> ORGANISM: Artificial Sequence
<220> FEATURE:
<223> OTHER INFORMATION: The sequence has been designed and synthesized

<400> SEQUENCE: 87

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Asp Lys Ala Met
145                 150                 155                 160

Ala Ile Ser Asp Pro Asn Ser Gln Val Gln Leu Val Glu Ser Gly Gly
                165                 170                 175

Gly Leu Val Gln Pro Gly Gly Ser Leu Arg Leu Ser Cys Glu Ala Ser
            180                 185                 190

Gly Phe Thr Leu Asp Tyr Tyr Gly Ile Gly Trp Phe Arg Gln Pro Pro
        195                 200                 205

Gly Lys Glu Arg Glu Ala Val Ser Tyr Ile Ser Ala Ser Ala Arg Thr
    210                 215                 220

Ile Leu Tyr Ala Asp Ser Val Lys Gly Arg Phe Thr Ile Ser Arg Asp
225                 230                 235                 240

Asn Ala Lys Asn Ala Val Tyr Leu Gln Met Asn Ser Leu Lys Arg Glu
                245                 250                 255

Asp Thr Ala Val Tyr Tyr Cys Ala Arg Arg Arg Phe Ser Ala Ser Ser
            260                 265                 270

Val Asn Arg Trp Leu Ala Asp Asp Tyr Asp Val Trp Gly Arg Gly Thr
        275                 280                 285

Gln Val Ala Val Ser Ser Glu Pro Lys Thr Pro Lys Pro Gln Thr Ser
    290                 295                 300

Ala Ile Ala Gly Gly Gly Gly Ser Gly Gly Gly Gly Ser Gly Gly Gly
305                 310                 315                 320

Gly Ser Leu Gln Ala Met Ala Ala Ala Ser Gln Val Gln Leu Val Glu
                325                 330                 335

Ser Gly Gly Gly Leu Val Gln Thr Gly Gly Ser Leu Arg Leu Ser Cys
            340                 345                 350

Ala Ser Ser Gly Ser Ile Ala Gly Phe Glu Thr Val Thr Trp Ser Arg
        355                 360                 365
```

```
Gln Ala Pro Gly Lys Ser Leu Gln Trp Val Ala Ser Met Thr Lys Thr
    370                 375                 380

Asn Asn Glu Ile Tyr Ser Asp Ser Val Lys Gly Arg Phe Ile Ile Ser
385                 390                 395                 400

Arg Asp Asn Ala Lys Asn Thr Val Tyr Leu Gln Met Asn Ser Leu Lys
                405                 410                 415

Pro Glu Asp Thr Gly Val Tyr Phe Cys Lys Gly Pro Glu Leu Arg Gly
            420                 425                 430

Gln Gly Ile Gln Val Thr Val Ser Ser Glu Pro Lys Thr Pro Lys Pro
        435                 440                 445

Gln Pro Ala Arg Arg
    450


<210> SEQ ID NO 88
<211> LENGTH: 6
<212> TYPE: PRT
<213> ORGANISM: Artificial Sequence
<220> FEATURE:
<223> OTHER INFORMATION: The sequence has been designed and synthesized

<400> SEQUENCE: 88

Gln Leu Gln Leu Val Glu
1               5


<210> SEQ ID NO 89
<211> LENGTH: 6
<212> TYPE: PRT
<213> ORGANISM: Artificial Sequence
<220> FEATURE:
<223> OTHER INFORMATION: The sequence has been designed and synthesized

<400> SEQUENCE: 89

Gln Val Gln Leu Val Glu
1               5


<210> SEQ ID NO 90
<211> LENGTH: 22
<212> TYPE: DNA
<213> ORGANISM: Artificial Sequence
<220> FEATURE:
<223> OTHER INFORMATION: The sequence has been designed and synthesized

<400> SEQUENCE: 90

tttgtttatc caccgaacta ag                                              22


<210> SEQ ID NO 91
<211> LENGTH: 22
<212> TYPE: DNA
<213> ORGANISM: Artificial Sequence
<220> FEATURE:
<223> OTHER INFORMATION: The sequence has been designed and synthesized

<400> SEQUENCE: 91

tcttcagaaa gggatccacc ag                                              22


<210> SEQ ID NO 92
<211> LENGTH: 22
<212> TYPE: DNA
<213> ORGANISM: Artificial Sequence
<220> FEATURE:
<223> OTHER INFORMATION: The sequence has been designed and synthesized

<400> SEQUENCE: 92
```

```
tggtggatcc ctttctgaag ac                                              22


<210> SEQ ID NO 93
<211> LENGTH: 18
<212> TYPE: DNA
<213> ORGANISM: Artificial Sequence
<220> FEATURE:
<223> OTHER INFORMATION: The sequence has been designed and synthesized

<400> SEQUENCE: 93

actgctccag tttcccac                                                   18


<210> SEQ ID NO 94
<211> LENGTH: 43
<212> TYPE: PRT
<213> ORGANISM: Artificial Sequence
<220> FEATURE:
<223> OTHER INFORMATION: The sequence has been designed and synthesized

<400> SEQUENCE: 94

Thr Ser Pro Ser Thr Val Arg Leu Glu Ser Arg Val Arg Glu Leu Glu
1               5                   10                  15

Asp Arg Leu Glu Glu Leu Arg Asp Glu Leu Glu Arg Ala Glu Arg Arg
            20                  25                  30

Ala Asn Glu Met Ser Ile Gln Leu Asp Glu Cys
        35                  40


<210> SEQ ID NO 95
<211> LENGTH: 505
<212> TYPE: PRT
<213> ORGANISM: Artificial Sequence
<220> FEATURE:
<223> OTHER INFORMATION: The sequence has been designed and synthesized

<400> SEQUENCE: 95

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Asp Lys Ala Met
145                 150                 155                 160

Ala Ile Ser Asp Pro Asn Ser Gln Val Gln Leu Val Glu Thr Gly Gly
                165                 170                 175

Leu Val Gln Pro Gly Gly Ser Leu Arg Leu Ser Cys Ala Ala Ser Gly
            180                 185                 190
```

```
Phe Thr Leu Asp Tyr Ser Ser Ile Gly Trp Phe Arg Gln Ala Pro Gly
        195                 200                 205

Lys Glu Arg Glu Gly Val Ser Cys Ile Ser Ser Ser Gly Asp Ser Thr
    210                 215                 220

Lys Tyr Ala Asp Ser Val Lys Gly Arg Phe Thr Thr Ser Arg Asp Asn
225                 230                 235                 240

Ala Lys Asn Thr Val Tyr Leu Gln Met Asn Ser Leu Lys Pro Asp Asp
                245                 250                 255

Thr Ala Val Tyr Tyr Cys Ala Ala Phe Arg Ala Thr Met Cys Gly Val
            260                 265                 270

Phe Pro Leu Ser Pro Tyr Gly Lys Asp Asp Trp Gly Lys Gly Thr Leu
        275                 280                 285

Val Thr Val Ser Ser Glu Pro Lys Thr Pro Lys Pro Gln Pro Thr Ser
    290                 295                 300

Ala Ile Ala Gly Gly Gly Gly Ser Gly Gly Gly Gly Ser Gly Gly Gly
305                 310                 315                 320

Gly Ser Leu Gln Ala Met Ala Ala Ala Gln Leu Gln Leu Val Glu Thr
                325                 330                 335

Gly Gly Gly Leu Val Gln Pro Gly Gly Ser Leu Arg Leu Ser Cys Ala
            340                 345                 350

Ala Ser Gly Phe Thr Phe Ser Asp Tyr Val Met Thr Trp Val Arg Gln
        355                 360                 365

Ala Pro Gly Lys Gly Pro Glu Trp Ile Ala Thr Ile Asn Thr Asp Gly
    370                 375                 380

Ser Thr Met Arg Asp Asp Ser Thr Lys Gly Arg Phe Thr Ile Ser Arg
385                 390                 395                 400

Asp Asn Ala Lys Asn Thr Leu Tyr Leu Gln Met Thr Ser Leu Lys Pro
                405                 410                 415

Glu Asp Thr Ala Leu Tyr Tyr Cys Ala Arg Gly Arg Val Ile Ser Ala
            420                 425                 430

Ser Ala Ile Arg Gly Ala Val Arg Gly Pro Gly Thr Gln Val Thr Val
        435                 440                 445

Ser Ser Glu Pro Lys Thr Pro Lys Pro Gln Pro Ala Arg Gln Thr Ser
    450                 455                 460

Pro Ser Thr Val Arg Leu Glu Ser Arg Val Arg Glu Leu Glu Asp Arg
465                 470                 475                 480

Leu Glu Glu Leu Arg Asp Glu Leu Glu Arg Ala Glu Arg Arg Ala Asn
                485                 490                 495

Glu Met Ser Ile Gln Leu Asp Glu Cys
            500                 505
```

<210> SEQ ID NO 96
<211> LENGTH: 5
<212> TYPE: PRT
<213> ORGANISM: Artificial Sequence
<220> FEATURE:
<223> OTHER INFORMATION: The sequence has been designed and synthesized

<400> SEQUENCE: 96

```
Asp Asp Asp Asp Lys
1               5
```

<210> SEQ ID NO 97
<211> LENGTH: 130
<212> TYPE: PRT
<213> ORGANISM: Artificial Sequence
<220> FEATURE:

<223> OTHER INFORMATION: The sequence was designed and synthesized

<400> SEQUENCE: 97

Ser Gly Gly Gly Leu Val Gln Pro Gly Gly Ser Leu Arg Leu Ser Cys
1               5                   10                  15

Ala Ala Ser Ala Gly Asn Leu Asp Tyr Tyr Ala Ile Gly Trp Phe Arg
            20                  25                  30

Gln Ala Pro Gly Lys Glu Arg Glu Gly Val Ser Cys Ile Ser Ser Ser
        35                  40                  45

Asp Gly Ser Thr Val Tyr Thr Asp Ser Val Lys Gly Arg Phe Thr Ile
    50                  55                  60

Ser Arg Asp Asn Thr Lys Asn Thr Val Asp Leu Gln Met Asp Asn Leu
65                  70                  75                  80

Lys Pro Glu Asp Thr Ala Val Tyr Tyr Cys Ala Thr Val Val Asn Tyr
                85                  90                  95

Tyr Cys Thr Ala Gly Gly Ser Ile His Ala Ser Pro Tyr Glu Ile Trp
            100                 105                 110

Gly Gln Gly Thr Gln Val Thr Val Ser Ser Ala His His Ser Glu Asp
        115                 120                 125

Pro Ser
    130

<210> SEQ ID NO 98
<211> LENGTH: 119
<212> TYPE: PRT
<213> ORGANISM: Artificial Sequence
<220> FEATURE:
<223> OTHER INFORMATION: The sequence was designed and synthesized

<400> SEQUENCE: 98

Ser Gly Gly Gly Leu Val His Pro Gly Gly Ser Leu Arg Leu Ser Cys
1               5                   10                  15

Ala Pro Ser Ala Ser Leu Pro Ser Thr Pro Phe Asn Pro Phe Asn Asn
            20                  25                  30

Met Val Gly Trp Tyr Arg Gln Ala Pro Gly Lys Gln Arg Glu Met Val
        35                  40                  45

Ala Ser Ile Gly Leu Arg Ile Asn Tyr Ala Asp Ser Val Lys Gly Arg
    50                  55                  60

Phe Thr Ile Ser Arg Asp Asn Ala Lys Asn Thr Val Asp Leu Gln Met
65                  70                  75                  80

Asp Ser Leu Arg Pro Glu Asp Ser Ala Thr Tyr Tyr Cys His Ile Glu
                85                  90                  95

Tyr Thr His Tyr Trp Gly Lys Gly Thr Leu Val Thr Val Ser Ser Glu
            100                 105                 110

Pro Lys Thr Pro Lys Pro Gln
        115

<210> SEQ ID NO 99
<211> LENGTH: 120
<212> TYPE: PRT
<213> ORGANISM: Artificial Sequence
<220> FEATURE:
<223> OTHER INFORMATION: The sequence was designed and synthesized

<400> SEQUENCE: 99

Ser Gly Gly Gly Leu Ala Gln Pro Gly Gly Ser Leu Arg Leu Ser Cys
1               5                   10                  15

Glu Ala Ser Gly Phe Gly Thr Trp Phe Arg Phe Asp Glu Asn Thr Val

```
            20                  25                  30

Asn Trp Tyr Arg Gln Pro Pro Gly Lys Ser Arg Glu Phe Asp Glu Leu
        35                  40                  45

Val Ala Arg Tyr Pro Lys Ser Gly Ile Val Thr Tyr Leu Asp Ser Val
    50                  55                  60

Lys Gly Arg Phe Thr Ile Ser Arg Asp Asn Ala Lys Lys Met Ala Phe
65                  70                  75                  80

Leu Gln Met Asp Asn Leu Lys Pro Glu Asp Thr Ala Val Tyr Tyr Cys
                85                  90                  95

Asn Val Gly Glu Phe Trp Gly Gln Gly Thr Gln Val Thr Ile Ser Ser
            100                 105                 110

Glu Pro Lys Thr Pro Lys Pro Gln
        115                 120


<210> SEQ ID NO 100
<211> LENGTH: 126
<212> TYPE: PRT
<213> ORGANISM: Artificial Sequence
<220> FEATURE:
<223> OTHER INFORMATION: The sequence was designed and synthesized

<400> SEQUENCE: 100

Ser Gly Gly Gly Leu Val Gln Pro Gly Gly Ser Leu Arg Leu Ser Cys
1               5                   10                  15

Val Val Ser Gly Ser Asp Phe Asn Thr Tyr Ile Met Gly Trp Tyr Arg
            20                  25                  30

Gln Val Pro Gly Lys Pro Arg Glu Leu Val Ala Asp Ile Thr Thr Glu
        35                  40                  45

Gly Lys Thr Asn Tyr Gly Gly Ser Val Lys Gly Arg Phe Thr Ile Ser
    50                  55                  60

Arg Asp Asn Ala Lys Asn Thr Val Tyr Leu Gln Met Phe Gly Leu Lys
65                  70                  75                  80

Pro Glu Asp Ala Gly Asn Tyr Val Cys Asn Ala Asp Trp Lys Met Gly
                85                  90                  95

Ala Trp Thr Ala Gly Asp Tyr Gly Ile Asp Tyr Trp Gly Lys Gly Thr
            100                 105                 110

Leu Val Thr Val Ser Ser Gly Pro Lys Thr Pro Lys Pro Gln
        115                 120                 125


<210> SEQ ID NO 101
<211> LENGTH: 122
<212> TYPE: PRT
<213> ORGANISM: Artificial Sequence
<220> FEATURE:
<223> OTHER INFORMATION: The sequence was designed and synthesized

<400> SEQUENCE: 101

Ser Gly Gly Gly Leu Val Gln Pro Gly Gly Ser Leu Arg Leu Ser Cys
1               5                   10                  15

Ala Ala Ser Gly Phe Thr Leu Gly Ser Arg Tyr Met Ser Trp Val Arg
            20                  25                  30

Gln Ala Pro Gly Glu Gly Phe Glu Trp Val Ser Ser Ile Glu Pro Ser
        35                  40                  45

Gly Thr Ala Trp Asp Gly Asp Ser Ala Lys Gly Arg Phe Thr Thr Ser
    50                  55                  60

Arg Asp Asp Ala Lys Asn Thr Leu Tyr Leu Gln Met Ser Asn Leu Gln
65                  70                  75                  80
```

```
Pro Glu Asp Thr Gly Val Tyr Tyr Cys Ala Thr Gly Tyr Arg Thr Asp
                85                  90                  95

Thr Arg Ile Pro Gly Gly Ser Trp Gly Gln Gly Thr Gln Val Thr Val
            100                 105                 110

Ser Ser Glu Pro Lys Thr Pro Lys Pro Gln
        115                 120


<210> SEQ ID NO 102
<211> LENGTH: 114
<212> TYPE: PRT
<213> ORGANISM: Artificial Sequence
<220> FEATURE:
<223> OTHER INFORMATION: The sequence was designed and synthesized

<400> SEQUENCE: 102

Ser Gly Gly Gly Leu Val Gln Pro Gly Gly Ser Leu Arg Leu Ser Cys
1               5                   10                  15

Gln Val Ser Gly Phe Thr Phe Gly Asp Trp Val Met Ser Trp Phe Arg
            20                  25                  30

Gln Ala Pro Gly Lys Glu Arg Glu Phe Val Ala Ser Ile Thr Ala Thr
        35                  40                  45

Ser Ser Leu Lys Tyr Tyr Ala Asp Ser Val Lys Gly Arg Phe Thr Ile
    50                  55                  60

Ser Arg Asp Asn Val Asn Asn Thr Leu Phe Leu Gln Met Asp Arg Leu
65                  70                  75                  80

Lys Ser Glu Asp Thr Ala Val Tyr Tyr Cys Arg Ser Pro Asn Tyr Trp
                85                  90                  95

Gly Gln Gly Thr Gln Val Thr Val Ser Ala Glu Pro Lys Thr Pro Lys
            100                 105                 110

Pro Gln


<210> SEQ ID NO 103
<211> LENGTH: 116
<212> TYPE: PRT
<213> ORGANISM: Artificial Sequence
<220> FEATURE:
<223> OTHER INFORMATION: The sequence was designed and synthesized

<400> SEQUENCE: 103

Ser Gly Gly Gly Leu Val Gln Val Gly Gly Ser Leu Arg Leu Ser Cys
1               5                   10                  15

Val Val Ser Gly Ser Asp Ile Ser Gly Ile Ala Met Gly Trp Tyr Arg
            20                  25                  30

Gln Ala Pro Gly Lys Arg Arg Glu Met Val Ala Asp Ile Phe Ser Gly
        35                  40                  45

Gly Ser Thr Asp Tyr Ala Gly Ser Val Lys Gly Arg Phe Thr Ile Ser
    50                  55                  60

Arg Asp Asn Ala Lys Lys Thr Ser Tyr Leu Gln Met Asn Asn Val Lys
65                  70                  75                  80

Pro Glu Asp Thr Gly Val Tyr Tyr Cys Arg Leu Tyr Gly Ser Gly Asp
                85                  90                  95

Tyr Trp Gly Gln Gly Thr Gln Val Thr Val Ser Ser Ala His His Ser
            100                 105                 110

Glu Asp Pro Ser
        115


<210> SEQ ID NO 104
<211> LENGTH: 126
```

<212> TYPE: PRT
<213> ORGANISM: Artificial Sequence
<220> FEATURE:
<223> OTHER INFORMATION: The sequence was designed and synthesized

<400> SEQUENCE: 104

Gly Gly Gly Gly Leu Val Gln Pro Gly Gly Ala Leu Arg Leu Ser Cys
1 5 10 15

Ala Ala Ser Val Phe Gly Met Asp Tyr Tyr Tyr Ile Gly Trp Val Arg
20 25 30

Gln Ala Pro Gly Lys Glu Arg Glu Gly Val Ser Cys Ile Ser Asn Ile
35 40 45

Gly Arg Thr His Tyr Ala Asp Ser Val Lys Gly Arg Phe Thr Ile Ser
50 55 60

Arg Asp Asn Ala Lys Asn Thr Val Tyr Leu Gln Met Asn Ser Leu Lys
65 70 75 80

Pro Glu Asp Thr Ala Val Tyr Tyr Cys Ala Ala Ala Pro Leu Val Gly
85 90 95

Asn Tyr Cys Pro Ala Ser Tyr Glu Tyr Glu Ser Trp Gly Gln Gly Thr
100 105 110

Gln Val Thr Val Ser Ser Ala His His Ser Glu Asp Pro Ser
115 120 125

<210> SEQ ID NO 105
<211> LENGTH: 130
<212> TYPE: PRT
<213> ORGANISM: Artificial Sequence
<220> FEATURE:
<223> OTHER INFORMATION: The sequence was designed and synthesized

<400> SEQUENCE: 105

Ser Gly Gly Gly Leu Val Gln Pro Gly Gly Ser Leu Arg Leu Ser Cys
1 5 10 15

Ala Ala Ser Gly Gln Ser Leu Asp Asn Tyr Ile Ile Gly Trp Phe Arg
20 25 30

Gln Ala Pro Gly Lys Glu Arg Glu Gly Val Ser Cys Ile Asp Arg Thr
35 40 45

Gly Thr Val Thr His Tyr Ala Asp Ser Val Lys Gly Arg Phe Thr Ile
50 55 60

Ser Thr Asp Asn Val Lys Asn Thr Val Tyr Leu Glu Met Asn Asp Leu
65 70 75 80

Lys Pro Glu Asp Thr Ala Thr Tyr Phe Cys Ala Ala Glu Arg Arg Trp
85 90 95

Gly Val Val Ser Val Cys Val Ile Ser Asp Tyr Tyr Phe Asp Ser Trp
100 105 110

Gly Gln Gly Thr Gln Val Thr Val Ser Ser Ala His His Ser Glu Asp
115 120 125

Pro Ser
130

<210> SEQ ID NO 106
<211> LENGTH: 127
<212> TYPE: PRT
<213> ORGANISM: Artificial Sequence
<220> FEATURE:
<223> OTHER INFORMATION: The sequence was designed and synthesized

<400> SEQUENCE: 106

Thr Gly Gly Gly Leu Val Gln Ala Gly Gly Ser Leu Arg Leu Ser Cys 1 5 10 15

Thr Ala Ser Gly Arg Thr Ser Ser Phe Tyr Ala Leu Ala Trp Phe Arg
20 25 30

Gln Gly Pro Gly Lys Glu Arg Glu Phe Val Ala Ala Ile Gly Trp Ile
35 40 45

Asp Gly Ser Thr Arg Tyr Thr Asp Ser Ala Lys Gly Arg Phe Thr Ile
50 55 60

Ser Arg Asp Ala Ala Lys Asn Thr Met Tyr Leu Gln Met Asn Ser Leu
65 70 75 80

Lys Pro Glu Asp Thr Ala Val Tyr Ser Cys Thr Ala Arg Thr Gln Tyr
85 90 95

Gly Gly Ser Ser Ala Asp Pro Lys Asn Tyr Gly Tyr Trp Gly Gln Gly
100 105 110

Thr Gln Val Thr Val Ser Ala Glu Pro Lys Thr Pro Lys Pro Gln
115 120 125

<210> SEQ ID NO 107
<211> LENGTH: 127
<212> TYPE: PRT
<213> ORGANISM: Artificial Sequence
<220> FEATURE:
<223> OTHER INFORMATION: The sequence was designed and synthesized

<400> SEQUENCE: 107

Thr Gly Gly Gly Leu Val Gln Ala Gly Gly Ser Leu Arg Leu Ser Cys
1 5 10 15

Ala Gly Ser Gly Arg Ser Phe Ser Ala Ala Val Met Gly Trp Phe Arg
20 25 30

Gln Ala Pro Gly Lys Glu Arg Glu Phe Val Ala Ala Leu Arg Gln Ile
35 40 45

Ile Gly Ser Thr His Tyr Ala Asp Ser Val Lys Gly Arg Phe Thr Ile
50 55 60

Ser Arg Asp Asn Ala Lys Asn Met Leu Tyr Leu Asp Met Asn Ser Leu
65 70 75 80

Lys Pro Thr Asp Thr Ala Ala Tyr Tyr Cys Thr Ala Gly Pro Pro Thr
85 90 95

Met Leu Asp Val Ser Thr Asp Arg Glu Tyr Asp Thr Trp Gly Gln Gly
100 105 110

Thr Gln Val Thr Val Ser Ser Ala His His Ser Glu Asp Pro Ser
115 120 125

<210> SEQ ID NO 108
<211> LENGTH: 127
<212> TYPE: PRT
<213> ORGANISM: Artificial Sequence
<220> FEATURE:
<223> OTHER INFORMATION: The sequence was designed and synthesized

<400> SEQUENCE: 108

Ser Gly Gly Gly Leu Val Gln Pro Gly Gly Ser Leu Arg Leu Ser Cys
1 5 10 15

Ala Thr Ser Gly Phe Thr Leu Glu Tyr Tyr Ala Ile Gly Trp Phe Arg
20 25 30

Gln Ala Pro Gly Lys Gly Arg Glu Gly Val Ala Cys Met Asn Ser Ser
35 40 45

Gly Gly Gly Thr Asn Tyr Ala Asp Ser Val Lys Gly Arg Phe Thr Ile
50 55 60

```
Ser Arg Asp Asn Ala Lys Lys Met Val Tyr Leu Gln Met Asn Ser Leu
65                  70                  75                  80

Lys Ser Glu Asp Thr Ala Val Tyr Tyr Cys Val Val Asp Asp Phe Arg
                85                  90                  95

Cys Gly Ser Arg Trp Ala Ala Tyr Leu Arg Ser Ser Trp Gly Gln Gly
            100                 105                 110

Thr Gln Val Thr Val Ser Ser Glu Pro Lys Thr Pro Lys Pro Gln
        115                 120                 125


<210> SEQ ID NO 109
<211> LENGTH: 127
<212> TYPE: PRT
<213> ORGANISM: Artificial Sequence
<220> FEATURE:
<223> OTHER INFORMATION: The sequence was designed and synthesized

<400> SEQUENCE: 109

Ser Gly Gly Gly Leu Val Gln Ser Gly Gly Ser Leu Arg Leu Ser Cys
1               5                   10                  15

Ala Ala Ser Val Leu Thr Leu Glu Tyr Tyr Ala Ile Gly Trp Phe Arg
            20                  25                  30

Gln Ala Pro Gly Lys Glu Arg Glu Gly Ile Ser Cys Thr Gly Ser Ser
        35                  40                  45

Gly Gly Ser Thr Val Tyr Ile Asp Ser Val Lys Gly Arg Phe Thr Val
    50                  55                  60

Val Arg Asp Asn Ala Lys Asn Met Val Tyr Leu Gln Met Asp Ser Leu
65                  70                  75                  80

Gln Pro Glu Asp Thr Ala Val Tyr Tyr Cys Ala Ala Asp Asp Leu Arg
                85                  90                  95

Cys Gly Arg Gly Trp Ser Ser Tyr Phe Arg Gly Ser Trp Gly Gln Gly
            100                 105                 110

Thr Gln Val Thr Val Ser Ser Glu Pro Lys Thr Pro Lys Pro Gln
        115                 120                 125


<210> SEQ ID NO 110
<211> LENGTH: 127
<212> TYPE: PRT
<213> ORGANISM: Artificial Sequence
<220> FEATURE:
<223> OTHER INFORMATION: The sequence was designed and synthesized

<400> SEQUENCE: 110

Ser Gly Gly Gly Leu Val Gln Pro Gly Gly Ser Leu Arg Leu Ser Cys
1               5                   10                  15

Thr Ala Ser Thr Leu Thr Leu Asn Tyr Tyr Ala Ile Gly Trp Phe Arg
            20                  25                  30

Gln Ala Pro Gly Lys Glu Arg Glu Gly Val Ser Cys Thr Gly Ser Ser
        35                  40                  45

Gly Gly Ser Thr Val Tyr Ile Asp Ser Val Lys Gly Arg Phe Thr Val
    50                  55                  60

Val Arg Asp Asn Ala Lys Asn Met Val Tyr Leu Gln Met Asp Ser Leu
65                  70                  75                  80

Gln Pro Glu Asp Thr Ala Val Tyr Tyr Cys Ala Ala Asp Asp Leu Arg
                85                  90                  95

Cys Gly Arg Gly Trp Ser Ser Tyr Phe Arg Gly Ser Trp Gly Gln Gly
            100                 105                 110

Thr Gln Val Thr Val Ser Ser Glu Pro Lys Thr Pro Lys Pro Gln
        115                 120                 125
```

<210> SEQ ID NO 111
<211> LENGTH: 469
<212> TYPE: PRT
<213> ORGANISM: Artificial Sequence
<220> FEATURE:
<223> OTHER INFORMATION: The sequence was designed and synthesized

<400> SEQUENCE: 111

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Asp Lys Ala Met
145                 150                 155                 160

Ala Ile Ser Asp Pro Asn Ser Gly Ala Pro Val Pro Tyr Pro Asp Pro
                165                 170                 175

Leu Glu Pro Arg Ala Ala Ala Gln Val Gln Leu Val Glu Ser Gly Gly
            180                 185                 190

Gly Leu Val Gln Val Gly Gly Ser Leu Arg Leu Ser Cys Val Val Ser
        195                 200                 205

Gly Ser Asp Ile Ser Gly Ile Ala Met Gly Trp Tyr Arg Gln Ala Pro
    210                 215                 220

Gly Lys Arg Arg Glu Met Val Ala Asp Ile Phe Ser Gly Gly Ser Thr
225                 230                 235                 240

Asp Tyr Ala Gly Ser Val Lys Gly Arg Phe Thr Ile Ser Arg Asp Asn
                245                 250                 255

Ala Lys Lys Thr Ser Tyr Leu Gln Met Asn Asn Val Lys Pro Glu Asp
            260                 265                 270

Thr Gly Val Tyr Tyr Cys Arg Leu Tyr Gly Ser Gly Asp Tyr Trp Gly
        275                 280                 285

Gln Gly Thr Gln Val Thr Val Ser Ser Ala His His Ser Glu Asp Pro
    290                 295                 300

Thr Ser Ala Ile Ala Gly Gly Gly Gly Ser Gly Gly Gly Gly Ser Gly
305                 310                 315                 320

Gly Gly Gly Ser Leu Gln Gly Gln Leu Gln Leu Val Glu Ser Gly Gly
                325                 330                 335

Gly Leu Val His Pro Gly Gly Ser Leu Arg Leu Ser Cys Ala Pro Ser
            340                 345                 350

Ala Ser Leu Pro Ser Thr Pro Phe Asn Pro Phe Asn Asn Met Val Gly
        355                 360                 365
```

```
Trp Tyr Arg Gln Ala Pro Gly Lys Gln Arg Glu Met Val Ala Ser Ile
    370                 375                 380

Gly Leu Arg Ile Asn Tyr Ala Asp Ser Val Lys Gly Arg Phe Thr Ile
385                 390                 395                 400

Ser Arg Asp Asn Ala Lys Asn Thr Val Asp Leu Gln Met Asp Ser Leu
                405                 410                 415

Arg Pro Glu Asp Ser Ala Thr Tyr Tyr Cys His Ile Glu Tyr Thr His
            420                 425                 430

Tyr Trp Gly Lys Gly Thr Leu Val Thr Val Ser Ser Glu Pro Lys Thr
        435                 440                 445

Pro Lys Pro Gln Pro Ala Arg Gln Gly Ala Pro Val Pro Tyr Pro Asp
    450                 455                 460

Pro Leu Glu Pro Arg
465


<210> SEQ ID NO 112
<211> LENGTH: 478
<212> TYPE: PRT
<213> ORGANISM: Artificial Sequence
<220> FEATURE:
<223> OTHER INFORMATION: The sequence was designed and synthesized

<400> SEQUENCE: 112

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Arg
        115                 120                 125

Gly Ser Gly Met Lys Glu Thr Ala Ala Ala Lys Phe Glu Arg Gln His
    130                 135                 140

Met Asp Ser Pro Asp Leu Gly Thr Asp Asp Asp Asp Lys Ala Met Ala
145                 150                 155                 160

Ile Ser Asp Pro Asn Ser Gly Ala Pro Val Pro Tyr Pro Asp Pro Leu
                165                 170                 175

Glu Pro Arg Ala Ala Ala Gln Val Gln Leu Val Glu Ser Gly Gly Gly
            180                 185                 190

Leu Val Gln Pro Gly Gly Ser Leu Arg Leu Ser Cys Ala Ala Ser Gly
        195                 200                 205

Phe Thr Leu Gly Ser Arg Tyr Met Ser Trp Val Arg Gln Ala Pro Gly
    210                 215                 220

Glu Gly Phe Glu Trp Val Ser Ser Ile Glu Pro Ser Gly Thr Ala Trp
225                 230                 235                 240

Asp Gly Asp Ser Ala Lys Gly Arg Phe Thr Thr Ser Arg Asp Asp Ala
                245                 250                 255
```

-continued

```
Lys Asn Thr Leu Tyr Leu Gln Met Ser Asn Leu Gln Glu Asp Thr Gly
            260                 265                 270

Val Tyr Tyr Cys Ala Thr Gly Tyr Arg Thr Asp Thr Arg Ile Pro Gly
        275                 280                 285

Gly Ser Trp Gly Gln Gly Thr Gln Val Thr Val Ser Ser Glu Pro Lys
    290                 295                 300

Thr Pro Lys Pro Gln Thr Ser Gly Gly Gly Gly Ser Gly Gly Gly Gly
305                 310                 315                 320

Ser Gly Gly Gly Gly Ser Gly Ala Pro Gln Val Gln Leu Val Glu Ser
                325                 330                 335

Gly Gly Gly Leu Val Gln Pro Gly Gly Ser Leu Arg Leu Ser Cys Val
            340                 345                 350

Val Ser Gly Ser Asp Phe Asn Thr Tyr Ile Met Gly Trp Tyr Arg Gln
        355                 360                 365

Val Pro Gly Lys Pro Arg Glu Leu Val Ala Asp Ile Thr Thr Glu Gly
    370                 375                 380

Lys Thr Asn Tyr Gly Gly Ser Val Lys Gly Arg Phe Thr Ile Ser Arg
385                 390                 395                 400

Asp Asn Ala Lys Asn Thr Val Tyr Leu Met Phe Gly Leu Lys Pro Glu
                405                 410                 415

Asp Ala Gly Asn Tyr Val Cys Asn Ala Asp Trp Lys Met Gly Ala Trp
            420                 425                 430

Thr Ala Gly Asp Tyr Gly Ile Asp Tyr Trp Gly Lys Gly Thr Leu Val
        435                 440                 445

Thr Val Ser Ser Gly Pro Lys Thr Pro Lys Pro Gln Thr Ser Ala Ala
    450                 455                 460

Ala Gly Ala Pro Val Pro Tyr Pro Asp Pro Leu Glu Pro Arg
465                 470                 475
```